US012312574B2

(12) United States Patent
Furusako et al.

(10) Patent No.: US 12,312,574 B2

(45) Date of Patent: May 27, 2025

(54) POLYMER-COATED CROSSLINKED ALGINATE GEL FIBER

(71) Applicant: MOCHIDA PHARMACEUTICAL CO., LTD., Tokyo (JP)

(72) Inventors: Shoji Furusako, Tokyo (JP); Tsutomu Satoh, Tokyo (JP); Tomohiro Narumi, Tokyo (JP); Shingo Sato, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 18/392,583

(22) Filed: Dec. 21, 2023

(65) Prior Publication Data

US 2024/0174959 A1 May 30, 2024

Related U.S. Application Data

(63) Continuation of application No. PCT/JP2022/024935, filed on Jun. 22, 2022.

(30) Foreign Application Priority Data

Jun. 23, 2021 (JP) ................................. 2021-104094
Dec. 27, 2021 (WO) .................. PCT/JP2021/048567

(51) Int. Cl.

| | |
|---|---|
| *C12M 1/12* | (2006.01) |
| *C08L 5/04* | (2006.01) |
| *C12M 1/00* | (2006.01) |
| *C12N 5/071* | (2010.01) |
| *C12N 11/04* | (2006.01) |

(52) U.S. Cl.

CPC ............... *C12M 25/10* (2013.01); *C08L 5/04* (2013.01); *C12M 23/20* (2013.01); *C12N 5/0676* (2013.01); *C12N 5/0682* (2013.01); *C12N 11/04* (2013.01)

(58) Field of Classification Search

CPC ......... C12M 25/10; C12M 23/20; C08L 5/04; C12N 11/04; C12N 5/06; C12N 5/0682; A61K 35/12

USPC .............................................................. 536/3

See application file for complete search history.

(56) References Cited

U.S. PATENT DOCUMENTS

| | | | | |
|---|---|---|---|---|
| 4,352,883 | A | 10/1982 | Lim | |
| 4,391,909 | A | 7/1983 | Lim | |
| 11,932,708 | B2 * | 3/2024 | Furusako | A61L 15/28 |
| 2012/0301963 | A1 | 11/2012 | Takeuchi et al. | |
| 2014/0127308 | A1 * | 5/2014 | Opara | A61K 35/54 424/490 |
| 2015/0190427 | A1 | 7/2015 | Hui et al. | |
| 2017/0130184 | A1 | 5/2017 | Takeuchi et al. | |
| 2018/0327703 | A1 | 11/2018 | Lei | |
| 2019/0282710 | A1 | 9/2019 | Fussenegger et al. | |
| 2019/0367901 | A1 | 12/2019 | Ohsumi et al. | |
| 2020/0392439 | A1 | 12/2020 | Takeuchi et al. | |
| 2021/0095053 | A1 | 4/2021 | Furusako et al. | |
| 2021/0340481 | A1 | 11/2021 | Furusako et al. | |
| 2021/0380727 | A1 | 12/2021 | Furusako et al. | |
| 2022/0259541 | A1 | 8/2022 | Onoe et al. | |
| 2022/0409773 | A1 | 12/2022 | Shimoda et al. | |
| 2023/0035986 | A1 | 2/2023 | Furusako et al. | |

FOREIGN PATENT DOCUMENTS

| | | | | |
|---|---|---|---|---|
| CA | 3103227 | * | 6/2019 | C08L 5/04 |
| CA | 3144606 | * | 6/2020 | A61K 35/39 |
| CN | 105078923 | A | 11/2015 | |
| JP | 60-160885 | A | 8/1985 | |
| JP | 61-293919 | A | 12/1986 | |
| JP | 7-298870 | A | 11/1995 | |
| JP | 2014-506926 | A | 3/2014 | |
| JP | 2014-136128 | A | 7/2014 | |
| JP | 2014-236698 | A | 12/2014 | |
| JP | 2016-508369 | A | 3/2016 | |
| JP | 2016-77229 | A | 5/2016 | |
| JP | 2018-534936 | A | 11/2018 | |
| JP | 2019-75993 | A | 5/2019 | |
| JP | 2019-520837 | A | 7/2019 | |
| JP | 6601931 | B1 | 11/2019 | |
| JP | 2021-16319 | A | 2/2021 | |
| WO | WO 98/49202 | A1 | 11/1998 | |
| WO | WO 01/52871 | A1 | 7/2001 | |
| WO | WO 2005/095626 | A1 | 10/2005 | |
| WO | WO 2010/139061 | A1 | 12/2010 | |
| WO | WO 2011/046105 | A1 | 4/2011 | |
| WO | WO 2014/171842 | A1 | 10/2014 | |
| WO | WO 2015/178427 | A1 | 11/2015 | |

(Continued)

OTHER PUBLICATIONS

Uludag et al, Advanced Drug Delivery Reviews, 2000, 42, 29-64.*
Darrabie et al., "Characteristics of Poly-L-Ornithine-coated alginate microcapsules", Biomaterials, vol. 26, 2005, pp. 6846-6852.
Decision of Refusal for Japanese Patent Application No. 2022-568561 issued on Dec. 5, 2023.
Hobbs et al., "Substitution of Polyornithine for Polylysine in Alginate Microcapsules", American Diabetes Association 60th Scientific Sessions, Abstract, No. 448-P, 2000, 1 page.
International Search Report (PCT/ISA/210) issued in PCT/JP2021/048567, dated Feb. 15, 2022.
International Search Report dated Aug. 30, 2022 for Application No. PCT/JP2022/024935 with an English translation.

(Continued)

*Primary Examiner* — Ganapathy Krishnan
(74) *Attorney, Agent, or Firm* — Birch, Stewart, Kolasch & Birch, LLP

(57) ABSTRACT

There has been demand for an additional method for producing antibodies. The present invention provides: a polymer-coated crosslinked alginate gel fiber in which a core layer containing a crosslinked alginate gel and either antibody-producing cells (e.g., antibody-producing CHO cells) or bioactive-substance-producing cells (e.g., MIN6 cells derived from pancreatic β cells) is coated with a cationic polymer; and a method for producing antibodies, a bioactive substance, etc., using the fiber.

20 Claims, 21 Drawing Sheets

(56) References Cited

FOREIGN PATENT DOCUMENTS

| | | |
|---|---|---|
| WO | WO 2018/151186 A1 | 8/2018 |
| WO | WO 2019/078251 A1 | 4/2019 |
| WO | WO 2019/123886 A1 | 6/2019 |
| WO | WO 2019/168058 A1 | 9/2019 |
| WO | WO 2019/240219 A1 | 12/2019 |
| WO | WO 2020/032221 A1 | 2/2020 |
| WO | WO 2020/262642 A1 | 12/2020 |
| WO | WO 2021/125255 A1 | 6/2021 |
| WO | WO 2021/125279 A1 | 6/2021 |
| WO | WO 2022/145419 A1 | 7/2022 |

OTHER PUBLICATIONS

Japanese Office Action dated Jul. 18, 2023 for Application No. 2022-568561 with an English translation.
Japanese Office Action dated Mar. 7, 2023 for Application No. 2022-568561 with an English translation.
Li et al., "Chemically crosslinked alginate porous microcarriers modified with bioactive molecule for expansion of human hepatocellular carcinoma cells", J. Biomed Mater Res Part B, vol. 102B, 2014, pp. 1648-1658.
Okada, "Design and Creation of Cytomedicine for Application to Cell Therapy", Yakugaku Zasshi, The Pharmaceutical Society of Japan, vol. 125, No. 8, 2005, pp. 601-615 with an English abstract.
Okada, "Research on Functional Evaluation of Immobilized Cells Using Polymer Carriers and Their Application to Cell Therapy, etc.", Research on Mosaka University, 1997, p. 8, 45 pages total with partial translation.
Strand et al., "Poly-L-Lysine Induces Fibrosis on Alginate Microcapsules via the Induction of Cytokines", Cell Transplantation, vol. 10, 2001, pp. 263-275.
Sugiura et al., "Tubular gel fabrication and cell encapsulation in laminar flow stream formed by microfabricated nozzle array", Lab Chip, vol. 8, 2008, pp. 1255-1257.
Sun et al., "Biological properties of sulfanilamide-loaded alginate hydrogel fibers based on ionic and chemical crosslinking for wound dressings", International Journal of Biological Macromolecules, vol. 157, 2020 (Available online Apr. 28, 2020), pp. 522-529.
Toda, "Use of Doorda, immobilised enzymes and cells", Biotechnology, vol. 96, No. 8, 2018, p. 467-471 with partial translation.
Uludag et al., "Technology of mammalian cell encapsulation", Advanced Drug Delivery Reviews, vol. 42, 2000, pp. 29-64.
Written Opinion of the International Searching Authority (PCT/ISA/237) issued in PCT/JP2021/048567, dated Feb. 15, 2022.
Yamada et al., "Microfluidic synthesis of chemically and physically anisotropic hydrogel microfibers for guided cell growth and networking", Soft Matter, vol. 8, 2012, pp. 3122-3130.
Yamaji, "Research on immobilized culture of floating animal cells", Doctoral thesis, Kyoto University, 1994, pp. 1-137, with a partial English translation.
Japanese Decision to Grant a Patent for Japanese Application No. 2023-194056, dated Feb. 27, 2024, with an English translation.
Japanese Notice of Reasons for Refusal for Japanese Application No. 2023-194056, dated Jan. 9, 2024, with an English translation.

* cited by examiner

POLYMER-COATED CROSSLINKED ALGINATE GEL FIBER

CROSS-REFERENCE TO RELATED APPLICATIONS

This application is Continuation of PCT International Application No. PCT/JP2022/024935, filed on Jun. 22, 2022, which claims priority under 35 U.S.C. § 119(a) to Patent Application No. 2021-104094, filed in Japan on Jun. 23, 2021, and PCT International Application No. PCT/JP2021/048567 filed on Dec. 27, 2021, all of which are hereby expressly incorporated by reference into the present application.

TECHNICAL FIELD

The present invention relates to a polymer-coated crosslinked alginate gel fiber for producing an antibody, a bioactive substance or the like, a method for manufacturing the fiber, and a method for manufacturing an antibody, a bioactive substance or the like using the fiber.

BACKGROUND ART

Hitherto, a variety of production methods of antibodies, bioactive substances (for example, interferon, erythropoietin, IL-2 (interleukin-2), CSF (colony-stimulating factor), TNF (tumor necrosis factor), and the like) and the like by culture using animal cells have been known.

In the case of antibody production, as antibody-producing cells, CHO cells (Chinese hamster ovary cells), Sp2/0 cells, NS0 cells and the like are used as host cells, and, especially, CHO cells are often in use for the manufacture of antibodies since CHO cells are cells for which suspension culture is possible and have a fast cell growth rate and mass production of target proteins by the mass culture of CHO cells is easy.

Recently, in the development and manufacture of antibody drugs, there has been a demand for stable production of antibody drugs and cost reduction, and, in order to achieve those, development of more highly productive efficient production systems (for example, continuous production methods, novel culture techniques for producing a necessary amount of an antibody with a small production facility and the like) has been attracting attention.

For the culture of antibody-producing cells, an antibody-producing cell line a cell is revived in a spinner flask or the like, then, expansion culture is performed while culture conditions such as the culture medium composition, the temperature, stirring conditions, gas exchange and the pH are controlled, and, in the end, culture is performed in a large production culture tank on a several to 10 thousands-liter scale.

In a case where an antibody-producing cell is continuously cultured in a high density, there are cases where (1) a method for separating a cell and a culture fluid, (2) an effective method for supplying oxygen and the like become problematic. Regarding (1) and (2), while a variety of improvements have been made, it is still required to solve a variety of other problems in order to efficiently produce antibodies.

Alginate gel fibers having a core-shell structure in which a variety of cells are contained in a core layer and a shell layer is composed of alginate gel are known (Patent Literature 1: WO 2011/046105 and Patent Literature 2: Japanese Patent Application Publication No. 2016-77229).

An alginate gel fiber having a core-shell structure in which an antibody-producing cell is contained in a core layer and a shell layer is composed of alginate gel is known (Patent Literature 3: WO 2020/032221).

Alginate gel hollow fibers in which a variety of cells are contained in a hollow part and an outer shell layer is alginate gel are known (Patent Literature 4: WO 2015/178427, Patent Literature 5: Japanese Patent No. 6601931 and Patent Literature 6: Japanese Patent Application Publication No. 2014-236698).

Bundles in which alginate hydrogel fibers comprising cells (specifically, human skin fibroblast, HEK 293T cells) are made to adhere together using an adhesive comprising nanoparticles having surfaces coated with a cationic water-soluble polymer are known (Patent Literature 7: WO 2019/078251 and Patent Literature 8: WO 2019/123886).

A nerve bundle for transplantation in which neural stem cells or alginate hydrogel fibers comprising neural stem cells are bundled using chitosan is known (Patent Literature 9: Japanese Patent Application Publication No. 2014-136128).

A cell structure in which a mixture comprising adherent cells (specifically, C2C12 cells), a microcarrier and polysaccharide gel (specifically, alginate gel) is coated with a polyamino acid (examples thereof include a sheet-like (plate-like) structure, a fiber-like (fibrous) structure, a spherical structure and the like) is known (Patent Literature 10: Japanese Patent Application Publication No. 2019-075993).

Tubular gel obtained by coating calcium alginate microfibers comprising cells (293/GFP cells) with poly-L-lysine and dissolving the microfibers in a sodium citrate solution is known (Non Patent Literature 1: PA-Lab Chip, 2008, 8, pp. 1255 to 1257).

Chemically modified alginic acid derivatives in which a cyclic alkyne group or an azide group is introduced into one or more arbitrary carboxyl groups of alginic acid through an amide bond and a divalent linker are known (Patent Literature 11: WO 2019/240219 and Patent Literature 12: WO 2021/125255).

An alginate gel fiber having a core-shell structure in which an antibody-producing cell is contained in a core layer and a shell layer is composed of crosslinked alginate gel formed of a chemically modified alginic acid derivative is known (Patent Literature 13: WO 2021/125279).

A microfiber including anisotropic calcium alginate hydrogel fibers, in which a core layer formed of propylene glycol alginate (PGA) containing cells (3T3 and HeLa cells) and a sodium alginate solution is sandwiched by shell layers formed of a sodium alginate solution, coated with poly-L-lysine is known (Non Patent Literature 2: Soft Matter (2012), 8 (11), pp. 3122 to 3130).

In Patent Literature 1 to 13 and Non Patent Literature 1 and 2, the polymer-coated crosslinked alginate gel fiber for producing an antibody, a bioactive substance or the like, the method for manufacturing the gel fiber, and the method for manufacturing an antibody or the like using the gel fiber of the present invention are not disclosed and are not even suggested.

CITATION LIST

Patent Literature

[Patent Literature 1] WO 2011/046105

[Patent Literature 2] Japanese Patent Application Publication No. 2016-77229

[Patent Literature 3] WO 2020/032221

[Patent Literature 4] WO 2015/178427

[Patent Literature 5] Japanese Patent No. 6601931

[Patent Literature 6] Japanese Patent Application Publication No. 2014-236698

[Patent Literature 7] WO 2019/078251

[Patent Literature 8] WO 2019/123886

[Patent Literature 9] Japanese Patent Application Publication No. 2014-136128

[Patent Literature 10] Japanese Patent Application Publication No. 2019-075993

[Patent Literature 11] WO 2019/240219

[Patent Literature 12] WO 2021/125255

[Patent Literature 13] WO 2021/125279

Non Patent Literature

[Non Patent Literature 1] PA-Lab Chip, 2008, 8, pp. 1255 to 1257

[Non Patent Literature 2] Soft Matter, (2012), 8(11), pp. 3122 to 3130

SUMMARY OF INVENTION

Technical Problem

There has been a demand for an alginate gel fiber comprising a cell enabling production of antibodies, bioactive substances or the like, especially, a more practical alginate gel fiber from which cells can be cultured for a long period of time (for example, seven days or longer, 14 days or longer, 28 days or longer or the like) with no decomposition of the fiber.

Solution to Problem

As a result of repeating intensive studies, the present inventors found that a novel polymer-coated crosslinked alginate gel fiber for producing an antibody, a bioactive substance or the like that comprises a cell enabling production of antibodies, bioactive substances or the like and is formed by coating crosslinked alginate gel that is obtained by performing a crosslinking reaction using chemically modified alginic acid derivatives represented by Formula (I) and Formula (II) shown in an embodiment [1] to be described below with a cationic polymer and a method for manufacturing the same. In addition, as a result of performing culture of a cell producing an antibody, a bioactive substance or the like using the polymer-coated crosslinked alginate gel fiber, the present inventors found that it is possible to continuously produce antibodies, bioactive substances or the like for a long period of time with no decomposition of the polymer-coated crosslinked alginate gel fiber and completed the present invention.

Effect of the Invention

Due to the present invention, a new polymer-coated crosslinked alginate gel fiber and a method for producing an antibody, a bioactive substance or the like using the gel fiber are provided. In several embodiments, a polymer-coated crosslinked alginate gel fiber enabling antibodies, bioactive substances or the like to be continuously produced for a long period of time by coating crosslinked alginate gel that is produced using a mixture comprising a cell enabling production of antibodies, bioactive substances or the like, chemically modified alginic acid derivatives represented by Formula (I) and Formula (II) shown in an embodiment [1] to be described below and the like with a cationic polymer is provided.

From examples to be described below, it was found that a polymer-coated crosslinked alginate gel fiber can be produced by coating crosslinked alginate gel (also referred to as a core layer) that is formed using a mixture comprising an antibody-producing cell (anti-GPVI antibody-producing CHO cell or Tocilizumab-producing CHO cell) or a bioactive substance-producing cell (MING cell derived from a pancreatic R cell), chemically modified alginic acid derivatives represented by Formula (I) and Formula (II) and the like with a cationic polymer of poly-L-ornithine, polyallylamine, polyethyleneimine or polymethylene-CO-guanidine (PMCG) (also referred to as a cationic polymer layer) and, as a result of performing culture using the fiber, antibodies or insulin can be continuously produced for a long period of time (a maximum of 47 days in the examples to be described below). The polymer-coated crosslinked alginate gel fiber of the present invention provides environments suitable for cells enabling production of antibodies, bioactive substances or the like, and antibodies, bioactive substances or the like produced in the core layer of the fiber continuously penetrate the core layer and the cationic polymer layer and are discharged outside the fiber.

The polymer-coated crosslinked alginate gel fiber of the present invention provides environments suitable for production of antibodies, bioactive substances or the like. Physical stress on the cell producing an antibody, a bioactive substance or the like that is encapsulated in the core layer is small, and it is expected that the encapsulated cell continuously produces antibodies, bioactive substances or the like for a long period of time. Therefore, a method for manufacturing an antibody, a bioactive substance or the like using such a fiber can be expected to significantly improve the production efficiency of antibodies, bioactive substances or the like. For example, in the case of antibody production, unlike suspension culture of antibodies where a large culture tank is required, production of antibodies with a small production facility is also expected. The method is also expected as a continuous production technique of the next-generation antibody drugs suitable for the manufacture of a variety of antibody drugs in small quantities.

BRIEF DESCRIPTION OF DRAWINGS

FIG. 4 is a schematic view for describing how a metabolite and a waste product, such as an antibody, a bioactive substance or the like produced in the core layer, a culture fluid (nutrient source) and oxygen penetrate the cationic polymer layer.

DESCRIPTION OF EMBODIMENTS

Specific Embodiments

Figure 1:
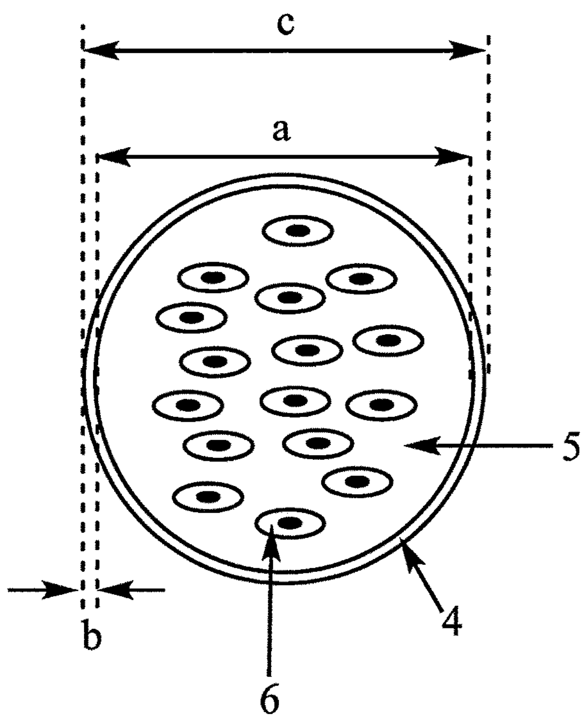
FIG. 1 is a cross-sectional view of a polymer-coated crosslinked alginate gel fiber.

Here, specific embodiments of a polymer-coated crosslinked alginate gel fiber, a method for manufacturing the fiber, and a method for manufacturing an antibody, a bioactive substance or the like using the fiber will be described. More specifically, the specific embodiments are as described in the following embodiments [1] to [7C-2].

[1] Embodiment 1 is as described below. A polymer-coated crosslinked alginate gel fiber comprising a core layer containing an antibody-producing cell or bioactive substance-producing cell embedded in crosslinked alginate gel that is obtained by performing a crosslinking reaction using chemically modified alginic acid derivatives represented by Formula (I) and Formula (II) (in the present specification, also referred to as "a cell enabling production of antibodies, bioactive substances or the like") and a cationic polymer layer coating the core layer. In addition, a polymer-coated crosslinked alginate gel fiber that is obtained by coating a core layer comprising a cell enabling production of antibodies, bioactive substances or the like and crosslinked alginate gel that is obtained by performing a crosslinking reaction using chemically modified alginic acid derivatives represented by Formula (I) and Formula (II) below with a cationic polymer (cationic polymer layer).

[Chemically Modified Alginic Acid Derivative Represented by Formula (I)]

Chemically modified alginic acid derivative represented by Formula (I) below:

[C1]

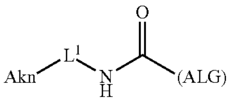

(I)

[in Formula (I), (ALG) represents alginic acid; —NHCO— represents an amide bond through an arbitrary carboxyl group of the alginic acid; Akn-$L^1$- (Akn represents a cyclic alkyne group; -$L^1$- is a divalent linker that bonds to the cyclic alkyne group (Akn)) is a group selected from the group consisting of partial structural formulae (in each formula, the right side of the cutting line is not included) shown in the following table].

TABLE 1-1

| No. | Akn-$L^1$- | |
|---|---|---|
| ALK-1a | 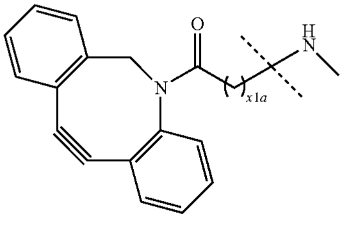 | x1a = 1-6 |

TABLE 1-1-continued
| No. | Akn-L[1]- | |
|---|---|---|
| ALK-1b | 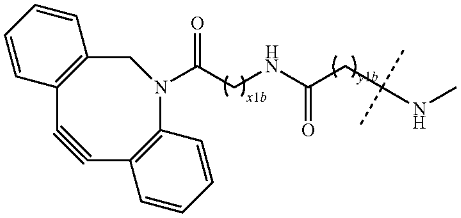 | x1b = 1-6<br>y1b = 1-6 |
| ALK-2 | 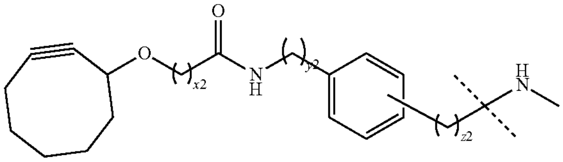 | x2 = 1-6<br>y2 = 0-6<br>z2 = 1-6 |
| ALK-3a | 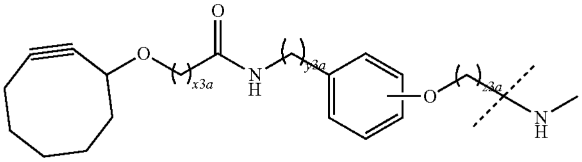 | x3a = 1-6<br>y3a = 0-6<br>z3a = 2-6 |
| ALK-3b | 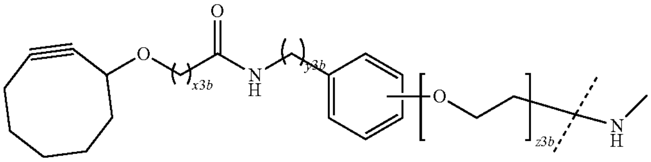 | x3b = 1-6<br>y3b = 0-6<br>z3b = 1-6 |
| ALK-4 | 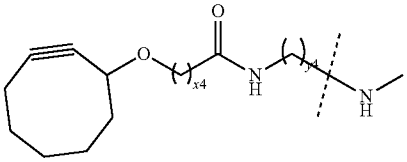 | x4 = 1-6<br>y4 = 2-6 |
| ALK-5a | 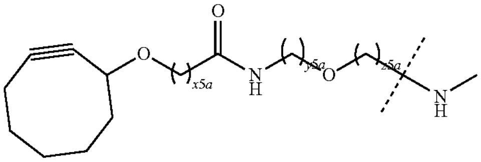 | x5a = 1-6<br>y5a = 2-6<br>z5a = 2-6 |
| ALK-5b | 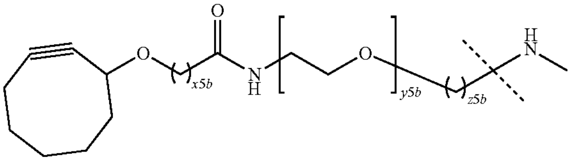 | x5b = 1-6<br>y5b = 1-6<br>z5b = 2-6 |
TABLE 1-2
| No. | Akn-L[1]- | |
|---|---|---|
| ALK-6 | 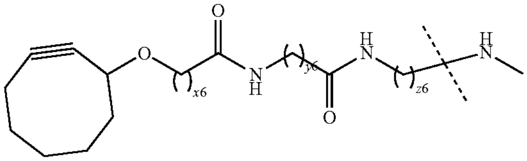 | x6 = 1-6<br>y6 = 1-6<br>z6 = 2-6 |

TABLE 1-2-continued

| No. | Akn-L[1]- | |
|---|---|---|
| ALK-7a | 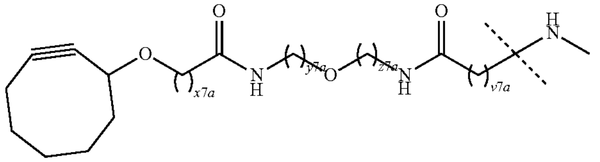 | x7a = 1-6<br>y7a = 2-6<br>z7a = 2-6<br>v7a = 1-6 |
| ALK-7b | 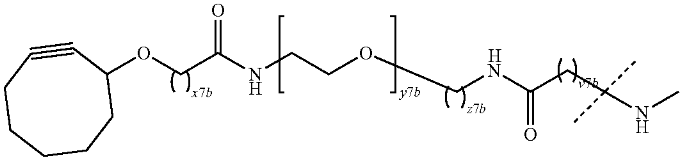 | x7b = 1-6<br>y7b = 1-6<br>z7b = 2-6<br>v7b = 1-6 |

[Chemically Modified Alginic Acid Derivative Represented by Formula (II)]

Chemically modified alginic acid derivative represented by Formula (II) below:

[C2]

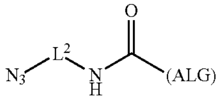

(II)

[in Formula (II), (ALG) represents alginic acid; —NHCO— represents an amide bond through an arbitrary carboxyl group of the alginic acid; -$L^2$- represents a linker selected from the group consisting of partial structural formulae (in each formula, the outsides of the cutting lines at both ends are not included) shown in the following table].

TABLE 2

| No. | -$L^2$- | |
|---|---|---|
| LN-1 | 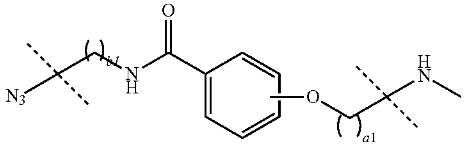 | a1 = 2-6<br>b1 = 2-6 |
| LN-2 | 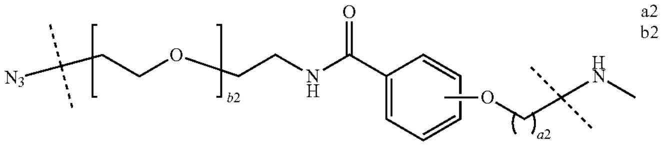 | a2 = 2-6<br>b2 = 1-6 |
| LN-3 | 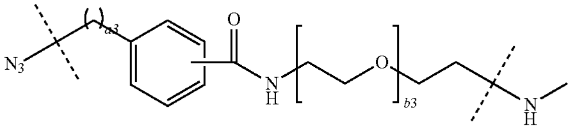 | a3 = 1-6<br>b3 = 1-6 |
| LN-4 | 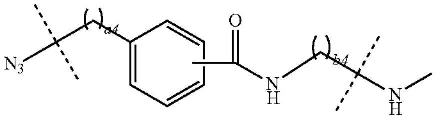 | a4 = 1-6<br>b4 = 2-6 |

TABLE 2-continued

| No. | $-L^2-$ | |
|---|---|---|
| LN-5 | 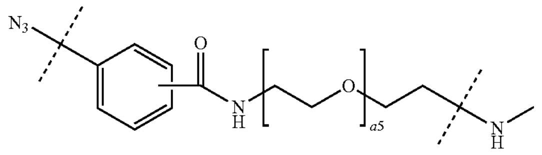 | a5 = 1-6 |
| LN-6 | 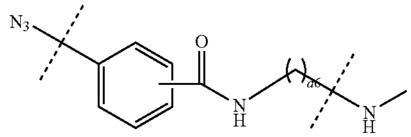 | a6 = 2-6 |

[1A] Embodiment 1A is as described below. A polymer-coated crosslinked alginate gel fiber comprising a core layer and a cationic polymer layer that is disposed on the outside of the core layer, in which the core layer comprises a cell enabling production of antibodies, bioactive substances or the like and crosslinked alginate gel in which a crosslink has been formed using chemically modified alginic acid derivatives represented by Formula (I) and Formula (II), and the cationic polymer layer is a cationic polymer. The chemically modified alginic acid derivatives represented by Formula (I) and Formula (II) are the same derivatives as defined in the embodiment [1].

[1-1-1] In the embodiment [1] or [1A], $Akn-L^1-$ in the chemically modified alginic acid derivative represented by Formula (I) is preferably a group selected from the group consisting of partial structural formulae (in each formula, the right side of the cutting line is not included) shown in the following table.

TABLE 3-1

| No. | $Akn-L^1-$ | |
|---|---|---|
| ALK-1a-1 | 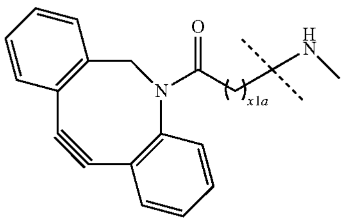 | x1a = 2-6 |
| ALK-1b-1 | 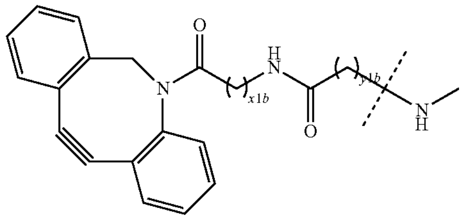 | x1b = 1-6<br>y1b = 1-6 |
| ALK-2-1 | 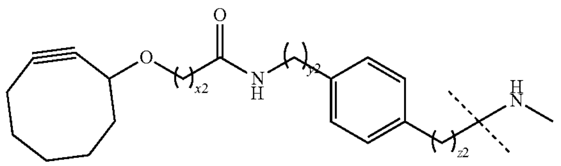 | x2 = 1-4<br>y2 = 0-6<br>z2 = 1-6 |
| ALK-3a-1 | 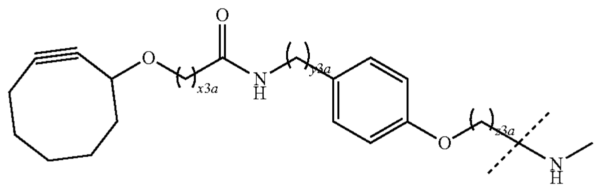 | x3a = 1-6<br>y3a = 0-6<br>z3a = 2-6 |

TABLE 3-1-continued
| No. | Akn-$L^1$- | |
|---|---|---|
| ALK-3b-1 | 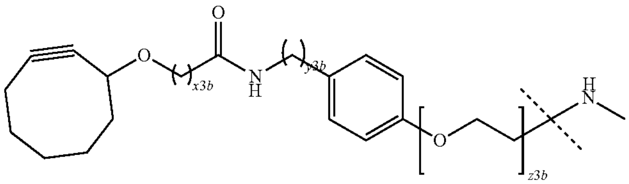 | x3b = 1-6<br>y3b = 0-6<br>z3b = 1-6 |
| ALK-4-1 | 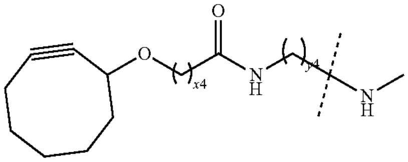 | x4 = 1-6<br>y4 = 2-6 |
| ALK-5a-1 | 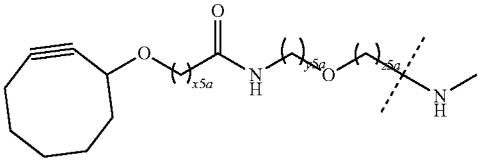 | x5a = 1-6<br>y5a = 2-6<br>z5a = 2-6 |
| ALK-5b-1 | 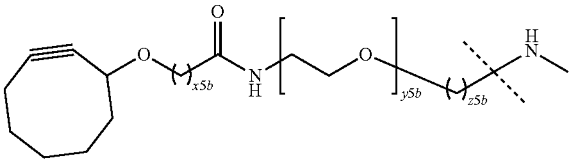 | x5b = 1-6<br>y5b = 1-6<br>z5b = 2-6 |
TABLE 3-2
| No. | Akn-$L^1$- | |
|---|---|---|
| ALK-6-1 | 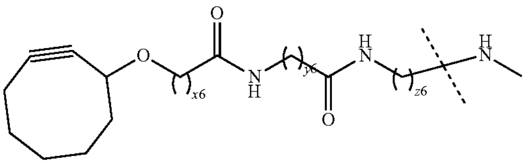 | x6 = 1-6<br>y6 = 1-6<br>z6 = 2-6 |
| ALK-7a-1 | 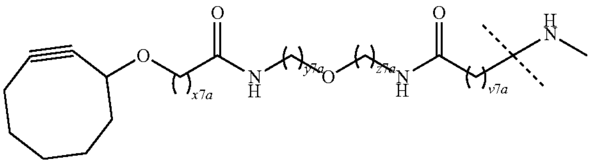 | x7a = 1-6<br>y7a = 2-6<br>z7a = 2-6<br>v7a = 1-6 |
| ALK-7b-1 | 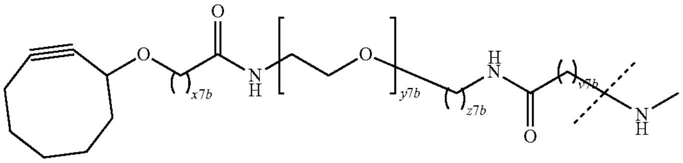 | x7b = 1-6<br>y7b = 1-6<br>z7b = 2-6<br>v7b = 1-6 |

[1-1-2] In the embodiment [1] or [1A], Akn-$L^1$- in the chemically modified alginic acid derivative represented by Formula (I) is more preferably a group selected from the group consisting of partial structural formulae (in each formula, the right side of the cutting line is not included) shown in the following table.

TABLE 3-3

| No. | Akn-$L^1$- | |
|---|---|---|
| ALK-1a-2 | 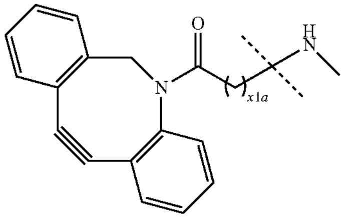 | x1a = 2-6 |
| ALK-1b-2 | 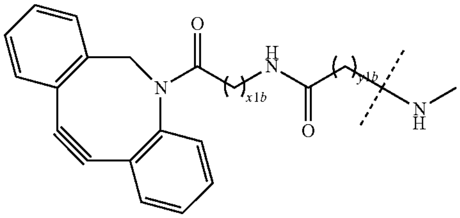 | x1b = 1-3<br>y1b = 1-3 |
| ALK-2-2 | 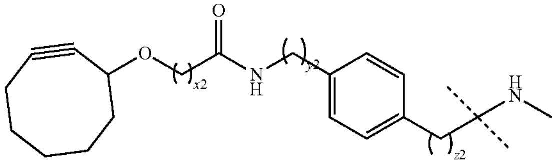 | x2 = 1-4<br>y2 = 1-6<br>z2 = 1-6 |
| ALK-3a-2 | 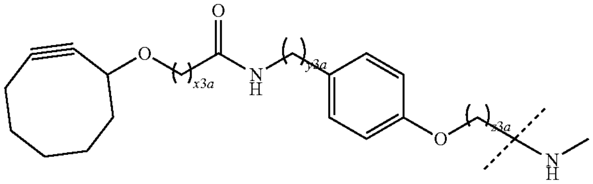 | x3a = 1-3<br>y3a = 0-3<br>z3a = 2-4 |
| ALK-3b-2 | 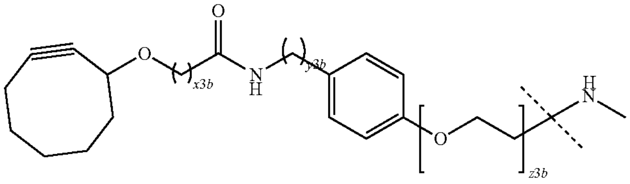 | x3b = 1-3<br>y3b = 0-3<br>z3b = 1-3 |
| ALK-4-2 | 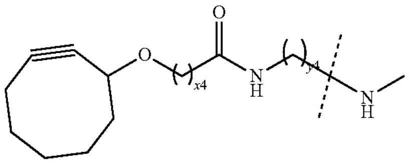 | x4 = 1-3<br>y4 = 2-4 |
| ALK-5a-2 | 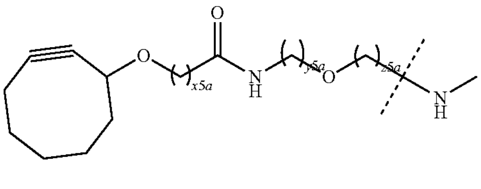 | x5a = 1-3<br>y5a = 2-4<br>z5a = 2-4 |

TABLE 3-3-continued

| No. | Akn-$L^1$- | |
|---|---|---|
| ALK-5b-2 | 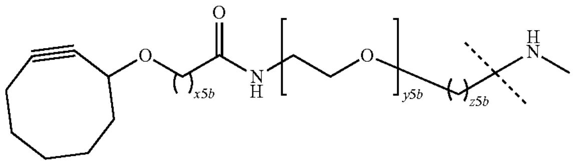 | x5b = 1-3<br>y5b = 1-3<br>z5b = 2-4 |

TABLE 3-4

| No. | Akn-$L^1$- | |
|---|---|---|
| ALK-6-2 | 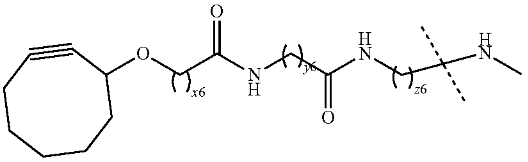 | x6 = 1-3<br>y6 = 1-3<br>z6 = 2-4 |
| ALK-7a-2 | 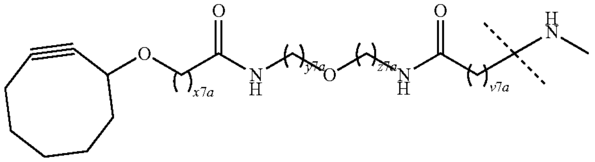 | x7a = 1-3<br>y7a = 2-4<br>z7a = 2-4<br>v7a = 1-3 |
| ALK-7b-2 | 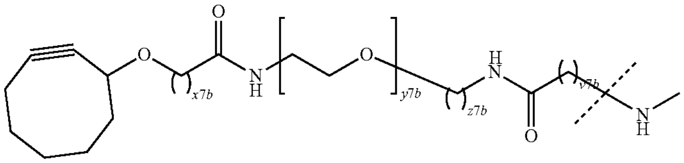 | x7b = 1-3<br>y7b = 1-3<br>z7b = 2-4<br>v7b = 1-3 |

[1-1-3] In the embodiment [1] or [1A], Akn-$L^1$- in the chemically modified alginic acid derivative represented by Formula (I) is still more preferably a group selected from the group consisting of the following partial structural formulae (in each formula, the right side of the cutting line is not included):

[C3]

ALK-1a-3a

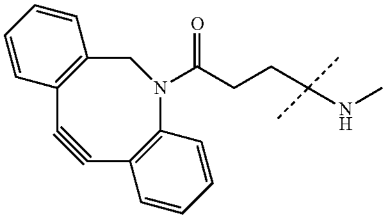

-continued

ALK-1a-3b

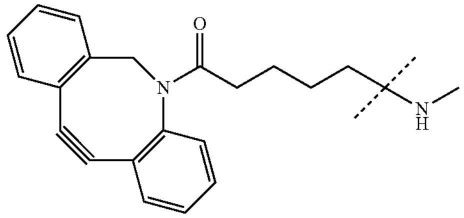

ALK-1b-3

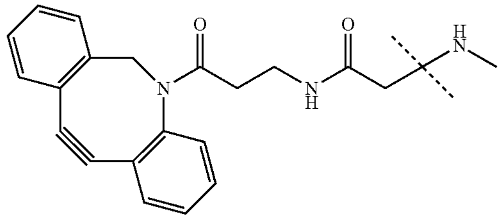

-continued

ALK-2-3

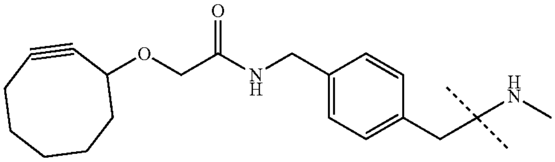

ALK-3a-3

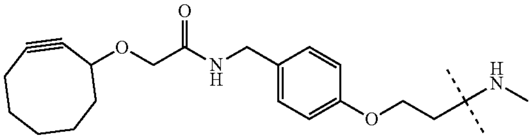

ALK-4-3

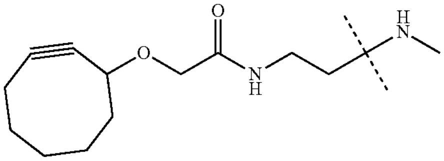

ALK-5a-3

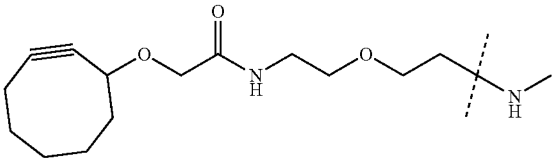

ALK-6-3a

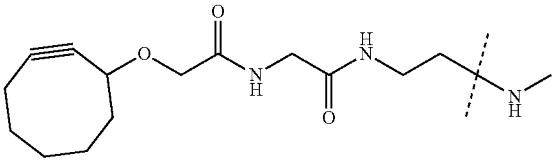

ALK-6-3b

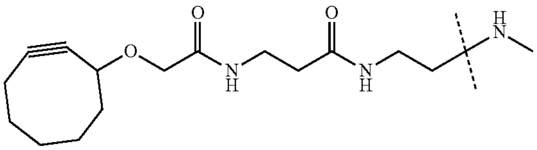

-continued

ALK-7a-3

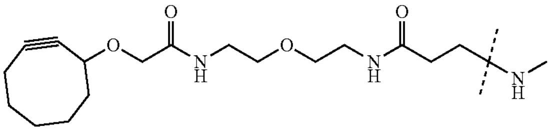

[1-1-4] In the embodiment [1] or [1A], Akn-L[1]- in the chemically modified alginic acid derivative represented by Formula (I) is particularly preferably a group selected from the following partial structural formulae (in each formula, the right side of the cutting line is not included):

[C4]

ALK-1a-3a

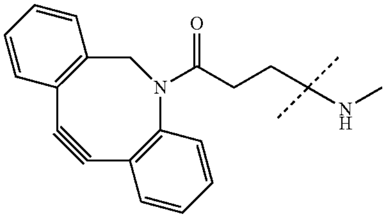

ALK-2-3

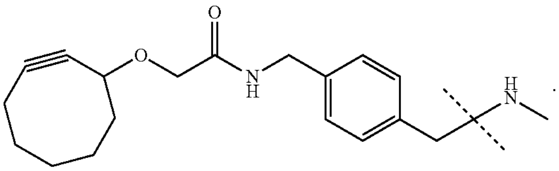

[1-1-5] In the embodiment [1] or [1A], Akn-L[1]- in the chemically modified alginic acid derivative represented by Formula (I) is a group selected from the group consisting of partial structural formulae (in each formula, the right side of the cutting line is not included) shown in the following table:

TABLE 3-5

| No. | Akn-L[1]- | |
|---|---|---|
| ALK-1a | 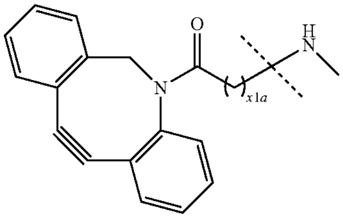 | x1a = 1-6 |
| ALK-2 | 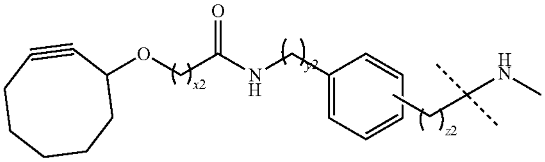 | x2 = 1-6<br>y2 = 0-6<br>z2 = 1-6 |

preferably a group selected from the group consisting of partial structural formulae (in each formula, the right side of the cutting line is not included) shown in the following table:

TABLE 3-6

| No. | $Akn-L^1-$ | |
|---|---|---|
| ALK-1a-1 | 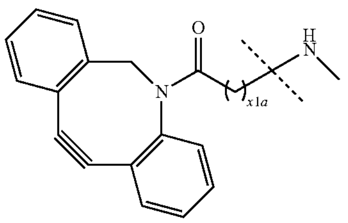 | x1a = 2-6 |
| ALK-2-1 | 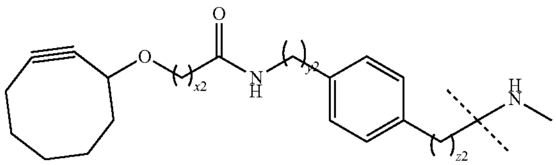 | x2 = 1-4<br>y2 = 0-6<br>z2 = 1-6 |

more preferably a group selected from the group consisting of partial structural formulae (in each formula, the right side of the cutting line is not included) shown in the following table:

TABLE 3-7

| No. | $Akn-L^1-$ | |
|---|---|---|
| ALK-1a-2 | 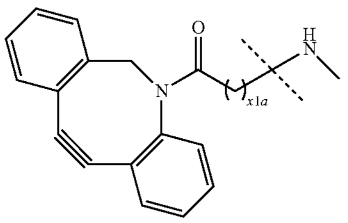 | x1a = 2-6 |
| ALK-2-2 | 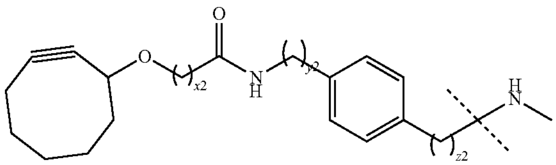 | x2 = 1-4<br>y2 = 1-6<br>z2 = 1-6 |

and still more preferably a group selected from the following partial structural formulae (in each formula, the right side of the cutting line is not included):

[C5]

ALK-1a-3a

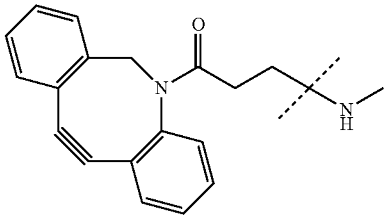

-continued

ALK-2-3

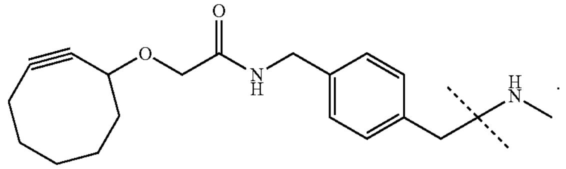

[1-2-1] In the embodiment [1] or [1A], $-L^2-$ in the chemically modified alginic acid derivative represented by Formula (II) is preferably a group selected from the group consisting of partial structural formulae (in each formula, the outsides of the cutting lines at both ends are not included) shown in the following table:

TABLE 4-1

| No. | $-L^2-$ | |
|---|---|---|
| LN-1-1 | 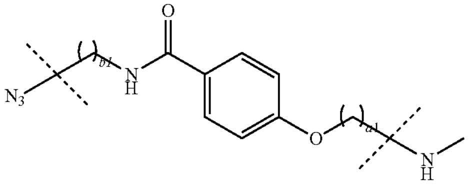 | a1 = 2-6<br>b1 = 2-6 |
| LN-2-1 | 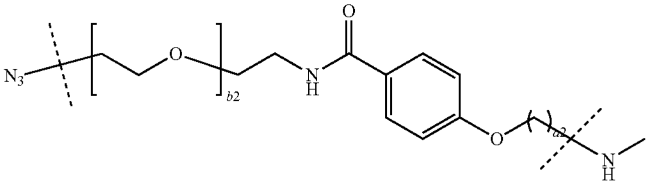 | a2 = 2-6<br>b2 = 1-6 |
| LN-3-1 | 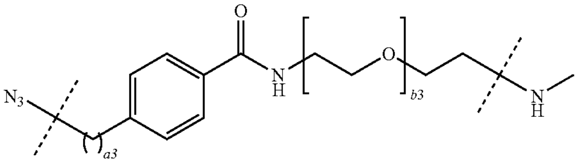 | a3 = 1-6<br>b3 = 1-6 |
| LN-4-1 | 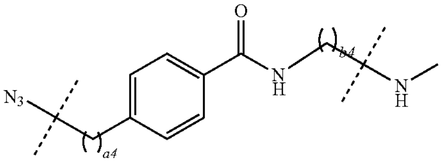 | a4 = 1-6<br>b4 = 2-6 |
| LN-5-1 | 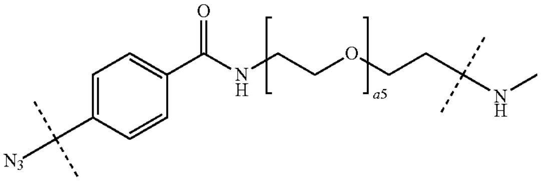 | a5 = 1-6 |
| LN-6-1 | 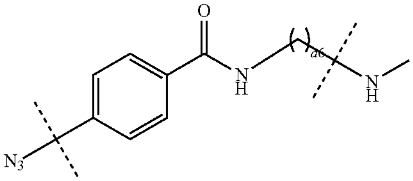 | a6 = 2-6 |

[1-2-2] In the embodiment [1] or [1A], $-L^2-$ in the chemically modified alginic acid derivative represented by Formula (II) is more preferably a group selected from the group consisting of partial structural formulae (in each formula, the outsides of the cutting lines at both ends are not included) shown in the following table:

TABLE 4-2

| No. | $-L^2-$ | |
|---|---|---|
| LN-1-2 | 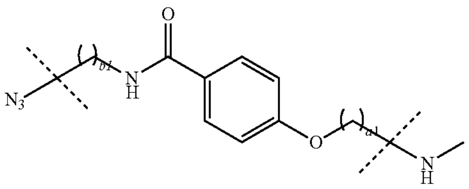 | a1 = 2-4<br>b1 = 2-4 |
| LN-2-2 | 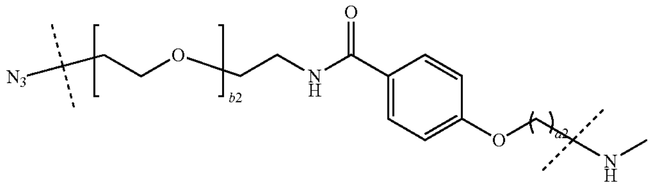 | a2 = 2-4<br>b2 = 1-3 |
| LN-3-2 | 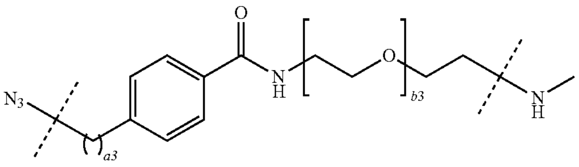 | a3 = 1-3<br>b3 = 1-3 |
| LN-4-2 | 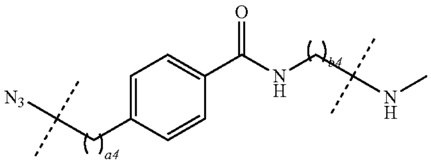 | a4 = 1-3<br>b4 = 2-4 |
| LN-5-2 | 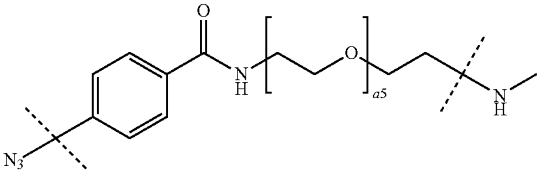 | a5 = 1-3 |
| LN-6-2 | 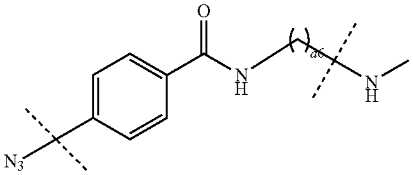 | a6 = 2-4 |

[1-2-3] In the embodiment [1] or [1A], $-L^2-$ in the chemically modified alginic acid derivative represented by Formula (II) is still more preferably a group selected from the group consisting of the following partial structural formulae (in each formula, the outsides of the cutting lines at both ends are not included):

[C6]

LN-1-3

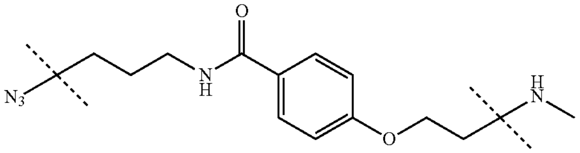

LN-2-3

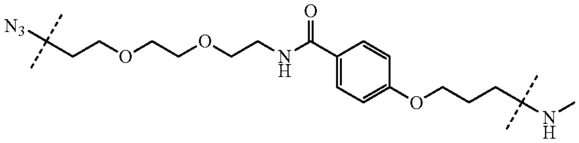

LN-3-3a

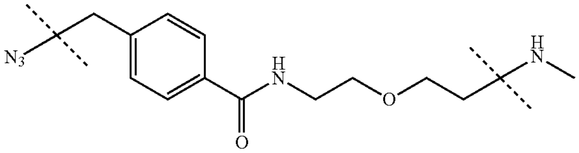

LN-3-3b

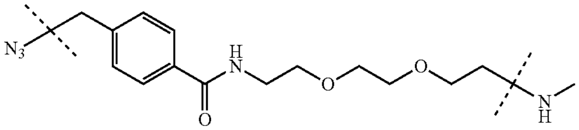

LN-4-3

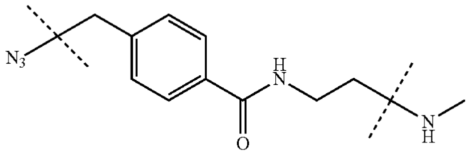

LN-5-3a

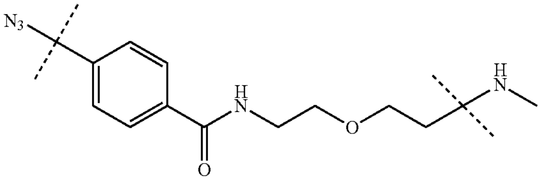

-continued

LN-5-3b

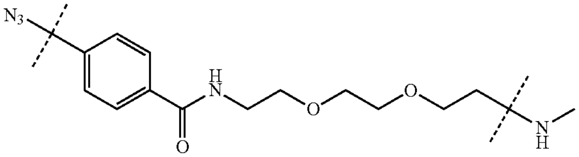

LN-6-3

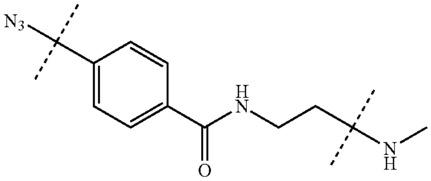

[1-2-4] In the embodiment [1] or [1A], $-L^2-$ in the chemically modified alginic acid derivative represented by Formula (II) is particularly preferably a group selected from the group consisting of the following partial structural formulae (in each formula, the outsides of the cutting lines at both ends are not included):

[C7]

LN-1-3

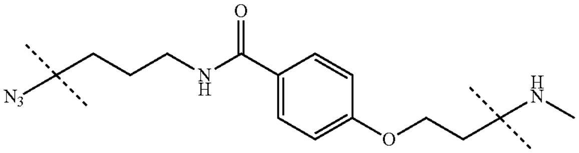

LN-3-3a

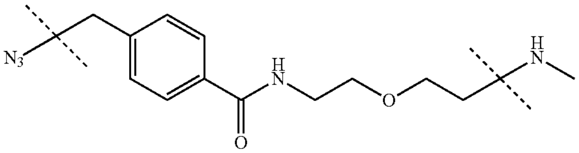

LN-5-3a

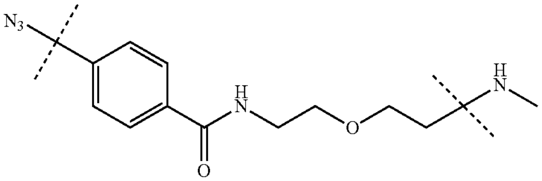

[1-2-5] In the embodiment [1] or [1A], $-L^2-$ in the chemically modified alginic acid derivative represented by Formula (II) is a group selected from the group consisting of partial structural formulae (in each formula, the outsides of the cutting lines at both ends are not included) shown in the following table:

TABLE 4-3
| No. | -L²- | |
|---|---|---|
| LN-1 | 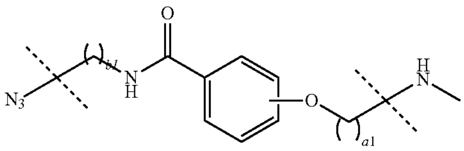 | a1 = 2-6<br>b1 = 2-6 |
| LN-3 | 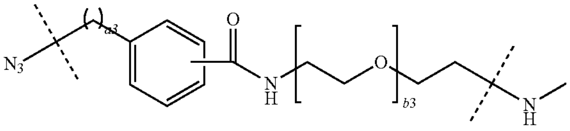 | a3 = 1-6<br>b3 = 1-6 |
| LN-5 | 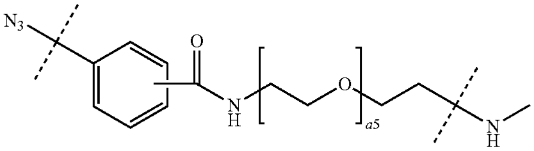 | a5 = 1-6 |
preferably a group selected from the group consisting of partial structural formulae (in each formula, the outsides of the cutting lines at both ends are not included) shown in the following partial structural formulae (in each formula, the right side of the cutting line is not included):
TABLE 4-4
| No. | -L²- | |
|---|---|---|
| LN-1-1 | 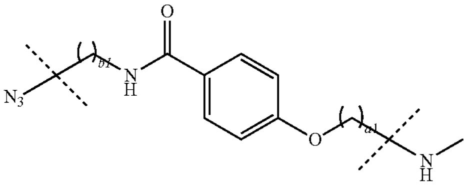 | a1 = 2-6<br>b1 = 2-6 |
| LN-3-1 | 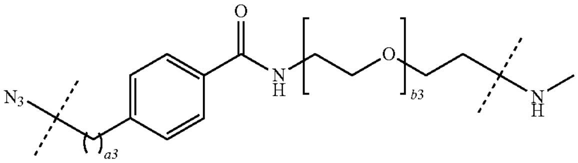 | a3 = 1-6<br>b3 = 1-6 |
| LN-5-1 | 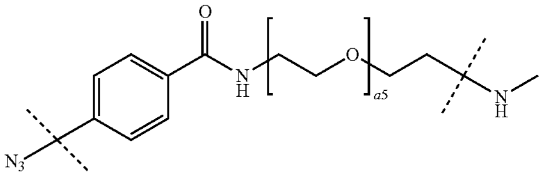 | a5 = 1-6 | more preferably a group selected from the group consisting of partial structural formulae (in each formula, the outsides of the cutting lines at both ends are not included) shown in the following partial structural formulae (in each formula, the right side of the cutting line is not included):

TABLE 4-5

| No. | —$L^2$— | |
|---|---|---|
| LN-1-2 | 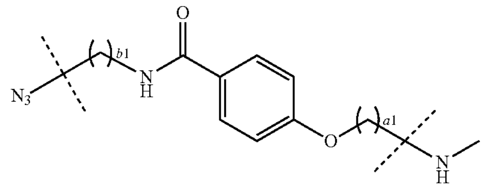 | a1 = 2-4<br>b1 = 2-4 |
| LN-3-2 | 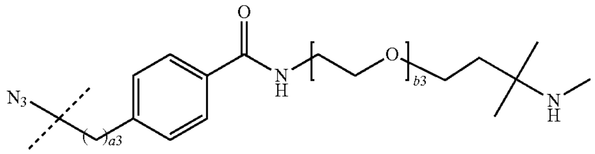 | a3 = 1-3<br>b3 = 1-3 |
| LN-5-2 | 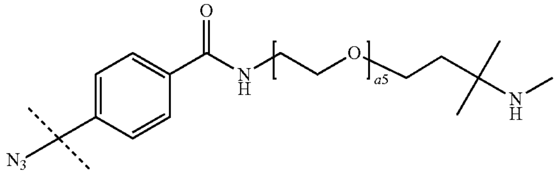 | a5 = 1-3 |

still more preferably a group selected from the group consisting of the following partial structural formulae (in each formula, the outsides of the cutting lines at both ends are not included).

[C8]

LN-1-3

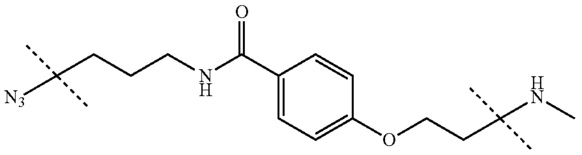

LN-3-3a

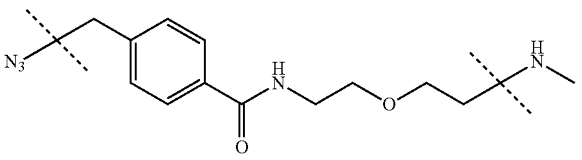

LN-5-3a

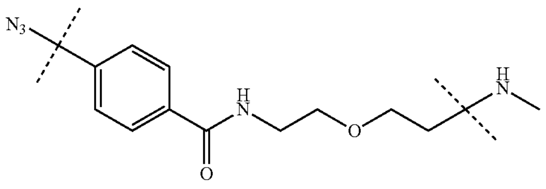

[1-2A] The use of the chemically modified alginic acid derivatives represented by Formula (I) and Formula (II) for which the definitions of Akn, -$L^1$- and -$L^2$- described in the embodiments [1] to [1-2-5] are appropriately combined makes it possible to arbitrarily form a preferable embodiment of crosslinked alginate gel in the core layer of the polymer-coated crosslinked alginate gel fiber of the present invention.

[1X] Embodiment 1X is as described below. A polymer-coated crosslinked alginate gel fiber that is obtained by coating a core layer comprising a cell enabling production of antibodies, bioactive substances or the like and crosslinked alginate gel in which a crosslink has been formed using a chemically modified alginic acid derivative represented by Formula (I-A) below and a chemically modified alginic acid derivative represented by Formula (II-A) below with a cationic polymer (cationic polymer layer).

[Chemically Modified Alginic Acid Derivative Represented by Formula (I-A)]

Chemically modified alginic acid derivative represented by Formula (I-A) below:

[C9]

(I-A)

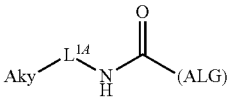

[in Formula (I-A), (ALG) represents alginic acid; —NHCO— represents an amide bond through an arbitrary carboxyl group of the alginic acid; -$L^{1A}$- is the following partial structural formula:

[C10]

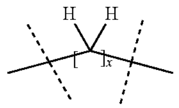

(in the formula, x is 1 to 50;

—$CH_2$— in the formula may be substituted by one to 15 groups such as —C(═O)—, —O—, —NH—, —N($C_{1-3}$ alkyl group)-, —S—, a $C_{3-8}$ cycloalkyl ring, a benzene ring, a five or six-membered aromatic heterocycle or a five or six-membered non-aromatic heterocycle;

hydrogen atoms in —$CH_2$— in the formula may be substituted by one to 10 groups such as a halogen atom, a hydroxyl group, an amino group, a $C_{1-3}$ alkyl group, a —O—$C_{1-3}$ alkyl group, —NH($C_{1-3}$ alkyl group)-, —N($C_{1-3}$ alkyl group)$_2$-, —COO-M (M=Na, K, ½Ca, a hydrogen atom or a $C_{1-3}$ alkyl group), a hydroxy $C_{1-3}$ alkyl group, a $C_{2-4}$ alkanoyl group, a —S—$C_{1-3}$ alkyl group, a —$SO_2$-$C_{1-3}$ alkyl group, a phenyl group, a benzyl group, a five or six-membered aromatic heterocycle or a five or six-membered non-aromatic heterocycle;

Aky is a cyclic alkyne group) (in the formula, the outsides of the cutting lines at both ends are not included)].

[Chemically Modified Alginic Acid Derivative Represented by Formula (II-A)]

Chemically modified alginic acid derivative represented by Formula (II-A) below:

[C11]

(II-A)

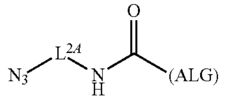

[in Formula (II-A), (ALG) represents alginic acid; —NHCO— represents an amide bond through an arbitrary carboxyl group of the alginic acid; -$L^{2A}$- is the following partial structural formula:

[C12]

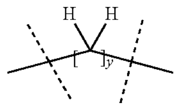

(in the formula, y is 1 to 50;

—$CH_2$— in the formula may be substituted by one to 15 groups such as —C(═O)—, —O—, —NH—, —N($C_{1-3}$ alkyl group)-, —S—, a $C_{3-8}$ cycloalkyl ring, a benzene ring, a five or six-membered aromatic heterocycle or a five or six-membered non-aromatic heterocycle;

hydrogen atoms in —$CH_2$— in the formula may be substituted by one to 10 groups such as a halogen atom, a hydroxyl group, an amino group, a $C_{1-3}$ alkyl group, a —O—$C_{1-3}$ alkyl group, —NH($C_{1-3}$ alkyl group)-, —N($C_{1-3}$ alkyl group)$_2$-, —COO-M (M=Na, K, ½Ca, a hydrogen atom or a $C_{1-3}$ alkyl group), a hydroxy $C_{1-3}$ alkyl group, a $C_{2-4}$ alkanoyl group, a —S—$C_{1-3}$ alkyl group, a —$SO_2$-$C_{1-3}$ alkyl group, a phenyl group, a benzyl group, a five or six-membered aromatic heterocycle or a five or six-membered non-aromatic heterocycle) (in the formula, the outsides of the cutting lines at both ends are not included)].

[1Y] Embodiment 1Y is as described below. A polymer-coated crosslinked alginate gel fiber comprising a core layer and a cationic polymer layer that is disposed on the outside of the core layer, in which the core layer comprises a cell enabling production of antibodies, bioactive substances or the like and crosslinked alginate gel in which a crosslink has been formed using a chemically modified alginic acid derivative represented by Formula (I-A) and a crosslinking is formed using a chemically modified alginic acid derivative represented by Formula (II-A), and the cationic polymer layer is a cationic polymer. The chemically modified alginic acid derivatives represented by Formula (I-A) and Formula (II-A) are the same as the definitions in the embodiment [1X].

[1X-1] In the embodiment [1X] or [1Y], in the chemically modified alginic acid derivative represented by Formula (I-A), regarding -$L^{1A}$-, it is preferable that x is 2 to 45, —$CH_2$— in -$L^{1A}$- may be substituted by one to 15 groups such as —C(═O)—, —O—, —NH—, —N($C_{1-3}$ alkyl group)-, a cyclohexane ring, a six-membered aromatic heterocycle, a six-membered non-aromatic heterocycle or a benzene ring, and hydrogen atoms in —$CH_2$— in -$L^{1A}$- may be substituted by one to 10 groups such as a hydroxyl group, an amino group, a $C_{1-3}$ alkyl group, a —O—$C_{1-3}$ alkyl group, —NH($C_{1-3}$ alkyl group), —N($C_{1-3}$ alkyl group)$_2$ or —COO-M (M=Na, K, ½Ca, a hydrogen atom or a $C_{1-3}$ alkyl group);

it is more preferable that x is 2 to 45, and —$CH_2$— in -$L^{1A}$- may be substituted by one to 15 groups such as —C(═O)—, —O—, —NH—, —N($C_{1-3}$ alkyl group)-, a cyclohexane ring or a benzene ring;

it is still more preferable that x is 2 to 45, and —$CH_2$— in -$L^{1A}$- may be substituted by one to 15 groups such as —C(═O)—, —O—, —NH— or a benzene ring;

it is particularly preferable that x is 3 to 25, and —$CH_2$— in -$L^{1A}$- may be substituted by one to 15 groups such as —C(═O)—, —O—, —NH— or a benzene ring;

it is most preferable that x is 3 to 15, and —$CH_2$— in -$L^{1A}$- may be substituted by one to 10 groups such as —C(═O)—, —O—, —NH— or a benzene ring;

specifically, -$L^{1A}$- is a linker selected from the following partial structural formulae:

[C13]

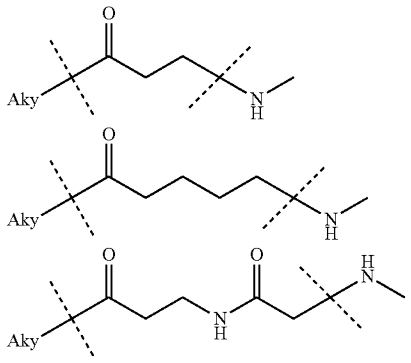

-continued

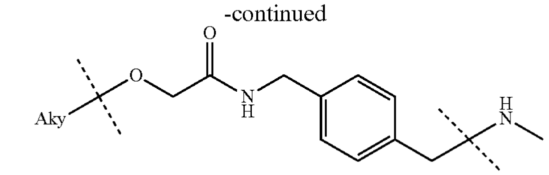

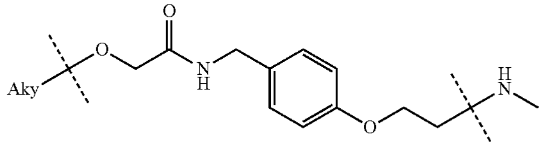

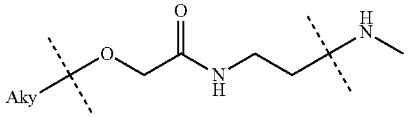

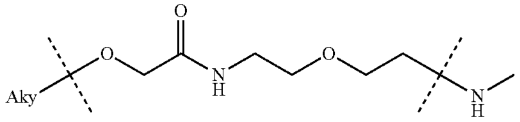

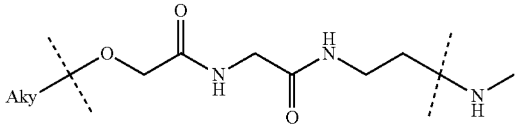

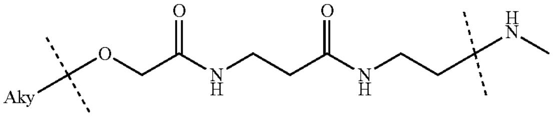

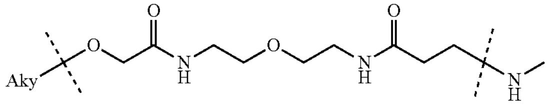

(in each formula, the outsides of the cutting lines at both ends are not included);

more specifically, -$L^{1A}$- is a linker selected from the following partial structural formulae:

[C14]

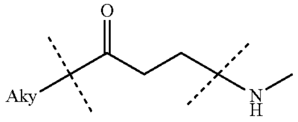

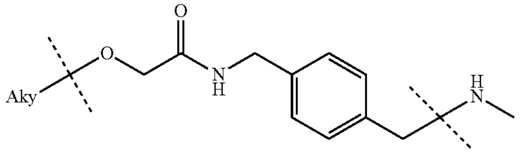

(in each formula, the outsides of the cutting lines at both ends are not included).

[1X-2] In the embodiment [1X] or [1Y], in the chemically modified alginic acid derivative represented by Formula (I-A), Aky is preferably a seven to nine-membered cyclic alkyne group (hydrogen atoms in —$CH_2$— of the cyclic alkyne group may be substituted by one to five groups selected from the group consisting of a halogen atom, a hydroxyl group, an amino group, a keto group, a $C_{1-3}$ alkyl group, a —O—$C_{1-3}$ alkyl group, —NH($C_{1-3}$ alkyl group)-, —N($C_{1-3}$ alkyl group)$_2$ and —COO-M (M=Na, K, ½Ca, a hydrogen atom or a $C_{1-3}$ alkyl group; one to three $C_{3-8}$ cycloalkyl rings, benzene rings or five or six-membered aromatic heterocycles may condense in the cyclic alkyne group);

more preferably an eight-membered cyclic alkyne group (hydrogen atoms in —$CH_2$— of the cyclic alkyne group may be substituted by one to five groups selected from the group consisting of a halogen atom, a keto group, a $C_{1-3}$ alkyl group or a —O—$C_{1-3}$ alkyl group; one to three cyclopropane rings, benzene rings or five-membered aromatic heterocycles may condense in the cyclic alkyne group);

still more preferably a group selected from the following partial structural formulae:

[C15]

(Aky-1)

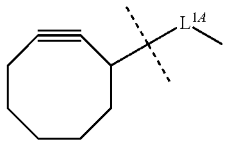

(Aky-2)

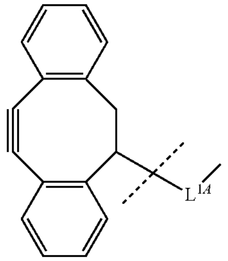

(Aky-3)

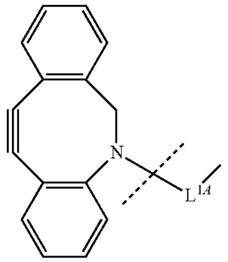

(Aky-4)

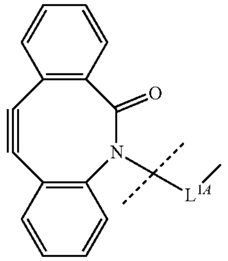

(Aky-5)

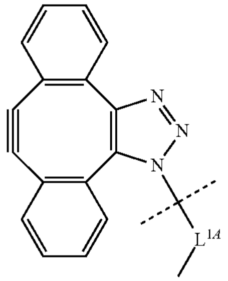

-continued (Aky-6)

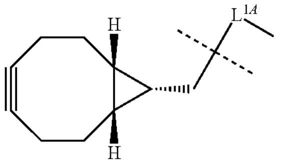

(Aky-7)

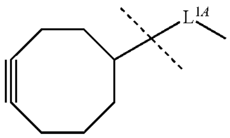

(Aky-8)

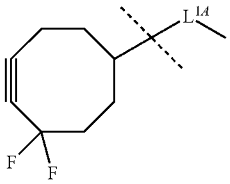

(Aky-9)

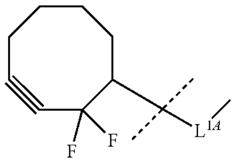

(Aky-10)

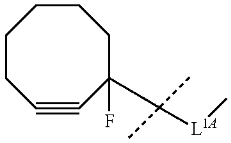

(Aky-11)

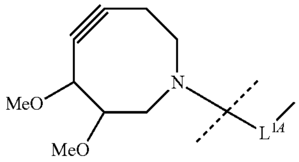

(Aky-12)

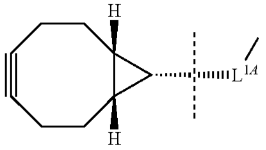

(in the formulae, the right sides of the cutting lines at both ends are not included);

particularly preferably a group selected from the following partial structural formulae:

[C16]

(Aky-1)

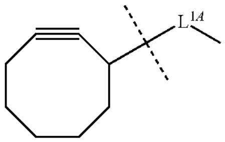

-continued (Aky-2)

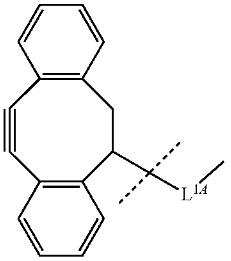

(Aky-3)

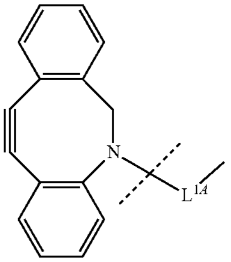

(Aky-4)

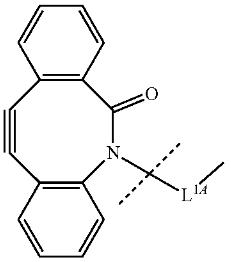

(Aky-6)

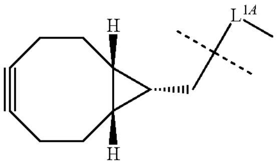

(in the formulae, the right sides of the cutting lines at both ends are not included);

most preferably a group selected from the following partial structural formulae:

[C17]

(Aky-1)

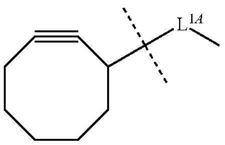

(Aky-3)

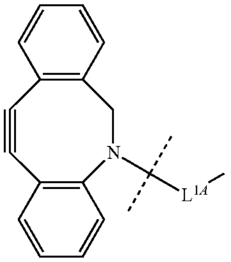

(in the formulae, the right sides of the cutting lines at both ends are not included).

[1X-3] In the embodiment [1X] or [1Y], in the chemically modified alginic acid derivative represented by Formula (II-A), regarding $-L^{2A}-$, it is preferable that y is 5 to 40, $—CH_2—$ in $-L^{2A}-$ may be substituted by one to 15 groups such as —C(═O)—, —O—, —NH—, —N($C_{1-3}$ alkyl group)-, a cyclohexane ring, a six-membered aromatic heterocycle, a six-membered non-aromatic heterocycle or a benzene ring, and hydrogen atoms in $—CH_2—$ in $-L^{2A}-$ may be substituted by one to 10 groups such as a hydroxyl group, an amino group, a $C_{1-3}$ alkyl group, a —O—$C_{1-3}$ alkyl group, —NH($C_{1-3}$ alkyl group)-, —N($C_{1-3}$ alkyl group)$_2$- or —COO-M (M=Na, K, ½Ca, a hydrogen atom or a $C_{1-3}$ alkyl group);

it is more preferable that y is 5 to 40, and $—CH_2—$ in $-L^{2A}-$ may be substituted by one to 10 groups such as —C(═O)—, —O—, —NH—, —N($C_{1-3}$ alkyl group)-, a cyclohexane ring or a benzene ring;

it is still more preferable that y is 5 to 40, and $—CH_2—$ in $-L^{2A}-$ may be substituted by one to 10 groups such as —C(═O)—, —O—, —NH—, —N($C_{1-3}$ alkyl group)- or a benzene ring;

it is particularly preferable that y is 5 to 20, and $—CH_2—$ in $-L^{2A}-$ may be substituted by one to 10 groups such as —C(═O)—, —O—, —NH— or a benzene ring;

it is most preferable that y is 5 to 15, and $—CH_2—$ in $-L^{2A}-$ may be substituted by one to 10 groups such as —C(═O)—, —O—, —NH— or a benzene ring;

specifically, for example, $-L^{2A}-$ is a linker selected from the following partial structural formulae:

[C18]

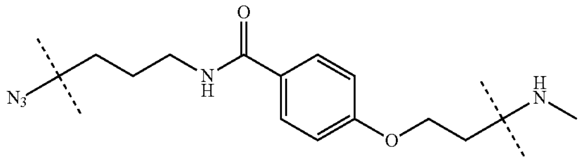

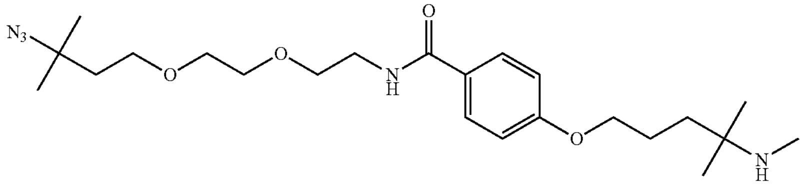

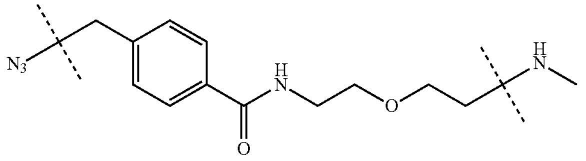

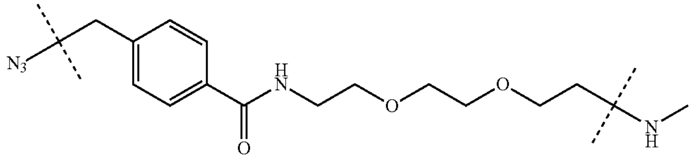

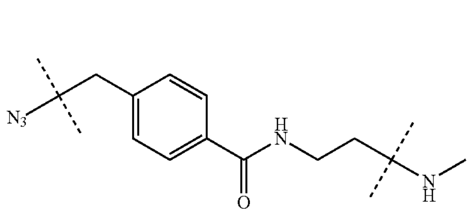

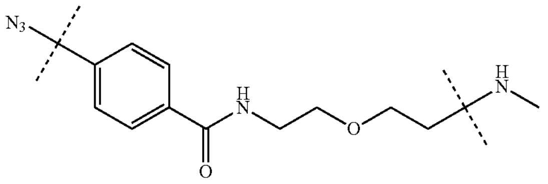

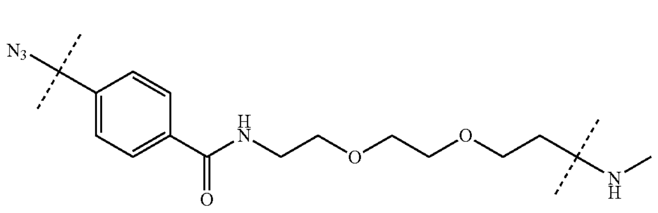

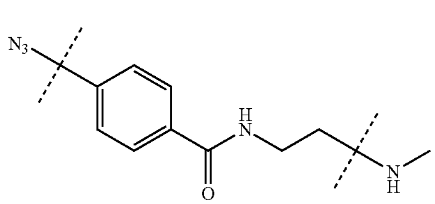

(in the formulae, the outsides of the cutting lines at both ends are not included); more specifically, $-L^{2A}-$ is a linker selected from the following partial structural formulae:

[C19]

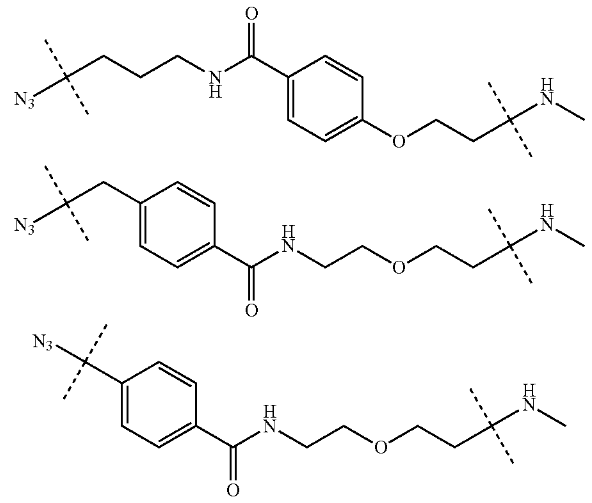

(in the formulae, the outsides of the cutting lines at both ends are not included).

[1X-4] The use of the chemically modified alginic acid derivatives represented by Formula (I-A) and Formula (II-A) for which the definitions of Aky, $-L^{1A}-$ and $-L^{2A}-$ described in the embodiment [1X], [1Y] and [1X-1] to [1X-3] are appropriately combined makes it possible to arbitrarily form a preferable embodiment of crosslinked alginate gel in the core layer of the polymer-coated crosslinked alginate gel fiber of the present invention.

[1-3] In the embodiment [1], [1A], [1X] or [1Y], the cell enabling production of antibodies, bioactive substances or the like, which is contained in the core layer of the polymer-coated crosslinked alginate gel fiber, is a cell selected from the group consisting of antibody (a variety of monoclonal antibodies such as human antibodies, humanized antibodies, chimeric antibodies and mouse antibodies)-producing cells, bioactive substance-producing cells and cells enabling production of a variety of useful substances useful as drug raw materials, chemical raw materials, food raw materials and the like.

[1-3-1] In the embodiment [1], [1A], [1X] or [1Y] the cell enabling production of antibodies, which is contained in the core layer of the polymer-coated crosslinked alginate gel fiber, (also referred to as the antibody-producing cell) is a hybridoma or a cultured cell transformed with an antibody expression vector, and a cultured cell that is used as a host thereof (host cell) is, for example, a cell selected from the group consisting of a CHO cell, a CHO cell subline, a COS cell, an Sp2/0 cell, an NS0 cell, an SP2 cell, a PERC6 cell, an YB2/0 cell, an YE2/0 cell, a 1R983F cell, a Namalwa cell, a Wil-2 cell, a Jurkat cell, a Vero cell, a Molt-4 cell, an HEK293 cell, a BHK cell, a HT-1080 cell, a KGH6 cell, a P3X63Ag8.653 cell, a $C_{127}$ cell, a JC cell, an LA7 cell, a ZR-45-30 cell, an hTERT cell, an $NM2C_5$ cell, a UACC-812 cell and the like.

[1-3-2] In the embodiment [1], [1A], [1X] or [1Y], in the antibody-producing cell that is contained in the core layer of the polymer-coated crosslinked alginate gel fiber, the host cell thereof is preferably a cell selected from the group consisting of a CHO cell, a CHO cell subline, a COS cell, an Sp2/0 cell, an NS0 cell, an SP2 cell and a PERC6 cell; more preferably a cell selected from the group consisting of a CHO cell, a CHO cell subline, an Sp2/0 cell and an NS0 cell; and still more preferably a CHO cell or a CHO cell subline.

[1-3-2-1] In the embodiment [1-3-2], the antibody-producing cell is preferably a floating cell or a cell or cell subline adapted so as to be floating-cultivable, and preferable examples, more preferable examples and still more preferable examples of such cells are as described in the embodiment [1-3-2].

[1-3-3] In the embodiment [1], [1A], [1X] or [1Y], the antibody-producing cell that is contained in the core layer of the polymer-coated crosslinked alginate gel fiber is, for example, an antibody-producing CHO cell in which a host cell thereof is a CHO cell, for example, a CHO cell selected from the group consisting of a muromonab-CD3-producing CHO cell, a trastuzumab-producing CHO cell, a rituximab-producing CHO cell, a palivizumab-producing CHO cell, an infliximab-producing CHO cell, a basiliximab-producing CHO cell, a tocilizumab-producing CHO cell, a gemtuzumab-producing CHO cell, a bevacizumab-producing CHO cell, an ibritumomab-producing CHO cell, an adalimumab-producing CHO cell, a cetuximab-producing CHO cell, a ranibizumab-producing CHO cell, an omalizumab-producing CHO cell, an eculizumab-producing CHO cell, a panitumumab-producing CHO cell, a ustekinumab-producing CHO cell, a golimumab-producing CHO cell, a canakinumab-producing CHO cell, a denosumab-producing CHO cell, a mogamulizumab-producing CHO cell, a certolizumab-producing CHO cell, an ofatumumab-producing CHO cell, a pertuzumab-producing CHO cell, a brentuximab-producing CHO cell, a natalizumab-producing CHO cell, a nivolumab-producing CHO cell, an alemtuzumab-producing CHO cell, a secukinumab-producing CHO cell, a ramucirumab-producing CHO cell, an ipilimumab-producing CHO cell, an evolocumab-producing CHO cell, a mepolizumab-producing CHO cell, an alirocumab-producing CHO cell, an ixekizumab-producing CHO cell, a brodalumab-producing CHO cell, an idarucizumab-producing CHO cell, an elotuzumab-producing CHO cell, a pembrolizumab-producing CHO cell, a sarilumab-producing CHO cell, a bezlotoxumab-producing CHO cell, a belimumab-producing CHO cell, a daratumumab-producing CHO cell, an avelumab-producing CHO cell, a dupilumab-producing CHO cell, an atezolizumab-producing CHO cell, a benralizumab-producing CHO cell, an inotuzumab-producing CHO cell, an emicizumab-producing CHO cell, a guselkumab-producing CHO cell, a durvalumab-producing CHO cell, an obinutuzumab-producing CHO cell, a vedolizumab-producing CHO cell, an anti-GPVI antibody-producing CHO cell and the like; for example, a CHO cell selected from the group consisting of a trastuzumab-producing CHO cell, a rituximab-producing CHO cell, an infliximab-producing CHO cell, a tocilizumab-producing CHO cell, an adalimumab-producing CHO cell, a nivolumab-producing CHO cell, and an anti-GPVI antibody-producing CHO cell; for example, a tocilizumab-producing CHO cell or an anti-GPVI antibody-producing CHO cell.

[1-3-4] In the embodiment [1], [1A], [1X] or [1Y], the cell enabling production of bioactive substances, which is contained in the core layer of the polymer-coated crosslinked alginate gel fiber, (also referred to as the bioactive substance-producing cell) is, for example, a cell selected from the group consisting of an insulin-secreting cell, a pancreatic islet, a pancreatic islet cell, a dopamine-secreting cell, a pituitary cell, a growth hormone-secreting cell, a parathyroid cell, a nerve growth factor-secreting cell, a blood coagulation factor-secreting cell, a hepatocyte, a parathyroid cell, an erythropoietin-secreting cell, a norepinephrine-secreting cell, a bioactive substance expression vector (genetically modified cell) and the like.

[1-3-5] In the embodiment [1], [1A], [1X] or [1Y], the bioactive substance-producing cell that is contained in the core layer of the polymer-coated crosslinked alginate gel fiber is preferably a cell selected from the group consisting of an insulin-secreting cell, a pancreatic islet and a pancreatic islet cell; more preferably a MING cell derived from a pancreatic β cell.

[1-4] In the embodiment [1], [1A], [1X] or [1Y], a component that can be additionally contained in the core layer of the polymer-coated crosslinked alginate gel fiber is, for example, a component selected from the group consisting of an alginic acid solution, alginate gel, a culture medium, a culture fluid, a collagen solution, methylcellulose, a sucrose solution and the like.

[1-4-1] In the embodiment [1], [1A], [1X] or [1Y], a component that can be additionally contained in the core layer of the polymer-coated crosslinked alginate gel fiber is preferably a component selected from the group consisting of an alginic acid solution, alginate gel, a culture medium and a culture fluid.

[1-5] In the embodiment [1], [1A], [1X] or [1Y], the weight-average molecular weight measured by gel filtration chromatography of the chemically modified alginic acid derivative represented by Formula (I), which is used to form the crosslinked alginate gel, that is contained in the core layer of the polymer-coated crosslinked alginate gel fiber is, for example, within a range of approximately 100,000 Da to approximately 3,000,000 Da; preferably within a range of approximately 300,000 Da to approximately 2,500,000 Da; more preferably within a range of approximately 500,000 Da to approximately 2,000,000 Da.

[1-6] In the embodiment [1], [1A], [1X] or [1Y], the weight-average molecular weight measured by gel filtration chromatography of the chemically modified alginic acid derivative represented by Formula (II), which is used to form the crosslinked alginate gel, that is contained in the core layer of the polymer-coated crosslinked alginate gel fiber is, for example, within a range of approximately 100,000 Da to approximately 3,000,000 Da; preferably within a range of approximately 300,000 Da to approximately 2,500,000 Da; more preferably within a range of approximately 500,000 Da to approximately 2,000,000 Da.

[1-7] In the embodiment [1] or [1A], the introduction rate of a reactive group (Akn-$L^1$-$NH_2$ group: Akn-$L^1$- is the same as the definition in the embodiment [1]) into the chemically modified alginic acid derivative represented by Formula (I), which is used to form the crosslinked alginate gel, that is contained in the core layer of the polymer-coated crosslinked alginate gel fiber is, for example, within a range of approximately 0.1 to approximately 30 mol %; preferably within a range of approximately 0.3 to approximately 20 mol %; more preferably within a range of approximately 0.5 to approximately 10 mol %.

[1-7X] In the embodiment [1X] or [1Y], the introduction rate of a reactive group (Aky-$L^1$-$NH_2$ group: Aky and -$L^{1A}$- are the same as the definitions in the embodiment [1X]) into the chemically modified alginic acid derivative represented by Formula (I-A), which is used to form the crosslinked alginate gel that is contained in the core layer of the polymer-coated crosslinked alginate gel fiber is, for example, within a range of approximately 0.1 to approximately 30 mol %; preferably within a range of approximately 0.3 to approximately 20 mol %; more preferably within a range of approximately 0.5 to approximately 10 mol %.

[1-8] In the embodiment [1] or [1A], the introduction rate of a reactive group ($N_3$-$L^2$-$NH_2$ group: -$L^2$- is the same as the definition in the embodiment [1]) into the chemically modified alginic acid derivative represented by Formula (II), which is used to form the crosslinked alginate gel, that is contained in the core layer of the polymer-coated crosslinked alginate gel fiber is, for example, within a range of approximately 0.1 to approximately 30 mol %; preferably within a range of approximately 0.3 to approximately 20 mol %; more preferably within a range of approximately 0.5 to approximately 15 mol %.

[1-8X] In the embodiment [1X] or [1Y], the introduction rate of a reactive group ($N_3$-$L^{2A}$-$NH_2$ group: -$L^{2A}$- is the same as the definition in the embodiment [1X]) into the chemically modified alginic acid derivative represented by Formula (II-A), which is used to form the crosslinked alginate gel that is contained in the core layer of the polymer-coated crosslinked alginate gel fiber is, for example, within a range of approximately 0.1 to approximately 30 mol %; preferably within a range of approximately 0.3 to approximately 20 mol %; more preferably within a range of approximately 0.5 to approximately 15 mol %.

[1-9] In the embodiment [1], [1A], [1X] or [1Y], the weight-average molecular weight measured by gel permeation chromatography (GPC) of alginic acid (for example, sodium alginate or the like) that is used to prepare an alginic acid solution that is used to form the alginic acid solution or the alginate gel that can be additionally contained in the core layer of the polymer-coated crosslinked alginate gel fiber is, for example, within a range of approximately 150,000 Da to approximately 2,500,000 Da; preferably within a range of approximately 300,000 Da to approximately 2,000,000 Da and more preferably within a range of approximately 700,000 Da to approximately 2,000,000 Da.

[1-9-1] In the embodiment [1], [1A], [1X] or [1Y], the weight-average molecular weight measured by gel permeation chromatography (GPC) of alginic acid (for example, sodium alginate or the like) that is used to prepare an alginic acid solution that is used to form the alginic acid solution or the alginate gel that can be additionally contained in the core layer of the polymer-coated crosslinked alginate gel fiber is, for example, within a range of approximately 150,000 Da to approximately 2,500,000 Da; preferably within a range of approximately 300,000 Da to approximately 2,500,000 Da; more preferably within a range selected from approximately 700,000 Da to approximately 1,400,000 Da, approximately 800,000 Da to approximately 1,500,000 Da, approximately 1,400,000 to approximately 2,000,000 Da or approximately 1,500,000 to approximately 2,500,000 Da.

[1-9-2] In the embodiment [1], [1A], [1X] or [1Y], the weight-average molecular weight measured by gel permeation chromatography (GPC) of alginic acid (for example, sodium alginate or the like) that is used to prepare an alginic acid solution that is used to form the alginic acid solution or the alginate gel that can be additionally contained in the core layer of the polymer-coated crosslinked alginate gel fiber is preferably a range selected from approximately 1,400,000 to approximately 2,000,000, approximately 700,000 to approximately 1,400,000 or approximately 800,000 to approximately 1,500,000; more preferably within a range of approximately 1,400,000 to approximately 2,000,000.

[1-10-1] In the embodiment [1] or [1A], the concentration of a solution of the chemically modified alginic acid derivative represented by Formula (I), which is used to form the crosslinked alginate gel, that is contained in the core layer of the polymer-coated crosslinked alginate gel fiber is, for example, within a range of approximately 0.01 to approximately 1.5 wt %; preferably within a range of approximately 0.05 to approximately 1.0 wt %; more preferably within a range of approximately 0.08 to approximately 0.75 wt %.

[1-10-1X] In the embodiment [1X] or [1Y], the concentration of a solution of the chemically modified alginic acid derivative represented by Formula (I-A), which is used to form the crosslinked alginate gel, that is contained in the core layer of the polymer-coated crosslinked alginate gel fiber is, for example, within a range of approximately 0.01 to approximately 1.5 wt %; preferably within a range of approximately 0.05 to approximately 1.0 wt %; more preferably within a range of approximately 0.08 to approximately 0.75 wt %.

[1-10-2] In the embodiment [1] or [1A], the concentration of a solution of the chemically modified alginic acid derivative represented by Formula (II), which is used to form the crosslinked alginate gel, that is contained in the core layer of the polymer-coated crosslinked alginate gel fiber is, for example, within a range of approximately 0.01 to approximately 1.5 wt %; preferably within a range of approximately 0.05 to approximately 1.0 wt %; more preferably within a range of approximately 0.08 to approximately 0.75 wt %.

[1-10-2X] In the embodiment [1X] or [1Y], the concentration of a solution of the chemically modified alginic acid derivative represented by Formula (II-A), which is used to form the crosslinked alginate gel, that is contained in the core layer of the polymer-coated crosslinked alginate gel fiber is, for example, within a range of approximately 0.01 to approximately 1.5 wt %; preferably within a range of approximately 0.05 to approximately 1.0 wt %; more preferably within a range of approximately 0.08 to approximately 0.75 wt %.

[1-10-3] In the embodiment [1] or [1A], the concentration of a solution mixture of the chemically modified alginic acid derivative represented by Formula (I) and the chemically modified alginic acid derivative represented by Formula (II), which are used to form the crosslinked alginate gel that is contained in the core layer of the polymer-coated crosslinked alginate gel fiber is, for example, within a range of approximately 0.02 to approximately 2.0 wt %; preferably within a range of approximately 0.1 to approximately 2.0 wt %; more preferably within a range of approximately 0.15 to approximately 1.5 wt %.

[1-10-3X] In the embodiment [1X] or [1Y], the concentration of a solution mixture of the chemically modified alginic acid derivative represented by Formula (I-A) and the chemically modified alginic acid derivative represented by Formula (II-A), which are used to form the crosslinked alginate gel that is contained in the core layer of the polymer-coated crosslinked alginate gel fiber is, for example, within a range of approximately 0.02 to approximately 2.0 wt %; preferably within a range of approximately 0.1 to approximately 2.0 wt %; more preferably within a range of approximately 0.15 to approximately 1.5 wt %.

[1-10-4] In the embodiment [1], [1A], [1X] or [1Y], the concentration of the alginic acid solution, which can be additionally contained in the core layer of the polymer-coated crosslinked alginate gel fiber, or the alginic acid solution, which is used to form the alginate gel is, for example, within a range of 0 to approximately 1.98 wt %; preferably within a range of 0 to approximately 1.8 wt %; more preferably within a range of 0 to approximately 1.7 wt %.

[1-10-4-1] In the embodiment [1], [1A], [1X] or [1Y], the concentration ($C_{ALG}$) of the alginic acid solution, which can be additionally contained in the core layer of the polymer-coated crosslinked alginate gel fiber, or the alginic acid solution, which is used to form the alginate gel is, for example, within a range of $0<C_{ALG}\leq$approximately 1.98 wt %; preferably within a range of $0<C_{ALG}\leq$approximately 1.8 wt %; more preferably within a range of $0<C_{ALG}\leq$approximately 1.7 wt %.

[1-11-1] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the total concentration of the concentration of the solution mixture comprising the chemically modified alginic acid derivatives represented by Formula (I) and Formula (II), which are used to form the core layer, and the concentration of the alginic acid solution is preferably within a range of approximately 0.5 to approximately 2.0 wt %; more preferably selected from approximately 1.0 wt %, approximately 1.5 wt % and approximately 2.0 wt %.

[1-11-1-1] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the total concentration ($C_{TOL}$) of the concentration of the solution mixture comprising the chemically modified alginic acid derivatives represented by Formula (I) and Formula (II), which are used to form the core layer, and the concentration of the alginic acid solution is, for example, $0<C_{TOL}\leq$approximately 2.0 wt %; preferably approximately 0.5 to approximately 2.0 wt %; more preferably approximately 1.0 to approximately 2.0 wt %; still more preferably a concentration selected from approximately 1.0 wt %, approximately 1.5 wt % and approximately 2.0 wt %.

[1-11-1-1X] In the embodiment [1X] or [1Y], in a case where the alginic acid solution or the alginate gel that is formed from the alginic acid solution is contained in the crosslinked alginate gel that is contained in the core layer of the polymer-coated crosslinked alginate gel fiber, the total concentration ($C_{TOL}$) of the concentration of the solution mixture comprising the chemically modified alginic acid derivatives represented by Formula (I-A) and Formula (II-A), which are used to form the core layer, and the concentration of the alginic acid solution is, for example, $0<C_{TOL}\leq$approximately 2.0 wt %; preferably approximately 0.5 to approximately 2.0 wt %; more preferably approximately 1.0 to approximately 2.0 wt %; still more preferably a concentration selected from approximately 1.0 wt %, approximately 1.5 wt % and approximately 2.0 wt %.

[1-11-2] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the combination of the concentration (C1 (wt %)) of the solution mixture comprising the chemically modified alginic acid derivatives represented by Formula (I) and Formula (II), which are used to form the core layer, and the concentration (C2 (wt %)) of the alginic acid solution is preferably a combination selected from the group consisting of (C1:C2)=(approximately 0.2: approximately 1.3), (approximately 0.5:approximately 1.0), (approximately 1.0:approximately 0.5), (approximately 0.66:approximately 1.34) and (approximately 0.34:approximately 0.66).

[1-11-2-1] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the combination of the concentration (C1 (wt %)) of the solution mixture comprising the chemically modified alginic acid derivatives represented by Formula (I) and Formula (II), which are used to form the core layer, and the concentration (C2 (wt %)) of the alginic acid solution is, for example, a combination of ranges satisfying formulae represented by 0<C2 (wt %)≤approximately 1.98 (wt %), 0<C1 (wt %)≤approximately 2.0 (wt %)−C2 (wt %) and 0<C1+C2 (wt %)≤approximately 2.0 (wt %);

preferably a combination selected from the group consisting of (C1:C2)=(approximately 0.2:approximately 1.3), (approximately 0.5:approximately 1.0), (approximately 1.0:approximately 0.5), (approximately 0.66: approximately 1.34) and (approximately 0.34:approximately 0.66).

[1-11-2-1X] In the embodiment [1X] or [1Y], in a case where the alginic acid solution or the alginate gel that is formed from the alginic acid solution is contained in the crosslinked alginate gel that is contained in the core layer of the polymer-coated crosslinked alginate gel fiber, the combination of the concentration (C1x (wt %)) of the solution mixture comprising the chemically modified alginic acid derivatives represented by Formula (I-A) and Formula (II-A), which are used to form the core layer, and the concentration (C2x (wt %)) of the alginic acid solution is, for example, a combination of ranges satisfying formulae represented by 0<C2x (wt %)≤approximately 1.98 (wt %), 0<C1x (wt %)≤approximately 2.0 (wt %)−C2x (wt %) and 0<C1x+C2x (wt %)≤approximately 2.0 (wt %);

preferably a combination selected from the group consisting of (C1x:C2x)=(approximately 0.2:approximately 1.3), (approximately 0.5:approximately 1.0), (approximately 1.0:approximately 0.5), (approximately 0.66:approximately 1.34) and (approximately 0.34:approximately 0.66).

[1-11-3] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the combination of the concentration (CIA (wt %)) of the solution of the chemically modified alginic acid derivative represented by Formula (I), the concentration (C1N (wt %)) of the solution of the chemically modified alginic acid derivative represented by Formula (II), which are used to form the core layer, and the concentration (C2 (wt %)) of the alginic acid solution is preferably a combination selected from the group consisting of (C1A:C1N:C2)=(approximately 0.1:approximately 0.1:approximately 1.3), (approximately 0.25:approximately 0.25:approximately 1.0), (approximately 0.5: approximately 0.5:approximately 0.5), (approximately 0.33: approximately 0.33:approximately 1.34) and (approximately 0.17:approximately 0.17:approximately 0.66).

[1-11-3-1] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the combination of the concentration (CIA (wt %)) of the solution of the chemically modified alginic acid derivative represented by Formula (I), the concentration (C1N (wt %)) of the solution of the chemically modified alginic acid derivative represented by Formula (II), which are used to form the core layer, and the concentration (C2 (wt %)) of the alginic acid solution is, for example, a combination of ranges satisfying formulae represented by 0<C2 (wt %)≤approximately 1.98 (wt %), 0<C1A (wt %)≤approximately 2.0 (wt %)−C2 (wt %), 0<C1N (wt %)≤approximately 2.0 (wt %)−C2 (wt %) and 0<C1A+C1N+C2 (wt %)≤approximately 2.0 (wt %);

preferably a combination selected from the group consisting of (C1A:C1N:C2)=(approximately 0.1:approximately 0.1:approximately 1.3), (approximately 0.25: approximately 0.25:approximately 1.0), (approximately 0.5:approximately 0.5:approximately 0.5), (approximately 0.33:approximately 0.33:approximately 1.34) and (approximately 0.17:approximately 0.17:approximately 0.66).

[1-11-3-1X] In the embodiment [1X] or [1Y], in a case where the alginic acid solution or the alginate gel that is formed from the alginic acid solution is contained in the crosslinked alginate gel that is contained in the core layer of the polymer-coated crosslinked alginate gel fiber, the combination of the concentration (C1Ax (wt %)) of the solution of the chemically modified alginic acid derivative represented by Formula (I-A), the concentration (C1Nx (wt %)) of the solution of the chemically modified alginic acid derivative represented by Formula (II-A), which are used to form the core layer, and the concentration (C2x (wt %)) of the alginic acid solution is, for example, a combination of ranges satisfying formulae represented by 0<C2x (wt %)≤approximately 1.98 (wt %), 0<C1Ax (wt %)≤approximately 2.0 (wt %)−C2x (wt %), 0<C1Nx (wt %)≤approximately 2.0 (wt %)−C2x (wt %) and 0<C1Ax+C1Nx+C2x (wt %)≤approximately 2.0 (wt %);

preferably a combination selected from the group consisting of (C1Ax:C1Nx:C2x)=(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34) and (approximately 0.17:approximately 0.17:approximately 0.66).

[1-11-4] In the embodiment [1] or [1A], the volume ratio (v1, v2) of the solutions of the individual derivatives in the solution mixture of the solution of the chemically modified alginic acid derivative represented by Formula (I) and the solution of the chemically modified alginic acid derivative represented by Formula (II), which are used to form the crosslinked alginate gel that is contained in the core layer of the polymer-coated crosslinked alginate gel fiber is, for example, a ratio in the case of v1+v2=15 and, for example, (v1:v2)=(7.5:7.5). Here, in v1+v2=15, 0<v1<15 and 0<v2<15.

[1-11-4X] In the embodiment [1X] or [1Y], the volume ratio (v1x, v2x) of the solutions of the individual derivatives in the solution mixture of the solution of the chemically modified alginic acid derivative represented by Formula (I-A) and the solution of the chemically modified alginic acid derivative represented by Formula (II-A), which are used to form the crosslinked alginate gel that is contained in the core layer of the polymer-coated crosslinked alginate gel fiber is, for example, a ratio in the case of v1x+v2x=15 and, for example, (v1x:v2x)=(7.5:7.5). Here, in v1x+v2x=15, 0<v1x<15 and 0<v2x<15.

[1-11-5] In the embodiment [1] or [1A], in a case where the alginic acid solution or the alginate gel that is formed from the alginic acid solution is contained in the crosslinked alginate gel that is contained in the core layer of the polymer-coated crosslinked alginate gel fiber, the volume ratio of the volumes (v1, v2, v3) of the individual solutions in the solution mixture of the solution of the chemically modified alginic acid derivative represented by Formula (I), the solution of the chemically modified alginic acid derivative represented by Formula (II), which are used to form the core layer, and the alginic acid solution is, for example, a ratio in the case of v1+v2+v3=15 and, for example, a combination of (v1:v2:v3)=(5:5:5), (2.5:2.5:10), (1:1:13) or the like. Here, in v1+v2+v3=15, 0<v1<15, 0<v2<15 and 0<v3<15.

[1-11-5X] In the embodiment [1X] or [1Y], in a case where the alginic acid solution or the alginate gel that is formed from the alginic acid solution is contained in the crosslinked alginate gel that is contained in the core layer of the polymer-coated crosslinked alginate gel fiber, the volume ratio of the volumes (v1x, v2x, v3x) of the individual solutions in the solution mixture of the solution of the chemically modified alginic acid derivative represented by Formula (I-A), the solution of the chemically modified alginic acid derivative represented by Formula (II-A), which are used to form the core layer, and the alginic acid solution is, for example, a ratio in the case of v1+v2+v3=15 and, for example, a combination of (v1:v2:v3)=(5:5:5), (2.5:2.5:10), (1:1:13) or the like. Here, in v1x+v2x+v3x=15, 0<v1x<15, 0<v2x<15 and 0<v3x<15.

[1-12] In the embodiment [1] or [1A], the crosslinked alginate gel that is contained in the core layer of the polymer-coated crosslinked alginate gel fiber comprises a chemical crosslink through a group represented by Formula (III-L) below:

[C20]

(III-L)

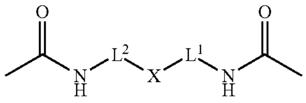

[in Formula (III-L), —CONH— and —NHCO— at both ends represent amide bonds through arbitrary carboxyl groups of the alginic acid;

—X— is a cyclic group selected from the group of partial structural formulae shown in the following table:

TABLE 5-1

| No. | —X— |
|---|---|
| CL-1 | 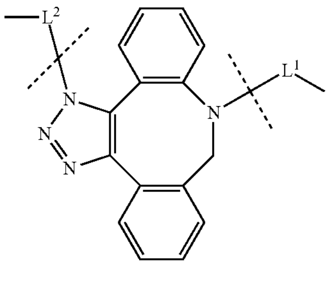 |

TABLE 5-1-continued

| No. | —X— |
|---|---|
| CL-1-r | 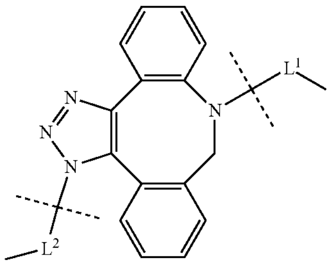 |
| CL-2 | 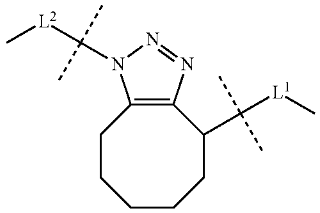 |
| CL-2-r | 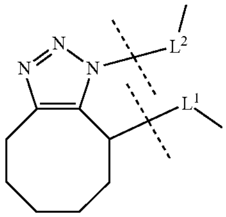 |

in a case where —X— is (CL-1) or (CL-1-r), -$L^1$- is a divalent linker (in each formula, the outsides of the cutting lines at both ends are not included) selected from the group of partial structural formulae shown in the following table:

TABLE 5-2

| No. | —$L^1$— | |
|---|---|---|
| LK-1a | 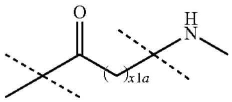 | x1a = 1-6 |
| LK-1b | 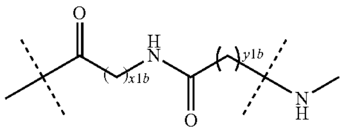 | x1b = 1-6<br>y1b = 1-6 |

and, in a case where —X— is (CL-2) or (CL-2-r), -$L^1$- is a divalent linker (in each formula, the outsides of the cutting lines at both ends are not included) selected from the group of partial structural formulae shown in the following table:

TABLE 5-3
| No. | —$L^1$— | |
| --- | --- | --- |
| LK-2 | 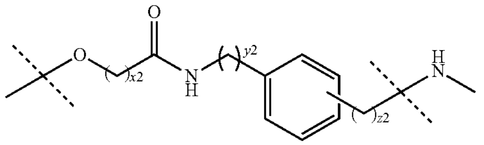 | x2 = 1-6<br>y2 = 0-6<br>z2 = 1-6 |
| LK-3a | 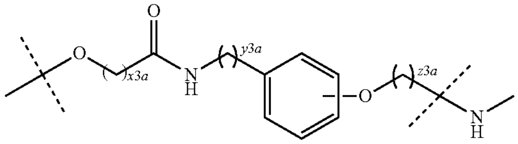 | x3a = 1-6<br>y3a = 0-6<br>z3a = 2-6 |
| LK-3b | 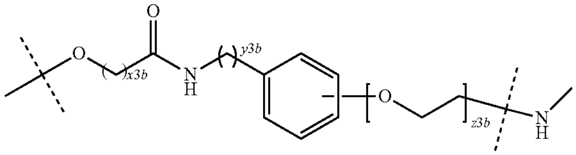 | x3b = 1-6<br>y3b = 0-6<br>z3b = 1-6 |
| LK-4 | 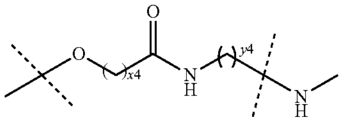 | x4 = 1-6<br>y4 = 2-6 |
| LK-5a | 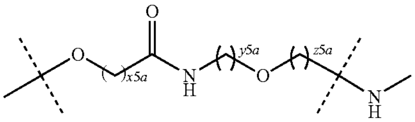 | x5a = 1-6<br>y5a = 2-6<br>z5a = 2-6 |
| LK-5b | 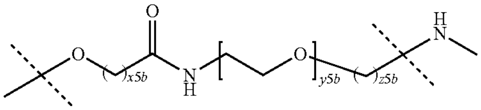 | x5b = 1-6<br>y5b = 1-6<br>z5b = 2-6 |
| LK-6 | 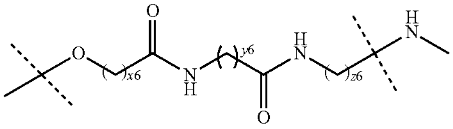 | x6 = 1-6<br>y6 = 1-6<br>z6 = 2-6 |
| LK-7a | 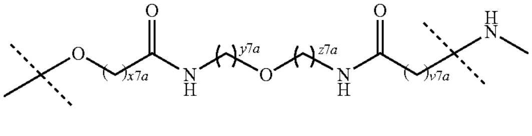 | x7a = 1-6<br>y7a = 2-6<br>z7a = 2-6<br>v7a = 1-6 |
| LK-7b | 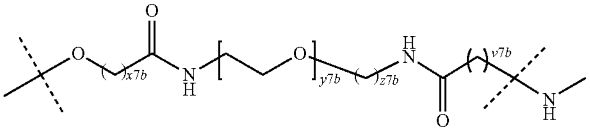 ; | x7b = 1-6<br>y7b = 1-6<br>z7b = 2-6<br>v7b =1-6 | and

-$L^2$- is the same as the definition of Formula (II) in the embodiment [1]].

[1-12-1] In Formula (III-L) shown in the embodiment [1-12], preferably, in a case where —X— is (CL-1) or (CL-1-r) in the embodiment [1-12], -$L^1$- is a divalent linker (in each formula, the outsides of the cutting lines at both ends are not included) selected from the group of partial structural formulae shown in the following table:

TABLE 6-1

| No. | —$L^1$— | |
|---|---|---|
| LK-1a-1 | 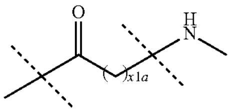 | x1a = 2-6 |
| LK-1b-1 | 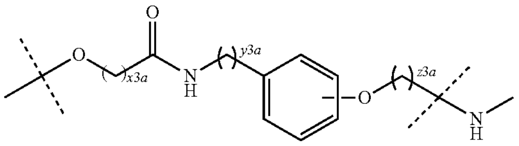 | x1b = 1-6<br>y1b = 1-6 |

in a case where —X— is (CL-2) or (CL-2-r), -$L^1$- is a divalent linker (in each formula, the outsides of the cutting lines at both ends are not included) selected from the group of partial structural formulae shown in the following table:

TABLE 6-2

| No. | —$L^1$— | |
|---|---|---|
| LK-2-1 | 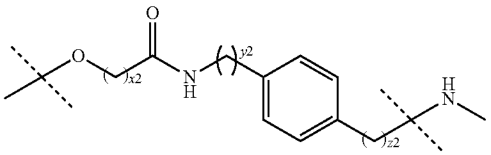 | x2 = 1-4<br>y2 = 0-6<br>z2 = 1-6 |
| LK-3a-1 | 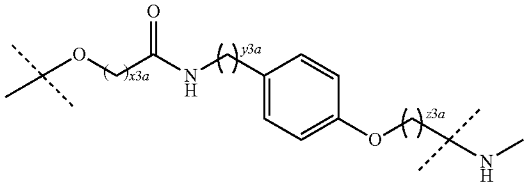 | x3a = 1-6<br>y3a = 0-6<br>z3a = 2-6 |
| LK-3b-1 | 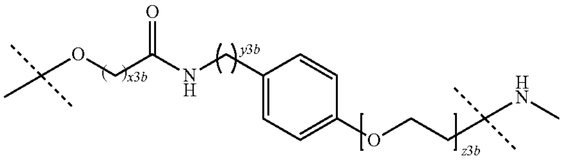 | x3b = 1-6<br>y3b = 0-6<br>z3b = 1-6 |
| LK-4-1 | 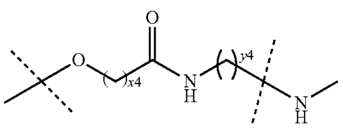 | x4 = 1-6<br>y4 = 2-6 |
| LK-5a-1 | 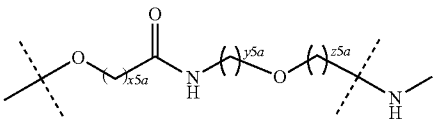 | x5 a = 1-6<br>y5a = 2-6<br>z5a = 2-6 |

TABLE 6-2-continued

| No. | $—L^1—$ | |
|---|---|---|
| LK-5b-1 | 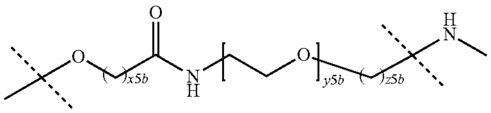 | x5b = 1-6<br>y5b = 1-6<br>z5b = 2-6 |
| LK-6-1 | 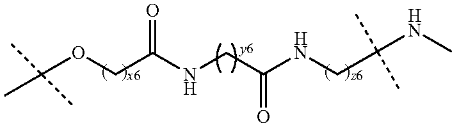 | x6 = 1-6<br>y6 = 1-6<br>z6 = 2-6 |
| LK-7a-1 | 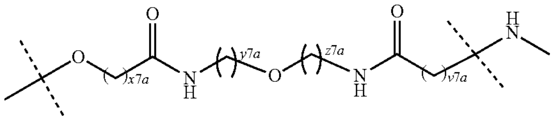 | x7a = 1-6<br>y7a = 2-6<br>z7a = 2-6<br>v7a = 1-6 |
| LK-7b-1 | 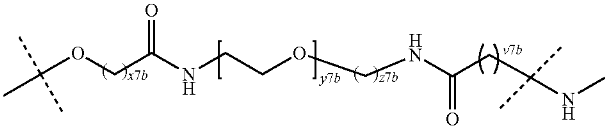 ; | x7b = 1-6<br>y7b = 1-6<br>z7b = 2-6<br>v7b = 1-6 |

more preferably, in a case where —X— is (CL-1) or (CL-1-r), $-L^1-$ is a divalent linker (in each formula, the outsides of the cutting lines at both ends are not included) selected from the group of partial structural formulae shown in the following table:

TABLE 6-3

| No. | $—L^1—$ | |
|---|---|---|
| LK-1a-2 | 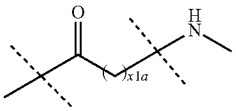 | x1a = 2-6 |

TABLE 6-3-continued

| No. | $—L^1—$ | |
|---|---|---|
| LK-1b-2 | 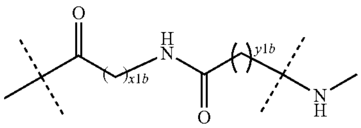 ; | x1b = 1-3<br>y1b = 1-3 |

in a case where —X— is (CL-2) or (CL-2-r), $-L^1-$ is a divalent linker (in each formula, the outsides of the cutting lines at both ends are not included) selected from the group of partial structural formulae shown in the following table:

TABLE 6-4

| No. | $—L^1—$ | |
|---|---|---|
| LK-2-2 | 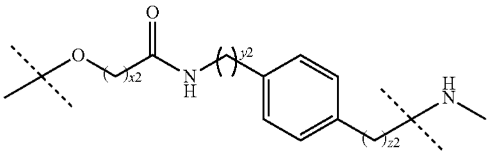 | x2 = 1-4<br>y2 = 1-6<br>z2 = 1-6 |
| LK-3a-2 | 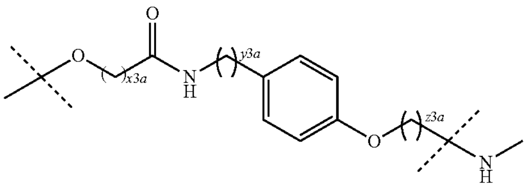 | x3a = 1-3<br>y3a = 0-3<br>z3a = 2-4 |
| LK-3b-2 | 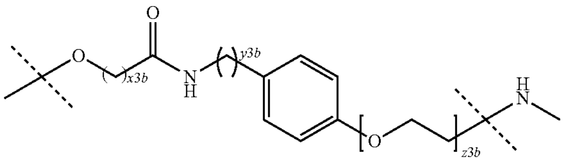 | x3b = 1-3<br>y3b = 0-3<br>z3b = 1-3 |

TABLE 6-4-continued

| No. | —$L^1$— | |
|---|---|---|
| LK-4-2 | 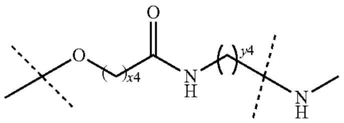 | x4 = 1-3<br>y4 = 2-4 |
| LK-5a-2 | 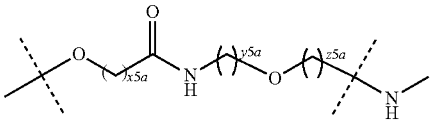 | x5a = 1-3<br>y5a = 2-4<br>z5a = 2-4 |
| LK-5b-2 | 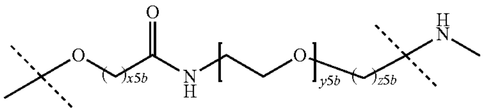 | x5b = 1-3<br>y5b = 1-3<br>z5b = 2-4 |
| LK-6-2 | 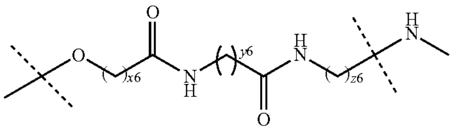 | x6 = 1-3<br>y6 = 1-3<br>z6 = 2-4 |
| LK-7a-2 | 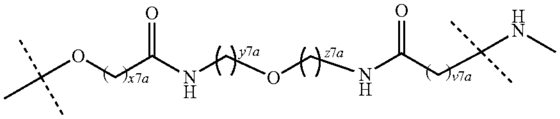 | x7a = 1-3<br>y7a = 2-4<br>z7a = 2-4<br>v7a = 1-3 |
| LK-7b-2 | 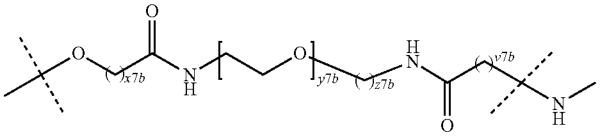 | x7b = 1-3<br>y7b = 1-3<br>z7b = 2-4<br>v7b = 1-3 |

still more preferably, in a case where —X— is (CL-1) or (CL-1-r), is a divalent linker (in each formula, the outsides of the cutting lines at both ends are not included) selected from the group of the following partial structural formulae:

[C21]

LK-1a-3a

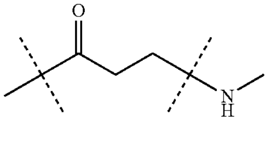

LIK-1a-3b

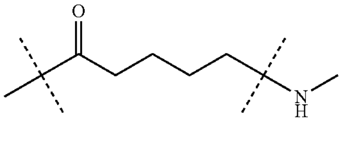

LK-1b-3

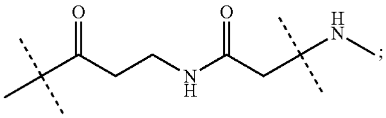

;

in a case where —X— is (CL-2) or (CL-2-r), -$L^1$- is a divalent linker (in each formula, the outsides of the cutting lines at both ends are not included) selected from the group of the following partial structural formulae:

[C22]

LK-2-3

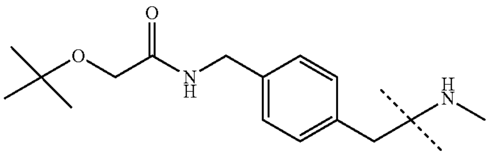

LK-3a-3

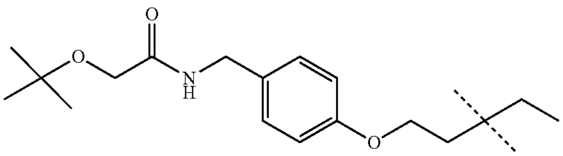

LK-4-3

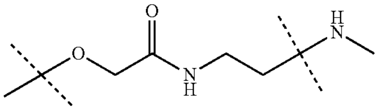

-continued

LK-5a-3

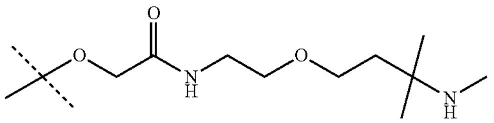

LK-6-3a

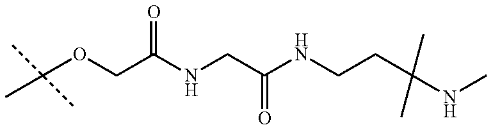

LK-6-3b

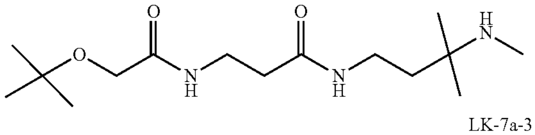

LK-7a-3

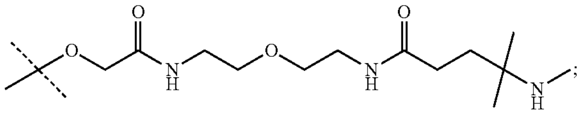

particularly preferably, in a case where —X— is (CL-1) or (CL-1-r), -$L^1$- is a divalent linker of the following partial structural formula (in each formula, the outsides of the cutting lines at both ends are not included):

[C23]

LK-1a-3a

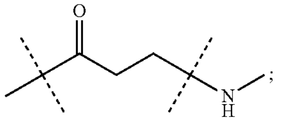

in a case where —X— is (CL-2) or (CL-2-r), -$L^1$- is a divalent linker of the following partial structural formula (in each formula, the outsides of the cutting lines at both ends are not included):

[C24]

LK-2-3

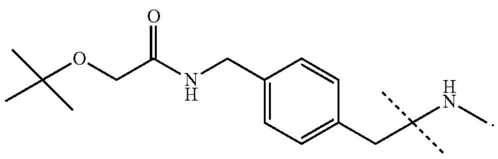

[1-12-2] In Formula (III-L) shown in the embodiment [1-12], preferable, more preferable, still more preferable and particularly preferable -$L^2$- are the same as the definitions described in the embodiments [1-2-1] to [1-2-4], respectively.

[1-12-3] In the embodiment [1-12], a preferable combination of -$L^2$-X-$L^1$- in the group represented by Formula (III-L) is as shown by a partial structure selected from the group of formulae in the following table:

TABLE 7-1

| -X- | -$L^1$- | -$L^2$- |
|---|---|---|
| CL-1 or CL-1-r | Linker selected from LK-1a-1 or LK-1b-1 | Linker selected from the group consisting of LN-1-1, LN-2-1, LN-3-1, LN-4-1, LN-5-1 and LN-6-1 |
| CL-2 or CL-2-r | Linker selected from the group consisting of LK-2-1, LK-3a-1, LK-3b-1, LK-4-1, LK-5a-1, LK-5b-1, LK-6-1, LK-7a-1 and LK-7b-1 | Linker selected from the group consisting of LN-1-1, LN-2-1, LN-3-1, LN-4-1, LN-5-1 and LN-6-1 |

(-$L^1$- in the table is the same as the definition of the preferable -$L^1$- described in the embodiment [1-12-1]; -$L^2$- is the same as the definition of the preferable -$L^2$- described in the embodiment [1-2-1]; —X— is as described in the embodiment [1-12]);

more preferably, the combination of -$L^2$-X-$L^1$- is as shown by a partial structure selected from the group of formulae in the following table:

TABLE 7-2

| -X- | -$L^1$- | -$L^2$- |
|---|---|---|
| CL-1 or CL-1-r | Linker selected from LK-1a-2 or LK-1b-2 | Linker selected from the group consisting of LN-1-2, LN-2-2, LN-3-2, LN-4-2, LN-5-2 and LN-6-2 |
| CL-2 or CL-2-r | Linker selected from the group consisting of LK-2-2, LK-3a-2, LK-3b-2, LK-4-2, LK-5a-2, LK-5b-2, LK-6-2, LK-7a-2 and LK-7b-2 | Linker selected from the group consisting of LN-1-2, LN-2-2, LN-3-2, LN-4-2, LN-5-2 and LN-6-2 |

(-$L^1$- in the table is the same as the definition of the more preferable -$L^1$- described in the embodiment [1-12-1]; -$L^2$- is the same as the definition of the more preferable -$L^2$-described in the embodiment [1-2-2]; —X— is as described in the embodiment [1-12]);

still more preferably, the combination of -$L^2$-X-$L^1$- is as shown by a partial structure selected from the group of formulae in the following table:

TABLE 7-3

| -X- | -$L^1$- | -$L^2$- |
|---|---|---|
| CL-1 or CL-1-r | Linker selected from the group consisting of LK-1a-3a, LK-1a-3b and LK-1b-3 | Linker selected from the group consisting of LN-1-3, LN-2-3, LN-3-3a, LN-3-3b, LN-4-3, LN-5-3a, LN-5-3b and LN-6-3 |
| CL-2 or CL-2-r | Linker selected from the group consisting of LK-2-3, LK-3a-3, LK-4-3, LK-5a-3, LK-6-3a, LK-6-3b and LK-7a-3 | Linker selected from the group consisting of LN-1-3, LN-2-3, LN-3-3a, LN-3-3b, LN-4-3, LN-5-3a, LN-5-3b and LN-6-3 |

(-$L^1$- in the table is the same as the definition of the still more preferable -$L^1$-described in the embodiment [1-12-1]; -$L^2$- is the same as the definition of the still more preferable -$L^2$- described in the embodiment [1-2-3]; —X— is as described in the embodiment [1-12]);

particularly preferably, the combination of $-L^2-X-L^1-$ is as shown by a partial structure selected from the group of formulae in the following table:

TABLE 7-4

| -X- | $-L^1-$ | $-L^2-$ |
|---|---|---|
| CL-1 or CL-1-r | Linker of LK-1a-3a | Linker selected from the group consisting of LN-1-3, LN-3-3a and LN-5-3a |
| CL-2 or CL-2-r | Linker of LK-2-3 | Linker selected from the group consisting of LN-1-3, LN-3-3a and LN-5-3a |

($-L^1-$ in the table is the same as the definition of the particularly preferable $-L^1-$described in the embodiment [1-12-1]; $-L^2-$ is the same as the definition of the particularly preferable $-L^2-$ described in the embodiment [1-2-4]; —X— is as described in the embodiment [1-12]).

[1-12A] In the embodiment [1] or [1A], the crosslinked alginate gel that is contained in the core layer of the polymer-coated crosslinked alginate gel fiber comprises a chemical crosslink through a group represented by Formula (III-L) shown in the embodiment [1-12] [in Formula (III-L), —CONH— and —NHCO— at both ends and —X— are the same as the definitions in the embodiment [1-12]; $-L^1-$ is the same as the group represented by the partial structural formula (LK-1a) shown in the embodiment [1-12] in a case where —X— is (CL-1) or (CL-1-r); $-L^1-$ is the same as the group represented by the partial structural formula (LK-2-1) shown in the embodiment [1-12] in a case where —X— is (CL-2) or (CL-2-r); $-L^2-$ is the same as a group selected from the partial structural formulae (LN-1), (LN-3) and (LN-5) shown in the embodiment [1]].

[1-12A-1] In the embodiment [1-12A], in a case where —X— is (CL-1) or (CL-1-r), the preferable, more preferable and still more preferable $-L^1-$ are the same as the groups represented by the partial structural formulae (LK-1a-1), (LK-1a-2), (LK-1a-3a) and (LK-1a-3b) shown in the embodiment [1-12-1], respectively; in a case where —X— is (CL-2) or (CL-2-r), the preferable, more preferable and still more preferable $-L^1-$ are the same as the groups represented by the partial structural formulae (LK-2-1), (LK-2-2) and (LK-2-3) shown in the embodiment [1-12-1], respectively; $-L^2-$ is preferably the same as the group represented by the partial structural formulae (LN-1-1), (LN-3-1) or (LN-5-1) shown in the embodiment [1-2-1], more preferably the same as the group represented by the partial structural formulae (LN-1-2), (LN-3-2) or (LN-5-2) shown in the embodiment [1-2-2] and still more preferably the same as the group represented by the partial structural formulae (LN-1-3), (LN-3-3a) or (LN-5-3a) shown in the embodiment [1-2-3].

[1-12A-2] In the embodiment [1-12A], preferable, more preferable and still more preferable combinations of $-L^2-X-L^1-$ in the group represented by Formula (III-L) are as shown by partial structures selected from the group of formulae in the following table:

TABLE 7-5

| | -X- | $-L^1-$ | $-L^2-$ |
|---|---|---|---|
| Preferable combination | CL-1 or CL-1-r CL-2 or CL-2-r | LK-1a-1 LK-2-1 | (LN-1-1), (LN-3-1) or (LN-5-1) |

TABLE 7-5-continued

| | -X- | $-L^1-$ | $-L^2-$ |
|---|---|---|---|
| More preferable combination | CL-1 or CL-1-r CL-2 or CL-2-r | LK-1a-2 LK-2-2 | (LN-1-2), (LN-3-2) or (LN-5-2) |
| Still more preferable combination | CL-1 or CL-1-r CL-2 or CL-2-r | LK-1a-3a LK-2-3 | (LN-1-3), (LN-3-3a) or (LN-5-3a) |

($-L^1-$ and $-L^2-$ in the table are the same as the definitions described in the embodiment [1-12A-1]; —X— is as described in the embodiment [1-12]).

[1-12X] In the embodiment [1X] or [1Y], the crosslinked alginate gel that is contained in the core layer of the polymer-coated crosslinked alginate gel fiber is crosslinked alginate gel bonded through a cyclic group represented by the following formula (III-Lx):

[C25]

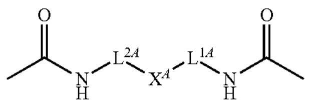

(III-Lx)

[in Formula (III-Lx), —CONH— and —NHCO— at both ends represent amide bonds through arbitrary carboxyl groups of the alginic acid;

$-L^{1A}-$ is the same as the definition in the embodiment [1X];

$-L^{2A}-$ is the same as the definition in the embodiment [1X];

$—X^A—$ is the following partial structural formula:

[C26]

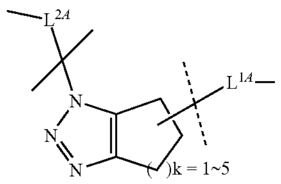

(in the formula, $—CH_2—$ in the $C_{5-9}$ cycloalkene ring may be substituted by one to four groups selected from —NH—, —S—, —O— or =C(=O); hydrogen atoms in $—CH_2—$ in the $C_{5-9}$ cycloalkene ring may be substituted by one to five groups selected from the group consisting of a halogen atom, a hydroxyl group, an amino group, a keto group, a $C_{1-3}$ alkyl group, a $—O—C_{1-3}$ alkyl group, a $—NHC_{1-3}$ alkyl group, $—N(C_{1-3}$ alkyl group$)_2$ or —COO-M (M=Na, K, ½Ca, a hydrogen atom or a $C_{1-3}$ alkyl group); one to three $C_{3-8}$ cycloalkyl rings, benzene rings or five or six-membered aromatic heterocycles may condense to the $C_{5-9}$ cycloalkene ring; in a case where the $C_{3-8}$ cycloalkyl rings, the benzene rings or the five or six-membered aromatic heterocycles condense to the $C_{5-9}$ cycloalkene ring, $-L^{1A}-$ may be substituted by the $C_{3-8}$ cycloalkyl ring, the benzene ring or the five or six-membered aromatic heterocycle)] (in the formulae, the outsides of the cutting lines at both ends are not included).

[1-12X-1] In the embodiment [1-12X], preferable, more preferable, still more preferable, particularly preferable and most preferable -$L^{1A}$- are the same as the definitions of -$L^{1A}$- described in the embodiments [1X-1].

[1-12X-2] In the embodiment [1-12X], preferable, more preferable, still more preferable, particularly preferable and most preferable -$L^{2A}$- are the same as the definitions of -$L^{2A}$- described in the embodiments [1X-3].

[1-12X-3] In the embodiment [1-12X], —$X^A$— is preferably a cyclic group selected from the group of the following partial structural formulae:

[C27]

(TZ-1)

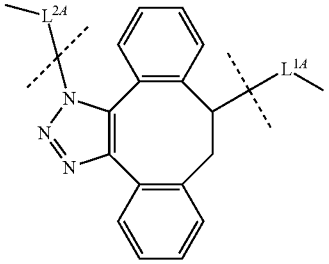

(TZ-2)

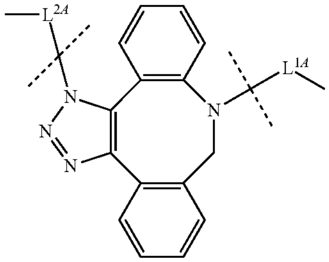

(TZ-3)

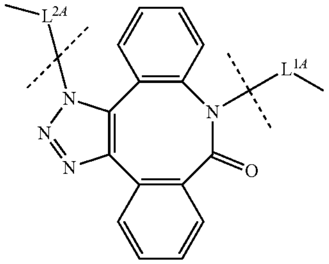

(TZ-4)

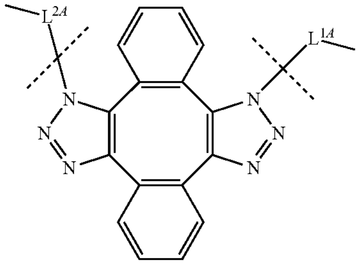

(TZ-5)

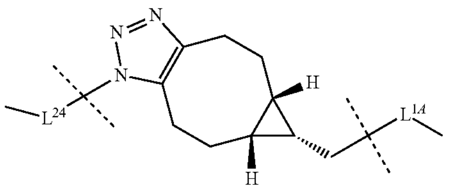

-continued (TZ-6)

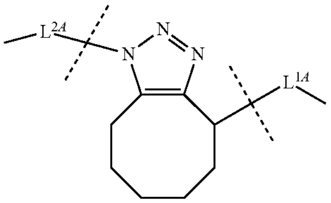

(TZ-7)

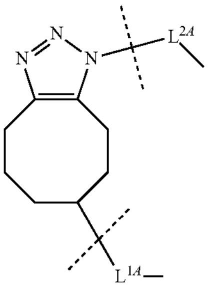

(TZ-8)

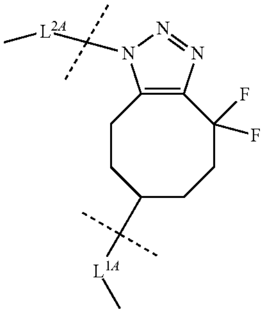

(TZ-9)

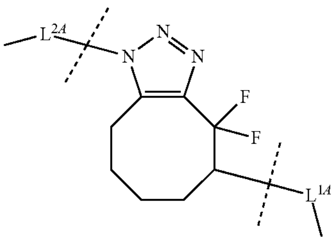

(TZ-10)

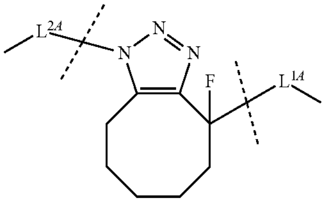

(TZ-11)

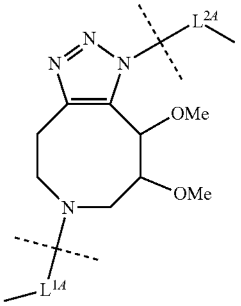

-continued
(TZ-12)
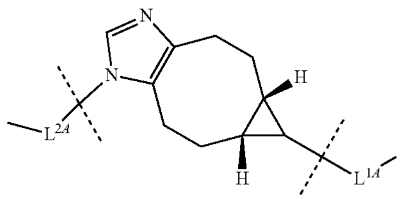
(TZ-1-r)
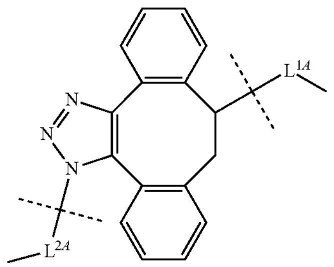
(TZ-2-r)
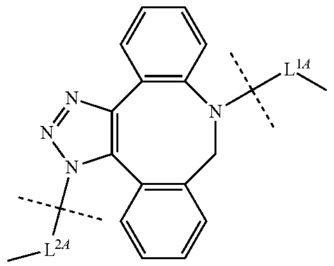
(TZ-3-r)
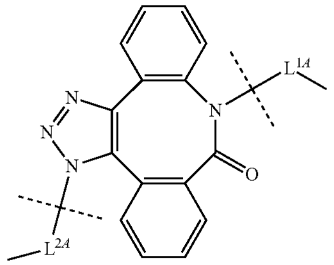
(TZ-4-r)
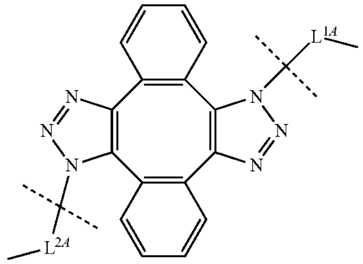
(TZ-5-r)
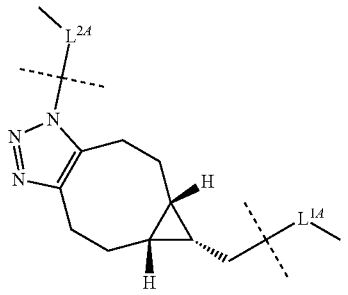
-continued
(TZ-6-r)
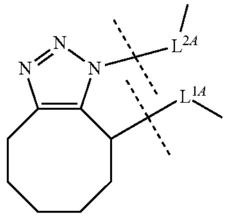
(TZ-7-r)
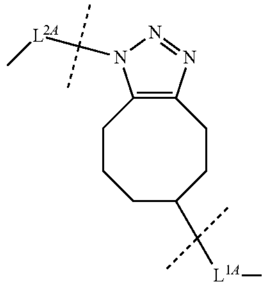
(TZ-8-r)
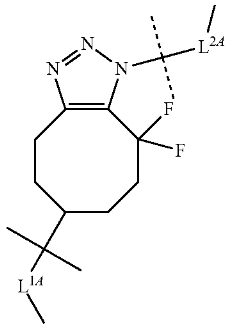
(TZ-9-r)
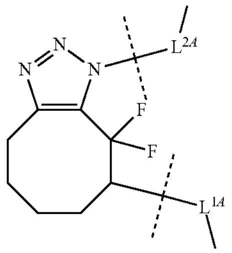
(TZ-10-r)
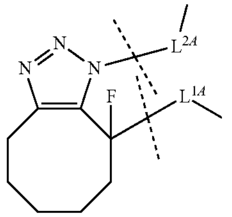
(TZ-11-r)
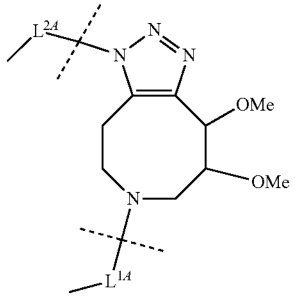

-continued
(TZ-12-r)
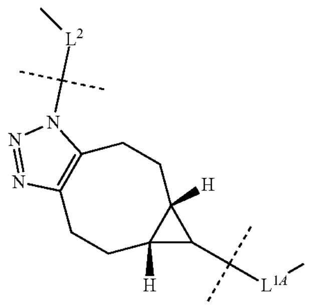
(in each formula, the outsides of the cutting lines at both ends are not included);
more preferably a cyclic group selected from the group of the following partial structural formulae:
[C28]
(TZ-1)
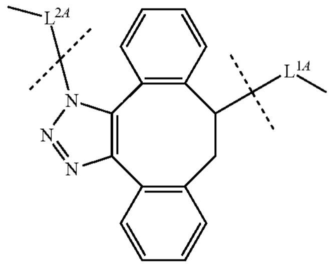
(TZ-2)
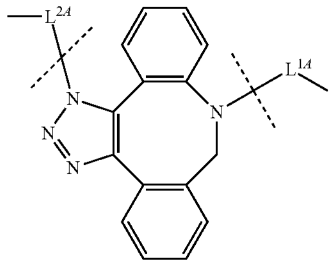
(TZ-3)
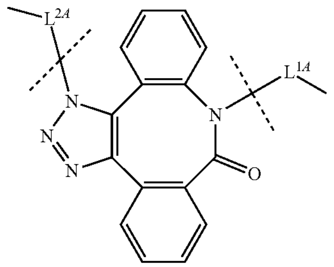
(TZ-5)
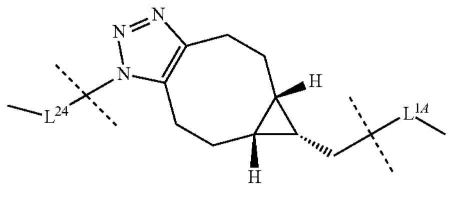
-continued
(TZ-6)
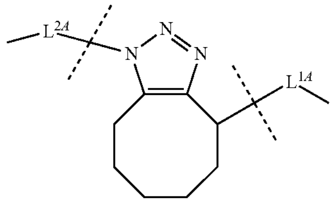
(TZ-1-r)
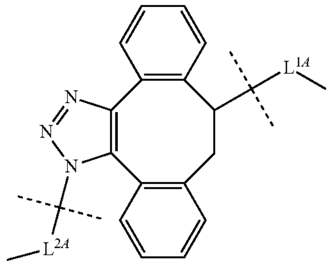
(TZ-2-r)
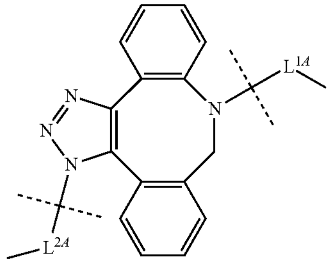
(TZ-3-r)
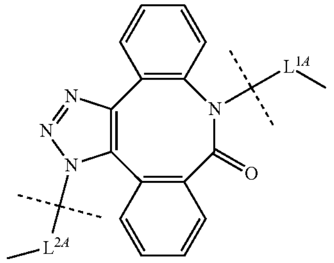
(TZ-5-r)
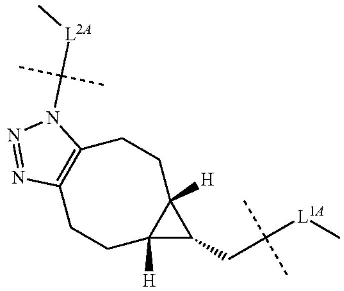
(TZ-6-r)
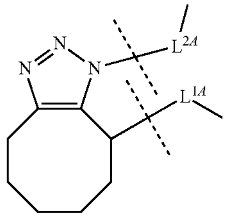

(in each formula, the outsides of the cutting lines at both ends are not included);

still more preferably a cyclic group selected from the group of the following partial structural formulae:

[C29]

(TZ-2)

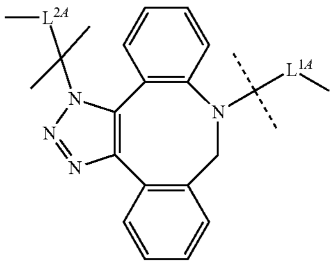

(TZ-2-r)

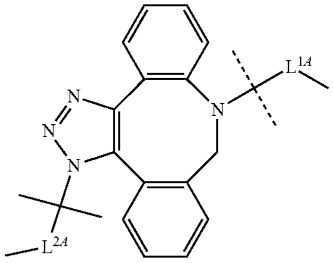

(TZ-6)

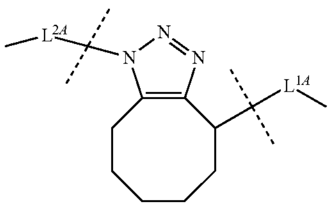

(TZ-6-r)

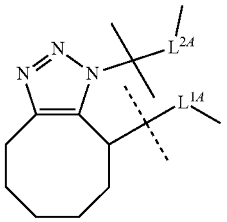

(in each formula, the outsides of the cutting lines at both ends are not included).

[1-12X-4] The appropriate combination of the definitions of -$L^{1A}$-, -$L^{2A}$- and —$X^A$— described in the embodiments [1-12X] to [1-12X-3] makes it possible to arbitrarily form a preferable embodiment of Formula (III-Lx) in the crosslinked alginate gel.

[1-13] In the embodiment [1] or [1A], the crosslinked alginate gel that is contained in the core layer comprises a chemical crosslink through a group represented by Formula (III-L) in the embodiment [1-12] [in Formula (III-L), each definition is the same as the definition in the embodiment [1-12]] or Formula (III-L) in the embodiment [1-12A] [in Formula (III-L), each definition is the same as the definition in the embodiment [1-12A]] and an ionic crosslinking through a divalent metal ion.

[1-13X] In the embodiment [1X] or [1Y], the crosslinked alginate gel that is contained in the core layer comprises a chemical crosslink through a group represented by Formula (III-Lx) in the embodiment [1-12X] [in Formula (III-Lx), each definition is the same as the definition in the embodiment [1-12X]] and an ionic crosslink through a divalent metal ion.

[1-13A] In the embodiment [1], [1A], [1X] or [1Y], the divalent metal ion that is used to form the ionic crosslinking in the crosslinked alginate gel that is contained in the core layer of the polymer-coated crosslinked alginate gel fiber is preferably a divalent metal ion selected from the group of a calcium ion, a magnesium ion, a barium ion, a strontium ion and a zinc ion; more preferably a calcium ion, a barium ion or a strontium ion; still more preferably a calcium ion or a barium ion.

[1-14] In the embodiment [1], [1A], [1X] or [1Y], for an aqueous solution comprising the divalent metal ion that is used to form the ionic crosslinking in the crosslinked alginate gel that is contained in the core layer of the polymer-coated crosslinked alginate gel fiber, it is possible to use an aqueous solution comprising a divalent metal ion selected from the group consisting of a calcium chloride aqueous solution, a calcium carbonate aqueous solution, a calcium gluconate aqueous solution, a barium chloride aqueous solution, a strontium chloride aqueous solution and the like as a supply source; a calcium chloride aqueous solution or a barium chloride aqueous solution is preferable.

[1-15-1] In the embodiment [1], [1A], [1X] or [1Y], the cationic polymer in the cationic polymer layer of the polymer-coated crosslinked alginate gel fiber is a cationic polymer selected from the group consisting of polyamino acids, basic polysaccharides, basic polymers and the like.

[1-15-2] In the embodiment [1], [1A], [1X] or [1Y], the cationic polymer in the cationic polymer layer of the polymer-coated crosslinked alginate gel fiber is preferably a cationic polymer selected from the group consisting of poly-L-ornithine (PLO), poly-D-ornithine (PDO), poly-DL-ornithine, poly-D-lysine (PDL), poly-L-lysine (PLL), poly-DL-lysine, poly-L-arginine (PLA), poly-D-arginine (PDA), poly-DL-arginine, poly-L-homoarginine (PLHA), poly-D-homoarginine (PDHA), poly-DL-homoarginine, poly-L-histidine (PLH), poly-D-histidine (PDH) and poly-DL-histidine, which are polyamino acids; more preferably poly-L-ornithine or poly-L-lysine; still more preferably poly-L-ornithine.

[1-15-3] In the embodiment [1], [1A], [1X] or [1Y], the cationic polymer in the cationic polymer layer of the polymer-coated crosslinked alginate gel fiber is chitosan.

[1-15-4] In the embodiment [1], [1A], [1X] or [1Y], the cationic polymer in the cationic polymer layer of the polymer-coated crosslinked alginate gel fiber is a cationic polymer selected from the group consisting of polymethylene-CO-guanidine (PMCG), polyallylamine (PAA), polyvinylamine (PVA), polyethyleneimine, allylamine-diallylamine copolymers and allylamine-maleic acid copolymers; preferably polyallylamine (PAA), polyethyleneimine or polymethylene-CO-guanidine (PMCG); more preferably polyethyleneimine or polymethylene-CO-guanidine (PMCG).

[1-16] In the embodiment [1], [1A], [1X] or [1Y], the outer diameter of the polymer-coated crosslinked alginate gel fiber is, for example, within a range of approximately 0.1 to approximately 2000 μm, approximately 0.2 to approximately 2000 μm, approximately 0.2 to approximately 1000 μm, approximately 0.5 to approximately 1000 μm, approximately 1 to approximately 1000 μm, approximately 10 to approximately 1000 μm, approximately 20 to approximately 1000 μm or the like.

The use of the chemically modified alginic acid derivatives represented by Formula (I) and Formula (II) for which the definitions of Akn, $-L^1-$, $-L^2-$ and X described in the above-described embodiments are appropriately combined makes it possible to arbitrarily form a preferable embodiment of crosslinked alginate gel in the core layer of the polymer-coated crosslinked alginate gel fiber of the embodiment.

The use of the chemically modified alginic acid derivatives represented by Formula (I-A) and Formula (II-A) for which the definitions of Aky, $-L^{1A}-$, $-L^{2A}-$ and $X^A$ described in the above-described embodiments are appropriately combined makes it possible to arbitrarily form a preferable embodiment of crosslinked alginate gel in the core layer of the polymer-coated crosslinked alginate gel fiber of the embodiment.

[1-17-1] The polymer-coated crosslinked alginate gel fiber of the embodiment [1] or [1A] is a polymer-coated crosslinked alginate gel fiber, in which, preferably, the alginic acid derivative represented by Formula (I), which is used to form the crosslinked alginate gel, is selected from the alginic acid derivatives described in the embodiment [1-1-1] or the preferable alginic acid derivatives of the embodiment [1-1-5] and the alginic acid derivative represented by Formula (II) is selected from the alginic acid derivatives described in the embodiment [1-2-1] or the preferable alginic acid derivatives of the embodiment [1-2-5]; the antibody-producing cell is selected from the cells described in the embodiments [1-3-1] to [1-3-3]; the cationic polymer layer is selected from the cationic polymers described in the embodiment [1-15-1].

[1-17-1B] The polymer-coated crosslinked alginate gel fiber of the embodiment [1] or [1A] is a polymer-coated crosslinked alginate gel fiber, in which, preferably, the alginic acid derivative represented by Formula (I), which is used to form the crosslinked alginate gel, is selected from the alginic acid derivatives described in the embodiment [1-1-1] or the preferable alginic acid derivatives of the embodiment [1-1-5] and the alginic acid derivative represented by Formula (II) is selected from the alginic acid derivatives described in the embodiment [1-2-1] or the preferable alginic acid derivatives of the embodiment [1-2-5]; the antibody-producing cell is selected from the cells described in embodiments [1B-3-1] to [1B-3-9]; the cationic polymer layer is selected from the cationic polymers described in the embodiment [1-15-1].

[1-17-2] The polymer-coated crosslinked alginate gel fiber of the embodiment [1] or [1A] is a polymer-coated crosslinked alginate gel fiber, in which, more preferably, the alginic acid derivative represented by Formula (I), which is used to form the crosslinked alginate gel, is selected from the alginic acid derivatives described in the embodiment [1-1-2] or the more preferable alginic acid derivatives of the embodiment [1-1-5] and the alginic acid derivative represented by Formula (II) is selected from the alginic acid derivatives described in the embodiment [1-2-2] or the more preferable alginic acid derivatives of the embodiment [1-2-5]; the antibody-producing cell is selected from the cells described in the embodiments [1-3-2] to [1-3-3]; the cationic polymer layer is selected from the cationic polymers described in the embodiments [1-15-2] to [1-15-4].

[1-17-2B] The polymer-coated crosslinked alginate gel fiber of the embodiment [1] or [1A] is a polymer-coated crosslinked alginate gel fiber, in which, more preferably, the alginic acid derivative represented by Formula (I), which is used to form the crosslinked alginate gel, is selected from the alginic acid derivatives described in the embodiment [1-1-2] or the more preferable alginic acid derivatives of the embodiment [1-1-5] and the alginic acid derivative represented by Formula (II) is selected from the alginic acid derivatives described in the embodiment [1-2-2] or the more preferable alginic acid derivatives of the embodiment [1-2-5]; the antibody-producing cell is selected from the cells described in embodiments [1B-3-2] to [1B-3-9]; the cationic polymer layer is selected from the cationic polymers described in the embodiments [1-15-2] to [1-15-4].

[1-17-3] The polymer-coated crosslinked alginate gel fiber of the embodiment [1] or [1A] is a polymer-coated crosslinked alginate gel fiber, in which, still more preferably, the alginic acid derivative represented by Formula (I), which is used to form the crosslinked alginate gel, is selected from the alginic acid derivatives described in the embodiment [1-1-3] and the alginic acid derivative represented by Formula (II) is selected from the alginic acid derivatives described in the embodiment [1-2-3]; the antibody-producing cell is selected from the cells described in the embodiments [1-3-2] to [1-3-3]; the cationic polymer layer is selected from the cationic polymers described in the embodiment [1-15-2] or [1-15-4].

[1-17-3B] The polymer-coated crosslinked alginate gel fiber of the embodiment [1] or [1A] is a polymer-coated crosslinked alginate gel fiber, in which, still more preferably, the alginic acid derivative represented by Formula (I), which is used to form the crosslinked alginate gel, is selected from the alginic acid derivatives described in the embodiment [1-1-3] and the alginic acid derivative represented by Formula (II) is selected from the alginic acid derivatives described in the embodiment [1-2-3]; the antibody-producing cell is selected from the cells described in embodiments [1B-3-3] or [1B-3-9]; the cationic polymer layer is selected from the cationic polymers described in the embodiment [1-15-2] or [1-15-4].

[1-17-4] The polymer-coated crosslinked alginate gel fiber of the embodiment [1] or [1A] is a polymer-coated crosslinked alginate gel fiber, in which, particularly preferably, the alginic acid derivative represented by Formula (I), which is used to form the crosslinked alginate gel, is selected from the alginic acid derivatives described in the embodiment [1-1-4] and the alginic acid derivative represented by Formula (II) is selected from the alginic acid derivatives described in the embodiment [1-2-4]; the antibody-producing cell is an antibody-producing CHO cell; the cationic polymer layer is selected from poly-L-ornithine, polyallylamine (PAA), polyethyleneimine or polymethylene-CO-guanidine (PMCG).

[1-17-5] In the embodiment [1-17-1] to [1-17-4], the crosslinked alginate gel in the polymer-coated crosslinked alginate gel fiber comprises any of the components that can be contained described in the embodiments [1-4] to [1-4-1].

Combination of the individual elements of the cell enabling production of antibodies, bioactive substances or the like, the chemically modified alginic acid derivatives represented by Formula (I) and Formula (II) that are used to form the crosslinked alginate gel and the cationic polymer (cationic polymer layer) in the polymer-coated crosslinked alginate gel fibers described in the embodiments makes it possible to arbitrarily form a preferable embodiment of a method for manufacturing a polymer-coated crosslinked alginate gel fiber.

[1-17X-1] The polymer-coated crosslinked alginate gel fiber of the embodiment [1X] or [1Y] is a polymer-coated crosslinked alginate gel fiber, in which, preferably, the alginic acid derivative, which is used to form the crosslinked alginate gel, is selected from the alginic acid derivatives represented by Formula (I-A) having the preferable -$L^{1A}$- described in the embodiment [1X-1] and the preferable Aky described in the embodiment [1X-2] and the alginic acid derivatives represented by Formula (II-A) having the preferable -$L^{2A}$- described in the embodiment [1X-3]; the antibody-producing cell is selected from the cells described in the embodiments [1-3-1] to [1-3-3]; the cationic polymer layer is selected from the cationic polymers described in the embodiment [1-15-1].

[1-17X-1B] The polymer-coated crosslinked alginate gel fiber of the embodiment [1X] or [1Y] is a polymer-coated crosslinked alginate gel fiber, in which, preferably, the alginic acid derivative, which is used to form the crosslinked alginate gel, is selected from the alginic acid derivatives represented by Formula (I-A) having the preferable -$L^{1A}$- described in the embodiment [1X-1] and the preferable Aky described in the embodiment [1X-2] and the alginic acid derivatives represented by Formula (II-A) having the preferable -$L^{2A}$- described in the embodiment [1X-3]; the antibody-producing cell is selected from the cells described in the embodiments [1B-3-1] to [1B-3-9]; the cationic polymer layer is selected from the cationic polymers described in the embodiment [1-15-1].

[1-17X-2] The polymer-coated crosslinked alginate gel fiber of the embodiment [1X] or [1Y] is a polymer-coated crosslinked alginate gel fiber, in which, more preferably, the alginic acid derivative, which is used to form the crosslinked alginate gel, is selected from the alginic acid derivatives represented by Formula (I-A) having the more preferable -$L^{1A}$-described in the embodiment [1X-1] and the more preferable Aky described in the embodiment [1X-2] and the alginic acid derivatives represented by Formula (II-A) having the more preferable -$L^{2A}$- described in the embodiment [1X-3]; the antibody-producing cell is selected from the cells described in the embodiments [1-3-2] to [1-3-3]; the cationic polymer layer is selected from the cationic polymers described in the embodiments [1-15-2] to [1-15-4].

[1-17X-2B] The polymer-coated crosslinked alginate gel fiber of the embodiment [1X] or [1Y] is a polymer-coated crosslinked alginate gel fiber, in which, more preferably, the alginic acid derivative, which is used to form the crosslinked alginate gel, is selected from the alginic acid derivatives represented by Formula (I-A) having the more preferable -$L^{1A}$-described in the embodiment [1X-1] and the more preferable Aky described in the embodiment [1X-2] and the alginic acid derivatives represented by Formula (II-A) having the more preferable -$L^{2A}$- described in the embodiment [1X-3]; the antibody-producing cell is selected from the cells described in the embodiments [1B-3-2] and [1B-3-9]; the cationic polymer layer is selected from the cationic polymers described in the embodiments [1-15-2] to [1-15-4].

[1-17X-3] The polymer-coated crosslinked alginate gel fiber of the embodiment [1X] or [1Y] is a polymer-coated crosslinked alginate gel fiber, in which, still more preferably, the alginic acid derivative, which is used to form the crosslinked alginate gel, is selected from the alginic acid derivatives represented by Formula (I-A) having the still more preferable -$L^{1A}$-described in the embodiment [1X-1] and the still more preferable Aky described in the embodiment [1X-2] and the alginic acid derivatives represented by Formula (II-A) having the still more preferable -$L^{2A}$- described in the embodiment [1X-3]; the antibody-producing cell is selected from the cells described in the embodiments [1-3-2] to [1-3-3]; the cationic polymer layer is selected from the cationic polymers described in the embodiments [1-15-2] or [1-15-4].

[1-17X-3B] The polymer-coated crosslinked alginate gel fiber of the embodiment [1X] or [1Y] is a polymer-coated crosslinked alginate gel fiber, in which, still more preferably, the alginic acid derivative, which is used to form the crosslinked alginate gel, is selected from the alginic acid derivatives represented by Formula (I-A) having the still more preferable -$L^{1A}$- described in the embodiment [1X-1] and the still more preferable Aky described in the embodiment [1X-2] and the alginic acid derivatives represented by Formula (II-A) having the still more preferable -$L^{2A}$- described in the embodiment [1X-3]; the antibody-producing cell is selected from the cells described in the embodiment [1B-3-3] or [1B-3-9]; the cationic polymer layer is selected from the cationic polymers described in the embodiments [1-15-2] or [1-15-4].

[1-17X-4] The polymer-coated crosslinked alginate gel fiber of the embodiment [1X] or [1Y] is a polymer-coated crosslinked alginate gel fiber, in which, particularly preferably, the alginic acid derivative, which is used to form the crosslinked alginate gel, is selected from the alginic acid derivatives represented by Formula (I-A) having the particularly preferable -$L^{1A}$- described in the embodiment [1X-1] and the particularly preferable Aky described in the embodiment [1X-2] and the alginic acid derivatives represented by Formula (II-A) having the particularly preferable -$L^{2A}$- described in the embodiment [1X-3]; the antibody-producing cell is an antibody-producing CHO cell; the cationic polymer layer is selected from poly-L-ornithine, polyallylamine (PAA), polyethyleneimine or polymethylene-CO-guanidine (PMCG).

[1-17X-5] The polymer-coated crosslinked alginate gel fiber of the embodiment [1X] or [1Y] is a polymer-coated crosslinked alginate gel fiber, in which, most preferably, the alginic acid derivative, which is used to form the crosslinked alginate gel, is selected from the alginic acid derivatives represented by Formula (I-A) having the most preferable -$L^{1A}$-described in the embodiment [1X-1] and the most preferable Aky described in the embodiment [1X-2] and the alginic acid derivatives represented by Formula (II-A) having the most preferable -$L^{2A}$- described in the embodiment [1X-3]; the antibody-producing cell is an antibody-producing CHO cell; the cationic polymer layer is selected from poly-L-ornithine, polyallylamine (PAA), polyethyleneimine or polymethylene-CO-guanidine (PMCG).

[1-17X-5-1] In the embodiment [1-17X-5], -$L^{1A}$- described in the alginic acid derivatives represented by Formula (I-A) is specifically a linker selected from the following partial structural formulae:

[C30]

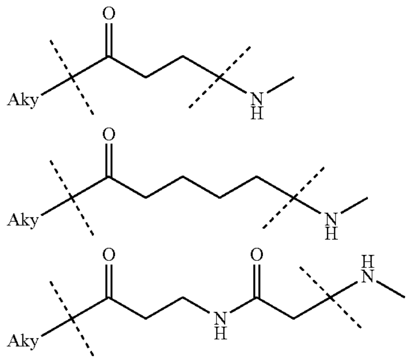

-continued

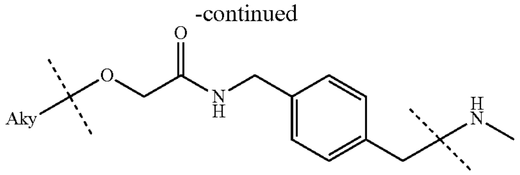

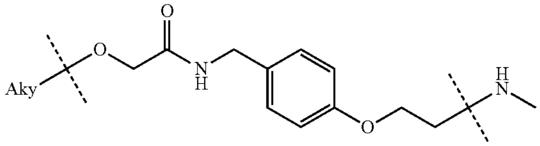

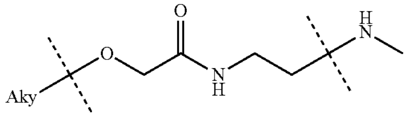

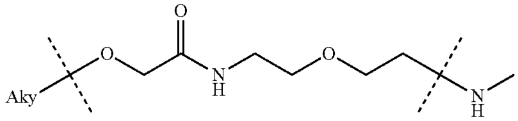

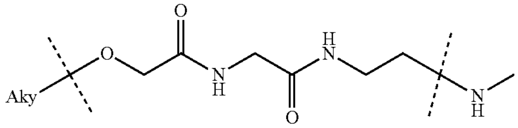

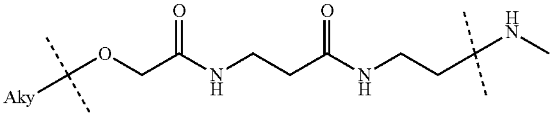

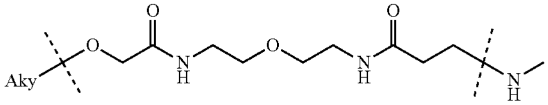

(in each formula, the outsides of the cutting lines at both ends are not included);

Aky is specifically a cyclic alkyne group selected from the following partial structural formulae:

[C31]

(Aky-1)

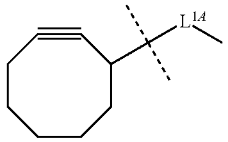

(Aky-3)

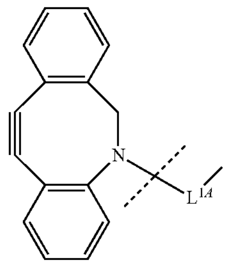

(in the formulae, the right sides of the cutting lines at both ends are not included); and -$L^{2A}$- described in the alginic acid derivatives represented by Formula (II-A) is specifically a linker selected from the following partial structural formulae:

[C32]

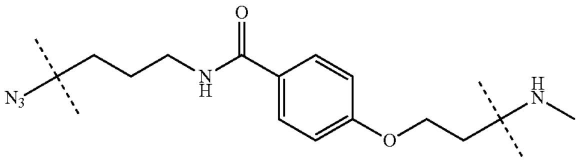

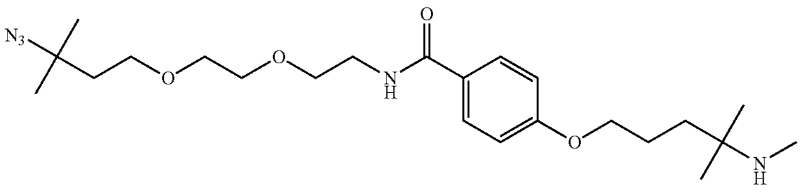

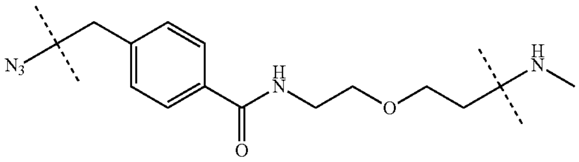

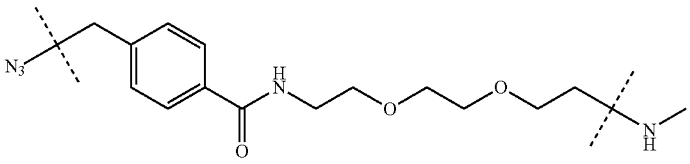

-continued

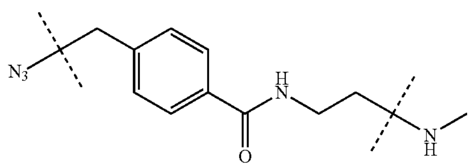

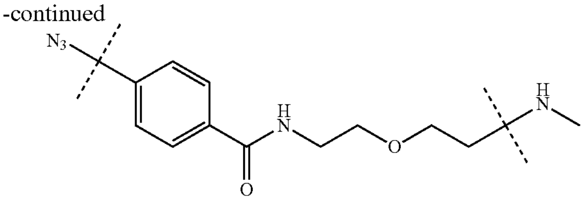

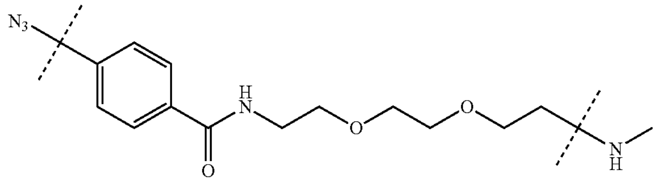

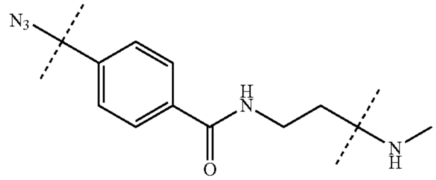

(in the formulae, the outsides of the cutting lines at both ends are not included).

[1-17X-6] In the embodiments [1-17X-1] to [1-17X-5-1], the crosslinked alginate gel in the polymer-coated crosslinked alginate gel fiber comprises any of the components that can be contained described in the embodiments [1-4] to [1-4-1].

Combination of the individual elements of the cell enabling production of antibodies, bioactive substances or the like, the chemically modified alginic acid derivatives represented by Formula (I-A) and Formula (II-A) that are used to form the crosslinked alginate gel and the cationic polymer (cationic polymer layer) in the polymer-coated crosslinked alginate gel fibers described in the embodiments makes it possible to arbitrarily form a preferable embodiment of a method for manufacturing a polymer-coated crosslinked alginate gel fiber.

[1B-3] In the embodiments [1], [1A], [1X] or [1Y], examples of the cell enabling production of antibodies, bioactive substances or the like that is contained in the core layer of the polymer-coated crosslinked alginate gel fiber include antibody (a variety of monoclonal antibodies such as human antibodies, humanized antibodies, chimeric antibodies and mouse antibodies or a variety of altered antibodies such as bispecific antibody, low-molecular-weight antibodies, glycoengineered antibodies thereof)-producing cells, bioactive substance (enzyme, cytokine, hormone, blood coagulation factor, vaccine or the like)-producing cells and cells enabling production of a variety of useful substances useful as drug raw materials, chemical raw materials, food raw materials and the like; an antibody-producing cell or a bioactive substance-producing cell is preferable.

[1B-3-1] In the embodiments [1], [1A], [1X] or [1Y], an antibody-producing cell that can be encapsulated in the core layer of the polymer-coated crosslinked alginate gel fiber is a hybridoma obtained from an antibody-producing B cell (antibody-producing hybridoma) or a cultured cell transformed with an antibody expression vector (antibody-producing genetically modified cell).

[1B-3-2] In the embodiments [1], [1A], [1X] or [1Y], the antibody-producing cell that can be encapsulated in the core layer of the polymer-coated crosslinked alginate gel fiber is preferably an antibody-producing genetically modified animal cell.

[1B-3-3] In the embodiment [1B-3-2], the animal cell that is used as a host is a CHO cell, a CHO cell subline (a CHO-K1 cell, a CHO-DG44 cell, a CHO-DXB11 cell, a CHO cell transformed such that a sugar chain is modified or the like), a COS cell, an Sp2/0 cell, an NS0 cell, an SP2 cell, a PERC6 cell, an YB2/0 cell, an YE2/0 cell, a 1R983F cell, a Namalwa cell, a Wil-2 cell, a Jurkat cell, a Vero cell, a Molt-4 cell, an HEK293 cell, a BHK cell, an HT-1080 cell, a KGH6 cell, a P3X63Ag8.653 cell, a C127 cell, a JC cell, an LA7 cell, a ZR-45-30 cell, an hTERT cell, an NM2C5 cell or a UACC-812 cell.

[1B-3-4] In the embodiment [1B-3-2], the animal cell that is used as a host is preferably a cell selected from a CHO cell, a CHO cell subline, a COS cell, an Sp2/0 cell, an NS0 cell, an SP2 cell, a PERC6 cell, an HEK293 cell, a BHK cell, an HT-1080 cell or a C127 cell; more preferably a cell selected from a CHO cell, a CHO cell subline, an Sp2/0 cell, an NS0 cell, an HEK293 cell or a BHK cell; still more preferably a CHO cell or a CHO cell subline.

[1B-3-5] In the embodiments [1], [1A], [1X] or [1Y], the antibody-producing cell that can be encapsulated in the core layer of the polymer-coated crosslinked alginate gel fiber is preferably a cell for which a host cell thereof is selected from a CHO cell, a CHO cell subline, an Sp2/0 cell or an NS0 cell; more preferably a CHO cell or a CHO cell subline.

[1B-3-6] In the embodiments [1], [1A], [1X] or [1Y], the antibody-producing cell that can be encapsulated in the core layer of the polymer-coated crosslinked alginate gel fiber is a cell from which antibodies that are used as biopharmaceuticals or biopharmaceutical raw materials are produced.

In the present specification, the antibody-producing cell that is contained in the core layer of the polymer-coated crosslinked alginate gel fiber is preferably a floating cell or a cell or cell subline adapted so as to be floating-cultivable.

[1B-3-7] In the embodiments [1], [1A], [1X] or [1Y], the antibody-producing cell that can be encapsulated in the core layer of the polymer-coated crosslinked alginate gel fiber is a cell selected from antibody-producing cells such as muromonab-CD3, trastuzumab, rituximab, palivizumab, infliximab, basiliximab, tocilizumab, bevacizumab, adalimumab, cetuximab, omalizumab, eculizumab, panitumumab, ustekinumab, golimumab, canakinumab, denosumab, ofatumumab, pertuzumab, natalizumab, nivolumab, alemtuzumab, secukinumab, ramucirumab, ipilimumab, evolocumab, mepolizumab, alirocumab, ixekizumab, brodalumab, elotuzumab, pembrolizumab, sarilumab, bezlotoxumab, belimumab, daratumumab, avelumab, dupilumab, atezolizumab, emicizumab, guselkumab, durvalumab, vedolizumab, romosozumab, risankizumab, necitumumab, ravulizumab, burosumab, isatuximab, tildrakizumab, satralizumab, galcanezumab, dinutuximab, fremanezumab, erenumab, casilibimab, imdevimab, anifloruмab, sotrovimab, ocrelizumab, naxitamab, aducanumab, tafacitamab, margetuximab, gantenerumab, tiragolumab, clovalimab, nemolizumab, katumasomab, pramotamab, falisimab, gemtuzumab, ibritumomab, brentuximab, inotuzumab, polatuzumab, enfortuzumab, sacituzumab, belantamab, roncastuximab, tisotumab, datopotab and patritumab; cells from which an antibody having an altered sugar chain is produced such as mogamulizumab, benralizumab, obinutuzumab and inevirizumab; cells from which a low-molecular-weight antibody composed of an antibody fragment is produced such as ranibizumab, idarucizumab, blinatumomab, brolucizumab, abciximab, capracizumab and certolizumab; and the like.

[1B-3-8] In the embodiments [1], [1A], [1X] or [1Y], the antibody-producing cell that can be encapsulated in the core layer of the polymer-coated crosslinked alginate gel fiber is an antibody-producing animal cell, preferably an antibody-producing CHO cell, an antibody-producing Sp2/0 cell or an antibody-producing NS0 cell; more preferably an antibody-producing CHO cell.

[1B-3-9] In the embodiment [1], [1A], [1X] or [1Y], the antibody-producing cell that can be encapsulated in the core layer of the polymer-coated crosslinked alginate gel fiber is preferably an antibody-producing CHO cell in which a host cell thereof is a CHO cell and, for example, a cell selected from a muromonab-CD3-producing CHO cell, a trastuzumab-producing CHO cell, a rituximab-producing CHO cell, a palivizumab-producing CHO cell, an infliximab-producing CHO cell, a basiliximab-producing CHO cell, a tocilizumab-producing CHO cell, a gemtuzumab-producing CHO cell, a bevacizumab-producing CHO cell, an ibritumomab-producing CHO cell, an adalimumab-producing CHO cell, a cetuximab-producing CHO cell, a ranibizumab-producing CHO cell, an omalizumab-producing CHO cell, an eculizumab-producing CHO cell, a panitumumab-producing CHO cell, a ustekinumab-producing CHO cell, a golimumab-producing CHO cell, a canakinumab-producing CHO cell, a denosumab-producing CHO cell, a mogamulizumab-producing CHO cell, a certolizumab-producing CHO cell, an ofatumumab-producing CHO cell, a pertuzumab-producing CHO cell, a brentuximab-producing CHO cell, a natalizumab-producing CHO cell, a nivolumab-producing CHO cell, an alemtuzumab-producing CHO cell, a secukinumab-producing CHO cell, a ramucirumab-producing CHO cell, an ipilimumab-producing CHO cell, an evolocumab-producing CHO cell, a mepolizumab-producing CHO cell, an alirocumab-producing CHO cell, an ixekizumab-producing CHO cell, a brodalumab-producing CHO cell, an idarucizumab-producing CHO cell, an elotuzumab-producing CHO cell, a pembrolizumab-producing CHO cell, a sarilumab-producing CHO cell, a bezlotoxumab-producing CHO cell, a belimumab-producing CHO cell, a daratumumab-producing CHO cell, an avelumab-producing CHO cell, a dupilumab-producing CHO cell, an atezolizumab-producing CHO cell, a benralizumab-producing CHO cell, an inotuzumab-producing CHO cell, an emicizumab-producing CHO cell, a guselkumab-producing CHO cell, a durvalumab-producing CHO cell, an obinutuzumab-producing CHO cell, a vedolizumab-producing CHO cell, a romosozumab-producing CHO cell, a risankizumab-producing CHO cell, a necitumumab-producing CHO cell, a ravulizumab-producing CHO cell, a burosumab-producing CHO cell, an isatuximab-producing CHO cell, a tildrakizumab-producing CHO cell, a satralizumab-producing CHO cell, a galcanezumab-producing CHO cell, a dinutuximab-producing CHO cell, a fremanezumab-producing CHO cell, an erenumab-producing CHO cell, a casilibimab-producing CHO cell, an imdevimab-producing CHO cell, an aniflorumab-producing CHO cell, a sotrovimab-producing CHO cell, an ocrelizumab-producing CHO cell, a naxitamab-producing CHO cell, an aducanumab-producing CHO cell, a tafacitamab-producing CHO cell, a margetuximab-producing CHO cell, a polatuzumab-producing CHO cell, an enfortuzumab-producing CHO cell, a sacituzumab-producing CHO cell, a belantamab-producing CHO cell, a roncastuximab-producing CHO cell, a tisotumab-producing CHO cell, an inevirizumab-producing CHO cell, a blinatumomab-producing CHO cell, a brolucizumab-producing CHO cell, an abciximab-producing CHO cell, a caplacizumab-producing CHO cell or an anti-GPVI antibody-producing CHO cell; a cell selected from a trastuzumab-producing CHO cell, a rituximab-producing CHO cell, an infliximab-producing CHO cell, a tocilizumab-producing CHO cell, an adalimumab-producing CHO cell, a nivolumab-producing CHO cell, or an anti-GPVI antibody-producing CHO cell.

[1B-3-10] In the embodiments [1], [1A], [1X] or [1Y], the bioactive substance-producing cell that is contained in the core layer of the polymer-coated crosslinked alginate gel fiber is the same as the bioactive substance-producing cell described in the embodiment [1-3-4].

[1B-3-11] In the embodiments [1], [1A], [1X] or [1Y], the bioactive substance-producing cell that is contained in the core layer of the polymer-coated crosslinked alginate gel fiber is a cell selected from the group consisting of an insulin-secreting cell, a pancreatic islet, a pancreatic islet cell or a MING cell derived from a pancreatic β cell.

[1B-3-12] In the embodiments [1], [1A], [1X] or [1Y], the bioactive substance-producing cell that can be encapsulated in the core layer of the polymer-coated crosslinked alginate gel fiber is a cultured cell transformed with a bioactive substance expression vector (bioactive substance-producing genetically modified cell).

[1B-3-13] In the embodiments [1], [1A], [1X] or [1Y], the bioactive substance-producing cell that can be encapsulated in the core layer of the polymer-coated crosslinked alginate gel fiber is a bioactive substance-producing genetically modified animal cell.

[1B-3-14] In the embodiment [1B-3-13], the animal cell that is used as a host is a cell selected from a CHO cell, a CHO cell subline, a COS cell, an Sp2/0 cell, an NS0 cell, an SP2 cell or a cell selected from a PERC6 cell, an HEK293 cell, a BHK cell, an HT-1080 cell or a C127 cell; preferably a cell selected from a CHO cell, a CHO cell subline, an Sp2/0 cell, an NS0 cell, an HEK293 cell or a BHK cell; more preferably a CHO cell or a CHO cell subline.

[1B-3-15] In the embodiments [1], [1A], [1X] or [1Y], the bioactive substance-producing cell that can be encapsulated in the core layer of the polymer-coated crosslinked alginate gel fiber is preferably a cell for which a host cell thereof is selected from a CHO cell, a CHO cell subline, an HEK293 cell or a BHK cell; more preferably a CHO cell or a CHO cell subline.

[1B-3-16] In the embodiments [1], [1A], [1X] or [1Y], the bioactive substance-producing cell that can be encapsulated in the core layer of the polymer-coated crosslinked alginate gel fiber is a cell from which bioactive substances that are used as biopharmaceuticals or biopharmaceutical raw materials are produced.

[1B-3-17] In the embodiments [1], [1A], [1X] or [1Y], the bioactive substance-producing cell that can be encapsulated in the core layer of the polymer-coated crosslinked alginate gel fiber is a cell selected from enzyme-producing cells such as alteplase, monteplase, imiglucerase, veraglucerase, agalsidase, laronidase, alglucosidase, avalglucosidase, idursulfase, gallsulfase, erosulfase, rasburicase, dornase, celluliponase, glucarpidase, hyaluronidase and asfotase; blood coagulation factor and blood-related protein-producing cells such as eptacog, octocog, rurioctocog, turoctocog, lonoctocog, damoctocog, simoctocog, nonacog, albutrepenonacog, catridecacog, efraloctocog, eftrenonacog, thrombomodulin, antithrombin, vonicog and albumin; hormone-producing cells such as insulin, insulin lispro, insulin aspart, insulin glargine, insulin detemir, insulin glulisine, insulin degludec, somatropin, somapcitan, mecacermin, carperitide, bosolitide, glucagon, follitropin, choriogonadotropin, dulaglutide, liraglutide, semaglutide, teduglutide, teriparatide and metreleptin; interferon-producing cells such as interferon alpha-2a, interferon alpha-2b, interferon beta-1a, interferon beta-1b and interferon gamma-1a; hematopoietic factor-producing cells such as epoetin, darbepoetin and romiplostim; cells from which cytokines such as filgrastim, lenograstim, tesseleukin, trafermin, verfermin, etanercept, aflibercept and denileukin, diftitox and receptors thereof are produced; cells from which cell surface antigens such as abatacept, cell surface receptors and ligands thereof are produced.

[1B-3-18] In the embodiments [1], [1A], [1X] or [1Y], the bioactive substance-producing cell that can be encapsulated in the core layer of the polymer-coated crosslinked alginate gel fiber is a bioactive substance-producing animal cell, preferably a bioactive substance-producing CHO cell, a bioactive substance-producing HEK 293 cell or a bioactive substance-producing BHK cell and more preferably a bioactive substance-producing CHO cell.

[1B-3-19] In the embodiments [1], [1A], [1X] or [1Y], the bioactive substance-producing cell that can be encapsulated in the core layer of the polymer-coated crosslinked alginate gel fiber is preferably a bioactive substance-producing cell CHO cell in which a host cell thereof is a CHO cell and, for example, a cell selected from an alteplase-producing CHO cell, an alglucosidase-producing CHO cell, a rurioctocog-producing CHO cell, a dulaglutide-producing CHO cell, an interferon beta-1a-producing CHO cell, a darbepoetin-producing CHO cell, an etanercept-producing CHO cell, an aflibercept-producing CHO cell or an abatacept-producing CHO cell.

[2] Embodiment 2 is as described below. A method for manufacturing a polymer-coated crosslinked alginate gel fiber that is formed by coating a core layer comprising a cell enabling production of antibodies, bioactive substances or the like and crosslinked alginate gel that is obtained by performing a crosslinking reaction using the chemically modified alginic acid derivative represented by Formula (I) and the chemically modified alginic acid derivative represented by Formula (II) described in the embodiment [1] with a cationic polymer, the method comprising step (1): a step of injecting a solution mixture comprising a cell enabling production of antibodies, bioactive substances or the like and the chemically modified alginic acid derivatives represented by Formula (I) and Formula (II) described in the embodiment [1] into a solution comprising a divalent metal ion to obtain a crosslinked alginate gel fiber (CLA) comprising the cell enabling production of antibodies, bioactive substances or the like in a core layer, and step (2): a step of bringing the crosslinked alginate gel fiber (CLA) comprising the cell enabling production of antibodies, bioactive substances or the like in the core layer obtained in the step (1) into contact with a solution comprising a cationic polymer, thereby obtaining a polymer-coated crosslinked alginate gel fiber (CFB) coated with a cationic polymer layer.

[2A] The polymer-coated crosslinked alginate gel fiber in the embodiment [2] is the polymer-coated crosslinked alginate gel fiber described in any of the embodiments ([1] to [1-17-5]).

[2-1] In the embodiment [2], the cell enabling production of antibodies, bioactive substances or the like that is used to manufacture the polymer-coated crosslinked alginate gel fiber is the same as the cell enabling production of antibodies, bioactive substances or the like described in any one of the embodiments [1-3] to [1-3-5].

[2-1-1] In the embodiment [2], the cell enabling production of antibodies, bioactive substances or the like that is used to manufacture the polymer-coated crosslinked alginate gel fiber is the same as the cell enabling production of antibodies, bioactive substances or the like described in any one of the embodiments [1B-3] to [1B-3-19].

[2-2] In the embodiment [2], the weight-average molecular weight measured by gel filtration chromatography of the chemically modified alginic acid derivative represented by Formula (I), which is used to manufacture the polymer-coated crosslinked alginate gel fiber, is, for example, within a range of approximately 100,000 Da to approximately 3,000,000 Da; preferably within a range of approximately 300,000 Da to approximately 2,500,000 Da; more preferably within a range of approximately 500,000 Da to approximately 2,000,000 Da.

[2-3] In the embodiment [2], the weight-average molecular weight measured by gel filtration chromatography of the chemically modified alginic acid derivative represented by Formula (II), which is used to manufacture the polymer-coated crosslinked alginate gel fiber, is, for example, within a range of approximately 100,000 Da to approximately 3,000,000 Da; preferably within a range of approximately 300,000 Da to approximately 2,500,000 Da; more preferably within a range of approximately 500,000 Da to approximately 2,000,000 Da.

[2-4] In the embodiment [2], the introduction rate of a reactive group: Akn-$L^1$-$NH_2$ group (Akn-$L^1$- is the same as the definitions in the embodiments [1] to [1-1-4]) into the chemically modified alginic acid derivative represented by Formula (I), which is used to manufacture the polymer-coated crosslinked alginate gel fiber, for example, within a range of approximately 0.1 to approximately 30 mol %; preferably within a range of approximately 0.3 to approximately 20 mol %; more preferably within a range of approximately 0.5 to approximately 10 mol %.

[2-5] In the embodiment [2], the introduction rate of a reactive group: $N_3$-$L^2$-$NH_2$ group (-$L^2$- is the same as the definitions in the embodiments [1] and [1-2-1] to [1-2-4]) into the chemically modified alginic acid derivative represented by Formula (II), which is used to manufacture the polymer-coated crosslinked alginate gel fiber, for example, within a range of approximately 0.1 to approximately 30 mol %; preferably within a range of approximately 0.3 to approximately 20 mol %; more preferably within a range of approximately 0.5 to approximately 15 mol %.

[2-6] In the embodiment [2], a component that can be added to the solution mixture comprising the cell enabling production of antibodies, bioactive substances or the like and the chemically modified alginic acid derivatives represented by Formula (I) and Formula (II) is, for example, a component selected from the group consisting of an alginic acid solution, a culture medium, a culture fluid, a collagen solution, methylcellulose, a sucrose solution, or a mixture thereof and the like; preferably a component selected from the group consisting of an alginic acid solution, a culture medium, a culture fluid, or a mixture thereof and the like.

[2-7] In the embodiment [2], the weight-average molecular weight measured by gel permeation chromatography (GPC) of alginic acid (for example, sodium alginate or the like) that is used to prepare the alginic acid solution that can be added to the solution mixture comprising the cell enabling production of antibodies, bioactive substances or the like and the chemically modified alginic acid derivatives represented by Formula (I) and Formula (II) is, for example, within a range of approximately 150,000 Da to approximately 2,500,000 Da; preferably within a range of approximately 300,000 Da to approximately 2,000,000 Da; more preferably within a range of approximately 700,000 Da to approximately 1,500,000 Da.

[2-7A] In the step (1) of the fiber manufacture in the embodiment [2], the weight-average molecular weight measured by gel permeation chromatography (GPC) of alginic acid (for example, sodium alginate or the like) that is used to prepare the alginic acid solution that can be added to the solution mixture comprising the cell enabling production of antibodies, bioactive substances or the like and the chemically modified alginic acid derivatives represented by Formula (I) and Formula (II) is, for example, within a range of approximately 150,000 Da to approximately 2,500,000 Da; preferably within a range of approximately 300,000 Da to approximately 2,500,000 Da; more preferably within a range selected from approximately 700,000 Da to approximately 1,400,000 Da, approximately 800,000 Da to approximately 1,500,000 Da, approximately 1,400,000 to approximately 2,000,000 Da or approximately 1,500,000 to approximately 2,500,000 Da.

[2-7B] In the step (1) of the fiber manufacture in the embodiment [2], the weight-average molecular weight measured by gel permeation chromatography (GPC) of alginic acid (for example, sodium alginate or the like) that is used to prepare the alginic acid solution that can be added to the solution mixture comprising the cell enabling production of antibodies, bioactive substances or the like and the chemically modified alginic acid derivatives represented by Formula (I) and Formula (II) is preferably within a range selected from approximately 1,400,000 to approximately 2,000,000, approximately 700,000 to approximately 1,400,000 or approximately 800,000 to approximately 1,500,000; more preferably within a range of approximately 1,400,000 to approximately 2,000,000.

[2-8] In the embodiment [2], the concentration of a solution of the chemically modified alginic acid derivative represented by Formula (I), which is used to manufacture the polymer-coated crosslinked alginate gel fiber is, for example, within a range of approximately 0.01 to approximately 1.5 wt %; preferably within a range of approximately 0.05 to approximately 1.0 wt %; more preferably within a range of approximately 0.08 to approximately 0.75 wt %.

In the present specification, "wt %" means "w/v %".

[2-9] In the embodiment [2], the concentration of a solution of the chemically modified alginic acid derivative represented by Formula (II), which is used to manufacture the polymer-coated crosslinked alginate gel fiber is, for example, within a range of approximately 0.01 to approximately 1.5 wt %; preferably within a range of approximately 0.05 to approximately 1.0 wt %; more preferably within a range of approximately 0.08 to approximately 0.75 wt %.

[2-10] In the embodiment [2], the concentration of the solution mixture of the chemically modified alginic acid derivative represented by Formula (I) and the chemically modified alginic acid derivative represented by Formula (II), which is used to manufacture the polymer-coated crosslinked alginate gel fiber, is, for example, within a range of approximately 0.02 to approximately 2.0 wt %; preferably within a range of approximately 0.1 to approximately 2.0 wt %; more preferably within a range of approximately 0.15 to approximately 1.5 wt %.

[2-11] In the embodiment [2], the concentration of the alginic acid solution that can be added to the solution mixture comprising the cell enabling production of antibodies, bioactive substances or the like and the chemically modified alginic acid derivatives represented by Formula (I) and Formula (II) is, for example, within a range of 0 to approximately 1.98 wt %; preferably within a range of 0 to approximately 1.8 wt %; more preferably within a range of 0 to approximately 1.7 wt %.

[2-11-1] In the embodiment [2], the concentration ($C_{ALG}$) of the alginic acid solution, which can be additionally contained in the solution mixture comprising the cell enabling production of antibodies, bioactive substances or the like and the chemically modified alginic acid derivatives represented by Formula (I) and Formula (II) is, for example, within a range of $0<C_{ALG}\leq$approximately 1.98 wt %; preferably within a range of $0<C_{ALG}\leq$approximately 1.8 wt %; more preferably within a range of $0<C_{ALG}\leq$approximately 1.7 wt %.

[2-11-1] In the embodiment [2], in a case where the alginic acid solution is added to the solution mixture comprising the cell enabling production of antibodies, bioactive substances or the like and the chemically modified alginic acid derivatives represented by Formula (I) and Formula (II), the total concentration of the concentration of the solution mixture comprising the chemically modified alginic acid derivatives represented by Formula (I) and Formula (II) and the concentration of the alginic acid solution is preferably within a range of approximately 0.5 to approximately 2.0 wt %; more preferably selected from approximately 1.0 wt %, approximately 1.5 wt % and approximately 2.0 wt %.

[2-11-1-1] In the embodiment [2], in a case where the alginic acid solution is added to the solution mixture comprising the cell enabling production of antibodies, bioactive substances or the like and the chemically modified alginic acid derivatives represented by Formula (I) and Formula (II), the total concentration ($C_{TOL}$) of the concentration of the solution mixture comprising the chemically modified alginic acid derivatives represented by Formula (I) and Formula (II) and the concentration of the alginic acid solution is, for example, $0<C_{TOL}\leq$approximately 2.0 wt %;

- preferably approximately 0.5 to approximately 2.0 wt %;
- more preferably approximately 1.0 to approximately 2.0 wt %;
- still more preferably a concentration selected from approximately 1.0 wt %, approximately 1.5 wt % and approximately 2.0 wt %.

[2-11-2] In the embodiment [2], in a case where the alginic acid solution is added to the solution mixture comprising the cell enabling production of antibodies, bioactive substances or the like and the chemically modified alginic acid derivatives represented by Formula (I) and Formula (II), the combination of the concentration (C1 (wt %)) of the solution mixture comprising the chemically modified alginic acid derivatives represented by Formula (I) and Formula (II) and the concentration (C2 (wt %)) of the alginic acid solution is preferably a combination selected from the group consisting of (C1:C2)=(approximately 0.2:approximately 1.3), (approximately 0.5:approximately 1.0), (approximately 1.0:approximately 0.5), (approximately 0.66:approximately 1.34) and (approximately 0.34:approximately 0.66).

[2-11-2-1] In the embodiment [2], in a case where the alginic acid solution is added to the solution mixture comprising the cell enabling production of antibodies, bioactive substances or the like and the chemically modified alginic acid derivatives represented by Formula (I) and Formula (II), the combination of the concentration (C1 (wt %)) of the solution mixture comprising the chemically modified alginic acid derivatives represented by Formula (I) and Formula (II) and the concentration (C2 (wt %)) of the alginic acid solution is for example, a combination of ranges satisfying formulae represented by $0<C2$ (wt %)≤approximately 1.98 (wt %),
$0<C1$ (wt %)≤approximately 2.0 (wt %)−C2 (wt %) and
$0<C1+C2$ (wt %)≤approximately 2.0 (wt %);
preferably a combination selected from the group consisting of (C1:C2)=(approximately 0.2:approximately 1.3), (approximately 0.5:approximately 1.0), (approximately 1.0:approximately 0.5), (approximately 0.66:approximately 1.34) and (approximately 0.34:approximately 0.66).

[2-11-3] In the embodiment [2], in a case where the alginic acid solution is added to the solution mixture comprising the cell enabling production of antibodies, bioactive substances or the like and the chemically modified alginic acid derivatives represented by Formula (I) and Formula (II), the combination of the concentration (C1A (wt %)) of the solution of the chemically modified alginic acid derivative represented by Formula (I), the concentration (C1N (wt %)) of the solution of the chemically modified alginic acid derivative represented by Formula (II) and the concentration (C2 (wt %)) of the alginic acid solution is preferably a combination selected from the group consisting of (C1A:C1N:C2)=(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34) and (approximately 0.17:approximately 0.17:approximately 0.66).

[2-11-3-1] In the embodiment [2], in a case where the alginic acid solution is added to the solution mixture comprising the cell enabling production of antibodies, bioactive substances or the like and the chemically modified alginic acid derivatives represented by Formula (I) and Formula (II), the combination of the concentration (C1A (wt %)) of the solution of the chemically modified alginic acid derivative represented by Formula (I), the concentration (C1N (wt %)) of the solution of the chemically modified alginic acid derivative represented by Formula (II) and the concentration (C2 (wt %)) of the alginic acid solution is, for example, a combination of ranges satisfying formulae represented by $0<C2$ (wt %)≤approximately 1.98 (wt %),
$0<C1A$ (wt %)≤approximately 2.0 (wt %)−C2 (wt %),
$0<C1N$ (wt %)≤approximately 2.0 (wt %)−C2 (wt %) and
$0<C1A+C1N+C2$ (wt %)≤approximately 2.0 (wt %);
preferably a combination selected from the group consisting of (C1A:C1N:C2)=(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34) and (approximately 0.17:approximately 0.17:approximately 0.66).

[2-12-1] In the embodiment [2], each volume ratio (v1, v2) of the solution of the chemically modified alginic acid derivative represented by Formula (I) and the solution of the chemically modified alginic acid derivative represented by Formula (II) in the solution mixture comprising the cell enabling production of antibodies, bioactive substances or the like and the chemically modified alginic acid derivatives represented by Formula (I) and Formula (II) is, for example, a ratio in the case of $v1+v2=15$ and, for example, (v1:v2)=(7.5:7.5). Here, in $v1+v2=15$, $0<v1<15$ and $0<v2<15$.

[2-12-2] In the embodiment [2], in a case where the alginic acid solution is added to the solution mixture comprising the cell enabling production of antibodies, bioactive substances or the like and the chemically modified alginic acid derivatives represented by Formula (I) and Formula (II), which is used to form the core layer of the polymer-coated crosslinked alginate gel fiber, the volume ratio of the volume (v1) of the chemically modified alginic acid derivative represented by Formula (I), the volume (v2) of the chemically modified alginic acid derivative represented by Formula (II) and the volume (v3) of the alginic acid solution in the solution mixture to which the alginic acid has been added is, for example, a ratio in the case of $v1+v2+v3=15$ and, for example, a combination of (v1:v2:v3)=(5:5:5), (2.5:2.5:10), (1:1:13) or the like. Here, in $v1+v2+v3=15$, $0<v1<15$, $0<v2<15$ and $0<v3<15$.

[2-13] In the embodiment [2], the divalent metal ion that is contained in the solution into which the solution mixture comprising the cell enabling production of antibodies, bioactive substances or the like and the chemically modified alginic acid derivatives represented by Formula (I) and Formula (II) is injected is a divalent metal ion selected from the group of a calcium ion, a magnesium ion, a barium ion, a strontium ion, a zinc ion and the like; preferably a calcium ion, a barium ion or a strontium ion; more preferably a calcium ion or a barium ion.

[2-14] In the embodiment [2], the solution into which the solution mixture comprising the cell enabling production of antibodies, bioactive substances or the like and the chemically modified alginic acid derivatives represented by Formula (I) and Formula (II) is injected is an aqueous solution comprising a divalent metal ion selected from the group consisting of a calcium chloride aqueous solution, a calcium carbonate aqueous solution, a calcium gluconate aqueous solution, a barium chloride aqueous solution, a strontium chloride aqueous solution and the like; preferably a calcium chloride aqueous solution or a barium chloride aqueous solution.

[2-15] In the embodiment [2] or [2-14], the concentration of the divalent metal ion is, for example, within a range of approximately 1 mM to approximately 1 M or a range of approximately 10 to approximately 500 mM; preferably approximately 10 to approximately 100 mM.

Figure 3:
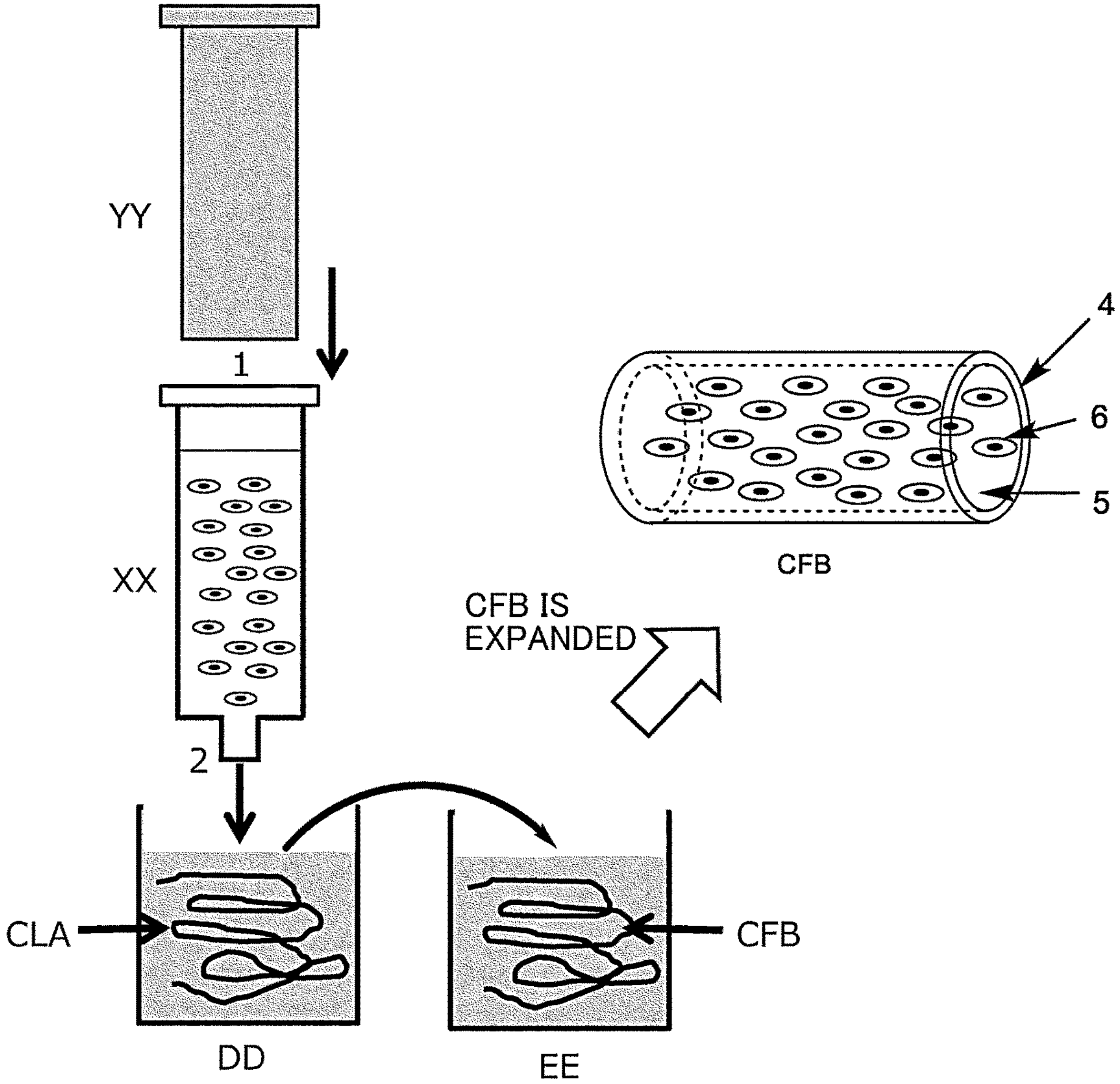
FIG. 3 is a schematic view for describing one embodiment of a manufacturing process of the polymer-coated crosslinked alginate gel fiber.

[2-16-1] In the embodiment [2], regarding the solution mixture comprising the cell enabling production of antibodies, bioactive substances or the like and the chemically modified alginic acid derivatives represented by Formula (I) and Formula (II), it is possible to use, for example, a device XX comprising an introduction port 1 and a discharge port 2, which is shown in FIG. 3, or the like, introduce the solution mixture from the introduction port 1 of the device XX and inject the solution mixture from the discharge port 2 of the device XX.

[2-16-2] In the embodiment [2-16-1], regarding the solution mixture comprising the cell enabling production of antibodies, bioactive substances or the like and the chemically modified alginic acid derivatives represented by Formula (I) and Formula (II), it is possible to inject the solution mixture from the discharge port 2 of the device XX using, for example, an extrusion tube YY as shown in FIG. 3 or the like.

[2-17] In the embodiment [2-16-2], as a combination of the device XX and the plunger YY, for example, an syringe can be used. In addition, as the syringe, it is possible to use a glass or plastic syringe.

[2-18] In the embodiments [2], [2-16-1] and [2-16-2], the injection rate (flow rate) of the solution mixture comprising the cell enabling production of antibodies, bioactive substances or the like and the chemically modified alginic acid derivatives represented by Formula (I) and Formula (II) is, for example, within a range of approximately 100 to approximately 10000 μL/minute.

[2-19-1] In the embodiment [2], the solution comprising a cationic polymer with which the crosslinked alginate gel fiber (CLA) comprising the cell enabling production of antibodies, bioactive substances or the like is brought into contact is a solution comprising a cationic polymer selected from the group consisting of polyamino acids (polymers of a basic amino acid), basic polysaccharides, basic polymers, salts thereof and the like.

[2-19-2] In the embodiment [2], the solution comprising a cationic polymer with which the crosslinked alginate gel fiber (CLA) comprising the cell enabling production of antibodies, bioactive substances or the like is brought into contact is preferably a solution comprising a cationic polymer selected from the group consisting of poly-L-ornithine (PLO), poly-D-ornithine (PDO), poly-DL-ornithine, poly-D-lysine (PDL), poly-L-lysine (PLL), poly-DL-lysine, poly-L-arginine (PLA), poly-D-arginine (PDA), poly-DL-arginine, poly-L-homoarginine (PLHA), poly-D-homoarginine (PDHA), poly-DL-homoarginine, poly-L-histidine (PLH), poly-D-histidine (PDH), poly-DL-histidine, which are polyamino acids, and a salt thereof; more preferably a solution comprising a cationic polymer selected from the group consisting of poly-L-ornithine, poly-L-lysine and a salt thereof; still more preferably a solution comprising a cationic polymer selected from poly-L-ornithine and a salt thereof.

[2-19-3] In the embodiment [2], the solution comprising a cationic polymer with which the crosslinked alginate gel fiber (CLA) comprising the cell enabling production of antibodies, bioactive substances or the like is brought into contact is, for example, a solution comprising a cationic polymer selected from the group consisting of chitosan, which is a basic polysaccharide, and a salt thereof.

[2-19-4] In the embodiment [2], the solution comprising a cationic polymer with which the crosslinked alginate gel fiber (CLA) comprising the cell enabling production of antibodies, bioactive substances or the like is brought into contact is, for example, a solution comprising a cationic polymer selected from the group consisting of polymethylene-CO-guanidine (PMCG), polyallylamine (PAA), polyvinylamine (PVA), polyethyleneimine, an allylamine-diallylamine copolymer, an allylamine-maleic acid copolymer, which are basic polymers, and a salt thereof.

[2-19-4-1] In the embodiment [2-19-4], the solution comprising a cationic polymer is preferably a solution comprising a cationic polymer selected from the group consisting of polyallylamine (PAA), polyethyleneimine, polymethylene-CO-guanidine (PMCG) and a salt thereof; more preferably a solution comprising a cationic polymer selected from the group consisting of polyethyleneimine, polymethylene-CO-guanidine (PMCG) or a salt thereof.

[2-20] In the embodiment [2], the solution comprising a cationic polymer with which the crosslinked alginate gel fiber (CLA) comprising the cell enabling production of antibodies, bioactive substances or the like is brought into contact may contain a component such as an aqueous solution containing a divalent metal ion (for example, a calcium chloride aqueous solution, a barium chloride aqueous solution or the like) or a buffer solution.

[2-21] In the embodiment [2], the temperature of the polymer-coated crosslinked alginate gel fiber during manufacturing is, for example, within a range of approximately 4° C. to approximately 37° C.

Combination of the methods for manufacturing a polymer-coated crosslinked alginate gel fiber described in the embodiments and individual elements makes it possible to arbitrarily form a preferable embodiment of the method for manufacturing a polymer-coated crosslinked alginate gel fiber.

[2-22] In the embodiments [2] to [2-21], the substitution of each of the chemically modified alginic acid derivatives represented by Formula (I) and Formula (II) by the chemically modified alginic acid derivatives represented by Formula (I-A) and Formula (II-A) described in the embodiment [1X] makes it possible to arbitrarily form a preferable embodiment of the method for manufacturing a polymer-coated crosslinked alginate gel fiber.

The substitution makes variables relating to the concentrations, volumes and the like of the chemically modified alginic acid derivatives represented by Formula (I-A) and Formula (II-A) replaced by the corresponding variables described in the embodiments [1-11-2-1X], [1-11-3-1X], [1-11-4X] and [1-11-5X].

[3] Embodiment 3 is as described below. A method for manufacturing an antibody, a bioactive substance or the like using a polymer-coated crosslinked alginate gel fiber that is formed by coating a core layer comprising a cell enabling production of antibodies, bioactive substances or the like and crosslinked alginate gel that is obtained by performing a crosslinking reaction using the chemically modified alginic acid derivative represented by Formula (I) and the chemically modified alginic acid derivative represented by Formula (II) described in the embodiment [1] with a cationic polymer. One embodiment of the manufacturing method is a method for manufacturing an antibody, a bioactive substance or the like in which the polymer-coated crosslinked alginate gel fiber is put into a culture container, a culture medium is added thereto, the polymer-coated crosslinked alginate gel fiber is immersed therein, and culture is performed.

[3A] The polymer-coated crosslinked alginate gel fiber in the embodiment [3] is the polymer-coated crosslinked alginate gel fiber described in any of the embodiments ([1] to [1-17-5]).

[3X] Embodiment 3X is as described below. A method for manufacturing an antibody, a bioactive substance or the like using a polymer-coated crosslinked alginate gel fiber that is formed by coating a core layer comprising a cell enabling production of antibodies, bioactive substances or the like and crosslinked alginate gel that is obtained by performing a crosslinking reaction using the chemically modified alginic acid derivative represented by Formula (I-A) and the chemically modified alginic acid derivative represented by Formula (II-A) described in the embodiment [1X] with a cationic polymer. One embodiment of the manufacturing method is a method for manufacturing an antibody, a bioactive substance or the like in which the polymer-coated crosslinked alginate gel fiber is put into a culture container, a culture medium is added thereto, the polymer-coated crosslinked alginate gel fiber is immersed therein, and culture is performed.

[3-1] In the embodiment [3] or [3X], the culture container is, for example, a container selected from the group consisting of a tissue culture plates, an Erlenmeyer flask, a T-flask, a spinner flask, a culture bag, an animal cell culture tank and the like; preferably an Erlenmeyer flask or an animal cell culture tank. For the culture, for example, any method of static culture, shaking culture or the like may be selected or any method of batch culture, fed-batch culture, continuous culture and the like may be used, but fed-batch culture or continuous culture is preferable.

[3-2] In any one of the embodiments [3] to [3-1], the temperature during the culture is, for example, within a range of approximately 28° C. to approximately 39° C. and is, for example, within a range of approximately 30° C. to approximately 37° C.

[3-3] In any one of the embodiments [3] to [3-2], the stirring rate during the culture is, for example, approximately 50 to approximately 500 rpm, approximately 50 to approximately 350 rpm, approximately 50 to approximately 250 rpm, approximately 50 to approximately 150 rpm and is, for example, approximately 125 rpm.

[3-4] In any one of the embodiments [3] to [3-3], as culture conditions, for example, the culture temperature is set within a range of approximately 28° C. to approximately 39° C., and the culture is performed with a culture device under a 5% $CO_2$ atmosphere at a stirring rate of approximately 125 rpm.

[3-5] In any one of the embodiments [3] to [3-4], the culture period is, for example, for seven days, 14 days, 28 days, 42 days, 56 days or 70 days.

In the present specification, in a case where the culture temperature is expressed with "approximately", the temperature may include up to the numerical value ±10% and up to the numerical value±20% in certain embodiments.

[3-6] In the embodiment [3], the cell enabling production of antibodies, bioactive substances or the like that is contained in the core layer of the polymer-coated crosslinked alginate gel fiber is the same as the cell enabling production of antibodies, bioactive substances or the like described in any one of the embodiments [1-3] to [1-3-5].

[3-6-1] In the embodiment [3], the cell enabling production of antibodies, bioactive substances or the like that is contained in the core layer of the polymer-coated crosslinked alginate gel fiber is the same as the cell enabling production of antibodies, bioactive substances or the like described in any one of the embodiments [1B-3] to [1B-3-19].

[3-7] In any one of the embodiments [3] to [3-6-1], the method for manufacturing an antibody, a bioactive substance or the like comprises addition of a cell growth inhibitor.

Combination of the methods for manufacturing an antibody, a bioactive substance or the like using a polymer-coated crosslinked alginate gel fiber described in the embodiments and individual elements makes it possible to arbitrarily form a preferable embodiment of the method for manufacturing an antibody, a bioactive substance or the like.

[4] In Embodiment 4, an antibody that is produced in the core layer of a polymer-coated crosslinked alginate gel fiber that is obtained by the method for manufacturing an antibody described in any one of the embodiments [3] to [3-7] and penetrates the cationic polymer layer is, for example, an antibody having an isotype selected from the group consisting of IgG, IgA, IgM, IgD, IgE and the like.

[5] In Embodiment 5, an antibody that is produced in the core layer of a polymer-coated crosslinked alginate gel fiber that is obtained by the method for manufacturing an antibody described in any one of the embodiments [3] to [3-7] and penetrates the cationic polymer layer is an antibody having a molecular weight within a range of, for example, approximately 45,000 to approximately 1,000,000 Da, approximately 3,000 to approximately 1,000,000 Da, approximately 20,000 to approximately 1,000,000 Da, approximately 20,000 to approximately 400,000 Da, approximately 45,000 to approximately 400,000 Da, approximately 20,000 to approximately 200,000 Da or approximately 45,000 to approximately 200,000 Da.

[6] In Embodiment 6, in the manufacturing method described in any one of the embodiments [3] to [3-7], insulin produced using an MING cell is, for example, insulin having a molecular weight within a range of approximately 5,000 to 10,000.

[6B] In Embodiment 6B, in the manufacturing methods described in the embodiments [3] to [3-7], a bioactive substance produced using a bioactive substance-producing cell is a bioactive substance having a molecular weight within a range of, for example, for example, approximately 3,000 to approximately 1,000,000 Da, approximately 20,000 to approximately 1,000,000 Da, approximately 45,000 to approximately 1,000,000 Da, approximately 20,000 to approximately 400,000 Da, approximately 45,000 to approximately 400,000 Da, approximately 20,000 to approximately 200,000 Da or approximately 45,000 to approximately 200,000 Da.

[7] In Embodiment 7, an antibody that is obtained in the methods for manufacturing an antibody described in any one of the embodiments [3] to [3-7] is, for example, muromonab-CD3 produced using a muromonab-CD3-producing CHO cell, trastuzumab produced using a trastuzumab-producing CHO cell, rituximab produced using a rituximab-producing CHO cell, palivizumab produced using a palivizumab-producing CHO cell, infliximab produced using an infliximab-producing CHO cell, basiliximab produced using a basiliximab-producing CHO cell, tocilizumab produced using a tocilizumab-producing CHO cell, gemtuzumab produced using a gemtuzumab-producing CHO cell, bevacizumab produced using a bevacizumab-producing CHO cell, ibritumomab produced using an ibritumomab-producing CHO cell, adalimumab produced using an adalimumab-producing CHO cell, cetuximab produced using a cetuximab-producing CHO cell, ranibizumab produced using a ranibizumab-producing CHO cell, omalizumab produced using an omalizumab-producing CHO cell, eculizumab produced using an eculizumab-producing CHO cell, panitumumab produced using a panitumumab-producing CHO cell, ustekinumab produced using a ustekinumab-producing CHO cell, golimumab produced using a golimumab-producing CHO cell, canakinumab produced using a canakinumab-producing CHO cell, denosumab produced using a denosumab-producing CHO cell, mogamulizumab produced using a mogamulizumab-producing CHO cell, certolizumab produced using a certolizumab-producing CHO cell, ofatumumab produced using an ofatumumab-producing CHO cell, pertuzumab produced using a pertuzumab-producing CHO cell, brentuximab produced using a brentuximab-producing CHO cell, natalizumab produced using a natalizumab-producing CHO cell, nivolumab produced using a nivolumab-producing CHO cell, alemtuzumab produced using an alemtuzumab-producing CHO cell, secukinumab produced using a secukinumab-producing CHO cell, ramucirumab produced using a ramucirumab-producing CHO cell, ipilimumab produced using an ipilimumab-producing CHO cell, evolocumab produced using an evolocumab-producing CHO cell, mepolizumab produced using a mepolizumab-producing CHO cell, alirocumab produced using an alirocumab-producing CHO cell, ixekizumab produced using an ixekizumab-producing CHO cell, brodalumab produced using a brodalumab-producing CHO cell, idarucizumab produced using an idarucizumab-producing CHO cell, elotuzumab produced using an elotuzumab-producing CHO cell, pembrolizumab produced using a pembrolizumab-producing CHO cell, sarilumab produced using a sarilumab-producing CHO cell, bezlotoxumab produced using a bezlotoxumab-producing CHO cell, belimumab produced using a belimumab-producing CHO cell, daratumumab produced using a daratumumab-producing CHO cell, avelumab produced using an avelumab-producing CHO cell, dupilumab produced using a dupilumab-producing CHO cell, atezolizumab produced using an atezolizumab-producing CHO cell, benralizumab produced using a benralizumab-producing CHO cell, inotuzumab produced using an inotuzumab-producing CHO cell, emicizumab produced using an emicizumab-producing CHO cell, guselkumab produced using a guselkumab-producing CHO cell, durvalumab produced using a durvalumab-producing CHO cell, obinutuzumab produced using an obinutuzumab-producing CHO cell, a vedolizumab-producing CHO cell or an anti-GPVI antibody produced using an anti-GPVI antibody-producing CHO cell.

[7-1], In the method for manufacturing an antibody described in any one of the embodiments [3] to [3-7], a producible antibody is, for example, trastuzumab produced using a trastuzumab-producing CHO cell, rituximab produced using a rituximab-producing CHO cell, infliximab produced using an infliximab-producing CHO cell, tocilizumab produced using a tocilizumab-producing CHO cell, adalimumab produced using an adalimumab-producing CHO cell, nivolumab produced using a nivolumab-producing CHO cell or an anti-GPVI antibody produced using an anti-GPVI antibody-producing CHO cell; for example, tocilizumab produced using a tocilizumab-producing CHO cell or an anti-GPVI antibody produced using an anti-GPVI antibody-producing CHO cell.

[7B] In Embodiment 7B, the antibody that is obtained in the method for manufacturing an antibody described in the embodiments [3] to [3-7] is an antibody such as muromonab-CD3, trastuzumab, rituximab, palivizumab, infliximab, basiliximab, tocilizumab, bevacizumab, adalimumab, cetuximab, omalizumab, eculizumab, panitumumab, ustekinumab, golimumab, canakinumab, denosumab, ofatumumab, pertuzumab, natalizumab, nivolumab, alemtuzumab, secukinumab, ramucirumab, ipilimumab, evolocumab, mepolizumab, alirocumab, ixekizumab, brodalumab, elotuzumab, pembrolizumab, sarilumab, bezlotoxumab, belimumab, daratumumab, avelumab, dupilumab, atezolizumab, emicizumab, guselkumab, durvalumab, vedolizumab, romosozumab, risankizumab, necitumumab, ravulizumab, burosumab, isatuximab, tildrakizumab, satralizumab, galcanezumab, dinutuximab, fremanezumab, erenumab, casilibimab, imdevimab, aniflorumab, sotrovimab, ocrelizumab, naxitamab, aducanumab, tafacitamab, margetuximab, gantenerumab, tiragolumab, clovalimab, nemolizumab, katumasomab, pramotamab, falisimab, gemtuzumab, ibritumomab, brentuximab, inotuzumab, polatuzumab, enfortuzumab, sacituzumab, belantamab, roncastuximab, tisotumab, datopotab or patritumab; an antibody having an altered sugar chain such as mogamulizumab, benralizumab, obinutuzumab or inevirizumab; a low-molecular-weight antibody composed of an antibody fragment such as ranibizumab, idarucizumab, blinatumomab, brolucizumab, abciximab, capracizumab or certolizumab.

[7C] In Embodiment 7C, the antibody that is obtained in the method for manufacturing an antibody described in the embodiments [3] to [3-7] is an antibody that is produced from a CHO cell such as a muromonab-CD3-producing CHO cell, a trastuzumab-producing CHO cell, a rituximab-producing CHO cell, a palivizumab-producing NS0 cell, a palivizumab-producing CHO cell, an infliximab-producing Sp2/0 cell, an infliximab-producing CHO cell, a basiliximab-producing Sp2/0 cell, a basiliximab-producing CHO cell, a tocilizumab-producing CHO cell, a bevacizumab-producing CHO cell, an adalimumab-producing CHO cell, a cetuximab-producing Sp2/0 cell, a cetuximab-producing CHO cell, an omalizumab-producing CHO cell, an eculizumab-producing NS0 cell, an eculizumab-producing CHO cell, a panitumumab-producing CHO cell, a ustekinumab-producing Sp2/0 cell, a ustekinumab-producing CHO cell, a golimumab-producing Sp2/0 cell, a golimumab-producing CHO cell, a canakinumab-producing Sp2/0 cell, a canakinumab-producing CHO cell, a denosumab-producing CHO cell, an ofatumumab-producing NS0 cell, an ofatumumab-producing CHO cell, a pertuzumab-producing CHO cell, a natalizumab-producing NS0 cell, a natalizumab-producing CHO cell, a nivolumab-producing CHO cell, an alemtuzumab-producing CHO cell, a secukinumab-producing CHO cell, a ramucirumab-producing NS0 cell, a ramucirumab-producing CHO cell, an ipilimumab-producing CHO cell, an evolocumab-producing CHO cell, a mepolizumab-producing CHO cell, an alirocumab-producing CHO cell, an ixekizumab-producing CHO cell, a brodalumab-producing CHO cell, an elotuzumab-producing NS0 cell, an elotuzumab-producing CHO cell, a pembrolizumab-producing CHO cell, a sarilumab-producing CHO cell, a bezlotoxumab-producing CHO cell, a belimumab-producing NS0 cell, a belimumab-producing CHO cell, a daratumumab-producing CHO cell, an avelumab-producing CHO cell, a dupilumab-producing CHO cell, an atezolizumab-producing CHO cell, an emicizumab-producing CHO cell, a guselkumab-producing CHO cell, a durvalumab-producing CHO cell, a vedolizumab-producing CHO cell, a romosozumab-producing CHO cell, a risankizumab-producing CHO cell, a necitumumab-producing NS0 cell, a necitumumab-producing CHO cell, a ravulizumab-producing CHO cell, a burosumab-producing CHO cell, an isatuximab-producing CHO cell, a tildrakizumab-producing CHO cell, a satralizumab-producing CHO cell, a galcanezumab-producing CHO cell, a dinutuximab-producing Sp2/0 cell, a dinutuximab-producing CHO cell, a fremanezumab-producing CHO cell, an erenumab-producing CHO cell, a casilibimab-producing CHO cell, an imdevimab-producing CHO cell, an aniflorumab-producing NS0 cell, an aniflorumab-producing CHO cell, a sotrovimab-producing CHO cell, an ocrelizumab-producing CHO cell, a naxitamab-producing CHO cell, an aducanumab-producing CHO cell, a tafacitamab-producing CHO cell, a margetuximab-producing CHO cell, a gemtuzumab-producing NS0 cell, a gemtuzumab-producing CHO cell, an ibritumomab-producing CHO cell, a brentuximab-producing CHO cell, an inotuzumab-producing CHO cell, a polatuzumab-producing CHO cell, an enfortuzumab-producing CHO cell, a sacituzumab-producing Sp2/0 cell, a sacituzumab-producing CHO cell, a belantamab-producing CHO cell, a roncastuximab-producing CHO cell, a tisotumab-producing CHO cell, a mogamulizumab-producing CHO cell, a benralizumab-producing CHO cell, an obinutuzumab-producing CHO cell, an inevirizumab-producing CHO cell, a ranibizumab-producing CHO cell, an idarucizumab-producing CHO cell, a blinatumomab-producing CHO cell, a brolucizumab-producing CHO cell, an abciximab-producing CHO cell, a caplacizumab-producing CHO cell, a certolizumab-producing CHO cell or an anti-GPVI antibody-producing CHO cell.

[7C-1] The antibody that is obtained in the method for manufacturing an antibody described in the embodiments [3] to [3-7] is an antibody that is produced from a CHO cell such as a muromonab-CD3-producing CHO cell, a trastuzumab-producing CHO cell, a rituximab-producing CHO cell, a palivizumab-producing CHO cell, an infliximab-producing CHO cell, a basiliximab-producing CHO cell, a tocilizumab-producing CHO cell, a gemtuzumab-producing CHO cell, a bevacizumab-producing CHO cell, an ibritumomab-producing CHO cell, an adalimumab-producing CHO cell, a cetuximab-producing CHO cell, a ranibizumab-producing CHO cell, an omalizumab-producing CHO cell, an eculizumab-producing CHO cell, a panitumumab-producing CHO cell, a ustekinumab-producing CHO cell, a golimumab-producing CHO cell, a canakinumab-producing CHO cell, a denosumab-producing CHO cell, a mogamulizumab-producing CHO cell, a certolizumab-producing CHO cell, an ofatumumab-producing CHO cell, a pertuzumab-producing CHO cell, a brentuximab-producing CHO cell, a natalizumab-producing CHO cell, a nivolumab-producing CHO cell, an alemtuzumab-producing CHO cell, a secukinumab-producing CHO cell, a ramucirumab-producing CHO cell, an ipilimumab-producing CHO cell, an evolocumab-producing CHO cell, a mepolizumab-producing CHO cell, an alirocumab-producing CHO cell, an ixekizumab-producing CHO cell, a brodalumab-producing CHO cell, an idarucizumab-producing CHO cell, an elotuzumab-producing CHO cell, a pembrolizumab-producing CHO cell, a sarilumab-producing CHO cell, a bezlotoxumab-producing CHO cell, a belimumab-producing CHO cell, a daratumumab-producing CHO cell, an avelumab-producing CHO cell, a dupilumab-producing CHO cell, an atezolizumab-producing CHO cell, a benralizumab-producing CHO cell, an inotuzumab-producing CHO cell, an emicizumab-producing CHO cell, a guselkumab-producing CHO cell, a durvalumab-producing CHO cell, an obinutuzumab-producing CHO cell, a vedolizumab-producing CHO cell, a romosozumab-producing CHO cell, a risankizumab-producing CHO cell, a necitumumab-producing CHO cell, a ravulizumab-producing CHO cell, a burosumab-producing CHO cell, an isatuximab-producing CHO cell, a tildrakizumab-producing CHO cell, a satralizumab-producing CHO cell, a galcanezumab-producing CHO cell, a dinutuximab-producing CHO cell, a fremanezumab-producing CHO cell, an erenumab-producing CHO cell, a casilibimab-producing CHO cell, an imdevimab-producing CHO cell, an aniflorumab-producing CHO cell, a sotrovimab-producing CHO cell, an ocrelizumab-producing CHO cell, a naxitamab-producing CHO cell, an aducanumab-producing CHO cell, a tafacitamab-producing CHO cell, a margetuximab-producing CHO cell, a polatuzumab-producing CHO cell, an enfortuzumab-producing CHO cell, a sacituzumab-producing CHO cell, a belantamab-producing CHO cell, a roncastuximab-producing CHO cell, a tisotumab-producing CHO cell, an inevirizumab-producing CHO cell, a blinatumomab-producing CHO cell, a brolucizumab-producing CHO cell, an abciximab-producing CHO cell, a caplacizumab-producing CHO cell or an anti-GPVI antibody-producing CHO cell.

[7C-2] The antibody that is obtained in the method for manufacturing an antibody described in the embodiments [3] to [3-7] is an antibody that is produced from a CHO cell such as a trastuzumab-producing CHO cell, a rituximab-producing CHO cell, an infliximab-producing CHO cell, a tocilizumab-producing CHO cell, an adalimumab-producing CHO cell, a nivolumab-producing CHO cell or an anti-GPVI antibody-producing CHO cell; an antibody that is produced from a tocilizumab-producing CHO cell or an anti-GPVI antibody-producing CHO cell; an antibody that is produced from a tocilizumab-producing CHO cell.

Hereinafter, each embodiment will be described in more detail. The chemically modified alginic acid derivative represented by Formula (I) and the chemically modified alginic acid derivative represented by Formula (II) can be substituted by the chemically modified alginic acid derivative represented by Formula (I-A) and the chemically modified alginic acid derivative represented by Formula (II-A), respectively.

1. Alginic Acid

Alginic acid that serves as a synthetic raw material of the chemically modified alginic acid derivatives represented by Formula (I), Formula (I-A), Formula (II) and Formula (II-A), and alginic acid that serves as a raw material of the alginic acid solution or alginate gel that can be contained in the core layer in the present specification will be described below.

Alginic acid mentioned in the present specification means at least one alginic acid selected from the group consisting of alginic acid, alginate ester and salts thereof (for example, sodium alginate) (referred to as "alginic acids" in some cases). Alginic acid that is used may naturally occur or may be a synthetic product, but is preferably a naturally-occurring alginic acid. Alginic acids that are preferably used are polymers that are bioabsorbable polysaccharides that are extracted from brown algae such as lessonia, macrocystis, *laminaria*, ascophyllum, durvillia, kajime, arame and kelp and contain two kinds of linearly polymerized uronic acids, such as D-mannuronic acid (M) and L-guluronic acid (G). More specifically, the alginic acids are block copolymers in which a homopolymer block of D-mannuronic acid (MM fraction), a homopolymer block of L-guluronic acid (GG fraction) and a block in which D-mannuronic acid and L-guluronic acid are arranged (M/G fractions) arbitrarily bond to one another.

Alginic acid is one kind of natural polysaccharide that is manufactured by being extracted from brown algae seaweed and purified and is a polymer in which D-mannuronic acid (M) and L-guluronic acid (G) are polymerized. The configuration rate (M/G ratio) of D-mannuronic acid to L-guluronic acid in alginic acid, that is, the gel strength varies mainly with the kind of a creature from which alginic acid is derived such as seaweed, is also affected by the habitat of the creature or seasons, and covers a high range from a high G type where the M/G ratio is approximately 0.2 to a high M type where the M/G ratio is approximately 5. The physicochemical properties of alginic acid vary with the M/G ratio of alginic acid, how M and G are arranged and the like, and there are cases where preferable uses vary. The gelling power of alginic acids and the properties of produced gel are affected by the M/G ratio, and it is known that, ordinarily, the gel strength becomes high in a case where the G ratio is high. Additionally, the M/G ratio also affects the hardness, fragility, water absorption, flexibility and the like of the gel. Therefore, as alginic acid that is used in the present invention, it is preferable to use alginic acid having an appropriate M/G ratio or an appropriate viscosity depending on the final intended use.

As industrial methods for manufacturing alginic acid, there are an acid method, a calcium method and the like, and, in the present invention, alginic acid manufactured by any method can be used. The quantitative value of alginic acid by the HPLC method is made by purification to be preferably within a range of 80 to 120 mass %, more preferably within a range of 90 to 110 mass % and still more preferably within a range of 95 to 105 mass %. In the present invention, alginic acid having a quantitative value by the HPLC method within the above-described range will be referred to as high-purity alginic acid. Alginic acid or a salt thereof that is used in the present invention is preferably high-purity alginic acid. As a commercially available product, it is possible to purchase and use, for example, KIMICA ALGIN series made commercially available by KIMICA Corporation, preferably, high-purity food and pharmaceutical grade alginic acid. The commercially available product can also be used after being further purified as appropriate. For example, it is preferable to perform a low endotoxin treatment. As a purification method or a low endotoxin treatment method, it is possible to adopt, for example, a method described in Japanese Patent Application Publication No. 2007-75425. In the present specification, "mass %" means "w/w %" or "w/v %".

A salt of alginic acid in "alginic acid" that is used in the present invention is a "monovalent metal salt of alginic acid", which is a salt made by ion-exchanging a proton ion in carboxylic acid of D-mannuronic acid or L-guluronic acid in alginic acid with a monovalent metal ion such as Na+ or K+. Specific examples of the monovalent metal salt of alginic acid include sodium alginate, potassium alginate and the like, and sodium alginate is particularly preferable.

In the present specification, there will be cases where alginic acid is expressed as (ALG)-COOH wherein (ALG) indicates alginic acid and —COOH indicates one arbitrary carboxyl group of alginic acid.

As alginic acid that is used in the present invention, alginic acid having an appropriate weight-average molecular weight depending on the final intended use is used. The weight-average molecular weight (GPC) of alginic acid that is used in the present invention is, for example, 10,000 to 10,000,000; preferably 100,000 to 5,000,000; more preferably 150,000 to 3,000,000.

In several embodiments, alginic acid refers to sodium alginate. As the sodium alginate, it is possible to use commercially available sodium alginate. Here, sodium alginate that will be used in examples to be described below is selected from sodium alginates A-1, A-2, A-3, B-1, B-2 and B-3 shown in the following table (sales agency: MOCHIDA PHARMACEUTICAL CO., LTD.). The viscosity, weight-average molecular weight and M/G ratio of an aqueous solution of 1 w/w % of each sodium alginate are shown in the following table.

TABLE 8

| Sodium alginate | Viscosity of 1 w/w % (mPa · s) | Weight-average molecular weight GPC | Weight-average molecular weight GPC-MALS | M/G ratio |
|---|---|---|---|---|
| A-1 | 10 to 40 | 300,000 to 700,000 | 60,000 to 130,000 | 0.5 to 1.8 |
| A-2 | 50 to 150 | 700,000 to 1,400,000 | 130,000 to 200,000 | |
| A-3 | 300 to 600 | 1,400,000 to 2,000,000 to | 200,000 to 400,000 | |
| B-1 | 10 to 40 | 150,000 to 800,000 | 60,000 to 130,000 | 0.1 to 0.5 |
| B-2 | 70 to 150 | 800,000 to 1,500,000 | 130,000 to 200,000 | |
| B-3 | 400 to 600 | 1,500,000 to 2,500,000 | 200,000 to 350,000 | |

Individual physical property values of the sodium alginates A-1, A-2, A-3, B-1, B-2 and B-3 were measured by a variety of methods to be described below. The measurement methods are not limited to the following methods, and there are cases where individual physical property values may differ from the above-described values depending on the measurement method.

[Measurement of Viscosity of Sodium Alginate]

The viscosity was measured according to The Japanese Pharmacopoeia (16*th* edition) using a rotational viscometer method (cone-plate rotating viscometer). Specific measurement conditions are a described below. A sample solution was prepared with using Milli-Q water. As a measurement device, a cone-plate rotational viscometer (viscotester RheoStress 600 (Thermo HAAKE GmbH) sensor: 35/1) was used. The rotating speed was set to 1 rpm at the time of measuring the 1 w/w % sodium alginate solution. As the readout time, the average value from one minute after the beginning to two minutes when the measurement was performed for two minutes was used. The average value of three times of measurement was used as the measurement value. The measurement temperature was set to 20° C.

[Measurement of Weight-Average Molecular Weight of Sodium Alginate]

The weight-average molecular weight was measured by two kinds of measurement methods of (1) gel permeation chromatography (GPC) and (2) GPC-MALS. The measurement conditions are as described below.

[Pretreatment Method]

A solution obtained by adding an eluent to the sample, dissolving the sample and then filtering the sample with a 0.45 μm membrane filter was used as a measurement solution.

(1) Gel Permeation Chromatography (GPC) Measurement

[Measurement Conditions (Relative Molecular Weight Distribution Measurement)]

Column: TSKgel GMPW-XL×2+G2500PW-XL (7.8 mm I.D.×300 mm×three)

Eluent: 200 mM sodium nitrate aqueous solution

Flow rate: 1.0 mL/min

Concentration: 0.05%

Detector: RI detector

Column temperature: 40° C.

Injection amount: 200 μL

Molecular weight standard: Standard pullulan, glucose (2) GPC-MALS Measurement

[Refractive Index Increment (Dn/Dc) Measurement (Measurement Conditions)]

Differential refractometer: Optilab T-rEX

Measurement wavelength: 658 nm

Measurement temperature: 40° C.

Solvent: 200 mM sodium nitrate aqueous solution

Sample concentration: 0.5 to 2.5 mg/mL (five concentrations)

[Measurement Conditions (Absolute Molecular Weight Distribution Measurement)]

Column: TSKgel GMPW-XL×2+G2500PW-XL (7.8 mm I.D.×300 mm×three)

Eluent: 200 mM sodium nitrate aqueous solution

Flow rate: 1.0 mL/min

Concentration: 0.05%

Detector: RI detector, light scattering detector (MALS)

Column temperature: 40° C.

Injection amount: 200 μL

In the present specification, there will be cases where Da (Dalton) is added as the unit to the molecular weights of alginic acid, alginic acid derivatives, crosslinked alginic acid and crosslinked alginic acid.

The configuration rates (M/G ratio) of D-mannuronic acid to L-guluronic acid in alginic acids vary mainly with the kind of a creature from which alginic acid is derived such as seaweed, are also affected by the habitat of the creature or seasons, and cover a high range from a high G type where the M/G ratio is approximately 0.2 to a high M type where the M/G ratio is approximately 5. The gelling power of alginic acids and the properties of produced gel are affected by the M/G ratio, and it is known that, ordinarily, the gel strength becomes high in a case where the G ratio is high. Additionally, the M/G ratio also affects the hardness, fragility, water absorption, flexibility and the like of the gel. The M/G ratios of alginic acids that are used and salts thereof are normally 0.1 to 4.0, 0.1 to 3.0 in certain embodiments, 0.1 to 2.0 in certain embodiments, 0.5 to 1.8 in certain embodiments and 0.8 to 1.2 in certain embodiments. In addition, the M/G ratios are 0.1 to 0.5 in other embodiments.

In addition, as alginic acid that is used in the present invention, it is preferable to use alginic acid having an appropriate viscosity or an appropriate M/G ratio depending on the final intended use.

In the present specification, a numerical range expressed using "to" indicates a range comprising numerical values before and after "to" as the minimum value and the maximum value, respectively.

In the present specification, "alginate ester" and "alginate salt" that are used are not particularly limited, but need to have no functional group that impairs crosslinking reactions to be caused to react with a crosslinking agent. Examples of the alginate ester preferably include propylene glycol alginate and the like.

Alginic acid is capable of having, for example, a monovalent salt of alginic acid and a divalent salt of alginic acid. Examples of the monovalent salt of alginic acid include sodium alginate, potassium alginate, ammonium alginate and the like, sodium alginate or potassium alginate is preferable, and sodium alginate is more preferable. Examples of the divalent salt of alginic acid include calcium alginate, magnesium alginate, barium alginate, strontium alginate and the like.

Alginic acid is a high-molecular-weight polysaccharide, it is difficult to accurately determine the molecular weight; however, ordinarily, the weight-average molecular weight is 1,000 to 10,000,000, preferably 10,000 to 8,000,000 and more preferably 20,000 to 3,000,000. It is known that, in the measurement of the molecular weights of naturally-occurring high-molecular-weight substances, values may differ depending on measurement methods.

In the case of specifying the molecular weight of the alginic acid derivative or alginic acid of the present invention or a salt thereof in the present specification, unless particularly otherwise described, the molecular weight is the weight-average molecular weight that is calculated by size exclusion chromatography (SEC). As alginic acid or a salt thereof that is used in the present invention, it is desirable to use alginic acid or salt thereof having an appropriate molecular weight distribution depending on the final intended use.

For example, depending on the measurement conditions of gel permeation chromatography (GPC) or gel filtration chromatography (both are also collectively referred to as size exclusion chromatography (SEC)) to be described in the following examples, the molecular weight is preferably 100,000 to 5,000,000 and more preferably 150,000 to 3,000,000. In addition, in certain embodiments, the molecular weight is preferably 500,000 to 3,000,000, more preferably 1,000,000 to 2,500,000 and still more preferably 1,000,000 to 2,000,000.

In addition, according to, for example, the GPC-MALS (SEC-MALS) method, it is possible to measure the absolute weight-average molecular weight. The weight-average molecular weight (absolute weight-average molecular weight) measured by the GPC-MALS method is preferably 10,000 or more, more preferably 50,000 or more and still more preferably 60,000 or more and is preferably 1,000,000 or less, more preferably 800,000 or less, still more preferably 700,000 or less and especially preferably 500,000 or less. A preferable range thereof is 10,000 to 1,000,000, more preferably 50,000 to 800,000 and still more preferably 60,000 to 500,000.

Normally, in the case of calculating the molecular weights of high-molecular-weight polysaccharides by a method in which the above-described SEC or SEC-MALS is used, a measurement error of approximately 10% to approximately 30% may be caused. For example, the fluctuation of the value may be caused within a range of 350,000 to 650,000 when the molecular weight is 500,000 and within a range of 700,000 to 1,300,000 when the molecular weight is 1,000,000. In the present specification, in a case where the molecular weight is expressed with "approximately" in the measurement, the temperature may include up to the numerical value ±10% and up to the numerical value±20% in certain embodiments.

Here, ordinarily, naturally-occurring high-molecular-weight substances are aggregates of molecules having a variety of molecular weights, not a single molecular weight, and are thus measured to have a molecular weight distribution with a certain constant width. A typical measurement method is gel filtration chromatography. Examples of typical information of a molecular weight distribution that is obtained by gel filtration chromatography include the weight-average molecular weight (Mw), the number-average molecular weight (Mn) and the dispersion ratio (Mw/Mn).

The weight-average molecular weight is a property where contribution of high-molecular-weight substances having a large molecular weight to the average molecular weight is emphasized and is represented by the following formula.

$$Mw=\Sigma(WiMi)/W=\Sigma(HiMi)/\Sigma(Hi)$$

The number-average molecular weight is calculated by dividing the total weight of high-molecular-weight substances by the total number of the high-molecular-weight substances.

$$Mn=W/\Sigma Ni=\Sigma(MiNi)/\Sigma Ni=\Sigma(Hi)/\Sigma(Hi/Mi)$$

Here, W is the total weight of the high-molecular-weight substances, Wi is the weight of the $i^{th}$ high-molecular-weight substance, Mi is the molecular weight in the $i^{th}$ elution time, Ni is the number of the molecular weights Mi and Hi is the height at the $i^{th}$ elution time.

It is known that, in the measurement of the molecular weights of naturally-occurring high-molecular-weight substances, values may differ depending on measurement methods (examples of hyaluronic acid: Chikako Yomota et. al. Bull. Natl. Health Sci., Vol. 117, pp. 135 to 139 (1999) and Chikako Yomota et. al. Bull. Natl. Inst. Health Sci., Vol. 121, pp. 30 to 33 (2003)). Regarding the measurement of the molecular weight of alginic acid, there is a publication where a method for calculating the molecular weight from the intrinsic viscosity and a method for calculating the molecular weight by SEC-MALLS (size exclusion chromatography with multiple angle laser light scattering detection) are described (ASTM F2064-00 (2006), published by ASTM International). In the present invention, as the weight-average molecular weight, it is possible to use a value calculated from a calibration curve obtained by measuring the molecular weights by such a normal method as described in the above-described publication, for example, size exclusion chromatography (SEC), and using pullulan as a standard substance.

In addition, in the present invention, as the weight-average molecular weight, it is possible to use an absolute molecular weight measured by such a normal method as described in the above-described publication, for example, size exclusion chromatography (SEC)-MALS.

Measurement of the molecular weights of alginic acids can be measured according to the normal methods.

In the case of specifying the molecular weight of alginic acid or a salt thereof in the present specification, unless particularly otherwise described, the molecular weight is the weight-average molecular weight that is calculated by gel filtration chromatography. As typical conditions in the case of using gel filtration chromatography in the measurement of the molecular weight, it is possible to adopt conditions in the present examples to be described below. As a column, for example, a Superose 6 Increase 10/300 GL column (GE Healthcare Corporation) can be used, as a developing solvent, for example, a 10 mmol/L phosphate buffer solution containing 0.15 mol/L of NaCl (pH: 7.4) can be used, and, as molecular weight standards, blue dextran, thyroglobulin, ferritin, aldolase, conalbumin, ovalbumin, ribonuclease A and aprotinin can be used.

The viscosity of alginic acid that is used in the present specification is not particularly limited, but is preferably 10 mPa s to 1000 mPa s and more preferably 50 mPa s to 800 mPa s in the case of measuring the viscosity as an aqueous solution of 1 w/w % alginic acids.

Measurement of the viscosity of an aqueous solution of alginic acid can be measured according to a normal method. For example, the viscosity can be measured using a coaxial double cylinder rotational viscometer, a single cylinder rotational viscometer (Brookfield viscometer), a cone-plate rotational viscometer (cone plate viscometer) or the like of the rotational viscometer method. Preferably, the viscosity measurement method in The Japanese Pharmacopoeia ($16^{th}$ edition) is desirably followed. More preferably, a cone-plate viscometer is used.

Immediately after being extracted from brown algae, alginic acids have a large molecular weight and a high viscosity, but the molecular weight becomes small, and the viscosity becomes low in the process of drying by heat, purification or the like. Alginic acids having different molecular weights can be manufactured by a method such as the management of conditions such as the temperature in the manufacturing process, selection of brown algae, which serves as a raw material, or the fractionation of the molecular weight in the manufacturing steps. Furthermore, it is also possible to produce alginic acids having intended molecular weights by mixing alginic acids with a different lot of alginic acids having different molecular weights or viscosities.

Alginic acid that is used in the present specification is alginic acid on which a low endotoxin treatment has not been performed in several embodiments or alginic acid on which a low endotoxin treatment has been performed in several different embodiments. A low endotoxin refers to the fact that the endotoxin level is so low that, substantially, inflammation or fever is not caused. More preferably, alginic acid on which a low endotoxin treatment has been performed is desirable.

The low endotoxin treatment can be performed by a well-known method or an equivalent method thereto. For example, the low endotoxin treatment can be performed by Suga et al.'s method in which sodium hyaluronate is purified (for example, refer to Japanese Patent Application Publication No. H09-324001 or the like), Yoshida et al.'s method in which β1,3-glucan is purified (for example, refer to Japanese Patent Application Publication No. H08-269102 or the like), William et al.'s method in which a biopolymer salt such as alginate or gellan gum is purified (for example, refer to Japanese Translation of PCT Application No. 2002-530440 or the like), James et al.'s method in which polysaccharide is purified (for example, refer to WO 93/13136 or the like), Lewis et al.'s method (for example, refer to the specification of U.S. Pat. No. 5,589,591 or the like), Herman Frank et al.s' method in which alginate is purified (for example, refer to Appl Microbiol Biotechnol (1994) 40: 638 to 643 or the like) or the like or an equivalent method thereto. The low endotoxin treatment is not limited thereto and can be performed by a well-known method such as washing, filtration with a filter (an endotoxin removal filter, a charged filter or the like), ultrafiltration, purification using a column (an endotoxin adsorption affinity column, a gel filtration column, an ion exchange resin column or the like), adsorption into a hydrophobic substance, resin, activated carbon or the like, an organic solvent treatment (extrusion with an organic solvent, precipitation and sedimentation by addition of an organic solvent or the like), a surfactant treatment (for example, refer to Japanese Patent Application Publication No. 2005-036036 or the like) or an appropriate combination thereof. A well-known method such as centrifugation may be appropriately combined with a step of these treatments. It is desirable to select the method as appropriate in accordance with the kind of alginic acid.

The endotoxin level can be confirmed by a well-known method and can be measured by, for example, a method in which a limulus reagent (LAL) is used, a method in which an ENDOSPECY (registered trademark) ES-24S set (SEIKAGAKU CORPORATION) is used or the like.

A method for treating the endotoxin that is used is not particularly limited, and, as a result, in the case of performing endotoxin measurement with a limulus reagent (LAL), the endotoxin content in alginic acids is preferably 500 endotoxin units (EU)/g or less, more preferably 100 EU/g or less, especially preferably 50 EU/g or less and particularly preferably 30 EU/g or less. In the present invention, "substantially containing no endotoxin" means that the endotoxin value measured by an endotoxin test in The Japanese pharmacopoeia is within the above-described numerical range. Sodium alginate on which the low endotoxin treatment has been performed can be procured from, for example, commercially available products such as Sea Matrix (registered trademark) (MOCHIDA PHARMACEUTICAL CO., LTD.) and PRONOVA™ UP LUG (FMC BioPolymer).

In several different embodiments, sodium alginate that serves as the synthetic raw material of the chemically modified alginic acid derivatives represented by Formula (I), Formula (I-A), Formula (II) and Formula (II-A) and sodium alginate that serves as the raw material of the alginic acid solution or the alginate gel that can be contained in the core layer in the present specification are not particularly limited and, for example, can be selected from sodium alginate A-1, A-2, A-3, B-1, B-2 or B-3 shown in Table 8.

In the present specification, the concentration of the alginic acid solution prepared using the sodium alginate (also referred to as the sodium alginate solution) is, for example, within a range of approximately 0.1 to approximately 3.3 wt %.

In the present specification, sodium alginate that serves as the synthetic raw material of the chemically modified alginic acid derivatives represented by Formula (I), Formula (I-A), Formula (II) and Formula (II-A) is preferably A-2, A-3, B-2 or B-3 shown in Table 8 and more preferably A-2 or A-3. In addition, the concentration of the sodium alginate solution that is used to synthesize the chemically modified alginic acid derivatives represented by Formula (I), Formula (I-A), Formula (II) and Formula (II-A) is preferably within a range of 1.5 to 2.0 wt %.

In the present specification, sodium alginate that is used to prepare the alginic acid solution that can be contained in the core layers of the polymer-coated crosslinked alginate gel fiber or the alginic acid solution that is used to form the alginate gel is preferably A-2, A-3, B-2 or B-3 shown in Table 8, more preferably A-2 or A-3 and still more preferably A-3. In addition, the concentration of the alginic acid solution prepared using the sodium alginate is preferably within a range of approximately 0.3 to approximately 1.5 wt %.

In the present specification, the alginic acid solution means a solution obtained by dissolving alginic acid in a solvent. The solvent is not particularly limited, and examples thereof include a culture medium, a cell culture medium, a culture fluid, an isotonic buffer solution, water, phosphate buffered saline (PBS), physiological saline and the like. A solution obtained by dissolving sodium alginate in the solvent is referred to as the sodium alginate solution.

In several embodiments, the solutions of the chemically modified alginic acid derivatives represented by Formula (I), Formula (I-A), Formula (II) and Formula (II-A), which are used to form the core layers of the polymer-coated crosslinked alginate gel fiber, and the alginic acid solution are not particularly limited, and it is also possible to mix a collagen solution, a culture medium, a culture fluid or the like. The solvent that is used to prepare the solution of the chemically modified alginic acid derivative represented by Formula (I), Formula (I-A), Formula (II) and Formula (II-A) and the alginic acid solution is as described below.

2. Chemically Modified Alginic Acid Derivative

In several embodiments, the chemically modified alginic acid derivatives in the present specification are derivatives in which a reactive group in a Huisgen reaction to be described below or a complementary reactive group of the above-described reactive group has been introduced into one or more arbitrary carboxyl groups of alginic acid through an amide bond and a divalent linker. More specifically, the chemically modified alginic acid derivatives are an alginic acid derivative represented by Formula (I) below:

[C33]

(I)

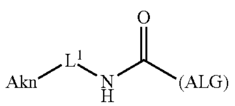

[in Formula (I), the definitions of (ALG), Akn-$L^1$- and —NH—CO— are the same as the definitions in Embodiment 1] and an alginic acid derivative represented by Formula (II) below:

[C34]

(II)

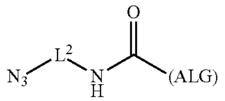

[in Formula (II), the definitions of (ALG), -$L^2$- and —NH—CO— are the same as the definitions in Embodiment 1].

The divalent linker (-$L^1$- or -$L^2$-) to be used can be selected from, specifically, the divalent linkers described in the above-described embodiments.

More specifically, the chemically modified alginic acid derivatives are an alginic acid derivative represented by Formula (I-A) below:

[C35]

(I-A)

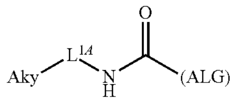

[in Formula (I-A), the definitions of (ALG), Aky-$L^{1A}$- and —NH—CO— are the same as the definitions in the embodiment 1X] and an alginic acid derivative represented by Formula (II-A) below:

[C36]

(II-A)

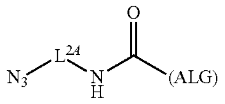

[in Formula (II-A), the definitions of (ALG), -$L^{2A}$- and —NH—CO— are the same as the definitions in the embodiment 1X].

The divalent linker (-$L^{1A}$- or -$L^{2A}$-) to be used can be selected from, specifically, the divalent linkers described in the embodiment [1X].

In the present specification, unless particularly otherwise described, examples of "halogen atom" include a fluorine atom, a chlorine atom, a bromine atom, an iodine atom or the like.

In the present specification, unless particularly otherwise described, examples of "$C_{1-3}$ alkyl group" include a methyl group, an ethyl group, a propyl group and an isopropyl group.

In the present specification, unless particularly otherwise described, "$C_{2-4}$ alkanoyl group" means "$C_{1-3}$ alkylcarbonyl group" in which a carbonyl group bonds to the "$C_{1-3}$ alkyl group", and examples thereof include an acetyl group, a propionyl group, a butyryl group or the like.

In the present specification, unless particularly otherwise described, examples of "$C_{3-8}$ cycloalkyl ring" include monocyclic or polycyclic saturated or unsaturated cycloalkyl rings having 3 to 8 carbon atoms, and examples thereof include a cyclopropane ring, a cyclobutene ring, a cyclopentane ring, a cyclohexane ring, a cycloheptane ring, a cyclooctane ring or the like.

In the present specification, unless particularly otherwise described, examples of "$C_{5-9}$ cycloalkene ring" include monocyclic cycloalkene rings having 5 to 9 carbon atoms, and examples thereof include a cyclopentene ring, a cyclohexene ring, a cycloheptene ring, a cyclooctene ring, a cyclononane ring or the like.

In the present specification, unless particularly otherwise described, "five or six-membered aromatic heterocycle" means a five or six-membered aromatic unsaturated ring containing one to four hetero atoms selected from the group consisting of a nitrogen atom, a sulfur atom and an oxygen atom.

In the present specification, unless particularly otherwise described, examples of the "five or six-membered aromatic heterocycles" include a pyrrole group, a furan group, a thiophene group, an imidazole group, a pyrazole group, an oxazole group, an isoxazole group, a thiazole group, an isothiazole group, a triazole group, an oxadiazole group, a furazane group, a thiadiazole group, a tetrazole group, a pyridine group, a pyridazine group, a pyrimidine group, a pyrazine group, a triazine group, a thiadiazine group or the like.

In the present specification, unless particularly otherwise described, "five or six-membered non-aromatic heterocycle" means a five or six-membered saturated ring containing one to four hetero atoms selected from the group consisting of an oxygen atom, a sulfur atom and a nitrogen atom.

In the present specification, unless particularly otherwise described, examples of the "five or six-membered non-aromatic heterocycles" include a pyrrolidine group, a tetrahydrofuran group, a thiolane group, a piperidine group, a dihydropyran group, a tetrahydropyran group, a tetrahydrothiopyran group, a piperazine group, a dioxane group, a morpholine group, a thiomorpholine group, a quinuclidine group or the like.

In the present specification, unless particularly otherwise described, "cyclic alkyne group" means "five to nine-membered cycloalkyne group" and also includes cycloalkyne groups in which —$CH_2$— in "five to nine-membered cycloalkyne group" are substituted by one to four groups selected from the group consisting of —NH—, —S—, —O— or =C(=O). In the cyclic alkyne group, hydrogen atoms in —$CH_2$— on the ring may be substituted by one to five groups selected from a halogen atom, a hydroxyl group, an amino group, a keto group, a $C_{1-3}$ alkyl group, a —O—$C_{1-3}$ alkyl group, a —NH($C_{1-3}$ alkyl group), —N($C_{1-3}$ alkyl group)$_2$ or —COO-M (M=Na, K, ½Ca, a hydrogen atom or a $C_{1-3}$ alkyl group) or the like; in addition, one to three rings selected from a $C_{3-8}$ cycloalkyl ring, a benzene ring and a five or six-membered aromatic heterocycle may condense in the cycloalkyne group.

In the present specification, unless particularly otherwise described, "five to nine-membered cycloalkyne group" means a group in which —$CH_2$—$CH_2$— of a monocyclic saturated cycloalkyl group having 5 to 9 carbon atoms has been substituted by and examples thereof include a cyclopentyne group, a cyclohexyne group, a cycloheptyne group, a cyclooctyne group, a cyclononyne group or the like. In addition, —$CH_2$— in "five to nine-membered cycloalkyne group" can also be substituted by one to four groups selected from the group consisting of —NH—, —S—, —O— or =C(=O).

In the present specification, unless particularly otherwise described, the cyclic alkyne group is preferably a seven to nine-membered cyclic alkyne group (a cycloalkyne group in which —$CH_2$— in a seven to nine-membered cycloalkyne group are substituted by one to four groups selected from the group consisting of —NH—, —S—, —O— or =C(=O)); hydrogen atoms in —$CH_2$— on the ring of a seven to nine-membered cyclic alkyne group may be substituted by one to five groups selected from groups such as a halogen atom, a hydroxyl group, an amino group, a keto group, a $C_{1-3}$ alkyl group, a —O—$C_{1-3}$ alkyl group, a —NH($C_{1-3}$ alkyl group), —N($C_{1-3}$ alkyl group)$_2$ and —COO-M (M=Na, K, ½Ca, a hydrogen atom or a $C_{1-3}$ alkyl group); in addition, one to three rings selected from a $C_{3-8}$ cycloalkyl ring, a benzene ring and a five or six-membered aromatic heterocycle may condense in the seven to nine-membered cyclic alkyne group);

more preferably a cyclooctyne group (a cycloalkyne group in which —$CH_2$— in a cyclooctyne group are substituted by one to four groups selected from the group consisting of —NH—, —S—, —O— or =C(=O)); hydrogen atoms in —$CH_2$— on the ring of the cyclooctyne group may be substituted by one to five groups selected from groups such as a halogen atom, a hydroxyl group, an amino group, a keto group, a $C_{1-3}$ alkyl group, a —O—$C_{1-3}$ alkyl group, a —NH($C_{1-3}$ alkyl group), —N($C_{1-3}$ alkyl group)$_2$ and —COO-M (M=Na, K, ½Ca, a hydrogen atom or a $C_{1-3}$ alkyl group); in addition, one to three rings selected from a $C_{3-8}$ cycloalkyl ring, a benzene ring and a five or six-membered aromatic heterocycle may condense in the cyclooctyne group);

still more preferably a group selected from the following partial structural formulae:

[C37]

(Aky-1)

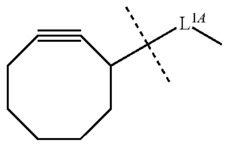

(Aky-2)

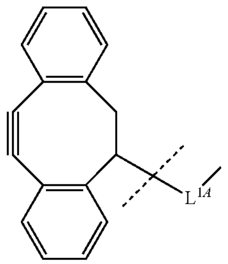

(Aky-3)

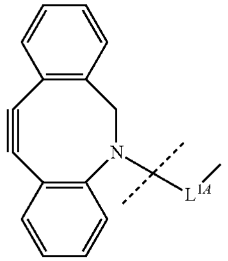

-continued (Aky-4)

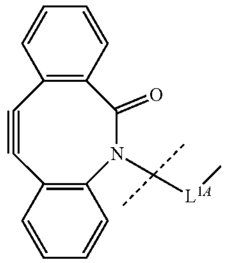

(Aky-5)

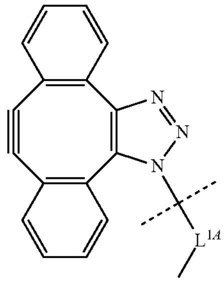

(Aky-6)

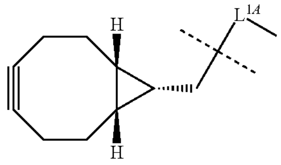

(Aky-7)

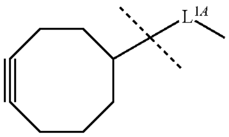

(Aky-8)

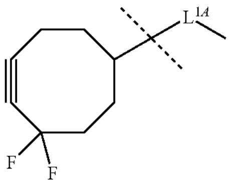

(Aky-9)

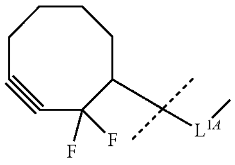

(Aky-10)

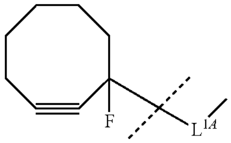

(Aky-11)

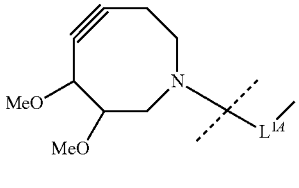

-continued (Aky-12)

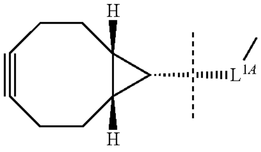

[in the formulae, the right sides of the cutting lines at both ends are not included];

particularly preferably a group selected from the following partial structural formulae:

[C38]

(Aky-1)

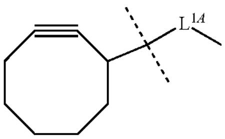

(Aky-2)

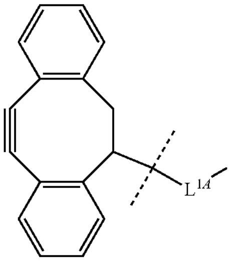

(Aky-3)

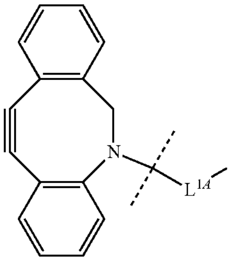

(Aky-4)

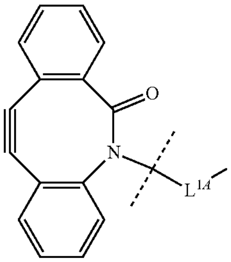

(Aky-6)

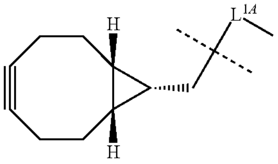

[in the formulae, the right sides of the cutting lines at both ends are not included];

most preferably a group selected from the following partial structural formulae:

[C39]

(Aky-1)

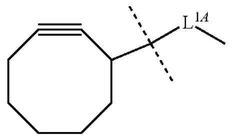

(Aky-3)

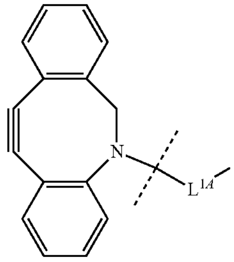

[in the formulae, the right sides of the cutting lines at both ends are not included].

In several embodiments, as the divalent linker ($-L^1-$ or $-L^2-$) in the present specification, it is also possible to use an arbitrary linker as long as the reaction with a cyclic alkyne group (Akn-) and an azide group (Huisgen reaction) is not impaired. Specific examples thereof include linear alkylene groups ($-(CH_2)_n-$, n=1 to 30) [a plurality of (for example, one to 10 or one to five) $-CH_2-$'s in the group may be substituted by groups such as —C(=O)—, —CONH—, —O—, —NH—, —S—, a cycloalkyl ring having 3 to 8 carbon atoms, a benzene ring, a heterocycle (a five or six-membered aromatic heterocycle or a five or six-membered non-aromatic heterocycle such as a pyridine ring, a piperidine ring or a piperazine ring); a plurality of (for example, one to 10 or one to five) hydrogen atoms in the linear alkylene group ($-CH_2-$) may be substituted by groups selected from groups of an oxo group (=O), $C_{1-6}$ alkyl groups (for example, groups such as a methyl group, an ethyl group, an n-propyl group and an iso-propyl group), halogen atoms (for example, a fluorine atom, a chlorine atom, a bromine atom, an iodine atom and the like), a hydroxyl group (—OH) and the like], but the divalent linker is not limited thereto.

In the —NH—CO— group of the chemically modified alginic acid derivative represented by Formula (I), Formula (I-A), Formula (II) or Formula (II-A), it is possible to substitute the hydrogen atom in the imino group (—NH—) into a methyl group to produce a —N(Me)-CO— group.

The bonding form between the linkers ($-L^1-$ and $-L^2-$) and alginic acid in the chemically modified alginic acid derivative represented by Formula (I) or Formula (II) is a —NH—CO— bond or a —N(Me)-CO— bond; preferably a —NH—CO— bond. —CO— in the —NH—CO— bond or the —N(Me)-CO— bond is derived from a carboxyl group of alginic acid.

The bonding form between the linkers ($-L^{1A}-$ and $-L^{2A}-$) and alginic acid in the chemically modified alginic acid derivative represented by Formula (I-A) or Formula (II-A) is a —NH—CO— bond or a —N(Me)-CO— bond; preferably a —NH—CO— bond. —CO— in the —NH—CO— bond or the —N(Me)-CO— bond is derived from a carboxyl group of alginic acid.

In the present specification, the chemically modified alginic acid derivative represented by Formula (I), Formula (I-A), Formula (II) or Formula (II-A) can be manufactured by, for example, a method for synthesizing a chemically modified alginic acid derivative to be described below.

The weight-average molecular weight measured by gel filtration chromatography of the chemically modified alginic acid derivative represented by Formula (I) or Formula I-A) in the present specification is within a range of approximately 100,000 Da to approximately 3,000,000 Da; preferably within a range of approximately 300,000 Da to approximately 2,500,000 Da; more preferably within a range of approximately 500,000 Da to approximately 2,000,000 Da. In addition, the weight-average molecular weight measured by gel filtration chromatography of the chemically modified alginic acid derivative represented by Formula (II) or Formula (II-A) is within a range of approximately 100,000 Da to approximately 3,000,000 Da; preferably within a range of approximately 300,000 Da to approximately 2,500,000 Da; more preferably within a range of approximately 500,000 Da to approximately 2,000,000 Da.

In the present specification, the Akn-$L^1$-NH— group in Formula (I) does not need to bond to all carboxyl groups in the alginic acid configuration unit, and the $N_3$-$L^2$-NH— group in Formula (II) does not need to bond to all carboxyl groups in the alginic acid configuration unit.

In the present specification, the Aky-$L^1$-NH— group in Formula (I-A) does not need to bond to all carboxyl groups in the alginic acid configuration unit, and the $N_3$-$L^{2A}$-NH— group in Formula (II-A) does not need to bond to all carboxyl groups in the alginic acid configuration unit.

In the present specification, in a case where the Akn-$L^1$-NH— group in Formula (I) is referred to as the reactive group, the $N_3$-$L^2$-NH— group in Formula (II) becomes the complementary reactive group. In addition, conversely, in a case where the $N_3$-$L^2$-NH— group in Formula (II) is referred to as the reactive group, the Akn-$L^1$-NH— group in Formula (I) becomes the complementary reactive group.

In the present specification, in a case where the Aky-$L^1$-NH— group in Formula (I-A) is referred to as the reactive group, the $N_3$-$L^{2A}$-NH— group in Formula (II-A) becomes the complementary reactive group. In addition, conversely, in a case where the $N_3$-$L^{2A}$-NH— group in Formula (II-A) is referred to as the reactive group, the Aky-$L^1$-NH— group in Formula (I-A) becomes the complementary reactive group.

In the present specification, the introduction rate of the reactive group into the chemically modified alginic acid derivative represented by Formula (I) or Formula (I-A) is, for example, within a range of approximately 0.1 to approximately 30 mol %; preferably within a range of approximately 0.3 to approximately 20 mol %; more preferably within a range of approximately 0.5 to approximately 10 mol %. In addition, the introduction rate of the reactive group into the chemically modified alginic acid derivative represented by Formula (II) or Formula (II-A) is, for example, within a range of approximately 0.1 to approximately 30 mol %; preferably within a range of approximately 0.3 to approximately 20 mol %; more preferably within a range of approximately 0.5 to approximately 15 mol %.

The introduction rate of the reactive group or the complementary reactive group is a value expressing, in percentage, the number of uronic acid monosaccharide units into which each reactive group has been introduced in uronic acid monosaccharide units, which are the repeating units of alginic acid. The introduction rate of the reactive group or the complementary reactive group can be obtained by a method described below in the examples to be described below.

In the present specification, the cyclic alkyne group (Akn) in Formula (I) and the azide group in Formula (II) form a triazole ring by the Huisgen reaction, whereby a crosslink is formed.

In the present specification, the cyclic alkyne group (Aky) in Formula (I-A) and the azide group in Formula (II-A) form a triazole ring by the Huisgen reaction, whereby a crosslink is formed.

In the present specification, the chemically modified alginic acid derivatives represented by Formula (I), Formula (I-A), Formula (II) or Formula (II-A) include a chemically modified alginic acid derivative in which a monovalent salt (for example, a sodium salt or the like) is formed in an arbitrary carboxyl group in the molecule.

3. Huisgen Reaction

The Huisgen reaction (1,3-dipolar cycloaddition) is a condensation reaction between compounds having a terminal azide group and a terminal alkyne group as shown in the following formula. As a result of the reaction, a disubstituted 1,2,3-triazole ring can be obtained with an efficient yield, and a surplus by-product is not generated, which is a characteristic. It is conceivable that a 1,4- or 1,5-disubstituted triazole ring can be generated by the reaction, and it is possible to obtain a triazole ring regioselectively using a copper catalyst (Cu catalyst).

[C40]

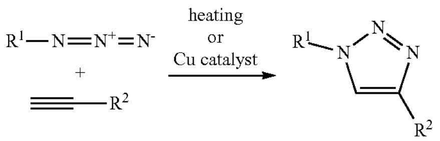

In addition, the Huisgen reaction where no copper catalyst is used has been reported by Wittig and Krebs. That is, the Huisgen reaction is a reaction where a cycloadduct can be obtained simply by mixing cyclooctyne and phenyl azide (in the following formula, $R^3$ is phenyl). In the present reaction, since the triple bond of cyclooctyne is significantly strained, elimination of the strain by a reaction with phenyl azide becomes a driving force, and the reaction progresses spontaneously, whereby no catalysts are required.

[C41]

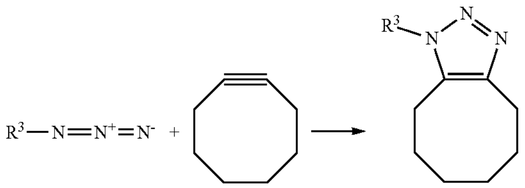

As described above, in the Huisgen reaction, it is possible to use an azide compound having a substituted primary azide, secondary azide, tertiary azide, aromatic azide or the like and a compound having a terminal or cyclic alkyne group that is a complementary reactive group of the azide group. In addition, in the Huisgen reaction, since almost only the azide group and the alkyne group react, it is possible to substitute a variety of functional groups (for example, an ester group, a carboxyl group, an alkenyl group, a hydroxyl group, an amino group and the like) into the reaction substrate.

In several embodiments, in order to easily and efficiently form a crosslink by a 1,2,3-triazole ring between alginic acid molecules within a short period of time without generating an undesirable by-product and using a copper catalyst to avoid cytotoxicity attributed to the copper catalyst, as the alkyne group in the Huisgen reaction, for example, the cyclic alkyne group (cyclooctyne group) described in the embodiment [1] is used.

In a preferable embodiment of a method for crosslinking the chemically modified alginic acid derivative, in the Huisgen reaction, an undesirable side reaction does not occur, and a by-product is almost not formed. Therefore, it becomes possible to incorporate a cell enabling production of antibodies, bioactive substances or the like into the core layer of the polymer-coated crosslinked alginate gel fiber of the present invention.

4. Method for Manufacturing Chemically Modified Alginic Acid Derivative

In the present specification, the chemically modified alginic acid derivative represented by Formula (I) or Formula (II) can be manufactured by a condensation reaction between an amine represented by Formula (AM-1) (Akn-$L^1$-$NH_2$: Akn-$L^1$- is the same as the definition in the embodiment [1]) or an amine represented by Formula (AM-2) ($N_3$-$L^2$-$NH_2$: -$L^2$- is the same as the definition in the embodiment [1]) and an arbitrary carboxyl group of alginic acid using an arbitrary condensing agent as shown in the following reaction formula. Detailed conditions for each reaction follow conditions described in WO 2019/240219.

[C42]

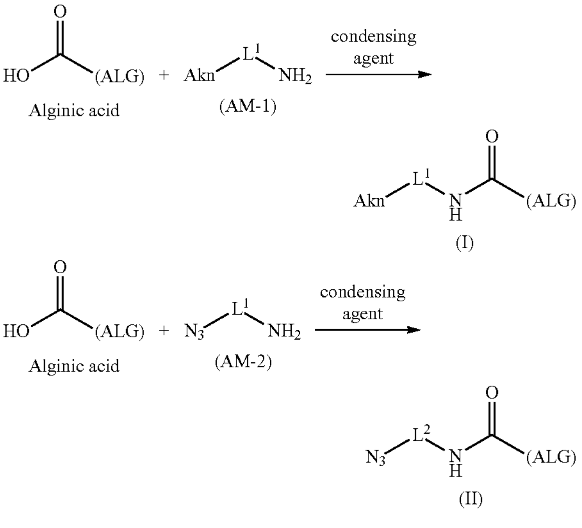

Alginic acid
(AM-1)
(I)
Alginic acid
(AM-2)
(II)

In the above-described method for manufacturing the chemically modified alginic acid derivative represented by Formula (I) or Formula (II), the introduction rate of the amine represented by Formula (AM-1) or Formula (AM-2) (which becomes the same meaning as the introduction rate of the reactive group into the chemically modified alginic acid derivative represented by Formula (I) or Formula (II) in the above-described embodiments) can be adjusted by appropriately selecting and combining reaction conditions of the following (i) to (v) and the like in consideration of the properties and the like of the amine. (i) An increase or decrease in the equivalent of the condensing agent, (ii) an increase or decrease in the reaction temperature, (iii) the extension or shortening of the reaction time, (iv) the adjustment of the concentration of alginic acid in the reaction substrate, (v) the addition of an organic solvent that is mixed with water to increase the solubility of the amine of Formula (AM-1) or Formula (AM-2) and the like.

In addition, in the condensation reaction, when the amines represented by Formula (AM-1) and Formula (AM-2) are substituted by the amines represented by Formula (AM-1A) and Formula (AM-2A), respectively, and the condensation reaction is performed in the same manner, it is possible to manufacture the chemically modified alginic acid derivative represented by Formula (I-A) or Formula (II-A). In each reaction formula, Aky-$L^{1A}$- in Aky-$L^{1A}$-$NH_2$ is the same as the definition in the embodiment [1X], and -$L^{2A}$- in $N_3$-$L^{2A}$-$NH_2$ is the same as the definition in the embodiment [1X].

[C43]

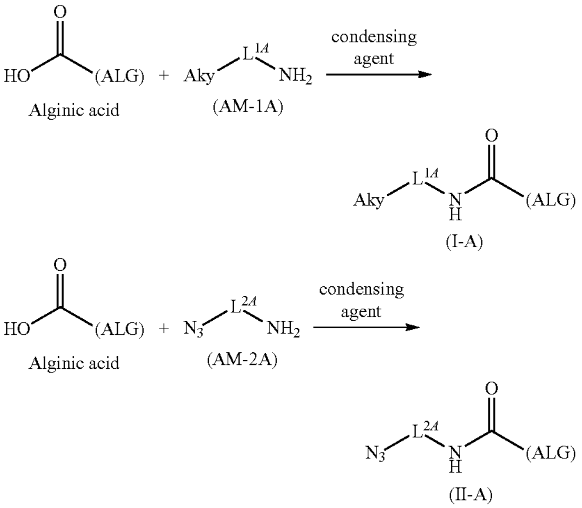

Alginic acid (AM-1A) (I-A)

Alginic acid (AM-2A) (II-A)

Hereinafter, a method for manufacturing, among the amines represented by Formula (AM-1) or Formula (AM-2), more specific amines that are used in the present specification will be described.

In each of the following manufacturing methods, the definitions of x1a, x1b, y1b, x2, y2, z2, x3a, y3a, z3a, x3b, y3b, z3b, x4, y4, x5a, y5a, z5a, x5b, y5b, z5b, x6, y6, z6, x7a, y7a, z7a, v7a, x7b, y7b, z7b, v7b, a1, b1, a2, b2, a3, b3, a4, b4, a5 and a6 are the same definitions as described in the embodiment [1]; $R^A$ is a $C_{1-6}$ alkyl group such as a methyl group or an ethyl group; $P^1$ is a protective group of an amino group selected from a —C(O)O-tert Bu group, a —C(O)O-Bn group, a —C(O)$CH_3$ group, a —C(O)$CF_3$ group, a —$SO_2$Ph, a —$SO_2$PhMe group, a —$SO_2$Ph($NO_2$) group and the like; E is a leaving group such as a halogen atom (a fluorine atom, a chlorine atom, a bromine atom, an iodine atom or the like), a —OTs group or a —OMs group, and X is a halogen atom (a fluorine atom, a chlorine atom, a bromine atom, an iodine atom or the like). In addition, in each of the following manufacturing methods, compounds represented by Formula (SM-A1), Formula (SM-A2), Formula (SM-B), Formula (SM-C1), Formula (SM-C2), Formula (SM-D), Formula (SM-E1), Formula (SM-E2), Formula (SM-F), Formula (SM-G1), Formula (SM-G2), Formula (SM-H), Formula (SM-J), Formula (SM-K), Formula (SM-L), Formula (RG-A1), Formula (RG-A2), Formula (RG-B1), Formula (RG-C1), Formula (RG-C2), Formula (RG-D1), Formula (RG-E1), Formula (RG-E2), Formula (RG-F1), Formula (RG-F2), Formula (RG-F3), Formula (RG-G1-1), Formula (RG-G1-2), Formula (RG-G1-3), Formula (RG-G2-1), Formula (RG-G2-2), Formula (RG-G2-3), Formula (RG-H1), Formula (RG-H2), Formula (RG-I1), Formula (RG-J1), Formula (RG-K), Formula (RG-L1) AND Formula (RG-M) are commercially available compounds or compounds that can be manufactured from commercially available compounds by manufacturing methods well known by publications.

In addition, in each of the following manufacturing methods, the protection and deprotection, the protection and deprotection of the protective group $P^1$, can be performed according to methods well known by publications, for example, a deprotection method described in "Protective Groups in Organic Synthesis $4^{th}$ Edition, 2007, John Wiley & Sons, Greene et al".

In addition, in each of the following manufacturing methods, condensation reactions mean the same reaction as the above-described condensation reaction.

[Manufacturing Method A]

A method for manufacturing amines represented by Formula (AM-1-1A) and Formula (AM-1-1B)

[C44]

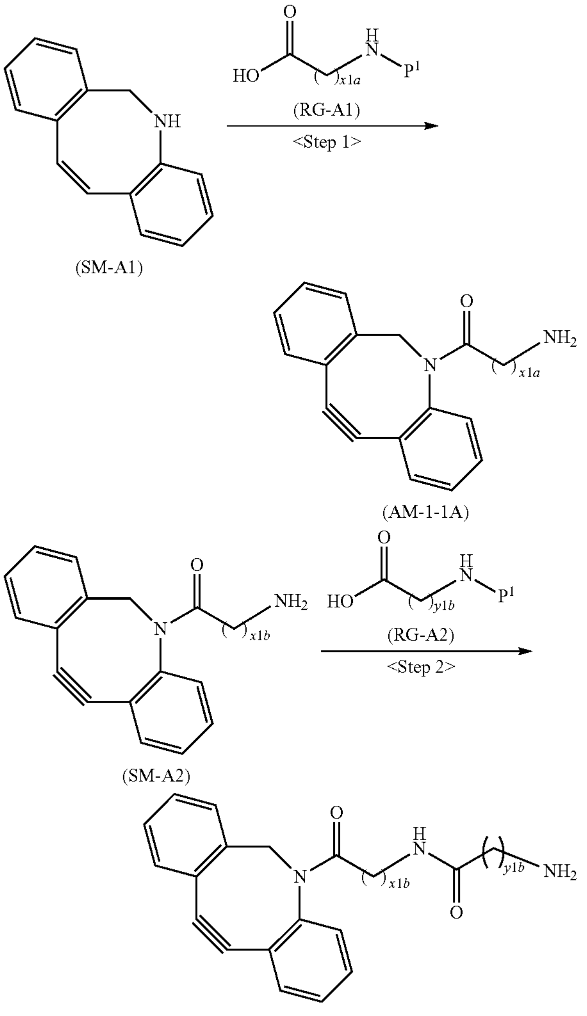

(SM-A1) (AM-1-1A) (SM-A2) (AM-1-1B)

<Step 1> Condensates are obtained by performing condensation reactions using a compound of Formula (SM-A) and a compound of Formula (RG-A1). Subsequently, bromine is added thereto, and then debromination reactions are performed using a base such as tert-BuOK, thereby forming alkyne groups. Subsequently, the protective groups $P^1$ are deprotected, whereby an amine represented by Formula (AM-1-1A) or a salt thereof can be manufactured.

<Step 2> Condensation reactions are performed using a compound of Formula (SM-A2) and a compound of Formula (RG-A2) that are obtained by the same method as in <Step 1> of the above-described [Manufacturing method A], and subsequently, the protective groups $P^1$ are deprotected, whereby an amine represented by Formula (AM-1-1B) or a salt thereof can be manufactured.

[Manufacturing Method B]

A method for manufacturing an amine represented by Formula (AM-1-2)

[C45]

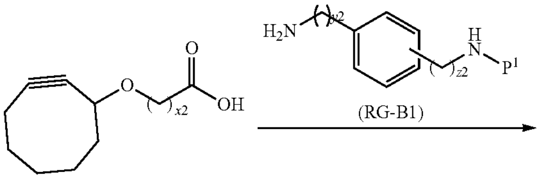

(RG-B1)

(SM-B)

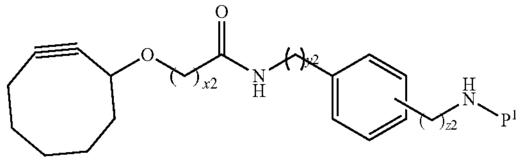

(AM-1-2)

Condensates are obtained by performing condensation reactions using a compound of Formula (SM-B) and a compound of Formula (RG-B1). Subsequently, the protective groups $P^1$ are deprotected, whereby an amine represented by Formula (AM-1-2) or a salt thereof can be manufactured.

[Manufacturing Method C] A Method for Manufacturing Amines Represented by Formula (AM-1-3A) and Formula (AM-1-3B)

[C46]

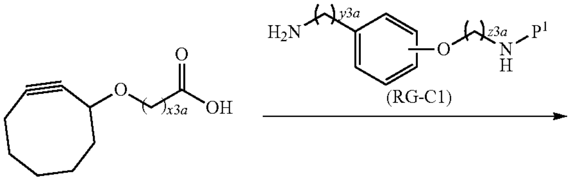

(RG-C1)

(SM-C1)

-continued

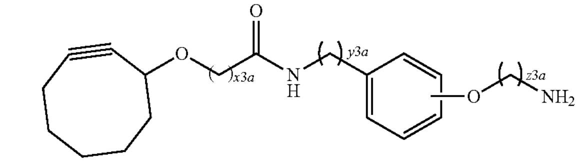

(AM-1-3A)

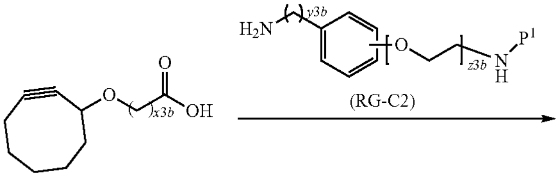

(RG-C2)

(SM-C2)

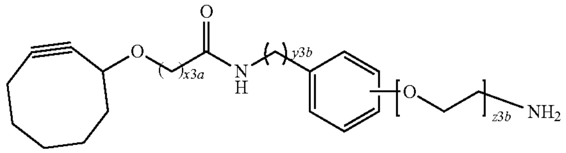

(AM-1-3B)

Condensation reactions are performed using a compound of Formula (SM-C1) and a compound of Formula (RG-C1), and condensates are obtained. Subsequently, the protective groups $P^1$ are deprotected, whereby an amine represented by Formula (AM-1-3A) or a salt thereof can be manufactured.

Condensation reactions are performed using a compound of Formula (SM-C2) and a compound of Formula (RG-C2), and condensates are obtained. Subsequently, the protective groups $P^1$ are deprotected, whereby an amine represented by Formula (AM-1-3B) or a salt thereof can be manufactured.

[Manufacturing Method D] A Method for Manufacturing an Amine Represented by Formula (AM-1-D):

[C47]

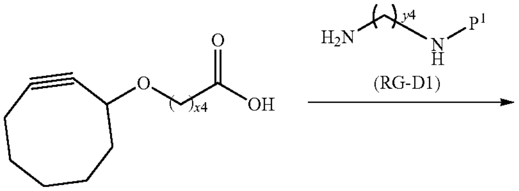

(RG-D1)

(SM-D)

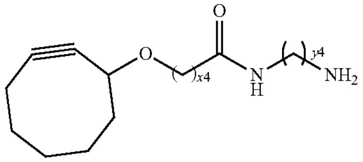

(AM-1-D)

Condensation reactions are performed using a compound of Formula (SM-D) and a compound of Formula (RG-D1), and condensates are obtained. Subsequently, the protective groups $P^1$ are deprotected, whereby an amine represented by Formula (AM-1-D) or a salt thereof can be manufactured.

[Manufacturing Method E] A Method for Manufacturing Amines Represented by Formula (AM-1-E1) and Formula (AM-1-E2)

[C48]

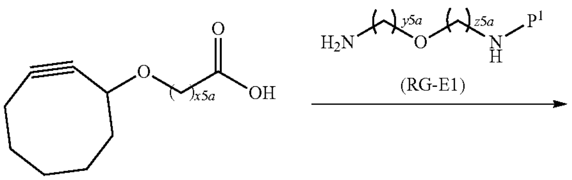

(SM-E1)

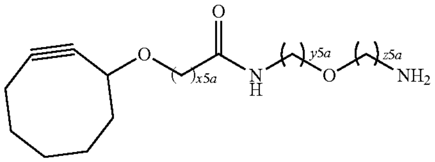

(AM-1-E1)

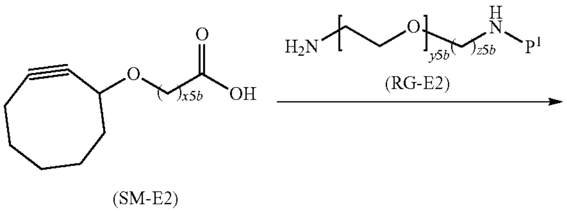

(SM-E2)

-continued

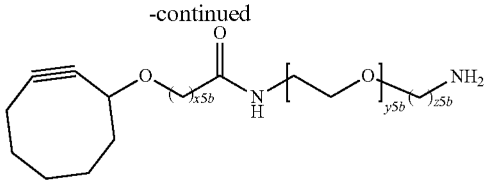

(AM-1-E2)

Condensation reactions are performed using a compound of Formula (SM-E1) and a compound of Formula (RG-E1), and condensates are obtained. Subsequently, the protective groups $P^1$ are deprotected, whereby an amine represented by Formula (AM-1-E1) or a salt thereof can be manufactured.

Condensation reactions are performed using a compound of Formula (SM-E2) and a compound of Formula (RG-E2), and condensates are obtained. Subsequently, the protective groups $P^1$ are deprotected, whereby an amine represented by Formula (AM-1-E2) or a salt thereof can be manufactured.

[Manufacturing Method F] A Method for Manufacturing an Amine Represented by Formula (AM-1-F):

[C49]

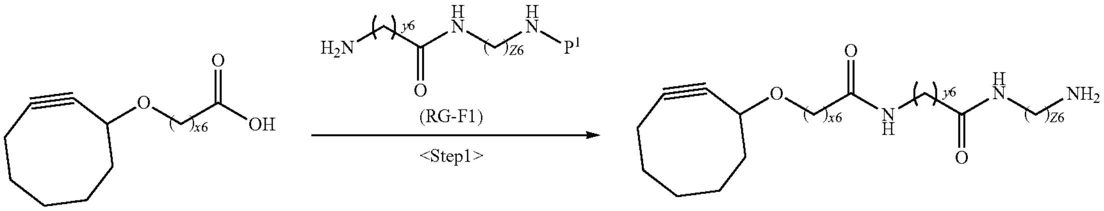

(SM-F)

(AM-1-F)

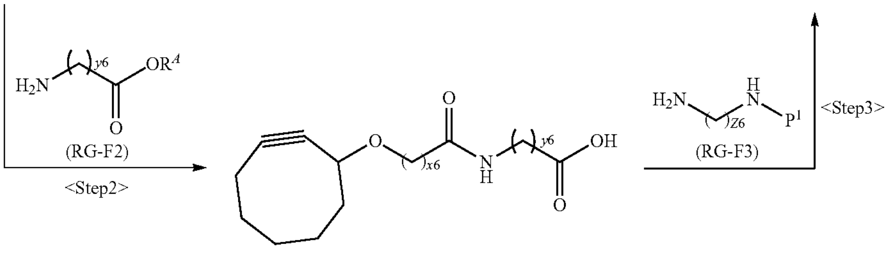

(IM-F1)

<Step 1> Condensation reactions are performed using a compound of Formula (SM-F) and a compound of Formula (RG-F1), and condensates are obtained. Subsequently, the protective groups $P^1$ are deprotected, whereby an amine represented by Formula (AM-1-F) or a salt thereof can be manufactured.

<Step 2> Condensation reactions are performed using a compound of Formula (SM-F) and a compound of Formula (RG-F2), and condensates are obtained. Subsequently, an ester group is hydrolyzed in a solvent that does not get involved in the reaction such as methanol, ethanol, tetrahydrofuran or water or a solvent mixture thereof in the presence of a base such as sodium hydroxide, whereby carboxylic acid represented by Formula (IM-F1) or a salt thereof can be manufactured.

<Step 3> Condensation reactions are performed using a compound of Formula (IM-F1) obtained in <Step 2> of [Manufacturing method F] and a compound of Formula (RG-F3), and condensates are obtained. Subsequently, the protective groups $P^1$ are deprotected, whereby an amine represented by Formula (AM-1-F) or a salt thereof can be manufactured.

[Manufacturing Method G] A Method for Manufacturing Amines Represented by Formula (AM-1-G1) and Formula (AM-1-G2)

[C50]

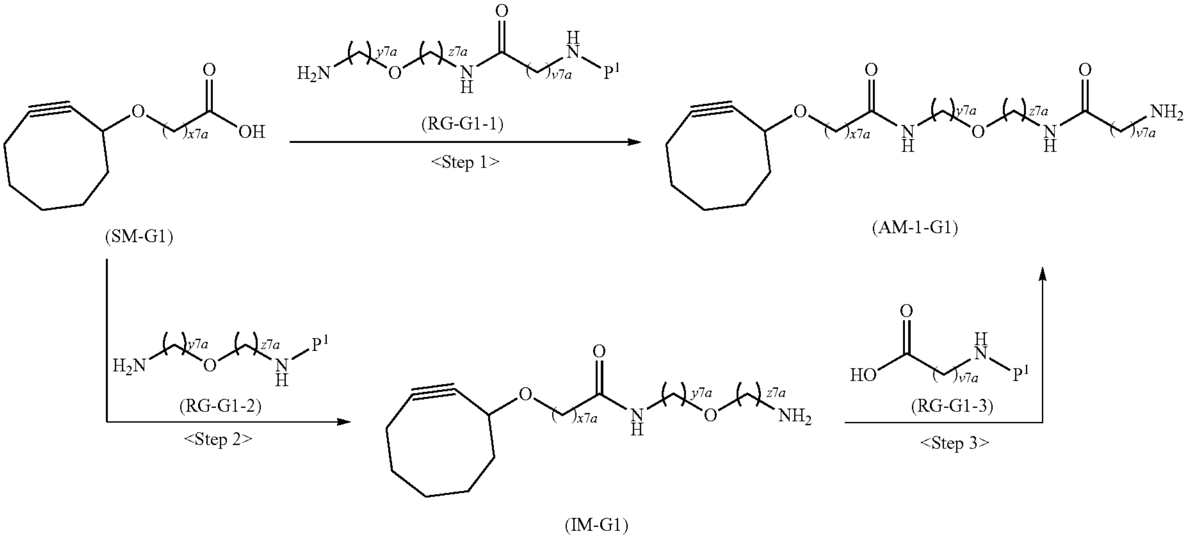

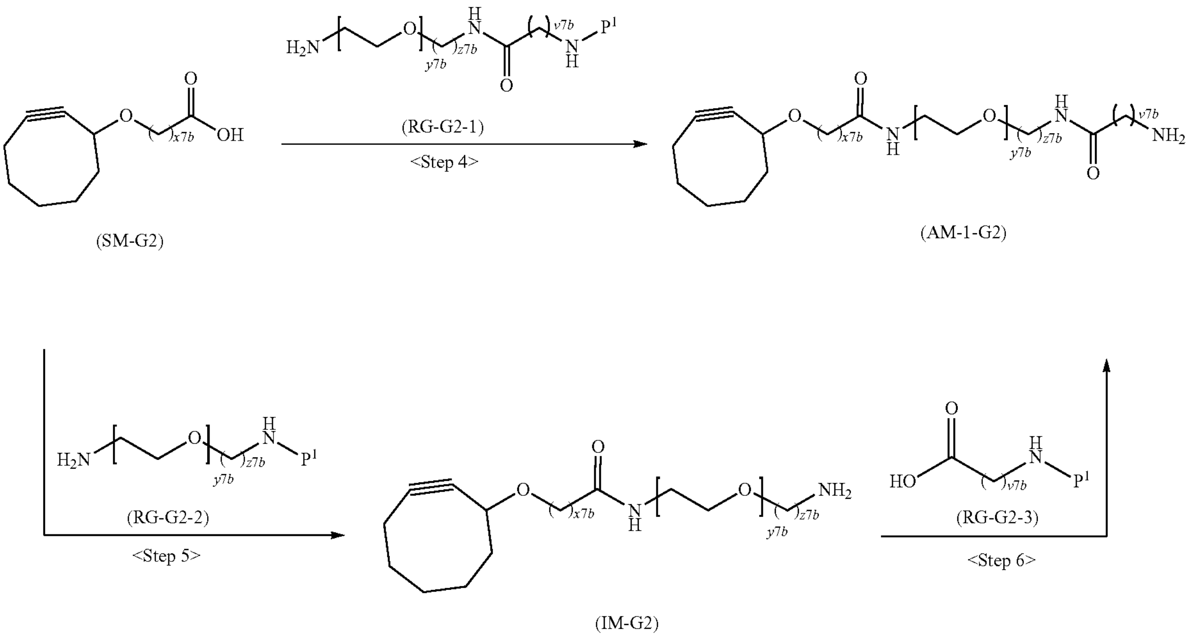

<Step 1> Condensation reactions are performed using a compound of Formula (SM-G1) and a compound of Formula (RG-G1-1), and condensates are obtained. Subsequently, the protective groups P' are deprotected, whereby an amine represented by Formula (AM-1-G1) or a salt thereof can be manufactured.

<Step 2> Condensation reactions are performed using a compound of Formula (SM-G1) and a compound of Formula (RG-G1-2), and condensates are obtained. Subsequently, an ester group is hydrolyzed, whereby carboxylic acid represented by Formula (IM-G1) or a salt thereof can be manufactured.

<Step 3> Condensation reactions are performed using a compound of Formula (IM-G1) obtained in <Step 2> of [Manufacturing method G] and a compound of Formula (RG-G1-3), and condensates are obtained. Subsequently, the protective groups P' are deprotected, whereby an amine represented by Formula (AM-1-G1) or a salt thereof can be manufactured.

<Step 4> Condensation reactions are performed using a compound of Formula (SM-G2) and a compound of Formula (RG-G2-1), and condensates are obtained. Subsequently, the protective groups P' are deprotected, whereby an amine represented by Formula (AM-1-G2) or a salt thereof can be manufactured.

<Step 5> Condensation reactions are performed using a compound of Formula (SM-G2) and a compound of Formula (RG-G2-2), and condensates are obtained. Subsequently, an ester group is hydrolyzed, whereby carboxylic acid represented by Formula (IM-G2) or a salt thereof (for example, a lithium salt, a sodium salt, a potassium salt or the like) can be manufactured.

<Step 6> Condensation reactions are performed using a compound of Formula (IM-G2) obtained in <Step 5> of [Manufacturing method G] and a compound of Formula (RG-G2-3), and condensates are obtained. Subsequently, the protective groups P' are deprotected, whereby an amine represented by Formula (AM-1-G2) or a salt thereof can be manufactured.

[Manufacturing Method H]

A method for manufacturing an amine represented by Formula (AM-2-H)

[C51]

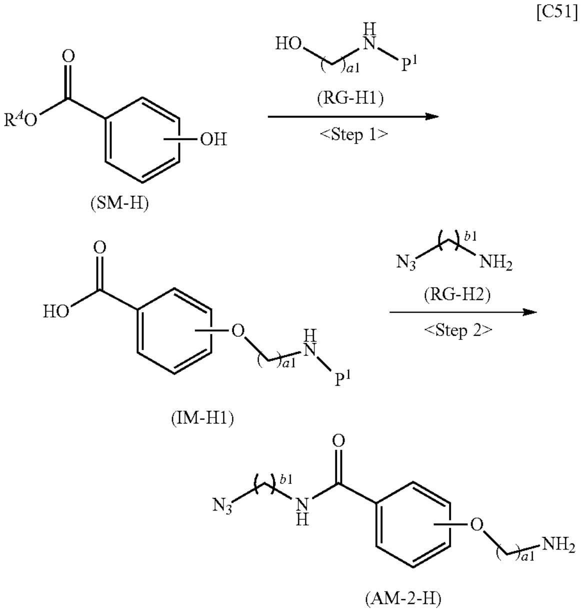

(SM-H)

(IM-H1)

(AM-2-H)

<Step 1> A compound represented by Formula (IM-H1) or a salt thereof (for example, a lithium salt, a sodium salt, a potassium salt or the like) can be manufactured by performing, using the compound of Formula (SM-H) and a compound of Formula (RG-H1), a Mitsunobu reaction in a solvent that does not get involved in a reaction such as tetrahydrofuran in the presence of reagents of (i) $PPh_3$ and $N_2(CO_2CHMe_2)_2$ according to a method well known by publications, for example, a method described in "European Journal of Organic Chemistry, 2014 (6), pp. 1280 to 1286; 2014" or the like and, subsequently, performing hydrolysis in the same manner as in the method described in <Step 2> of [Manufacturing method F].

<Step 2> Condensation reactions are performed using a compound of Formula (IM-H1) obtained in <Step 1> of [Manufacturing method H] and a compound of Formula (RG-H2), and condensates are obtained. Subsequently, the protective groups $P^1$ are deprotected, whereby an amine represented by Formula (AM-2-H) or a salt thereof can be manufactured.

[Manufacturing Method I]

A method for manufacturing an amine represented by Formula (AM-24)

[C52]

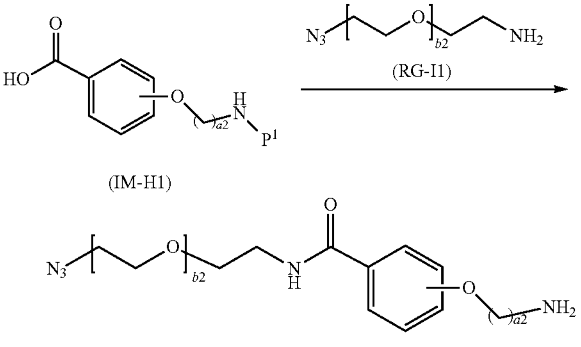

(IM-H1)

(AM-2-I)

<Step 1A> Condensation reactions are performed using a compound of Formula (IM-H1) obtained in <Step 1> of [Manufacturing method H] and a compound of Formula (RG-II), and condensates are obtained. Subsequently, the protective groups $P^1$ are deprotected, whereby an amine represented by Formula (AM-24) or a salt thereof can be manufactured.

[Manufacturing Method J]

A method for manufacturing an amine represented by Formula (AM-2-J)

[C53]

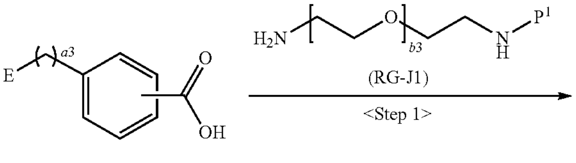

(SM-J)

-continued

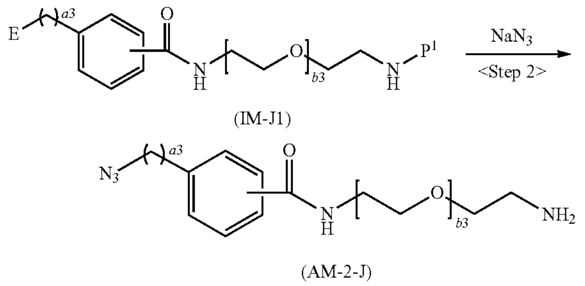

(IM-J1)

(AM-2-J)

<Step 1> Condensation reactions are performed using a compound of Formula (SM-J) and a compound of Formula (RG-J1), whereby Formula (IM-J1) can be manufactured.

<Step 2> An amine represented by Formula (AM-2-J) or a salt thereof can be manufactured by reacting $NaN_3$ in a solvent that does not get involved in a reaction such as dimethyl sulfoxide using the compound of (IM-J1) obtained in <Step 1> of [Manufacturing method J] according to a method well known by publications, for example, a method described in "Organometallics, 29 (23), pp. 6619 to 6622; 2010" or the like and then deprotecting the protective group $P^1$.

[Manufacturing Method K]

A method for manufacturing an amine represented by Formula (AM-2-K)

[C54]

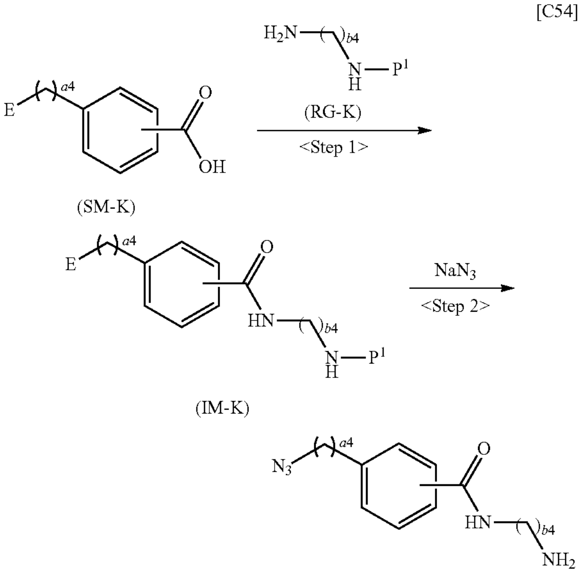

(SM-K)

(IM-K)

(AM-2-K)

<Step 1> Condensation reactions are performed using a compound of Formula (SM-K) and a compound of Formula (RG-K), whereby Formula (IM-K) can be manufactured.

<Step 2> An amine represented by Formula (AM-2-K) or a salt thereof can be manufactured by performing the same reaction as in <Step 2> of [Manufacturing method J] and the deprotection of the protective group $P^1$ using the compound of Formula (IM-K) that is obtained in <Step 1> of [Manufacturing method K].

[Manufacturing Method L]

A method for manufacturing an amine represented by Formula (AM-2-L)

[C55]

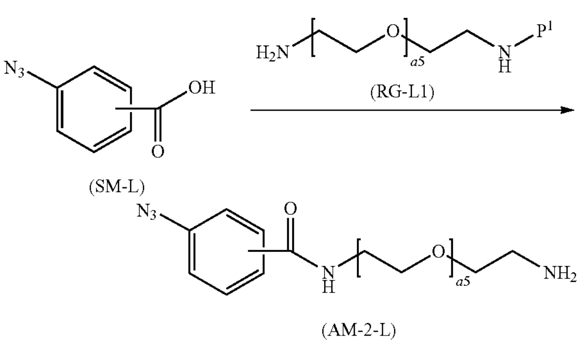

(SM-L)

(AM-2-L)

Condensation reactions are performed using a compound of Formula (SM-L) and a compound of Formula (RG-L1), and condensates are obtained. Subsequently, the protective groups $P^1$ are deprotected, whereby an amine represented by Formula (AM-2-L) or a salt thereof can be manufactured.

[Manufacturing Method M]

A method for manufacturing an amine represented by Formula (AM-2-M)

[C56]

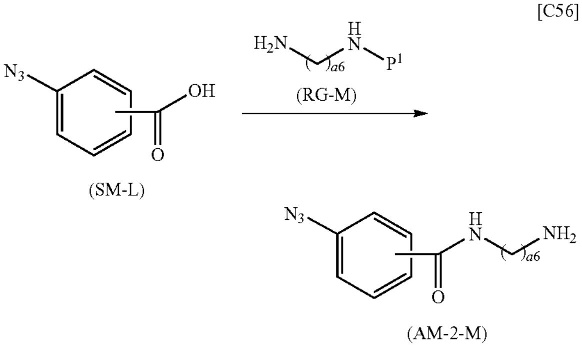

(SM-L)

(AM-2-M)

Condensation reactions are performed using a compound of Formula (SM-L) and a compound of Formula (RG-M), and condensates are obtained. Subsequently, the protective groups $P^1$ are deprotected, whereby an amine represented by Formula (AM-2-M) or a salt thereof can be manufactured.

In the case of amines other than amines represented by Formula (AM-1) or Formula (AM-2) that can be manufactured by the [Manufacturing method A] to [Manufacturing method M], for example, the linker $-L^1-$ in Formula (AM-1) or the linker $-L^2-$ in Formula (AM-2) is a linear alkylene group ($-(CH_2)_n-$, n=1 to 30) [a plurality of (for example, one to 10 or one to five) $-CH_2-$'s in the group may be substituted by groups such as $-C(=O)-$, $-CONH-$, $-O-$, $-NH-$, $-S-$, a cycloalkyl ring having 3 to 8 carbon atoms, a benzene ring, a heterocycle (a five or six-membered aromatic heterocycle or a five or six-membered non-aromatic heterocycle such as a pyridine ring, a piperidine ring or a piperazine ring); a plurality of (for example, one to 10 or one to five) hydrogen atoms in the linear alkylene group ($-CH_2-$) may be substituted by groups selected from groups of an oxo group ($=O$), $C_{1-6}$ alkyl groups (for example, groups such as a methyl group, an ethyl group, an n-propyl group and an iso-propyl group), halogen atoms (for example, a fluorine atom, a chlorine atom, a bromine atom, an iodine atom and the like), a hydroxyl group (—OH) and the like], desired amines can be manufactured by appropriately combining methods well known by publications, for example, synthesis methods described in “The Fifth Series of Experimental Chemistry, each book, 2007, Maruzen Co., Ltd.”, “Comprehensive Organic Transformations, A Guide to Functional Group Preparations, 3rd Edition (Edited by Richard C. Larock), 2018”, “Strategic Applications of Named Reactions in Organic Synthesis, (Edited by Laszlo Kurti, Barbara Czako), Academic Press, 2005” and the like.

As the amine represented by Formula (AM-1A) or Formula (AM-2A) [the definitions of Aky, $-L^{1A}-$ and $-L^{2A}-$ in each formula are the same as the definitions in the embodiment [1X]], a desired amine can be manufactured by appropriately combining synthesis methods well known by publications, for example, synthesis methods described in WO 2019/240219, WO 2021/125255, “The Fifth Series of Experimental Chemistry, each book, 2007, Maruzen Co., Ltd.”, “Comprehensive Organic Transformations, A Guide to Functional Group Preparations, 3rd Edition (Edited by Richard C. Larock), 2018”, “Strategic Applications of Named Reactions in Organic Synthesis, (Edited by Laszlo Kurti, Barbara Czako), Academic Press, 2005” and the like (an oxidation and reduction reaction, an $—O—CH_2—$ bond formation reaction, a halogenation reaction, an azidation reaction, an addition/elimination reaction, a condensation reaction, a protection/deprotection and the like) using a commercially available compound or a compound that can be manufactured by a method well known by publications from a commercially available compound.

[C57]

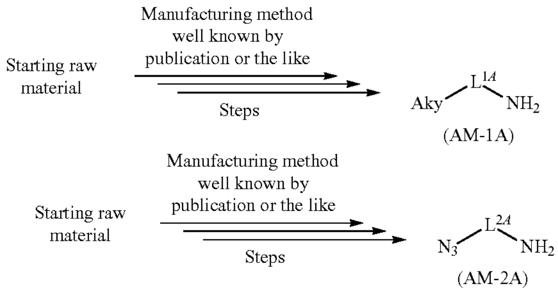

(AM-1A)

(AM-2A)

In the present specification, there are cases where the amine represented by Formula (AM-1), Formula (AM-1A), Formula (AM-2) and Formula (AM-2A) (also comprising a subordinate formula of each formula) forms a pharmaceutically acceptable salt (for example, an acid addition salts; for example, hydrochloride, hydrobromide, sulfate, acetate, trifluoroacetate, p-toluenesulfonate or the like).

Compounds in the present specification are capable of forming a salt and can be obtained by a normal method by, for example, mixing a solution comprising an appropriate amount of an acid or a base to form an intended salt and then performing fractional filtration or distilling away the solvent mixture. As a review regarding salts, Handbook of Pharmaceutical Salts: Properties, Selection, and Use, Stahl & Wermuth (Wiley-VCH, 2002) has been published, and the present book comprises detailed description.

In the present specification, the amine represented by Formula (AM-1), Formula (AM-1A), Formula (AM-2) and Formula (AM-2A) (also comprising a subordinate formula of each formula) or a salt thereof is capable of forming a solvate with a solvent such as water, ethanol or glycerol.

In the present specification, unless particularly otherwise described, in a case where a cyclic group has a variable substituent as a substituent, it means that the variable substituent does not bond to a specific carbon atom of the cyclic group. For example, it means that a variable substituent Rs in Formula A below is capable of substituting any of carbon atoms i, ii, iii, iv and v in Formula A.

[C58]

Formula A

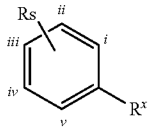

5-1. Crosslinked Alginate Gel

In the present specification, the crosslinked alginate gel that is contained in the core layers of the polymer-coated crosslinked alginate gel fiber may be crosslinked alginate gel having (i) a crosslink through a divalent metal ionic bond, (ii) a crosslink through a chemical bond or (iii) a crosslink through both a divalent metal ionic bond and a chemical bond, which is formed using the chemically modified alginic acid derivative described in the above-described section “2. Chemically modified alginic acid derivative”, (which can also be referred to as crosslinked alginic acid or chemically crosslinked alginic acid). The crosslinked alginate gel that is contained in the core layer of the polymer-coated crosslinked alginate gel fiber is crosslinked alginate gel comprising, as a crosslink, both a chemical crosslink by a triazole ring that is formed by performing the Huisgen reaction (crosslinking reaction) and an ionic crosslinking that is formed by making a divalent metal ion (for example, a calcium ion or the like) coexist. In addition, the crosslinked alginate gel that is contained in the core layer of the polymer-coated crosslinked alginate gel fiber is crosslinked alginate gel comprising, as a crosslink, a chemical crosslink by a triazole ring that is formed by performing the Huisgen reaction (crosslinking reaction).

In the following description, the chemically modified alginic acid derivative represented by Formula (I) and the chemically modified alginic acid derivative represented by Formula (II) can be substituted by the chemically modified alginic acid derivative represented by Formula (I-A) and the chemically modified alginic acid derivative represented by Formula (II-A), respectively.

In the present specification, the crosslinked alginate gel that is contained in the core layers of the polymer-coated crosslinked alginate gel fiber can be obtained by performing the Huisgen reaction (crosslinking reaction), which forms a chemical crosslink between the chemically modified alginic acid derivatives represented by Formula (I) and Formula (II), using the chemically modified alginic acid derivatives. In addition, the crosslinked alginate gel can be obtained by forming an ionic crosslinking between the chemically modified alginic acid derivatives represented by Formula (I) and Formula (II) by making divalent metal ions coexist in the chemically modified alginic acid derivatives. In addition, the crosslinked alginate gel can be obtained by performing the Huisgen reaction (crosslinking reaction) using the chemically modified alginic acid derivatives represented by Formula (I) and Formula (II) to form a chemical crosslink between the derivatives and, furthermore, making divalent metal ions coexist.

In the present specification, "a crosslink is formed", "a crosslink has been formed" or "a crosslinking reaction is performed" means that a chemical crosslink (chemical bond) is formed between the chemically modified alginic acid derivatives represented by Formula (I) and Formula (II) by performing the Huisgen reaction using the chemically modified alginic acid derivatives represented by Formula (I) and Formula (II), that an ionic crosslinking (ionic bond) is formed between individual derivatives of the chemically modified alginic acid derivatives represented by Formula (I) and Formula (II) by making divalent metal ions coexist in the chemically modified alginic acid derivatives represented by Formula (I) and Formula (II) or that both a chemical crosslink by the Huisgen reaction and an ionic crosslinking by a divalent metal ion are formed. In addition, the above-described expression also means that an ionic crosslinking is formed in alginic acid (sodium alginate or the like) by making a divalent metal ion coexist in the alginic acid.

The time during which an ionic crosslinking is formed by bringing divalent metal ions into contact with the chemically modified alginic acid derivatives represented by Formula (I) and Formula (II) and ionically crosslinked alginate gel is produced is, for example, an instant (for example, one to five seconds) to several hours (for example, one to three hours). In addition, the time during which the Huisgen reaction progressed between the chemically modified alginic acid derivatives represented by Formula (I) and Formula (II) to form a chemical crosslink and chemically crosslinked alginate gel is produced is, for example, several seconds to 24 hours, several seconds to 12 hours or several seconds to 30 minutes.

The divalent metal ion that is used to obtain the crosslinked alginate gel is not particularly limited, examples thereof include a calcium ion, a magnesium ion, a barium ion, a strontium ion, a zinc ion and the like, a calcium ion, a barium ion or a strontium ion is preferable, and a calcium ion or a barium ion is more preferable.

The solution comprising the divalent metal ion is not particularly limited, examples thereof include solutions comprising a calcium ion (for example, aqueous solutions such as a calcium chloride aqueous solution, a calcium carbonate aqueous solution, a calcium gluconate aqueous solution), solutions comprising a barium ion (for example, aqueous solutions such as a barium chloride aqueous solution) and solutions comprising a strontium ion (for example, aqueous solutions such as a strontium chloride aqueous solution), a solution comprising a calcium ion or a solution comprising a barium ion is preferable, and a calcium chloride aqueous solution or a barium chloride aqueous solution is more preferable.

The divalent metal ion concentration (for example, the calcium ion or barium ion concentration) of the solution comprising the divalent metal ion is not particularly limited and is, for example, within a range of approximately 1 mM to approximately 1 M or a range of approximately 10 to approximately 500 mM and preferably approximately 10 to approximately 100 mM.

A solvent that is used to prepare the solution or the like comprising the divalent metal ion is not particularly limited, examples thereof include tap water, pure water (for example, distilled water, ion-exchanged water, RO water, RO-EDI water and the like), ultrapure water (MilliQ water), a culture medium, a cell culture medium, a culture fluid, phosphate buffered saline (PBS), physiological saline and the like, and physiological saline or ultrapure water is preferable.

In a case where an ionic crosslinking and a chemical crosslink are present in the crosslinked alginate gel that is contained in the core layer of the fibers, the reaction of the ionic crosslinking is instant and reversible whereas the reaction of the chemical crosslink relatively slowly progresses under relatively mild conditions and is irreversible. When the chemical crosslink and the ionic crosslinking are appropriately combined using these properties, it becomes possible to efficiently produce the crosslinked alginate gel of the present invention. For example, when a solution mixture of the chemically modified alginic acid derivatives represented by Formula (I) and Formula (II) is injected into the solution comprising the divalent metal ion using a device XX in "9. Method for manufacturing polymer-coated crosslinked alginate gel fiber" to be described below, an ionic crosslinking is formed, and it is possible to instantly produce crosslinked alginate gel having a fibrous shape. In addition, when the Huisgen reaction (crosslinking reaction) progresses between the chemically modified alginic acid derivatives represented by Formula (I) and Formula (II) at the same time, and a chemical crosslink is formed, crosslinked alginate gel having a fibrous shape comprising both an ionic crosslinking and a chemical crosslink can be obtained. The physical properties of the crosslinked alginate gel can be adjusted by a method of changing the concentration of an aqueous solution comprising a divalent metal ion to be used (for example, a calcium chloride aqueous solution) or the introduction rate of the reactive group that is introduced into the chemically modified alginic acid derivative or the like.

The crosslinked alginate gel that is contained the core layers of the polymer-coated crosslinked alginate gel fiber of the present invention can be produced in a fibrous shape (also referred to as "crosslinked alginate gel fiber") using the above-described crosslinking reaction and the chemically modified alginic acid derivatives represented by Formula (I) and Formula (II). The crosslinked alginate gel fiber can be produced by adding an alginic acid (for example, sodium alginate) solution to the solution mixture of the chemically modified alginic acid derivatives represented by Formula (I) and Formula (II) at the time of producing the crosslinked alginate gel fiber.

Regarding the length of the crosslinked alginate gel fiber, a crosslinked alginate gel fiber having a desired length can be obtained by, for example, cutting the solution mixture that is injected at the time of injecting the solution mixture containing the cell enabling production of antibodies, bioactive substances or the like and the chemically modified alginic acid derivatives represented by Formula (I) and Formula (II) from the discharge port 2 of the device XX at certain intervals using a cutting tool such as scissors or a cutter in "9. Method for manufacturing polymer-coated crosslinked alginate gel fiber" described below.

The length of the crosslinked alginate gel fiber is not particularly limited, and examples thereof include lengths described in "9. Method for manufacturing polymer-coated crosslinked alginate gel fiber" described below.

In the present invention, as one of the methods for strengthening the fiber structure (for example, acquisition of long-term stability or the like), chemical crosslinking (Huisgen reaction) is used. In a case where culture is performed in a culture fluid using the crosslinked alginate gel fiber having both an ionic crosslinking and a chemical crosslink produced as described above, the divalent metal ion that forms the ionic crosslinking is gradually and reversibly discharged, only the chemical crosslink remains in the crosslinked alginate gel fiber, the gel structure is held by the irreversible chemical crosslink, and it is possible to stably and continuously culture the crosslinked alginate gel fiber.

The crosslinked alginate gel of the present invention that is formed by performing a crosslinking reaction using the chemically modified alginic acid derivatives represented by Formula (I) and Formula (II) is not particularly limited and may contain other components such as a collagen solution, collagen gel, a culture medium, a cell culture medium, a culture fluid, methylcellulose, a sucrose solution, an alginic acid solution and alginate gel.

In the case of being simply mentioned in the present specification, "alginate gel" means alginate gel in which an ionic crosslinking has been formed by making a divalent metal ion coexist in alginic acid (for example, sodium alginate) or a solution thereof.

5-2. Chemical Crosslink in Crosslinked Alginate Gel

In the present specification, the crosslinked alginate gel can be obtained by mixing the chemically modified alginic acid derivatives represented by Formula (I) and Formula (II) and performing the Huisgen reaction. In addition, the crosslinked alginate gel fiber can also be obtained by mixing the chemically modified alginic acid derivatives represented by Formula (I-A) and Formula (II-A) and performing a Huisgen reaction.

In the present specification, the crosslinked alginate gel forms a three-dimensional network structure through a chemical crosslink (a crosslink by a triazole ring that is formed of an alkyne group and an azide group). A preferable chemically modified alginic acid derivative is a derivative that improves the stability of the crosslinked alginate gel after crosslinking. The physical properties of the crosslinked alginate gel can be adjusted with, for example, the introduction rate of each reactive group in the chemically modified alginic acid represented by Formula (I) or Formula (II), which is a raw material.

Crosslinked alginate gel in several embodiments is crosslinked alginate gel crosslinked through a group represented by Formula (III-L) below:

[C59]

(III-L)

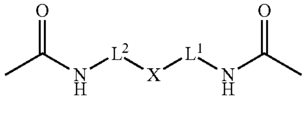

[in Formula (III-L), —CONH— and —NHCO— at both ends represent amide bonds through an arbitrary carboxyl group of alginic acid; $-L^1-$, $-L^2-$ and —X— are the same as the definitions in the embodiment [1-12]].

In the present specification, the crosslinked alginate gel forms a three-dimensional network structure through a chemical crosslink (a crosslink by a triazole ring that is formed of an alkyne group and an azide group). A preferable chemically modified alginic acid derivative is a derivative that improves the stability of the crosslinked alginate gel after crosslinking. The physical properties of the crosslinked alginate gel can be adjusted with, for example, the introduction rate of each reactive group in the chemically modified alginic acid represented by Formula (I-A) or Formula (II-A), which is a raw material.

Crosslinked alginate gel in several embodiments is crosslinked alginate gel crosslinked through a group represented by Formula (III-Lx) below:

[C60]

(III-Lx)

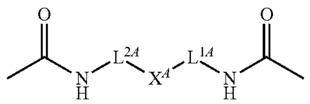

[in Formula (III-Lx), —CONH— and —NHCO— at both ends represent amide bonds through an arbitrary carboxyl group of alginic acid; $-L^{1A}-$, $-L^{2A}-$ and $—X^A—$ are the same as the definitions in the embodiment [1-12X]].

In the following description, Formula (I) and Formula (II) can be substituted by Formula (I-A) and Formula (II-A), respectively.

In several embodiments, the mixing ratio between the chemically modified alginic acid derivative represented by Formula (I) and the chemically modified alginic acid derivative represented by Formula (II) at the time of producing the crosslinked alginate gel is, for example, 1:1.0 to 4.0, 1:1.0 to 3.0, 1:1.0 to 2.0, 1:1.0 to 1.5 or 1:1 and preferably 1:1.0 to 3.0 in terms of the weight ratio between the chemically modified alginic acid derivative represented by Formula (I) and the chemically modified alginic acid derivative represented by Formula (II).

In several embodiments, the mixing ratio between the chemically modified alginic acid derivative represented by Formula (II) and the chemically modified alginic acid derivative represented by Formula (I) at the time of producing the crosslinked alginate gel is, for example, 1:1.0 to 4.0, 1:1.0 to 3.0, 1:1.0 to 2.0, 1:1.0 to 1.5 or 1:1 in terms of the weight ratio between the chemically modified alginic acid derivative represented by Formula (II) and the chemically modified alginic acid derivative represented by Formula (I).

In several embodiments, the mixing ratio between the chemically modified alginic acid derivative represented by Formula (I) and the chemically modified alginic acid derivative represented by Formula (II) at the time of producing the crosslinked alginate gel is, for example, 1:1.0 to 4.0, 1:1.0 to 3.0, 1:1.0 to 2.0, 1:1.0 to 1.5 or 1:1; preferably 1:1.0 to 3.0, in terms of, more preferably, the introduction rate (mol %) ratio of the reactive group between the chemically modified alginic acid derivative represented by Formula (I) and the chemically modified alginic acid derivative represented by Formula (II).

In several embodiments, the mixing ratio between the chemically modified alginic acid derivative represented by Formula (II) and the chemically modified alginic acid derivative represented by Formula (I) at the time of producing the crosslinked alginate gel is, for example, 1:1.0 to 4.0, 1:1.0 to 3.0, 1:1.0 to 2.0, 1:1.0 to 1.5 or 1:1 and, more preferably, the introduction rate (mol %) ratio of the reactive group between the chemically modified alginic acid derivative represented by Formula (II) and the chemically modified alginic acid derivative represented by Formula (I).

In the crosslinked alginate gel, all of the carboxyl groups in the alginic acid configuration unit do not need to have the crosslink of Formula (III-L). The introduction rate (also referred to as the crosslink rate) of the crosslink represented by Formula (III-L) in the crosslinked alginate gel is, for example, within a range of approximately 0.1% to approximately 80%, approximately 0.3% to approximately 60%, approximately 0.5% to approximately 30% or approximately 1.0% to approximately 10%.

In the crosslinked alginate gel, all of the carboxyl groups in the alginic acid configuration unit do not need to have the crosslink of Formula (III-Lx). The introduction rate (also referred to as the crosslink rate) of the crosslink represented by Formula (III-Lx) in the crosslinked alginate gel is, for example, within a range of approximately 0.1% to approximately 80%, approximately 0.3% to approximately 60%, approximately 0.5% to approximately 30% or approximately 1.0% to approximately 10%.

The concentration of the solution of the alginic acid derivative represented by Formula (I) or Formula (II) in the Huisgen reaction for obtaining the crosslinked alginate gel that is contained in the core layers of the polymer-coated crosslinked alginate gel fiber of the present invention is, for example, within a range of approximately 0.01 to approximately 1.5 wt %; preferably within a range of approximately 0.05 to approximately 1.0 wt %; more preferably within a range of approximately 0.08 to approximately 0.75 wt %.

The concentration of the solution of the alginic acid derivative represented by Formula (I-A) or Formula (II-A) in the Huisgen reaction for obtaining the crosslinked alginate gel that is contained in the core layers of the polymer-coated crosslinked alginate gel fiber of the present invention is, for example, within a range of approximately 0.01 to approximately 1.5 wt %; preferably within a range of approximately 0.05 to approximately 1.0 wt %; more preferably within a range of approximately 0.08 to approximately 0.75 wt %.

In the Huisgen reaction for obtaining the crosslinked alginate gel that is contained in the core layers of the polymer-coated crosslinked alginate gel fiber of the present invention where the alginic acid derivatives represented by Formula (I) or Formula (II) are used, in a case where the alginic acid solution is added to the solution mixture of the alginic acid derivatives represented by Formula (I) and Formula (II), the concentration ($C_{ALG}$) of the alginic acid solution is, for example, within a range of $0<C_{ALG}\leq$approximately 1.98 wt %; preferably within a range of $0<C_{ALG}\leq$approximately 1.8 wt %; more preferably within a range of $0<C_{ALG}\leq$approximately 1.7 wt %.

In the Huisgen reaction for obtaining the crosslinked alginate gel that is contained in the core layers of the polymer-coated crosslinked alginate gel fiber of the present invention where the alginic acid derivatives represented by Formula (I-A) or Formula (II-A) are used, in a case where the alginic acid solution is added to the solution mixture of the alginic acid derivatives represented by Formula (I-A) and Formula (II-A), the concentration ($C_{ALG}$) of the alginic acid solution is, for example, within a range of $0<C_{ALG}\leq$approximately 1.98 wt %; preferably within a range of $0<C_{ALG}\leq$approximately 1.8 wt %; more preferably within a range of $0<C_{ALG}\leq$approximately 1.7 wt %.

Regarding the reaction temperature of the Huisgen reaction (the temperature at the time of producing the crosslinked alginate gel and the crosslinked alginate gel fiber), normally, the outside temperature is approximately 4° C. to approximately 60° C. and preferably approximately 15° C. to approximately 37° C.

6. Polymer-Coated Crosslinked Alginate Gel Fiber

In the following description, the chemically modified alginic acid derivative represented by Formula (I) and the chemically modified alginic acid derivative represented by Formula (II) can be substituted by the chemically modified alginic acid derivative represented by Formula (I-A) and the chemically modified alginic acid derivative represented by Formula (II-A), respectively.

In the present specification, a polymer-coated crosslinked alginate gel fiber means a fiber-like (fibrous) structure that is obtained by coating a core layer comprising a cell enabling production of antibodies, bioactive substances or the like and crosslinked alginate gel that is obtained by performing a crosslinking reaction using chemically modified alginic acid derivatives represented by Formula (I) and Formula (II) with a cationic polymer (cationic polymer layer) (a method for manufacturing the polymer-coated crosslinked alginate gel fiber will be described below).

Alternatively, the polymer-coated crosslinked alginate gel fiber is a fiber-like (fibrous) structure comprising a core layer and a cationic polymer layer that is disposed on the outside of the core layer. The core layer comprises a cell enabling production of antibodies, bioactive substances or the like and crosslinked alginate gel in which a crosslink has been formed using the chemically modified alginic acid derivatives represented by Formula (I) and Formula (II), and the cationic polymer layer is a cationic polymer.

Alternatively, the polymer-coated crosslinked alginate gel fiber is a fiber-like (fibrous) structure comprising a core layer and a cationic polymer layer that is disposed on the outside of the core layer. The core layer comprises a cell enabling production of antibodies, bioactive substances or the like and crosslinked alginate gel, the crosslinked alginate gel comprises a crosslink that is obtained by performing a crosslink reaction using the chemically modified alginic acid derivatives represented by Formula (I) and Formula (II), and the cationic polymer layer is a cationic polymer.

FIG. 1 shows a cross-sectional view of an example of the polymer-coated crosslinked alginate gel fiber formed by coating a crosslinked alginate gel fiber with a cationic polymer. This polymer-coated crosslinked alginate gel fiber has an outer diameter c and comprises a core layer 5 having a diameter a and a cationic polymer layer 4 having a thickness b, and the core layer 5 comprises crosslinked alginate gel in which cells 6 producing antibodies, bioactive substances or the like are included. The crosslinked alginate gel in the core layer 5 is crosslinked alginate gel formed by performing a crosslinking reaction using the chemically modified alginic acid derivatives represented by Formula (I) and Formula (II).

The core layers of polymer-coated crosslinked alginate gel fibers of several embodiments may contain, aside from the crosslinked alginate gel formed by performing a crosslinking reaction using the chemically modified alginic acid derivatives represented by Formula (I) and Formula (II) described in the embodiment [1], other components such as a collagen solution, collagen gel, a culture medium, a cell culture medium, a culture fluid, methylcellulose, a sucrose solution, an alginic acid solution and alginate gel which are not particularly limited as long as the components do not have cytotoxicity; preferably may contain a component selected from the group consisting of an alginic acid solution, alginate gel, a culture medium and a culture fluid.

"Polymer-coated crosslinked alginate gel fiber" is, for example, a fibrous structure in which the outer diameter (c in FIG. 1) of a fiber is, for example, approximately 0.1 to approximately 2000 μm and is thus also referred to as "polymer-coated crosslinked alginate microfiber" in some cases.

The cross-sectional shape of the polymer-coated crosslinked alginate gel fiber in a direction perpendicular to the central axis is not limited to a circular shape and may be an asymmetric structure or a deformed shape, and, for example, the cross-sectional shape may be a variety of shapes such as a circular shape, an elliptical shape or a polygonal shape (for example, a triangular shape, a square shape, a pentagonal shape or the like) and is preferably a circular cross-sectional shape as shown in FIG. 1.

The outer diameter (in the case of a non-circular shape, the major axis or the maximum diameter is regarded as the outer diameter) of the polymer-coated crosslinked alginate gel fiber is, for example, within a range of approximately 0.1 to approximately 2000 μm, approximately 0.2 μm to approximately 2000 μm, approximately 0.2 μm to approximately 1000 μm, approximately 0.5 to approximately 1000 μm, approximately 1 to approximately 1000 μm, approximately 10 to approximately 1000 μm, approximately 20 to approximately 1000 μm or the like.

The diameter of the core layer of the polymer-coated crosslinked alginate gel fiber is, for example, within a range of approximately 0.1 to approximately 2000 μm, approximately 0.2 μm to approximately 2000 μm, approximately 1 to approximately 1000 μm, approximately 2 to approximately 500 μm, approximately 2 to approximately 200 μm or the like. In addition, the diameter is, for example, within a range of approximately 0.1 to approximately 2000 μm, approximately 0.2 μm to approximately 2000 μm, approximately 0.2 to approximately 1000 μm, approximately 0.5 to approximately 1000 μm, approximately 1 to approximately 1000 μm, approximately 10 to approximately 1000 μm, approximately 20 to approximately 1000 μm or the like. The diameter of the cross section of the core layer is preferably less than the diameter of the fiber cross section and 50% or more.

The thickness of the polymer layer (b) of the polymer-coated crosslinked alginate gel fiber can be obtained from "(outer diameter of polymer-coated crosslinked alginate gel fiber−diameter of core layer)/2 (b=(c−a)/2 in FIG. 1)". The thickness of the polymer layer is, for example, approximately 0.1 to approximately 200 μm, approximately 1 to approximately 200 μm, approximately 5 μm to approximately 200 μm or the like.

The values of the diameter and outer diameter of the core layer in the polymer-coated crosslinked alginate gel fiber and the inner diameter of the polymer layer can be measured, for example, from an image obtained with a phase-contrast optical microscope after the fiber is produced using a cationic polymer that emits fluorescence for the polymer layer. The values are expressed as the average values of measurement values at several sites in the polymer-coated crosslinked alginate gel fiber. The core layer and the polymer layer in the polymer-coated crosslinked alginate gel fiber normally have substantially uniform thicknesses, and it is preferable that each layer has thickness uniformity within a range of ±10%.

The length of the polymer-coated crosslinked alginate gel fiber is not particularly limited, and examples thereof include lengths of approximately 0.01 to approximately 100 m, approximately 0.1 to approximately 75 m and approximately 0.3 to approximately 50 m described in "9. Method for manufacturing polymer-coated crosslinked alginate gel fiber" described below.

In the present specification, the core layers of polymer-coated crosslinked alginate gel fibers of several embodiments can be formed using a solution mixture of the chemically modified alginic acid derivatives represented by, in which a cell enabling production of antibodies, bioactive substances or the like is contained. In that case, the concentration of the solution of the chemically modified alginic acid derivative represented by Formula (I) or Formula (II) is, for example, each within a range of approximately 0.01 to approximately 1.5 wt %; preferably within a range of approximately 0.05 to approximately 1.0 wt %; more preferably within a range of approximately 0.08 to approximately 0.75 wt %.

Alternatively, the concentration of the solution mixture of the chemically modified alginic acid derivatives represented by Formula (I) and Formula (II) is, for example, within a range of approximately 0.02 to approximately 2.0 wt %; preferably within a range of approximately 0.1 to approximately 2.0 wt %; more preferably within a range of approximately 0.15 to approximately 1.5 wt %.

Alternatively, in a case where an alginic acid solution is added to the solution mixture of the chemically modified alginic acid derivatives represented by Formula (I) and Formula (II), the concentration ($C_{ALG}$) of the alginic acid is, for example, within a range of $0<C_{ALG}\leq$approximately 1.98 wt %; preferably within a range of $0<C_{ALG}\leq$approximately 1.8 wt %; more preferably within a range of $0<C_{ALG}\leq$approximately 1.7 wt %.

In the present specification, in a case where an alginic acid solution is added to the solution mixture of the chemically modified alginic acid derivatives represented by Formula (I) and Formula (II), which is used to form the core layer of the polymer-coated crosslinked alginate gel fiber and in which a cell enabling production of antibodies, bioactive substances or the like is contained, the combination of the concentration (C1 (wt %)) of the solution mixture comprising the chemically modified alginic acid derivatives represented by Formula (I) and Formula (II) and the concentration (C2 (wt %)) of the alginic acid solution is not particularly limited and is, for example, a combination of ranges satisfying formulae represented by 0<C2 (wt %)≤approximately 1.98 (wt %), 0<C1 (wt %)≤approximately 2.0 (wt %)−C2 (wt %), and 0<C1+C2 (wt %)≤approximately 2.0 (wt %);

examples thereof include combinations such as (C1:C2)=(approximately 0.2:approximately 1.3), (approximately 0.5:approximately 1.0), (approximately 1.0:approximately 0.5), (approximately 0.66:approximately 1.34), (approximately 0.34:approximately 0.66) and (approximately 0.16:approximately 0.34). Aside from these concentrations, the solution mixture can be prepared in an appropriate combination of the concentrations C1 and C2.

In the present specification, in a case where an alginic acid solution is added to the solution mixture of the chemically modified alginic acid derivatives represented by Formula (I-A) and Formula (II-A), which is used to form the core layer of the polymer-coated crosslinked alginate gel fiber and in which a cell enabling production of antibodies, bioactive substances or the like is contained, the combination of the concentration (C1x (wt %)) of the solution mixture comprising the chemically modified alginic acid derivatives represented by Formula (I-A) and Formula (II-A) and the concentration (C2x (wt %)) of the alginic acid solution is, for example, a combination of ranges satisfying formulae represented by 0<C2x (wt %)≤approximately 1.98 (wt %), 0<C1x (wt %)≤approximately 2.0 (wt %)−C2x (wt %) and 0<C1x+C2x (wt %)≤approximately 2.0 (wt %), and examples thereof include combinations such as (C1x:C2x)=(approximately 0.2:approximately 1.3), (approximately 0.5:approximately 1.0), (approximately 1.0:approximately 0.5), (approximately 0.66:approximately 1.34), (approximately 0.34:approximately 0.66) and (approximately 0.16:approximately 0.34). Aside from these concentrations, the solution mixture can be prepared in an appropriate combination of the concentrations C1x and C2x.

In the present specification, in a case where an alginic acid solution is added to the solution mixture of the chemically modified alginic acid derivatives represented by Formula (I) and Formula (II), which is used to form the core layer of the polymer-coated crosslinked alginate gel fiber and in which a cell enabling production of antibodies, bioactive substances or the like is contained, the combination of the concentration (C1A (wt %)) of the solution of the chemically modified alginic acid derivative represented by Formula (I), the concentration (C1N (wt %)) of the solution of the chemically modified alginic acid derivative represented by Formula (II) and the concentration (C2 (wt %)) of the alginic acid solution is not particularly limited and is, for example, a combination of ranges satisfying formulae represented by $0<C1A\leq$approximately $2.0-C2$, $0<C1N\leq$approximately $2.0-C2$, $0<C2\leq$approximately 1.98 and $0<C1A+C1N+C2\leq$approximately 2.0; examples thereof include combinations of (C1A:C1N:C2)=(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34), (approximately 0.17:approximately 0.17:approximately 0.66), (approximately 0.08:approximately 0.08:approximately 0.34) and the like. Aside from these concentrations, the solution mixture can be prepared in an appropriate combination of the concentrations C1A, C1N and C2.

In the present specification, in a case where an alginic acid solution is added to the solution mixture of the chemically modified alginic acid derivatives represented by Formula (I-A) and Formula (II-A), which is used to form the core layer of the polymer-coated crosslinked alginate gel fiber and in which a cell enabling production of antibodies, bioactive substances or the like is contained, the combination of the concentration (C1Ax (wt %)) of the solution of the chemically modified alginic acid derivative represented by Formula (I-A), the concentration (C1Nx (wt %)) of the solution of the chemically modified alginic acid derivative represented by Formula (II-A) and the concentration (C2x (wt %)) of the alginic acid solution is not particularly limited and is, for example, a combination of ranges satisfying formulae represented by $0<C2x$ (wt %)$\leq$approximately 1.98 (wt %), $0<C1Ax$ (wt %)$\leq$approximately 2.0 (wt %)$-C2x$ (wt %), $0<C1Nx$ (wt %)$\leq$approximately 2.0 (wt %)$-C2x$ (wt %) and $0<C1Ax+C1Nx+C2x$ (wt %)$\leq$approximately 2.0 (wt %), and examples thereof include combinations such as (C1Ax:C1Nx:C2x)=(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34), (approximately 0.17:approximately 0.17:approximately 0.66) and (approximately 0.08:approximately 0.08:approximately 0.34). Aside from these concentrations, the solution mixture can be prepared in an appropriate combination of the concentrations C1Ax, C1Nx and C2x.

In the present specification, each volume ratio (v1, v2) of the solution of the chemically modified alginic acid derivative represented by Formula (I) and the solution of the chemically modified alginic acid derivative represented by Formula (II) in the solution mixture comprising the cell enabling production of antibodies, bioactive substances or the like and the chemically modified alginic acid derivatives represented by Formula (I) and Formula (II), which is used to form the core layer of the polymer-coated crosslinked alginate gel fiber, is, for example, a ratio in the case of $v1+v2=15$ and, for example, (v1:v2)=(7.5:7.5). Here, in $v1+v2=15$, $0<v1<15$ and $0<v2<15$.

In the present specification, each volume ratio (v1x, v2x) of the solution of the chemically modified alginic acid derivative represented by Formula (I-A) and the solution of the chemically modified alginic acid derivative represented by Formula (II-A) in the solution mixture comprising the cell enabling production of antibodies, bioactive substances or the like and the chemically modified alginic acid derivatives represented by Formula (I-A) and Formula (II-A), which is used to form the core layer of the polymer-coated crosslinked alginate gel fiber, is, for example, a ratio in the case of $v1x+v2x=15$ and, for example, (v1x:v2x)=(7.5:7.5). Here, in $v1x+v2x=15$, $0<v1x<15$ and $0<v2x<15$.

In the present specification, in a case where the alginic acid solution is added to the solution mixture comprising the cell enabling production of antibodies, bioactive substances or the like and the chemically modified alginic acid derivatives represented by Formula (I) and Formula (II), which is used to form the core layer of the polymer-coated crosslinked alginate gel fiber, the volume ratio of the volume (v1) of the chemically modified alginic acid derivative represented by Formula (I), the volume (v2) of the chemically modified alginic acid derivative represented by Formula (II) and the volume (v3) of the alginic acid solution in the solution mixture to which the alginic acid solution has been added is, for example, a ratio in the case of $v1+v2+v3=15$ and, for example, a combination of (v1:v2:v3)=(5:5:5), (2.5:2.5:10), (1:1:13) or the like. Here, in $v1+v2+v3=15$, $0<v1<15$, $0<v2<15$ and $0<v3<15$.

In the present specification, in a case where the alginic acid solution is added to the solution mixture comprising the cell enabling production of antibodies, bioactive substances or the like and the chemically modified alginic acid derivatives represented by Formula (I-A) and Formula (II-A), which is used to form the core layer of the polymer-coated crosslinked alginate gel fiber, the volume ratio of the volume (v1x) of the chemically modified alginic acid derivative represented by Formula (I-A), the volume (v2x) of the chemically modified alginic acid derivative represented by Formula (II-A) and the volume (v3x) of the alginic acid solution in the solution mixture to which the alginic acid solution has been added is, for example, a ratio in the case of $v1x+v2x+v3x=15$ and, for example, a combination of (v1x:v2x:v3x)=(5:5:5), (2.5:2.5:10), (1:1:13) or the like. Here, in $v1x+v2x+v3x=15$, $0<v1x<15$, $0<v2x<15$ and $0<v3x<15$.

In the present specification, in a case where an alginic acid solution is added to the solution mixture of the chemically modified alginic acid derivatives represented by Formula (I) and Formula (II) or the chemically modified alginic acid derivatives represented by Formula (I-A) and Formula (II-A), which is used to form the core layer of the polymer-coated crosslinked alginate gel fiber and in which a cell enabling production of antibodies, bioactive substances or the like is contained, the molecular weight of alginic acid (for example, sodium alginate or the like) that is used to prepare the alginic acid solution is not particularly limited, and the weight-average molecular weight measured by gel permeation chromatography (GPC) is, for example, within a range of approximately 150,000 Da to approximately 2,500,000 Da, a range of approximately 300,000 Da to approximately 2,000,000 Da, a range of approximately 700,000 Da to approximately 2,000,000 Da or the like.

In the present specification, in a case where an alginic acid solution is added to the solution mixture of the chemically modified alginic acid derivatives represented by Formula (I) and Formula (II) or the chemically modified alginic acid derivatives represented by Formula (I-A) and Formula (II-A), which is used to form the core layer of the polymer-coated crosslinked alginate gel fiber and in which a cell enabling production of antibodies, bioactive substances or the like is contained, the molecular weight of alginic acid (for example, sodium alginate or the like) that is used to prepare the alginic acid solution is not particularly limited, and the weight-average molecular weight measured by gel permeation chromatography (GPC) is, for example, within a range of approximately 150,000 Da to approximately 2,500,000 Da, a range of approximately 300,000 Da to approximately 2,500,000 Da, a range of approximately 700,000 Da to approximately 1,400,000 Da, approximately 800,000 Da to approximately 1,500,000 Da, approximately 1,400,000 to approximately 2,000,000 Da, approximately 1,500,000 to approximately 2,500,000 Da or the like.

A solvent that is used to prepare the solution of the chemically modified alginic acid derivative represented by Formula (I), Formula (I-A), Formula (II) or Formula (II-A), the alginic acid solution or the like, which is used to produce the core layer of the polymer-coated crosslinked alginate gel fiber, is not particularly limited, examples thereof include a culture medium, a cell culture medium, a culture fluid, an isotonic buffer solution, phosphate buffered saline (PBS), physiological saline and the like, and a culture medium, a cell culture medium, a culture fluid, physiological saline or an isotonic buffer solution is preferable.

7. Cationic Polymer

A polycation refers to a compound having two or more cationic groups in one molecule, and the cationic group refers to a cation group or a group from which a cation group can be derived. Examples of the cationic group include groups such as amino groups; monoalkylamino groups such as a methylamino group and an ethylamino group; dialkylamino groups such as a dimethylamino group and a diethylamino group; imino groups; guanidino groups and the like. The amino group may be a —$NH_3^+$ group to which a proton bond through a coordination-bond.

In the present specification, the cationic polymer refers to a polymer having two or more cationic group in one molecule. Examples of the cationic polymer include polymers obtained by polymerizing monomers having a cationic group. In addition, it is preferable that the cationic polymer is so hydrophilic as to be soluble in water and has a characteristic of becoming positively charged when the cationic group is dissociated in water. As the cationic polymer, a polymer having two or more amino groups in one molecule is particularly preferable.

Figure 2:
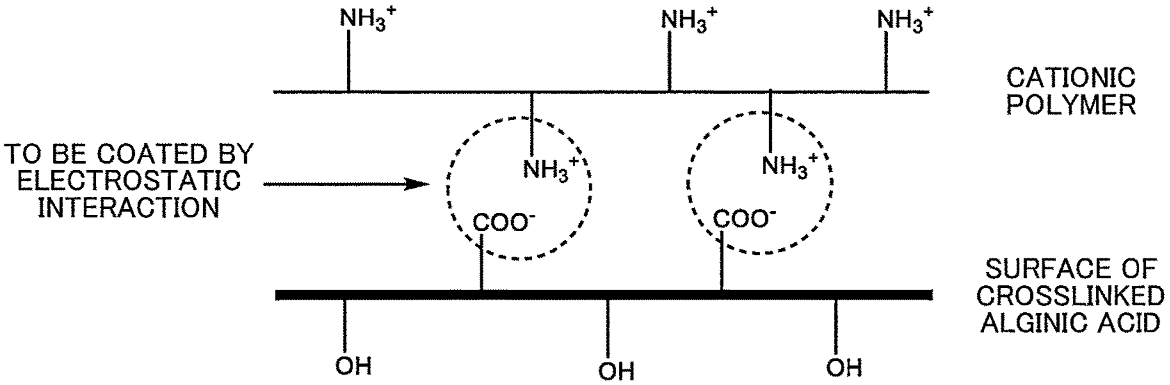
FIG. 2 is a schematic view of a core layer and a cationic polymer layer in the polymer-coated crosslinked alginate gel fiber.

In the present specification, the cationic polymer is preferably a substance capable of increasing the strength of the crosslinked alginate gel fiber when the surface of the crosslinked alginate gel fiber is coated with the cationic polymer by an electrostatic interaction between a carboxyl group in the crosslinked alginate gel fiber and a cationic group in the cationic polymer on the surface of the crosslinked alginate gel fiber that is formed by performing a crosslinking reaction using the chemically modified alginic acid derivatives represented by Formula (I) and Formula (II), which comprises a cell enabling production of antibodies, bioactive substances or the like or the crosslinked alginate gel fiber that is formed by performing a crosslinking reaction using the chemically modified alginic acid derivatives represented by Formula (I-A) and Formula (II-A), which comprises a cell enabling production of antibodies, bioactive substances or the like (refer to FIG. 2). In addition, the cationic polymer is preferably a substance enabling antibodies, bioactive substances or the like produced from the cell enabling production of antibodies, bioactive substances or the like, which is contained in the core layer, to penetrate the cationic polymer coating the core layer (polymer layer) and be discharged to the outside of the polymer-coated crosslinked alginate gel fiber.

In the present specification, examples of the cationic polymer include cationic polymers such as polyamino acids (polymers of basic amino acids), basic polysaccharides (for example, chitosan and the like), basic polymers (polymethylene-CO-guanidine (PMCG), polyallylamine (PAA), polyvinylamine (PVA), polyethyleneimine, allylamine-diallylamine copolymers, allylamine-maleic acid copolymers and the like), and the cationic polymer is preferably a cationic polymer selected from the group consisting of poly-L-ornithine (PLO), poly-D-ornithine (PDO), poly-DL-ornithine, poly-D-lysine (PDL), poly-L-lysine (PLL), poly-DL-lysine, poly-L-arginine (PLA), poly-D-arginine (PDA), poly-DL-arginine, poly-L-homoarginine (PLHA), poly-D-homoarginine (PDHA), poly-DL-homoarginine, poly-L-histidine (PLH), poly-D-histidine (PDH) and poly-DL-histidine, which are polyamino acids; a cationic polymer selected from the group consisting of polymethylene-CO-guanidine (PMCG), polyallylamine (PAA) and polyethyleneimine, which are basic polymers; more preferably poly-L-ornithine (PLO), poly-L-lysine (PLL), polymethylene-CO-guanidine (PMCG), polyallylamine (PAA) or polyethyleneimine; still more preferably poly-L-ornithine (PLO), polymethylene-CO-guanidine (PMCG) or polyethyleneimine.

In the present specification, examples of the cationic polymer that is used to prepare the solution comprising the cationic polymer include polyamino acids, basic polysaccharides, basic polymers, which have been described above, and salts thereof (hydrochlorides, hydrobromides and the like). As the cationic polymer, a commercially available product or a polymer prepared from a commercially available product can be used.

In the present specification, the degree of polymerization of the cationic polymer is not particularly limited, and examples thereof include a degree of polymerization of 50 to 6,000, a degree of polymerization of 50 to 2,000, a degree of polymerization of 100 to 1,500 and the like. In the case of poly-L-ornithine, the degree of polymerization is, for example, 130 to 1,300, in the case of polyallylamine, the degree of polymerization is, for example, 50 to 1,800, and, in the case of chitosan, the degree of polymerization is, for example, 60 to 6,000.

In the present specification, the weight-average molecular weight (Mw) of the cationic polymer is not particularly limited and is, for example, within a range of 500 to 1,000,000, a range of 1,000 to 500,000, a range of 3,000 to 300,000, a range of 5,000 to 100,000, a range of 10,000 to 50,000 or the like. The weight-average molecular weight (Mw) of the cationic polymer can be measured by gel permeation chromatography (GPC).

For example, in the case of poly-L-ornithine, it is possible to use commercially available poly-L-ornithine hydrobromide [for example, molecular weight: 70,000 to 150,000

(manufactured by FUJIFILM Wako Pure Chemical Corporation), molecular weight: 15,000 to 30,000, 30,000 to 70,000 or 5,000 to 15,000 (manufactured by Sigma-Aldrich) or the like]; for example, in the case of polyallylamine, it is possible to use commercially available polyallylamine [for example, molecular weight: 1,600, 3,000, 5,000, 8,000, 15,000 or 25,000 (manufactured by Nitto Boseki Co., Ltd.), to 15,000, to 65,000 (manufactured by Sigma-Aldrich) or the like], commercially available polyallylamine hydrochloride [for example, molecular weight: 1,600, 3,000, 5,000, 15,000 or 100,000 (manufactured by Nitto Boseki Co., Ltd.), to 17,500 or 50,000 (manufactured by Sigma-Aldrich) or the like]; for example, in the case of chitosan, it is possible to use commercially available chitosan [for example, molecular weight: to 15,000 (manufactured by FUJIFILM Wako Pure Chemical Corporation), 5,000, 50,000, 100,000, 160, 000 or 180,000 (manufactured by Sigma-Aldrich) or the like].

Chitosan, which is one of the cationic polymers, is a deacetylated product of chitin, and, from the viewpoint of the water solubility, it is possible to use chitosan having a degree of deacetylation, for example, within a range of 40% to 100%, within a range of 45% to 90%, within a range of 50% to 80% or the like.

The concentration of the solution comprising the cationic polymer is not particularly limited, but needs to be a concentration high enough to uniformly coat the surface of the alginate gel fiber and is, for example, a concentration of approximately 0.01 to approximately 10.0 wt %, approximately 0.01 to approximately 5.0 wt % or approximately 0.02 to approximately 1.0 wt %, preferably approximately 0.02 to approximately 5.0 wt % and more preferably a concentration of approximately 0.05 to approximately 1.0 wt %.

The viscosity of the solution comprising the cationic polymer is not particularly limited and is, for example, within a range of 10.0 to 500.0 mPa·s, within a range of 20.0 to 300.0 mPa·s, within a range of 50.0 to 200.0 mPa·s or the like.

It is possible to use two or more kinds of cationic polymers in the solution comprising the cationic polymer.

A solvent in the solution comprising the cationic polymer is not particularly limited as long as the solvent is capable of dissolving the cationic polymer, examples thereof include water (tap water, pure water (for example, distilled water, ion-exchanged water, RO water, RO-EDI water and the like), ultrapure water (MilliQ water)), aqueous solutions of inorganic salts (phosphate buffered saline (PBS), physiological saline and the like) and the like, and pure water, water or physiological saline, which are capable of further increasing the charge amount of the cationic polymer, is preferable.

8. Cell that is Contained in Core Layer

In the present specification, the cell that can be encapsulated in the core layers of the polymer-coated crosslinked alginate gel fiber is not particularly limited, and examples thereof include antibody (a variety of monoclonal antibodies such as human antibodies, humanized antibodies, chimeric antibodies and mouse antibodies or a variety of altered antibodies such as bispecific antibody, low-molecular-weight antibodies, glycoengineered antibodies thereof)-producing cells, bioactive substance (enzyme, cytokine, hormone, blood coagulation factor, vaccine or the like)-producing cells and cells enabling production of a variety of useful substances useful as drug raw materials, chemical raw materials, food raw materials and the like. The cell is preferably an antibody-producing cell or a bioactive substance-producing cell.

In the present specification, examples of the antibody-producing cell that can be encapsulated in the core layers of the polymer-coated crosslinked alginate gel fiber include a hybridoma obtained from an antibody-producing B cell (antibody-producing hybridoma) or a cultured cell transformed with an antibody expression vector (antibody-producing genetically modified cell).

In the present specification, examples of the bioactive substance-producing cell that can be encapsulated in the core layers of the polymer-coated crosslinked alginate gel fiber include a cultured cell transformed with a bioactive substance expression vector (bioactive substance-producing genetically modified cell).

A cultured cell that can be used as a host of genetical modification is not particularly limited, and examples thereof include microorganisms such as bacteria or yeast, plant cells, insect cells or animal cells.

Examples of the microorganisms that can be used as the host include *Escherichia coli*, budding yeast, fission yeast, *Pichia* yeast and the like, and examples of the insect cells that can be used as the host include Sf9 cells, Sf21 cells, High Five cells and the like.

As the animal cells that can be used as the host, it is possible to appropriately select cells from a CHO cell, a CHO cell subline (a CHO-K1 cell, a CHO-DG44 cell, a CHO-DXB11 cell, a CHO cell transformed such that a sugar chain is modified or the like), a COS cell, an Sp2/0 cell, an NS0 cell, an SP2 cell, a PERC6 cell, an YB2/0 cell, an YE2/0 cell, a 1R983F cell, a Namalwa cell, a Wil-2 cell, a Jurkat cell, a Vero cell, a Molt-4 cell, an HEK293 cell, a BHK cell, an HT-1080 cell, a KGH6 cell, a P3X63Ag8.653 cell, a C127 cell, a JC cell, an LA7 cell, a ZR-45-30 cell, an hTERT cell, an NM2C5 cell, a UACC-812 cell and the like (these cells are cells described in the ATCC cell line catalog, which can be procured from American Type Culture Collection). In the present specification, unless particularly otherwise described, “CHO cell” means cells also comprising “CHO cell subline”, and other cells also each means cells comprising cell sublines thereof.

In the present specification, the antibody-producing cell that can be encapsulated in the core layers of the polymer-coated crosslinked alginate gel fiber is preferably an animal cell transformed with an antibody expression vector, that is, an antibody-producing genetically modified animal cell. Alternatively, the bioactive substance-producing cell that can be encapsulated in the core layers is preferably an animal cell transformed with a bioactive substance expression vector, that is, a bioactive substance-producing genetically modified animal cell.

The animal cell that is used as the host is specifically a CHO cell, a CHO cell subline, a COS cell, an Sp2/0 cell, an NS0 cell, an SP2 cell or a PERC6 cell, an HEK293 cell, a BHK cell, an HT-1080 cell or a C127 cell; more preferably a cell selected from the group consisting of a CHO cell, a CHO cell subline, an Sp2/0 cell, an NS0 cell, an HEK293 cell and a BHK cell; still more preferably a CHO cell or a CHO cell subline. In addition, in certain embodiments, the host cell of the antibody-producing cell is preferably a CHO cell, a CHO cell subline, an Sp2/0 cell or an NS0 cell; more preferably a CHO cell or a CHO cell subline. In addition, the host cell of the bioactive substance-producing cell is preferably a CHO cell, a CHO cell subline, an HEK293 cell or a BHK cell; more preferably a CHO cell or a CHO cell subline.

In the present specification, the antibody-producing cell that can be contained in the core layers of the polymer-coated crosslinked alginate gel fiber is not particularly limited, and examples thereof include cells from which antibodies that are used as biopharmaceuticals or biopharmaceutical raw materials are produced. In addition, the bioactive substance-producing cell is not particularly limited, and examples thereof include cells from which bioactive substances that are used as biopharmaceuticals or biopharmaceutical raw materials are produced.

Examples of the biopharmaceuticals include drugs for a variety of diseases such as a variety of cancers, autoimmune diseases, inflammatory diseases, eye diseases, blood diseases, cranial nerve diseases, hereditary rare diseases, endocrine and metabolic system diseases, cardiovascular diseases, respiratory diseases, digestive diseases, skin diseases, muscle and bone diseases and infectious diseases.

Among the biopharmaceuticals, specific targets of antibody drugs are not particularly limited, examples thereof include C5 (complement), CD3, CD19, CD20, CD22, CD25, CD30, CD33, CD38, CD52, CD79, IL-1β, IL-4R, IL-5, IL-6, IL-6R, IL-12, IL-17, IL-17R, IL-23, IFNAR, PCSK9, CGRP, CGRPR, GD2 (ganglioside), HER2, HER3, TROP2, BCMA, PD-1, PD-L1, CTLA-4, LAG-3, TIM-3, TIGIT, KIR, SLAMF7, RANKL, TNF-α, BLyS, EGFR, VEGF, VEGFR, FGF, nectin, integrin, EpCAM, CCR4, TfR, TF, FIXa, FX, GPVI, sclerostin, amyloid β, IgE, a variety of viruses and the like (comprising subtypes, subunits and fragments thereof), and cells from which antibodies for these targets are produced can be contained in the core layer.

In the present specification, the antibody-producing cell that can be contained in the core layers of the polymer-coated crosslinked alginate gel fiber is not particularly limited, and specific examples thereof include muromonab-CD3, trastuzumab, rituximab, palivizumab, infliximab, basiliximab, tocilizumab, bevacizumab, adalimumab, cetuximab, omalizumab, eculizumab, panitumumab, ustekinumab, golimumab, canakinumab, denosumab, ofatumumab, pertuzumab, natalizumab, nivolumab, alemtuzumab, secukinumab, ramucirumab, ipilimumab, evolocumab, mepolizumab, alirocumab, ixekizumab, brodalumab, elotuzumab, pembrolizumab, sarilumab, bezlotoxumab, belimumab, daratumumab, avelumab, dupilumab, atezolizumab, emicizumab, guselkumab, durvalumab, vedolizumab, romosozumab, risankizumab, necitumumab, ravulizumab, burosumab, isatuximab, tildrakizumab, satralizumab, galcanezumab, dinutuximab, fremanezumab, erenumab, casilibimab, imdevimab, aniflorumab, sotrovimab, ocrelizumab, naxitamab, aducanumab, tafacitamab, margetuximab, gantenerumab, tiragolumab, clovalimab, nemolizumab, katumasomab, pramotamab, falisimab, gemtuzumab, ibritumomab, brentuximab, inotuzumab, polatuzumab, enfortuzumab, sacituzumab, belantamab, roncastuximab, tisotumab, datopotab and patritumab; cells from which an antibody having an altered sugar chain is produced such as mogamulizumab, benralizumab, obinutuzumab and inevirizumab; cells from which a low-molecular-weight antibody composed of an antibody fragment is produced such as ranibizumab, idarucizumab, blinatumomab, brolucizumab, abciximab, capracizumab and certolizumab; and the like.

In the present specification, the antibody-producing cell that can be contained in the core layers of the polymer-coated crosslinked alginate gel fiber is not particularly limited, and specific examples thereof include antibody-producing animal cells, an antibody-producing CHO cell, an antibody-producing Sp2/0 cell or an antibody-producing NS0 cell is preferable; an antibody-producing CHO cell is more preferable.

More specifically, the antibody-producing animal cells are not particularly limited and examples thereof include a muromonab-CD3-producing CHO cell, a trastuzumab-producing CHO cell, a rituximab-producing CHO cell, a palivizumab-producing NS0 cell, a palivizumab-producing CHO cell, an infliximab-producing Sp2/0 cell, an infliximab-producing CHO cell, a basiliximab-producing Sp2/0 cell, a basiliximab-producing CHO cell, a tocilizumab-producing CHO cell, a bevacizumab-producing CHO cell, an adalimumab-producing CHO cell, a cetuximab-producing Sp2/0 cell, a cetuximab-producing CHO cell, an omalizumab-producing CHO cell, an eculizumab-producing NS0 cell, an eculizumab-producing CHO cell, a panitumumab-producing CHO cell, a ustekinumab-producing Sp2/0 cell, a ustekinumab-producing CHO cell, a golimumab-producing Sp2/0 cell, a golimumab-producing CHO cell, a canakinumab-producing Sp2/0 cell, a canakinumab-producing CHO cell, a denosumab-producing CHO cell, an ofatumumab-producing NS0 cell, an ofatumumab-producing CHO cell, a pertuzumab-producing CHO cell, a natalizumab-producing NS0 cell, a natalizumab-producing CHO cell, a nivolumab-producing CHO cell, an alemtuzumab-producing CHO cell, a secukinumab-producing CHO cell, a ramucirumab-producing NS0 cell, a ramucirumab-producing CHO cell, an ipilimumab-producing CHO cell, an evolocumab-producing CHO cell, a mepolizumab-producing CHO cell, an alirocumab-producing CHO cell, an ixekizumab-producing CHO cell, a brodalumab-producing CHO cell, an elotuzumab-producing NS0 cell, an elotuzumab-producing CHO cell, a pembrolizumab-producing CHO cell, a sarilumab-producing CHO cell, a bezlotoxumab-producing CHO cell, a belimumab-producing NS0 cell, a belimumab-producing CHO cell, a daratumumab-producing CHO cell, an avelumab-producing CHO cell, a dupilumab-producing CHO cell, an atezolizumab-producing CHO cell, an emicizumab-producing CHO cell, a guselkumab-producing CHO cell, a durvalumab-producing CHO cell, a vedolizumab-producing CHO cell, a romosozumab-producing CHO cell, a risankizumab-producing CHO cell, a necitumumab-producing NS0 cell, a necitumumab-producing CHO cell, a ravulizumab-producing CHO cell, a burosumab-producing CHO cell, an isatuximab-producing CHO cell, a tildrakizumab-producing CHO cell, a satralizumab-producing CHO cell, a galcanezumab-producing CHO cell, a dinutuximab-producing Sp2/0 cell, a dinutuximab-producing CHO cell, a fremanezumab-producing CHO cell, an erenumab-producing CHO cell, a casilibimab-producing CHO cell, an imdevimab-producing CHO cell, an aniflorumab-producing NS0 cell, an aniflorumab-producing CHO cell, a sotrovimab-producing CHO cell, an ocrelizumab-producing CHO cell, a naxitamab-producing CHO cell, an aducanumab-producing CHO cell, a tafacitamab-producing CHO cell, a margetuximab-producing CHO cell, a gemtuzumab-producing NS0 cell, a gemtuzumab-producing CHO cell, an ibritumomab-producing CHO cell, a brentuximab-producing CHO cell, an inotuzumab-producing CHO cell, a polatuzumab-producing CHO cell, an enfortuzumab-producing CHO cell, a sacituzumab-producing Sp2/0 cell, a sacituzumab-producing CHO cell, a belantamab-producing CHO cell, a roncastuximab-producing CHO cell, a tisotumab-producing CHO cell, a mogamulizumab-producing CHO cell, a benralizumab-producing CHO cell, an obinutuzumab-producing CHO cell, a inevirizumab-producing CHO cell, a ranibizumab-producing CHO cell, an idarucizumab-producing CHO cell, a caplacizumab-producing CHO cell, a certolizumab-producing CHO cell, an anti-GPVI antibody-producing CHO cell and the like.

Examples of the antibody-producing CHO cell include a muromonab-CD3-producing CHO cell, a trastuzumab-producing CHO cell, a rituximab-producing CHO cell, a palivizumab-producing CHO cell, an infliximab-producing CHO cell, a basiliximab-producing CHO cell, a tocilizumab-producing CHO cell, a gemtuzumab-producing CHO cell, a bevacizumab-producing CHO cell, an ibritumomab-producing CHO cell, an adalimumab-producing CHO cell, a cetuximab-producing CHO cell, a ranibizumab-producing CHO cell, an omalizumab-producing CHO cell, an eculizumab-producing CHO cell, a panitumumab-producing CHO cell, a ustekinumab-producing CHO cell, a golimumab-producing CHO cell, a canakinumab-producing CHO cell, a denosumab-producing CHO cell, a mogamulizumab-producing CHO cell, a certolizumab-producing CHO cell, an ofatumumab-producing CHO cell, a pertuzumab-producing CHO cell, a brentuximab-producing CHO cell, a natalizumab-producing CHO cell, a nivolumab-producing CHO cell, an alemtuzumab-producing CHO cell, a secukinumab-producing CHO cell, a ramucirumab-producing CHO cell, an ipilimumab-producing CHO cell, an evolocumab-producing CHO cell, a mepolizumab-producing CHO cell, an alirocumab-producing CHO cell, an ixekizumab-producing CHO cell, a brodalumab-producing CHO cell, an idarucizumab-producing CHO cell, an elotuzumab-producing CHO cell, a pembrolizumab-producing CHO cell, a sarilumab-producing CHO cell, a bezlotoxumab-producing CHO cell, a belimumab-producing CHO cell, a daratumumab-producing CHO cell, an avelumab-producing CHO cell, a dupilumab-producing CHO cell, an atezolizumab-producing CHO cell, a benralizumab-producing CHO cell, an inotuzumab-producing CHO cell, an emicizumab-producing CHO cell, a guselkumab-producing CHO cell, a durvalumab-producing CHO cell, an obinutuzumab-producing CHO cell, a vedolizumab-producing CHO cell, a romosozumab-producing CHO cell, a risankizumab-producing CHO cell, a necitumumab-producing CHO cell, a ravulizumab-producing CHO cell, a burosumab-producing CHO cell, an isatuximab-producing CHO cell, a tildrakizumab-producing CHO cell, a satralizumab-producing CHO cell, a galcanezumab-producing CHO cell, a dinutuximab-producing CHO cell, a fremanezumab-producing CHO cell, an erenumab-producing CHO cell, a casilibimab-producing CHO cell, an imdevimab-producing CHO cell, an aniflorumab-producing CHO cell, a sotrovimab-producing CHO cell, an ocrelizumab-producing CHO cell, a naxitamab-producing CHO cell, an aducanumab-producing CHO cell, a tafacitamab-producing CHO cell, a margetuximab-producing CHO cell, a polatuzumab-producing CHO cell, an enfortuzumab-producing CHO cell, a sacituzumab-producing CHO cell, a belantamab-producing CHO cell, a roncastuximab-producing CHO cell, a tisotumab-producing CHO cell, an inevirizumab-producing CHO cell, a blinatumomab-producing CHO cell, a brolucizumab-producing CHO cell, an abciximab-producing CHO cell, a caplacizumab-producing CHO cell, an anti-GPVI antibody-producing CHO cell and the like;

The antibody-producing CHO cell is, for example, a CHO cell selected from the group consisting of a trastuzumab-producing CHO cell, a rituximab-producing CHO cell, an infliximab-producing CHO cell, a tocilizumab-producing CHO cell, an adalimumab-producing CHO cell, a nivolumab-producing CHO cell and an anti-GPVI antibody-producing CHO cell; for example, a tocilizumab-producing CHO cell.

Antibodies produced as described above can also be modified and altered after the production, and specific examples thereof include PEGylation, drug conjugation modification, radiolabeling and the like. That is, cells that are used to produce antibodies that serve as a raw material in the production of modified antibodies such as PEGylated antibodies and antibody-drug conjugates (raw material antibody-producing cells) can be exemplified as the cells that can be encapsulated in the core layer. The raw material antibody-producing cells are not particularly limited, examples of the raw material antibody-producing cell for PEGylated antibodies include cells from which raw material antibody fragments of certolizumab pegol are produced, specifically, a certolizumab-producing CHO cell and the like; examples of the raw material antibody-producing cell for antibody-drug conjugates include raw material antibody-producing cells such as gemtuzumab ozogamicin, ibritumomab tiuxetan, trastuzumab emtansine, trastuzumab deruxtecan, brentuximab vedotin, inotuzumab ozogamicin, cetuximab salotarocan sodium, polatuzumab vedotin, enfortumab vedotin-ejfv, sacituzumab govitecan, belantamab mafodotin, roncastuximabu tecilin, tisotumab vedotin, datopotamab deruxtecan and patritumab deruxtecan, and specific examples thereof include gemtuzumab-producing NS0 cells, ibritumomab-producing CHO cells, trastuzumab-producing CHO cells, brentuximab-producing CHO cells, inotuzumab-producing CHO cells, cetuximab-producing Sp2/0 cells, polatuzumab-producing CHO cells, enfortuzumab-producing CHO cells, sacituzumab-producing Sp2/0 cells, belantamab-producing CHO cells, roncastuximab-producing CHO cells, tisotumab-producing CHO cells and the like.

In addition, cells from which a fusion protein of an antibody or an antibody fragment and other protein or peptide is produced also can be contained in the core layer, and examples thereof include pavinafspalpha-producing CHO cells, vintorafspalpha-producing CHO cells and the like.

“Antibodies” will be described in detail in “12. Classification of antibodies” and “13. Method for producing and purifying antibody and bioactive substance”.

In the present specification, the bioactive substance means a substance and a compound group that develop physiological and pharmacological actions on creatures. Examples of the substance and compound group that develop physiological and pharmacological actions on creatures include enzymes, insulin, alkaloids, cytokines (interferons, interleukins, chemokines, tumor necrosis factors and the like), plant hormones, neurotransmitters, pheromones, hormones (animal hormones), growth factors, growth regulators, growth inhibitors, activators, hematopoietic factors, blood coagulation factors, vaccines (attenuated vaccines, inactivated vaccines, protein vaccines and the like) and the like.

In addition, the receptors, cell surface antigens and cell surface receptors of these substances and ligands thereof are also substances that develop physiological and pharmacological actions, which are included in the bioactive substance. Furthermore, in addition to bioactive substances that living bodies originally have, substances obtained by modifying or altering bioactive substances, substances that activate or impair bioactivity and fusion proteins obtained by combining a plurality of bioactive substances or partial regions or fragments thereof are also included in the bioactive substance as long as physiological and pharmacological actions are developed, and, in the present specification, such substances comprising these substances are referred to as the bioactive substance. In the present specification, the bioactive substance is preferably a protein bioactive substance, that is, a bioactive substance composed of a protein or a peptide.

In the present specification, the bioactive substance-producing cell that can be contained in the core layers of the polymer-coated crosslinked alginate gel fiber is not particularly limited, and, as described above, examples thereof include cells from which bioactive substances that are used as biopharmaceuticals or biopharmaceutical raw materials are produced.

The bioactive substance that is used as biopharmaceuticals is not particularly limited, examples thereof include enzymes such as t-PA, glucocerebrosidase, galactosidase, hyaluronidase, iduronidase, glucosidase, sulfatase, uric acid oxidase, DNase, adenosine deaminase, tripeptidyl peptidase, hyaluronidase, phenylalanine ammonia lyase and alkaline phosphatase; blood coagulation factors and blood-related proteins such as FVIIa, FVIII, FIX, FXIII, thrombomodulin, antithrombin and albumin; hormones such as insulin, growth hormone, diuretic peptide, gonadotropin, GLP-1, GLP-2, parathyroid hormone and leptin; interferons such as IFN-α, IFN-β and IFN-γ; hematopoietic factors such as erythropoietin and thrombopoietin; cytokines and receptors thereof such as G-CSF, IL-2, IL-10, IL-2R, IL-4R, IL-5R, IL-6R, IL-17R, TNFR, EGF, EGFR, FGF, VEGF, VEGFR, PDGF, PDGFR and TGF-β; cell surface antigens such as CTLA-4, cell surface receptors and ligands thereof; proteins and peptides for vaccines such as hepatitis B virus-derived antigens, papilloma virus-derived antigens, varicella-zoster virus-derived antigens and SARS-CoV-2-derived antigens; and the like, subtypes, subunits and active fragments thereof are also included, and cells from which these bioactive substances are produced can be contained in the core layer.

In the present specification, structurally altered substances are also included in the bioactive substance, examples thereof include substances to which amino acid sequence alteration has been added so as to change the activity of the substances, and specific examples include insulin analogs, GLP-1 analogs, erythropoietin analogs and the like. In addition, substances composed of the amino acid sequence of a partial region or fragment of the original substance are also included, the substances may be substances obtained by combining the amino acid sequences of a plurality of partial regions or fragments thereof; specific examples thereof include insulin analogues, FVIII analogues, parathyroid hormone analogues and the like. Furthermore, fusion proteins obtained by combining two or more kinds of substances or partial regions or fragments thereof are also included, and examples thereof include fusion proteins of an enzyme and an antibody, fusion proteins of a cytokine receptor and an antibody Fc portion, fusion proteins of a cell surface antigen extracellular domain and an antibody Fc portion, fusion proteins of a blood coagulation factor and an antibody Fc portion, fusion proteins of a blood coagulation factor and a plasma protein and the like. Cells from which these structurally altered bioactive substances are produced can be contained in the core layer.

Bioactive substances produced as described above can also be modified and altered after the production, and specific examples thereof include PEGylation, sugar chain modification, drug conjugation modification, radiolabeling and the like. That is, in the production of modified proteins and peptides such as PEGylated protein or fatty acid attached peptide, the bioactive substances can be used for the production of proteins and peptides, which serve as raw materials, specific examples thereof include cells from which raw material proteins and peptides such as PEGylated FVIII, PEGylated erythropoietin and fatty acid-added Insulin analogues are produced, and cells from which bioactive substances that serve as those raw materials are produced (raw material bioactive substance-producing cells) can be contained in the core layer.

In the present specification, the bioactive substance-producing cell that can be contained in the core layers of the polymer-coated crosslinked alginate gel fiber is not particularly limited, and specific examples thereof include enzyme-producing cells such as alteplase, monteplase, imiglucerase, veraglucerase, agalsidase, laronidase, alglucosidase, avalglucosidase, idursulfase, gallsulfase, erosulfase, rasburicase, dornase, celluliponase, glucarpidase, hyaluronidase and asfotase; blood coagulation factor and blood-related protein-producing cells such as eptacog, octocog, rurioctocog, turoctocog, lonoctocog, damoctocog, simoctocog, nonacog, albutrepenonacog, catridecacog, efraloctocog, eftrenonacog, thrombomodulin, antithrombin, vonicog and albumin; hormone-producing cells such as insulin, insulin lispro, insulin aspart, insulin glargine, insulin detemir, insulin glulisine, insulin degludec, somatropin, somapcitan, mecacermin, carperitide, bosolitide, glucagon, follitropin, choriogonadotropin, dulaglutide, liraglutide, semaglutide, teduglutide, teriparatide and metreleptin; interferon-producing cells such as interferon alpha-2a, interferon alpha-2b, interferon beta-1a, interferon beta-1b and interferon gamma-1a; hematopoietic factor-producing cells such as epoetin, darbepoetin and romiplostim; cells from which cytokines such as filgrastim, lenograstim, tesseleukin, trafermin, verfermin, etanercept, aflibercept and denileukin diftitox and receptors thereof are produced; and cells from which cell surface antigens such as abatacept, cell surface receptors and ligands thereof are produced, and cells from which subtypes, subunits and active fragments thereof are produced are also included.

In the present specification, the bioactive substance-producing cell that can be contained in the core layers of the polymer-coated crosslinked alginate gel fiber is not particularly limited, and specific examples thereof include bioactive substance-producing animal cells, bioactive substance-producing CHO cells, bioactive substance-producing HEK 293 cells or bioactive substance-producing BHK cells are preferable, and bioactive substance-producing CHO cells are more preferable.

More specifically, the bioactive substance-producing animal cell is not particularly limited, examples thereof include bioactive substance-producing CHO cells such as alteplase-producing CHO cells, imiglucerase-producing CHO cells, agalsidase-producing CHO cells, laronidase-producing CHO cells, alglucosidase-producing CHO cells, avalglucosidase-producing CHO cells, idursulfase-producing CHO cells, galsulfase-producing CHO cells, erosulfase-producing CHO cells, dornase-producing CHO cells, celluliponase-producing CHO cells, hyaluronidase-producing CHO cells, asfotase-producing CHO cells, rurioctocog-producing CHO cells, turoctocog-producing CHO cells, ronoctocog-producing CHO cells, nonacog-producing CHO cells, albutrepenonacog-producing CHO cells, thrombomodulin-producing CHO cells, antithrombin-producing CHO cells, bonicog-producing CHO cells, follitropin-producing CHO cells, chriogonadotropin-producing CHO cells, dulaglutide-producing CHO cells, interferon beta-1a producing CHO cells, epoetin-producing CHO cells, darbepoetin-producing CHO cells, lenograstim-producing CHO cells, etanercept-producing CHO cells, aflibercept-producing CHO cells and abatacept-producing CHO cells; bioactive substance-producing HEK 293 cells such as simoctocog-producing HEK 293 cells, eflaloctocog-producing HEK 293 cells and eftrenonacog-producing HEK 293 cells; bioactive substance-producing BHK cells such as monteplase-producing BHK cells, eptacog-producing BHK cells, octocog-producing BHK cells and damoctocog-producing BHK cells; bioactive substance-producing HT-1080 cells such as bellaglucerase-producing HT-1080 cells, agalsidase-producing HT-1080 cells and idursulphase-producing HT-1080 cells; bioactive substance-producing PERC6 cells such as follitropin-producing PERC6 cells; and the like;

Examples of the bioactive substance-producing CHO cells include alteplase-producing CHO cells, alglucosidase-producing CHO cells, rurioctocog-producing CHO cells, dulaglutide-producing CHO cells, interferon beta-1a-producing CHO cells, darbepoetin-producing CHO cells, etanercept-producing CHO cells, aflibercept-producing CHO cells, abatacept-producing CHO cells and the like.

The bioactive substances exemplified herein are, in some cases, expressed as the names of substances that have been modified or altered after being produced, and those may contain cells from which the bioactive substance that serves as a raw material thereof is produced in the core layer. For example, in PEGylated bioactive substances such as elapegademase, pegvariase, rurioctocog alfa pegol, turoctocog alfa pegol, damoctocog alfa pegol, nonacog beta pegol, pegvisomant, peginterferon alfa-2a, peginterferon alfa-2b, epoetin beta pegol, pegfilgrastim and pegverfermin, it is possible to contain cells from which the bioactive substance that serves as a raw material thereof is produced in the core layer.

The cell enabling production of bioactive substances also include, in addition to the above-described bioactive substance-producing genetically modified cells, natural cells or cells on which an artificial alteration operation has been performed and also include cell masses composed of a plurality of cells, and examples thereof include an insulin-secreting cell, a pancreatic islet, a pancreatic islet cell, a dopamine-secreting cell, a pituitary cell, a growth hormone-secreting cell, a parathyroid cell, a nerve growth factor-secreting cell, a blood coagulation factor-secreting cell, a hepatocyte, a parathyroid cell, an erythropoietin-secreting cell, a norepinephrine-secreting cell and the like. In the present specification, in certain embodiments, the bioactive substance-producing cell is an insulin-secreting cell, a pancreatic islet, a pancreatic islet cell or a MING cell derived from a pancreatic β cell.

"Insulin-secreting cell" means a cell having an insulin-secreting function and, for example, means a β cell that secrete insulin in cells configuring a pancreatic islet. In addition, "insulin-secreting cell" may be a cell given an insulin-secreting function by differentiation, maturation, alteration or the like, and, for example, cells having an insulin-secreting function obtained by differentiating a stem cell such as an iPS cell, an ES cell or a somatic stem cell (for example, a mesenchymal stem cell), cells having an insulin-secreting function obtained by maturing a juvenile cell or a progenitor cell and cells given an insulating-secreting function by genetic recombination can also be included. Here, the differentiation or maturation of the cell comprises the culture of the cell, that is, cells obtained by differentiation or maturation may include cells obtained by culturing.

"Pancreatic islet" is a cell mass composed of an average of approximately 2000 pancreatic islet cells, which is also referred to as a separate name of islets of Langerhans. The pancreatic islet is composed of five kinds of cells: an α-cell that secretes glucagon, a β-cell that secretes insulin, a 6-cell that secretes somatostatin, an ε-cell that secretes ghrelin, and a PP (pancreatic polypeptide) cell that secretes pancreatic polypeptide.

In the present specification, "pancreatic islet cell" may be a cell comprising at least one kind of cell of the above-described five kinds of cells configuring the pancreatic islet, but preferably comprises at least the β-cell. In several embodiments, the pancreatic islet cell may be a mixture comprising all of the α-cell, the β-cell, the δ-cell, the ε-cell and the PP cell and may be a cell comprising the cells in the pancreatic islet.

In addition, "pancreatic islet cell" may be a cell that has become a pancreatic islet cell by differentiation, maturation, alteration or the like. In this case, "pancreatic islet cell" may also include, for example, a pancreatic islet cell obtained by differentiating a stem cell such as an iPS cell, an ES cell or a somatic stem cell (for example, a mesenchymal stem cell) and a pancreatic islet cell obtained by maturing a juvenile cell or a progenitor cell.

In the case of being used in a transplantation use, "insulin-secreting cell" or "pancreatic islet (comprising the pancreatic islet cell)" preferably has viability and functions favorable enough to recover the patient's morbidity when transplanted into a patient. Examples of the functions of the insulin-secreting cell, the pancreatic islet or the pancreatic islet cell include secretion of insulin, and it is preferable that glucose responsiveness be maintained even after transplantation.

Donors of "insulin-secreting cell", "pancreatic islet" or "pancreatic islet cell" are animals, preferably vertebrates and more preferably mammals, specific examples thereof include human, pigs, monkeys, rats, mice and the like, and human or pig is still more preferable. In several embodiments, the donors of "insulin-secreting cell", "pancreatic islet" or "pancreatic islet cell" are pigs from the viewpoint of donor shortage elimination. "Insulin-secreting cell", "pancreatic islet" or "pancreatic islet cell" may be any of a pancreatic islet or pancreatic islet cell obtained from an animal, which is a donor, or an insulin-secreting cell or pancreatic islet cell obtained from a donor-derived cell and may be, for example, an insulin-secreting cell or pancreatic islet cell differentiated from a human-derived ES cell or iPS cell.

In a case where "insulin-secreting cell", "pancreatic islet" or "pancreatic islet cell" is derived from a pig, insulin-secreting cells or pancreatic islet cells obtained from an adult porcine islet, a fetal, neonatal or perinatal porcine islet or the pancreatic islet are exemplary examples. The pancreatic islet may be used after being appropriately cultured, and a pancreatic islet obtained by maturing a fetal, neonatal or perinatal porcine islet may be used.

Examples of the blood coagulation factor-secreting cell include factor VIII-secreting cells and factor IX-secreting cells.

9. Method for Manufacturing Polymer-Coated Crosslinked Alginate Gel Fiber

In the following description, the chemically modified alginic acid derivative represented by Formula (I) and the chemically modified alginic acid derivative represented by Formula (II) can be substituted by the chemically modified alginic acid derivative represented by Formula (I-A) and the chemically modified alginic acid derivative represented by Formula (II-A), respectively.

Here, a method for manufacturing a polymer-coated crosslinked alginate gel fiber in which crosslinked alginate gel (core layer) that comprises a cell enabling production of antibodies, bioactive substances or the like and is formed by performing a crosslinking reaction using the chemically modified alginic acid derivatives represented by Formula (I) and Formula (II) is coated with a cationic polymer (cationic polymer layer) is provided. For example, a method for manufacturing the fiber comprising the use of a device XX shown in FIG. 3 is provided.

Hereinafter, a method for manufacturing the polymer-coated crosslinked alginate gel fiber will be described.

The method for manufacturing the polymer-coated crosslinked alginate gel fiber is not particularly limited and is, for example, performed using the device XX shown in FIG. 3. The device XX herein is a device that is preferably used to produce the polymer-coated crosslinked alginate gel fiber.

The device XX is, for example, a device in which, as shown in FIG. 3, a micro flow channel comprising one introduction port and one discharge port can be produced, and a solution is introduced from the introduction port and made to flow at an appropriate speed, whereby the solution has a fiber shape (fibrous shape) and is discharged from the discharge port.

The device XX is, for example, capable of injecting the solution mixture comprising the cell enabling production of antibodies, bioactive substances or the like and the chemically modified alginic acid derivatives represented by Formula (I) and Formula (II), which has been introduced from the introduction port of the device XX, from the discharge port of the device XX by extruding the solution mixture using an extrusion tube YY as shown in FIG. 3.

As a device comprising the device XX and the extrusion tube YY, for example, an syringe can be used. In the case of the syringe, the device XX becomes an outer tube, and the extrusion tube YY for extruding the solution introduced into the device XX from the discharge port becomes an inner tube. In the case of using the syringe, it is possible to use a glass or plastic syringe.

As shown in FIG. 3, as a container that receives the fiber-like substance that is discharged from the discharge port 2 of the device XX, a container DD, such as a beaker comprising a solution having a divalent metal ion, is used. Alternatively, as a container for coating the surface of the crosslinked alginate gel fiber CLA with the cationic polymer, a container EE, such as a beaker comprising a solution having a cationic polymer, is used.

FIG. 3 is a schematic view for describing one embodiment of a manufacturing process of the polymer-coated crosslinked alginate gel fiber. As one example, a production method where a solution mixture of the chemically modified alginic acid derivatives comprising a cell (a cell enabling production of antibodies, bioactive substances or the like) and represented by Formula (I) and Formula (II) is used will be described.

The polymer-coated crosslinked alginate gel fiber can be manufactured by, for example, a method comprising the following steps (S) to (2).

Step (S): A step of introducing a solution mixture comprising a cell enabling production of antibodies, bioactive substances or the like and the chemically modified alginic acid derivatives represented by Formula (I) and Formula (II) from the introduction port 1 of the device XX, step (1): A step of injecting the solution mixture comprising a cell enabling production of antibodies, bioactive substances or the like and the chemically modified alginic acid derivatives represented by Formula (I) and Formula (II) into a solution comprising a divalent metal ion from the discharge port 2 of the device XX and bringing the solution mixture into contact with the divalent metal ion to obtain a crosslinked alginate gel fiber (CLA) comprising the cell enabling production of antibodies, bioactive substances or the like, and step (2): a step of bringing the crosslinked alginate gel fiber (CLA) comprising a cell enabling production of antibodies, bioactive substances or the like obtained in the step (1) into contact with a solution comprising a cationic polymer, thereby obtaining a polymer-coated crosslinked alginate gel fiber (CFB) that is formed by being coated with a cationic polymer layer.

In the step (S), the cell enabling production of antibodies, bioactive substances or the like, which is described as the above-described cell that is contained in the core layer, is suspended or dissolved in a solution comprising the chemically modified alginic acid derivatives represented by Formula (I) and Formula (II). At this time, it is also possible to add, aside from the cell enabling production of antibodies, bioactive substances or the like, a component such as an alginic acid solution, a culture medium, a culture fluid, a collagen solution, methylcellulose or a sucrose solution.

In the step (1), the solution mixture (or suspension) comprising a cell enabling production of antibodies, bioactive substances or the like and the chemically modified alginic acid derivatives represented by Formula (I) and Formula (II) prepared in the step (S) is slowly discharged to the solution comprising a divalent metal ion, whereby the discharged solution sequentially gelates, which makes it possible to manufacture a fiber-like (fibrous) structure. The solution mixture is brought into contact with the solution comprising a divalent metal ion, whereby ionic crosslinking progresses between the chemically modified alginic acid derivatives represented by Formula (I) and Formula (II), at the same time, chemical crosslinking by a Huisgen reaction also progresses, and gel can be produced.

In the step (2), the crosslinked alginate gel fiber comprising a cell enabling production of antibodies, bioactive substances or the like obtained in the step (1) is brought into contact with a solution comprising a cationic polymer, whereby the surface of the crosslinked alginate gel fiber comprising a cell enabling production of antibodies, bioactive substances or the like is coated with a cationic polymer layer.

The polymer-coated crosslinked alginate gel fiber (CFB) of the present invention can be manufactured by performing the steps (S) to (2).

In the present specification, "contact" means that a certain solution (for example, the solution of the chemically modified alginic acid derivative) or gel (for example, crosslinked alginate gel) is immersed in or added to another solution (for example, the solution comprising a divalent metal ion or the solution comprising a cationic polymer) or the like.

The flow rate (injection rate) of the solution mixture comprising the cell enabling production of antibodies, bioactive substances or the like and the chemically modified alginic acid derivatives represented by Formula (I) and Formula (II), which is injected from the discharge port 2 of the device XX, may be, for example, approximately 100 to approximately 10000 μL/minute. For example, the flow rate in the case of producing a polymer-coated crosslinked alginate gel fiber comprising an anti-GPVI antibody-producing CHO cell or a tocilizumab-producing CHO cell in the core layer is, for example, 250 μL/minute, 4 mL/minute, 10 mL/minute or the like, and the flow rate in the case of producing a polymer-coated crosslinked alginate gel fiber comprising a MING cell in the core layer is, for example, 125 μL/minute. The flow rate (injection rate) can be adjusted using a cylinder pump or the like, which makes it possible to manufacture fibers having a variety of sizes. Alternatively, it also becomes possible to manufacture fibers in which the diameter of the core layer can be adjusted by changing the size (diameter) of the discharge port 2 of the device XX.

A needle for luer lock syringe (metal needle), a syringe tube, a glass capillary and the like are appropriately combined and connected to the discharge port 2 of the device XX, whereby it is possible to discharge the solution mixture comprising the cell enabling production of antibodies, bioactive substances or the like and the chemically modified alginic acid derivatives represented by Formula (I) and Formula (II) to the solution comprising a divalent metal ion.

Regarding the solution mixture comprising the cell enabling production of antibodies, bioactive substances or the like and the chemically modified alginic acid derivatives represented by Formula (I) and Formula (II), which is introduced from the introduction port 1 of the device XX, for example, the chemically modified alginic acid derivatives represented by Formula (I) and Formula (II) described in the embodiment [1] are used, and a solvent (for example, a culture medium, a cell culture medium, a culture fluid, an isotonic buffer, a phosphate buffered saline, a physiological saline and the like) is added to prepare a solution mixture of the chemically modified alginic acid derivatives represented by Formula (I) and Formula (II) having a predetermined concentration (for example, the concentration of the solution of each chemically modified alginic acid derivative is approximately 0.01 to approximately 1.5 wt %, and the concentration of the solution mixture of the chemically modified alginic acid derivatives represented by Formula (I) and Formula (II) is approximately 0.02 to approximately 2.0 wt %).

In a case where an alginic acid solution is added to the solution mixture comprising the cell enabling production of antibodies, bioactive substances or the like and the chemically modified alginic acid derivatives represented by Formula (I) and Formula (II), which is introduced from the introduction port 1 of the device XX, the total concentration of the concentration of the solution mixture comprising the chemically modified alginic acid derivatives represented by Formula (I) and Formula (II) and the concentration of the alginic acid solution is prepared to, for example, a range of approximately 0.5 to approximately 2.0 wt %.

In a case where the alginic acid solution is added to the solution mixture comprising the cell enabling production of antibodies, bioactive substances or the like and the chemically modified alginic acid derivatives represented by Formula (I) and Formula (II), which is introduced from the introduction port 1 of the device XX, the combination of the concentration (C1 (wt %)) of the solution mixture comprising the chemically modified alginic acid derivatives represented by Formula (I) and Formula (II) and the concentration (C2 (wt %)) of the alginic acid solution is not particularly limited and is, for example, a combination of ranges satisfying formulae represented by $0<C2$ (wt %)≤approximately 1.98 (wt %), $0<C1$ (wt %)≤approximately 2.0 (wt %)−C2 (wt %) and $0<C1+C2$ (wt %)≤approximately 2.0 (wt %), and examples thereof include combinations such as (C1:C2) =(approximately 0.2:approximately 1.3), (approximately 0.5:approximately 1.0), (approximately 1.0:approximately 0.5), (approximately 0.66:approximately 1.34), (approximately 0.34:approximately 0.66) and (approximately 0.16:approximately 0.34). Aside from these concentrations, the solution mixture can be prepared in an appropriate combination of the concentrations C1 and C2.

In a case where the alginic acid solution is added to the solution mixture comprising the cell enabling production of antibodies, bioactive substances or the like and the chemically modified alginic acid derivatives represented by Formula (I-A) and Formula (II-A), which is introduced from the introduction port 1 of the device XX, the combination of the concentration (C1x (wt %)) of the solution mixture comprising the chemically modified alginic acid derivatives represented by Formula (I-A) and Formula (II-A) and the concentration (C2x (wt %)) of the alginic acid solution is not particularly limited and is, for example, a combination of ranges satisfying formulae represented by $0<C2x$ (wt %)≤approximately 1.98 (wt %), $0<C1x$ (wt %)≤approximately 2.0 (wt %)−C2x (wt %) and $0<C1x+C2x$ (wt %)≤approximately 2.0 (wt %), and examples thereof include combinations such as (C1x:C2x)=(approximately 0.2:approximately 1.3), (approximately 0.5:approximately 1.0), (approximately 1.0:approximately 0.5), (approximately 0.66:approximately 1.34), (approximately 0.34:approximately 0.66) and (approximately 0.16:approximately 0.34). Aside from these concentrations, the solution mixture can be prepared in an appropriate combination of the concentrations C1 and C2.

In a case where the alginic acid solution is added to the solution mixture comprising the cell enabling production of antibodies, bioactive substances or the like and the chemically modified alginic acid derivatives represented by Formula (I) and Formula (II), which is introduced from the introduction port 1 of the device XX, the combination of the concentration (C1A (wt %)) of the solution of the chemically modified alginic acid derivative represented by Formula (I), the concentration (C1N (wt %)) of the solution of the chemically modified alginic acid derivative represented by Formula (II) and the concentration (C2 (wt %)) of the alginic acid solution is not particularly limited and is, for example, a combination of ranges satisfying formulae represented by $0<C2$ (wt %)≤approximately 1.98 (wt %), $0<C1A$ (wt %)≤approximately 2.0 (wt %)−C2 (wt %), $0<C1N$ (wt %)≤approximately 2.0 (wt %)−C2 (wt %) and $0<C1A+C1N+C2$ (wt %)≤approximately 2.0 (wt %), and examples thereof include combinations of (C1A:C1N:C2) =(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34), (approximately 0.17:approximately 0.17:approximately 0.66), (approximately 0.08:approximately 0.08:approximately 0.34) and the like. Aside from these concentrations, the solution mixture can be prepared in an appropriate combination of the concentrations C1A, C1N and C2.

In a case where the alginic acid solution is added to the solution mixture comprising the cell enabling production of antibodies, bioactive substances or the like and the chemically modified alginic acid derivatives represented by Formula (I-A) and Formula (II-A), which is introduced from the introduction port 1 of the device XX, the combination of the concentration (C1Ax (wt %)) of the solution of the chemically modified alginic acid derivative represented by Formula (I-A), the concentration (C1Nx (wt %)) of the solution of the chemically modified alginic acid derivative represented by Formula (II-A) and the concentration (C2x (wt %)) of the alginic acid solution is not particularly limited and is, for example, a combination of ranges satisfying formulae represented by 0<C2x (wt %)≤approximately 1.98 (wt %), 0<C1Ax (wt %)≤approximately 2.0 (wt %)−C2x (wt %), 0<C1Nx (wt %)≤approximately 2.0 (wt %)−C2x (wt %) and 0<C1Ax+C1Nx+C2x (wt %)≤approximately 2.0 (wt %), and examples thereof include combinations such as (C1Ax:C1Nx:C2x)=(approximately 0.1:approximately 0.1:approximately 1.3), (approximately 0.25:approximately 0.25:approximately 1.0), (approximately 0.5:approximately 0.5:approximately 0.5), (approximately 0.33:approximately 0.33:approximately 1.34), (approximately 0.17:approximately 0.17:approximately 0.66) and (approximately 0.08:approximately 0.08:approximately 0.34). Aside from these concentrations, the solution mixture can be prepared in an appropriate combination of the concentrations C1Ax, C1Nx and C2x.

Each volume ratio (v1, v2) of the solution of the chemically modified alginic acid derivative represented by Formula (I) and the solution of the chemically modified alginic acid derivative represented by Formula (II) in the solution mixture comprising the cell enabling production of antibodies, bioactive substances or the like and the chemically modified alginic acid derivatives represented by Formula (I) and Formula (II), which is introduced from the introduction port 1 of the device XX, is, for example, a ratio in the case of v1+v2=15 and, for example, (v1:v2)=(7.5:7.5). Here, in v1+v2=15, 0<v1<15 and 0<v2<15.

Each volume ratio (v1x, v2x) of the solution of the chemically modified alginic acid derivative represented by Formula (I-A) and the solution of the chemically modified alginic acid derivative represented by Formula (II-A) in the solution mixture comprising the cell enabling production of antibodies, bioactive substances or the like and the chemically modified alginic acid derivatives represented by Formula (I-A) and Formula (II-A), which is introduced from the introduction port 1 of the device XX, is, for example, a ratio in the case of v1x+v2x=15 and, for example, (v1x:v2x)=(7.5:7.5). Here, in v1x+v2x=15, 0<v1x<15 and 0<v2x<15.

In a case where the alginic acid solution is added to the solution mixture comprising the cell enabling production of antibodies, bioactive substances or the like and the chemically modified alginic acid derivatives represented by Formula (I) and Formula (II), which is introduced from the introduction port 1 of the device XX, the volume ratio of the volume (v1) of the chemically modified alginic acid derivative represented by Formula (I), the volume (v2) of the chemically modified alginic acid derivative represented by Formula (II) and the volume (v3) of the alginic acid solution in the solution mixture to which the alginic acid solution has been added is, for example, a ratio in the case of v1+v2+v3=15 and, for example, a combination of (v1:v2:v3)=(5:5:5), (2.5:2.5:10), (1:1:13) or the like. Here, in v1+v2+v3=15, 0<v1<15, 0<v2<15 and 0<v3<15.

In a case where the alginic acid solution is added to the solution mixture comprising the cell enabling production of antibodies, bioactive substances or the like and the chemically modified alginic acid derivatives represented by Formula (I-A) and Formula (II-A), which is introduced from the introduction port 1 of the device XX, the volume ratio of the volume (v1x) of the chemically modified alginic acid derivative represented by Formula (I-A), the volume (v2x) of the chemically modified alginic acid derivative represented by Formula (II-A) and the volume (v3x) of the alginic acid solution in the solution mixture to which the alginic acid solution has been added is, for example, a ratio in the case of v1x+v2x+v3x=15 and, for example, a combination of (v1x:v2x:v3x)=(5:5:5), (2.5:2.5:10), (1:1:13) or the like. Here, in v1x+v2x+v3x=15, 0<v1x<15, 0<v2x<15 and 0<v3x<15.

A crosslinked alginate gel fiber (CLA) having a desired length can be obtained by cutting the solution mixture that is injected at the time of injecting the solution mixture containing the cell enabling production of antibodies, bioactive substances or the like and the chemically modified alginic acid derivatives represented by Formula (I) and Formula (II) from the discharge port 2 of the device XX at certain intervals using a cutting tool such as scissors or a cutter. The length of the crosslinked alginate gel fiber (CLA) is not particularly limited, and examples thereof include approximately 0.01 m to approximately 100 m, approximately 0.1 m to approximately 75 m, approximately 0.3 m to approximately 50 m, approximately 0.5 m to approximately 30 m, approximately 1.0 m to approximately 10 m, approximately 1.0 m to approximately 2.0 m, approximately 2.0 m to approximately 3.0 m, approximately 3.0 m to approximately 4.0 m, approximately 4.0 m to approximately 5.0 m, approximately 5.0 m to approximately 6.0 m, approximately 6.0 m to approximately 7.0 m, approximately 7.0 m to approximately 8.0 m, approximately 8.0 m to approximately 9.0 m, approximately 9.0 m to approximately 10 m, approximately 1 cm to approximately 5 cm, approximately 5 cm to approximately 10 cm, approximately 10 cm to approximately 20 cm, approximately 20 cm to approximately 30 cm, approximately 30 cm to approximately 40 cm, approximately 40 cm to approximately 50 cm, approximately 50 cm to approximately 60 cm, approximately 60 cm to approximately 70 cm, approximately 70 cm to approximately 80 cm, approximately 80 cm to approximately 90 cm, approximately 90 cm to approximately 1.0 m, approximately 90 cm to approximately 1.0 m and the like.

A crosslinked alginate gel fiber (CLA) having a desired length can be obtained by cutting the solution mixture that is injected at the time of injecting the solution mixture containing the cell enabling production of antibodies, bioactive substances or the like and the chemically modified alginic acid derivatives represented by Formula (I-A) and Formula (II-A) from the discharge port 2 of the device XX at certain intervals using a cutting tool such as scissors or a cutter. The length of the crosslinked alginate gel fiber (CLA) is not particularly limited, and examples thereof include the same lengths as described above.

The outer diameter of the polymer-coated crosslinked alginate gel fiber (CFB) to be produced is not particularly limited, is as described above and is, for example, within a range of approximately 0.1 to approximately 2000 approximately 0.2 to approximately 2000 approximately 0.2 to approximately 1000 approximately 0.5 to approximately 1000 approximately 1 to approximately 1000 approximately 10 to approximately 1000 approximately 20 to approximately 1000 μm or the like.

The length of the polymer-coated crosslinked alginate gel fiber (CFB) is not particularly limited, is as described above and may be, for example, approximately 0.3 to approximately 50 m. In addition, the adjustment of the length of the crosslinked alginate gel fiber (CLA) makes it possible to obtain a polymer-coated crosslinked alginate gel fiber (CFB) having a length of approximately 0.01 m to approximately 100 m, approximately 0.1 m to approximately 75 m, approximately 0.3 m to approximately 50 m, approximately 0.5 m to approximately 30 m, approximately 1.0 m to approximately 10 m, approximately 1.0 m to approximately 2.0 m, approximately 2.0 m to approximately 3.0 m, approximately 3.0 m to approximately 4.0 m, approximately 4.0 m to approximately 5.0 m, approximately 5.0 m to approximately 6.0 m, approximately 6.0 m to approximately 7.0 m, approximately 7.0 m to approximately 8.0 m, approximately 8.0 m to approximately 9.0 m, approximately 9.0 m to approximately 10 m, approximately 1 cm to approximately 5 cm, approximately 5 cm to approximately 10 cm, approximately 10 cm to approximately 20 cm, approximately 20 cm to approximately 30 cm, approximately 30 cm to approximately 40 cm, approximately 40 cm to approximately 50 cm, approximately 50 cm to approximately 60 cm, approximately 60 cm to approximately 70 cm, approximately 70 cm to approximately 80 cm, approximately 80 cm to approximately 90 cm, approximately 90 cm to approximately 1.0 m, approximately 90 cm to approximately 1.0 m or the like.

The cross-sectional shape of the polymer-coated crosslinked alginate gel fiber (CFB) is as described above, and examples thereof include a circular shape, an elliptical shape, a polygonal shape such as a square shape or a pentagonal shape, or the like.

The solution comprising a divalent metal ion with which the solution mixture comprising the cell enabling production of antibodies, bioactive substances or the like and the chemically modified alginic acid derivatives represented by Formula (I) and Formula (II) or the solution mixture comprising the cell enabling production of bioactive substances or the like and the chemically modified alginic acid derivatives represented by Formula (I-A) and Formula (II-A), which is injected from the discharge port 2 of the device XX, is brought into contact is as described in the "5-1. Crosslinked alginate gel", and examples thereof include solutions in which a calcium ion, a magnesium ion, a barium ion, a strontium ion, a zinc ion or the like is contained.

The concentration of the divalent metal ion in the solution comprising a divalent metal ion is, for example, within a range of approximately 1 mM to approximately 1 M or a range of approximately 10 to approximately 500 mM; preferably approximately 10 to approximately 100 mM.

A solvent that is used to prepare the solution comprising a divalent metal ion is as described in the "5-1. Crosslinked alginate gel", and examples thereof include water, physiological saline and the like.

The time during which the solution mixture comprising the cell enabling production of antibodies, bioactive substances or the like and the chemically modified alginic acid derivatives represented by Formula (I) and Formula (II), which is injected from the discharge port 2 of the device XX, is brought into contact with the solution comprising a divalent metal ion is, for example, approximately one minute to 60 minutes, one minute to 30 minutes or the like.

The solution comprising a cationic polymer with which the crosslinked alginate gel fiber (CLA) that is obtained in the step (2) of the method for manufacturing the polymer-coated crosslinked alginate gel fiber is brought into contact is the solution comprising a cationic polymer described in the "7. Cationic polymer", and examples thereof include solutions comprising a polyamino acid, a basic polysaccharide, a basic polymer or the like.

The concentration of the solution comprising a cationic polymer with which the crosslinked alginate gel fiber (CLA) is brought into contact is as described in the "7. Cationic polymer" and is, for example, approximately 0.02 to approximately 0.2 wt %, approximately 0.05 to approximately 0.1 wt % or the like.

The solution comprising a cationic polymer with which the crosslinked alginate gel fiber (CLA) is brought into contact may contain a component such as an aqueous solution having a divalent metal ion (for example, a calcium chloride aqueous solution, a barium chloride aqueous solution or the like), a sodium chloride aqueous solution or a buffer solution for adjusting the pH of the solution (an aqueous solution of acetic acid, sodium acetate, sodium hydroxide, hydroxyethylpiperazine ethane sulfonic acid or the like).

The time during which the crosslinked alginate gel fiber (CLA) is brought into contact with the solution comprising a cationic polymer is, for example, approximately one minute to 60 minutes, one minute to 30 minutes or the like.

In several embodiments, the temperature of the polymer-coated crosslinked alginate gel fiber during manufacturing is, for example, within a range of approximately 4° C. to approximately 37° C.

The manufacturing method makes it possible to easily obtain polymer-coated crosslinked alginate gel fibers having a core layer in which a certain number of cells enabling production of antibodies, bioactive substances or the like are contained.

In several embodiments, when the polymer-coated crosslinked alginate gel fiber is cultured in a culture fluid, an antibody-producing cell, a bioactive substance-producing cell or the like is cultured, and it is possible to produce antibodies, bioactive substances or the like. Appropriate exchange of culture fluids makes it possible for the polymer-coated crosslinked alginate gel fiber to continuously culture antibody-producing cells, bioactive substance-producing cells and the like for several weeks to several months.

The strength of the polymer-coated crosslinked alginate gel fiber can be measured by a shaking collapse test, a tensile strength test or the like according to a method well-known to a person skilled in the art.

In a case where "approximately" is used in the description in the present specification, unless particularly otherwise, values of up to the numerical value±20% and preferably up to the numerical value ±10% can also be included.

10. Method for Culturing Antibody-Producing Cell, Bioactive Substance-Producing Cell or the Like Here, a method for manufacturing an antibody, a bioactive substance or the like using the polymer-coated crosslinked alginate gel fiber comprising a cell enabling production of antibodies, bioactive substances or the like in the core layer, which are produced by the above-described manufacturing methods, is provided. For example, the polymer-coated crosslinked alginate gel fiber is put into a culture container, a culture medium is added thereto, the polymer-coated crosslinked alginate gel fiber is immersed therein, and culture is performed, whereby it is possible to manufacture antibodies, bioactive substances or the like. Hereinafter, "the method for manufacturing an antibody, a bioactive substance or the like" will be referred to as "the method for culturing an antibody-producing cell, a bioactive substance-producing cell or the like" in some cases.

Figure 4:
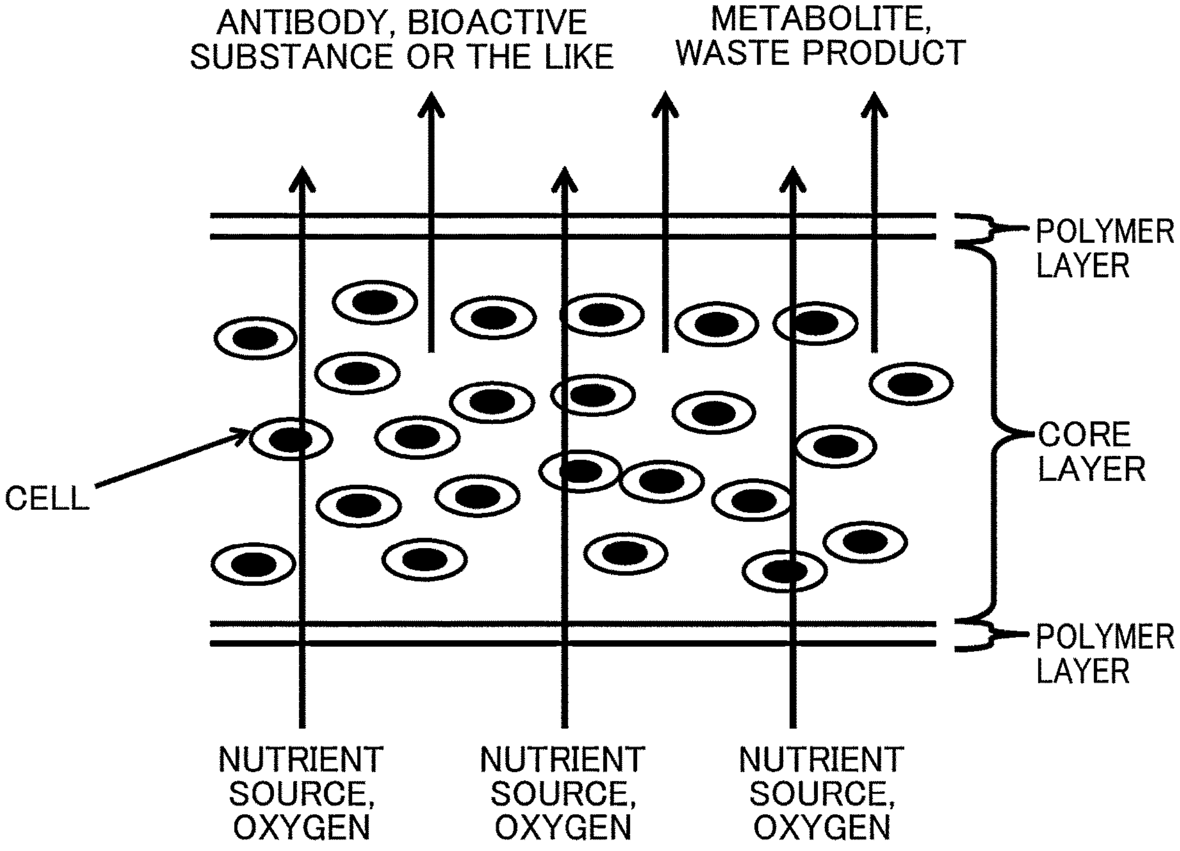
FIG. 4 is a lateral section of the polymer-coated crosslinked alginate gel fiber.
Figure 5:
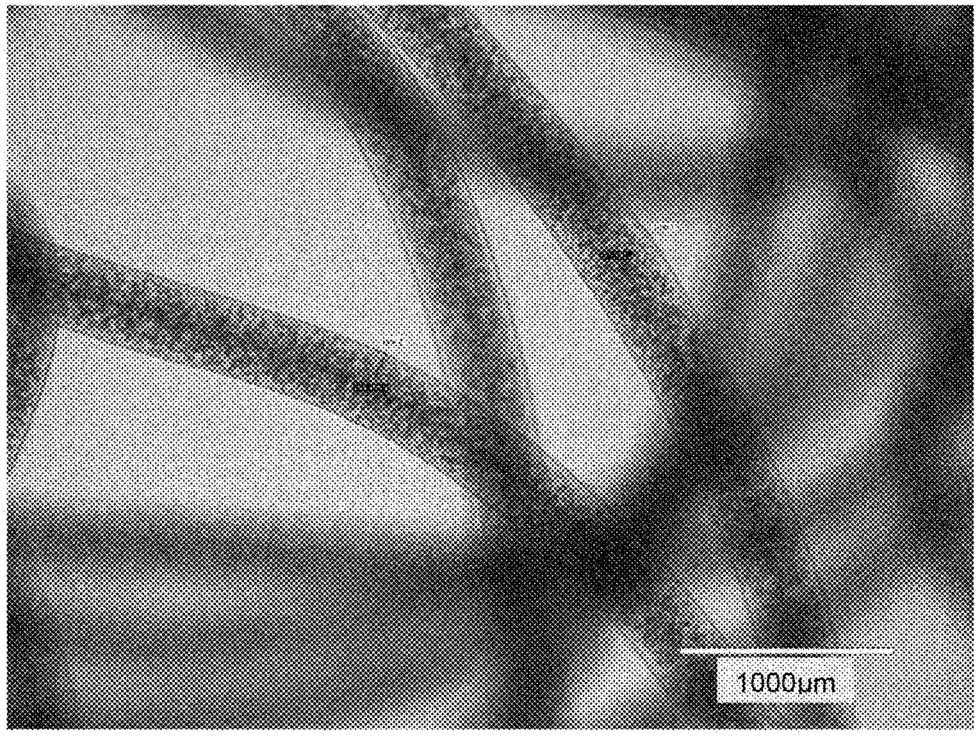
FIG. 5 is a photograph of a polymer-coated crosslinked alginate gel fiber (FB2-A-5-c1) of (Example F2-C) before culture.
Figure 6:
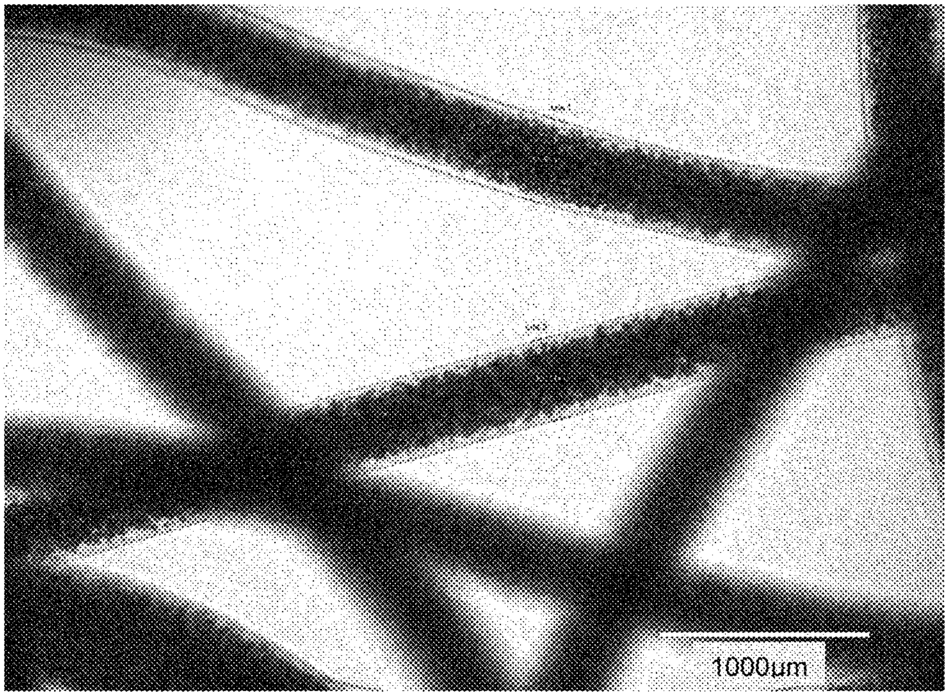
FIG. 6 is a photograph of the polymer-coated crosslinked alginate gel fiber (FB2-A-5-c1) of (Example F2-C) after culture.

According to a preferable embodiment of the method for culturing an antibody-producing cell, a bioactive substance-producing cell or the like, after the polymer-coated crosslinked alginate gel fiber comprising a cell enabling production of antibodies, bioactive substances or the like in the core layer is produced by the above-described manufacturing method, it is possible to immerse the polymer-coated crosslinked alginate gel fiber in a culture fluid to begin the culture of an antibody-producing cell, a bioactive substance-producing cell or the like at an early stage. Therefore, it is possible to immediately perform the supply of a culture fluid (nutrient source) and oxygen to the core layer as shown in FIG. 4, that is, culturing becomes possible without causing the necrosis of the antibody-producing cell, the bioactive substance-producing cell or the like, which is contained in the core layer. In a particularly preferable embodiment, it is possible to produce antibodies, bioactive substances and the like while the necrosis of the antibody-producing cell, the bioactive substance-producing cell or the like in the core layer of the polymer-coated crosslinked alginate gel fiber is sufficiently prevented.

The polymer-coated crosslinked alginate gel fiber of the present invention comprising a cell enabling production of antibodies, bioactive substances or the like in the core layer has sufficient permeability with respect to components such as a culture fluid (nutrient source) and oxygen that are present outside the fiber during the culture.

Hereinafter, an example of a method for culturing an antibody-producing cell will be specifically described, but the method is not limited thereto. The polymer-coated crosslinked alginate gel fiber comprising an antibody-producing cell in the core layer produced by the above-described manufacturing method is put into a vent cap-attached Erlenmeyer shake flask (Corning Incorporated, Cat. 431143), a culture medium (30 mL) having a composition in Table 31 below is added thereto, the gel fiber is immersed in the culture medium, and then the antibody-producing cell is cultured while being shaken in an incubator at 37° C. under a 5% $CO_2$ atmosphere under a condition of 125 rpm using a shaker (PHC Holdings Corporation's MIR-S100C). During the culture period, once two to three days, 1.8 mL of the culture medium is extracted, 1.8 mL of a feed solution (manufactured by Fujifilm Irvine Scientific, catalog No. JX F003) or a culture medium having a composition in Table 31 is added thereto, and the total amount of the culture medium is held at 30 mL. In addition, during the culture period, half the amount of the culture medium is exchanged once a week.

In addition, hereinafter, an example of a method for culturing a bioactive substance-producing cell will be specifically described, but the method is not limited thereto. The polymer-coated crosslinked alginate gel fiber comprising a bioactive substance-producing cell in the core layer produced by the above-described manufacturing method is put into an ultralow adhesive surface dish, a culture medium (5 mL) having a composition in Table 35 below is added thereto, and the bioactive substance-producing cell is placed still and cultured in an incubator at 37° C. under a 5% $CO_2$ atmosphere.

A technique for manufacturing an antibody, a bioactive substance or the like using a certain embodiment of a polymer-coated crosslinked alginate gel fiber is excellent in that antibody-producing cells, bioactive substance-producing cells or the like that are contained in the core layer do not grow up to more than a certain number, whereby physical stress on cells is small and thus the encapsulated antibody-producing cells, bioactive substance-producing cells or the like have a possibility of continuously producing antibodies, bioactive substances or the like for a long period of time.

In a particularly preferable embodiment, the method has a possibility of significantly improving the production and purification efficiency of antibodies (for example, the use of a preferable embodiment of the polymer-coated crosslinked alginate gel fiber also makes it possible to culture antibodies in small production facilities unlike suspension culture for which a large culture tank is required) and can be expected as a continuous production technique of next-generation antibody drugs also suitable for the manufacturing of a variety of items of antibody drugs in small quantities.

Antibodies (for example, an anti-GPVI antibody and tocilizumab) or bioactive substances (for example, insulin) produced by culturing may be stored in the core layer of the polymer-coated crosslinked alginate gel fiber and are preferably stored in a culture fluid outside the polymer-coated crosslinked alginate gel fiber after penetrating the core layer and the cationic polymer layer of the polymer-coated crosslinked alginate gel fiber.

Antibodies, bioactive substances or the like can be recovered and purified with reference to a description below.

In a preferable embodiment, as shown in FIG. 4, antibodies, bioactive substances or the like produced in the core layer of the polymer-coated crosslinked alginate gel fiber penetrate the core layer and the cationic polymer layer and are discharged outside the fiber, which makes it possible to form a cycle enabling the continuous culture of antibodies, bioactive substances or the like. At this time, a metabolite and a waste product may also be discharged outside the fiber.

Actually, in examples to be described below, as cells that were contained in the core layers, cells selected from anti-GPVI antibody-producing cells, tocilizumab-producing CHO cells or MING cells were used, as the chemically modified alginic acid derivative represented by Formula (I) that is used to form the crosslinked alginate gel in the core layer, a chemically modified alginic acid derivative selected from the following formulae:

[C61]

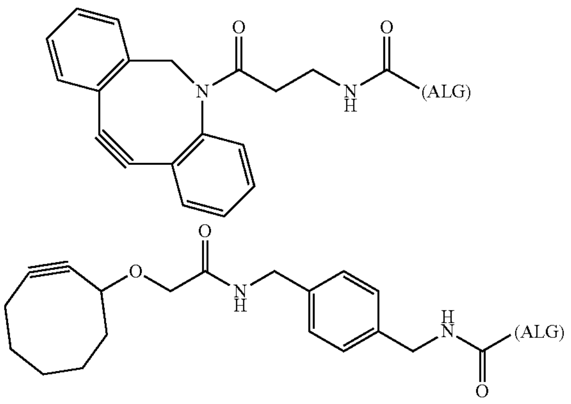

[in the formulae, (ALG) represents alginic acid; —NHCO— represents an amide bond through an arbitrary carboxyl group of the alginic acid] was used, as the chemically modified alginic acid derivative represented by Formula (II) that is used to form the crosslinked alginate gel in the core layer, a chemically modified alginic acid derivative selected from the following formulae:

[C62]

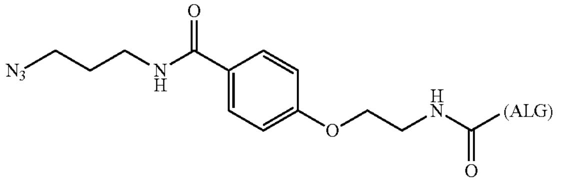

-continued

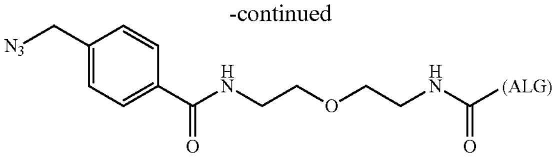

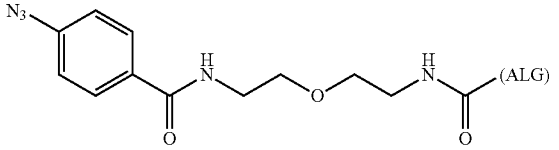

[in the formulae, (ALG) represents alginic acid; —NHCO— represents an amide bond through an arbitrary carboxyl group of the alginic acid] was used, and, as the cationic polymer in the cationic polymer layer, poly-L-ornithine, polyallylamine (PAA), polyethyleneimine or polymethylene-CO-guanidine (PMCG) was used to produce polymer-coated crosslinked alginate gel fibers.

In addition, it was possible to confirm places where the polymer-coated crosslinked alginate gel fiber obtained above was cultured and the fact that the produced antibodies (anti-GPVI antibody or tocilizumab) or bioactive substances (insulin) penetrated the core layer and the cationic polymer layer and were stored in the culture fluid.

A culture container where the polymer-coated crosslinked alginate gel fiber comprising a cell enabling production of antibodies, bioactive substances or the like in the core layer is cultured is, for example, a container selected from the group consisting of a tissue culture plate, an Erlenmeyer flask, a T-flask, a spinner flask, a culture bag, an animal cell culture tank and the like; preferably an Erlenmeyer flask or an animal cell culture tank. For culturing, any method of static culture, shaking/rocking culture and the like may be selected.

For improvement in the productivity of antibodies, bioactive substances or the like, an increase in the number of cells such as antibody-producing cells and bioactive substance-producing cells per culture is effective; however, conversely, such an increase causes excessive growth, degrades culture environments and may cause the shortening of the culture period. In the methods for manufacturing an antibody, a bioactive substance or the like of several embodiments, as a method for decreasing physical stress on cells, which is attributed to the excessive growth of the antibody-producing cell, the bioactive substance-producing cell or the like that is contained in the core layer of the polymer-coated crosslinked alginate gel fiber, for example, a method in which the antibody-producing cell, the bioactive substance-producing cell or the like that is contained in the core layer does not grow up to more than a certain number, methods such as the control of the culture temperature during culture and the addition of a cell growth inhibitor to culture fluids are exemplified.

In the methods for manufacturing an antibody, a bioactive substance or the like of several embodiments, the culture temperature is, for example, within a range of approximately 28° C. to approximately 39° C. and, for example, within a range of 30° C. to 37° C.

In the methods for manufacturing an antibody, a bioactive substance or the like of several embodiments, the culture temperature from the beginning to end of the culture can also timely changed. For example, it is possible to set the temperature at the time of beginning culture to approximately 37° C. and, at a stage after a certain time of culture, change the temperature to approximately 30° C.

In the methods for manufacturing an antibody, a bioactive substance or the like of several embodiments, the culture period is, for example, seven days or longer, 10 days or longer, 20 days or longer, 30 days or longer, 40 days or longer, 50 days or longer, 60 days or longer or 70 days or longer.

In the methods for manufacturing an antibody, a bioactive substance or the like of several embodiments, the culture period is, for example, seven days, 14 days, 28 days, 35 days, 42 days, 49 days, 56 days, 63 days or 70 days.

In the methods for manufacturing an antibody of several embodiments, it is also possible to add a cell growth inhibitor to the culture fluid. The cell growth inhibitor is an agent capable of inhibiting excessive cell growth during the culture period, and examples thereof include additives such as dimethyl sulfoxide, sodium butyrate, valproic acid, lithium chloride, valeric acid and methotrexate (MTX). The timing of adding the cell growth inhibitor to the culture fluid can be any of at the beginning of culture or in the middle of culture (when a required number of cells have grown). In the present specification, in a case where culture is performed using an anti-GPVI antibody-producing cell, methotrexate (MTX) is added.

In the present specification, as the cell culture medium, it is possible to use a commercially available culture base, a prepared culture medium or a self-made culture medium. Alternatively, it is also possible to use natural culture media (for example, a soybean-casein digest culture medium (SCD culture medium) and the like) or a synthetic culture medium (a culture medium in which all of the variety of nutrients necessary for growth are supplemented with chemicals). Alternatively, the cell culture medium is not particularly limited, but needs to be a basic culture medium comprising necessary components for cell survival and growth (inorganic salt, carbohydrate, hormone, essential amino acid, non-essential amino acid, vitamin and the like), and examples thereof include Dulbecco's modified eagle medium (DMEM), minimum essential medium (MEM), RPMI-1640, Basal medium eagle (BME), Dulbecco's modified eagle's medium: nutrient mixture F-12 (DMEM/F-12), glasgow minimum essential medium (glasgow MEM), a G016 culture medium, DMED (high glucose) and the like.

Alternatively, the culture medium may further contain serum. The serum is not particularly limited, and examples thereof include FBS/FCS (fetal bovine/calf serum), NCS (newborn calf serum), CS (calf serum), HS (horse serum) and the like. The concentration of the serum that is contained in the culture medium is, for example, 2 wt % or more and 10 wt % or less.

In the polymer-coated crosslinked alginate gel fiber of the present invention, since both ends of the crosslinked alginate gel fiber of the core layer are coated with the cationic polymer, leakage of a large number (for example, $1\times10^5$/mL or more cells) of cells such as antibody-producing cells or bioactive substance-producing cells that are contained in the core layer to the outside of the fiber during the culture period is prevented, suppressed or decreased.

11. Method for Calculating Number of Living Cells in Core Layer

Hereinafter, an example of a method for measuring the number of living cells in antibody-producing cells that are contained in the core layer of the polymer-coated crosslinked alginate gel fiber comprising the antibody-producing cells in the beginning of culture, in the middle of culture or after culture will be specifically described, but the method is not limited thereto.

A crosslinked alginate gel fiber, polymer-coated crosslinked alginate gel fiber comprising antibody-producing cells (0.2 mL) was moved to a 15 mL tube (centrifuge tube (with printed scales, bulk), model No: 2325-015-MYP), and a G016 culture medium (4.5 mL), which is a composition in Table 31 to be described below, is added thereto up to approximately 4.5 mL based on the scales of the tube. Subsequently, 30 μL of 1 mg/mL alginate lyase (poly α-guluronate lyase recombinant *Zobellia galactanivorans*) (Creative enzymes, Cat #NATE-1563) was added thereto and shaking-stirred at 30° C. and 125 rpm for one hour or longer. During the shaking stirring, the pipetting of the solution or the addition of the alginate lyase was performed as appropriate until the crosslinked alginate gel fiber uniformly dissolves. After uniform dissolution of the crosslinked alginate gel fiber is confirmed, the amount of the liquid is confirmed, and the G016 culture medium is added thereto, thereby adjusting the amount to 5 mL. A part of the solution is collected, and the number of cells is counted. The average value of two times of measurement is regarded as the number of living cells in the crosslinked alginate gel fiber.

12. Classification of Antibodies

Antibodies are referred to as mouse antibodies, rat antibodies, rabbit antibodies, human antibodies and the like depending on immune animal species during production. In order to reduce immunogenicity at the time of using antibodies in human beings, as altered antibodies obtained by converting partial regions of antibodies derived from different species into human sequences, there are chimeric antibodies and humanized antibodies, which are used as biopharmaceuticals. In addition, there are also antibodies produced from human antibody genes using a mouse into which human antibody genes have been integrated, which are referred to as human-type antibodies or simply human antibodies, which are used as biopharmaceuticals.

In addition to the above-described variety of antibodies, a variety of altered antibodies, which are referred to as next-generation antibodies, also have been developed, and, in the present specification, altered antibodies are also included in "antibodies". For example, there are multivalent antibodies that are antibodies exhibiting specificity with respect to two or more antigens, and, particularly, antibodies exhibiting bispecificity are referred to as bispecific antibodies, which are one of highly functionalized antibodies. There are also low-molecular-weight antibodies, which are antibodies given a low molecular weight by removing an Fc portion of an antibody, examples thereof include Fab, $F(ab')_2$, scFv (single-chain Fv), VHH and the like, which are used as biopharmaceuticals. Furthermore, bispecific low-molecular-weight antibodies also have been produced, and, for example, scFv-scFv is used as a biopharmaceutical. Antibodies in which an Fc region or the like is mutated to alter a sugar chain are also one example of altered antibodies. It is also possible to produce glycoengineered antibodies by transforming a host cell in advance to alter a sugar chain, and examples thereof include defucose-depleted antibodies. In the present specification, fusion proteins of an antibody or antibody fragment and a different protein or peptide are also exemplified as one example of altered antibodies, that is, antibodies; however, in the case of fusion proteins with the bioactive substance, the fusion proteins are also included in bioactive substances.

Antibodies are classified into classes (isotypes) and subclasses as shown in a table below depending on a difference in the structure of a constant region.

Classification of Human Ig

TABLE 9

| Class (isotype) | Subclass | Ratio in Ig (%) | Molecular weight (approximately) |
|---|---|---|---|
| IgG | IgG1 | 65 | 150,000 |
| | IgG2 | 25 | 150,000 |
| | IgG3 | 7 | 170,000 |
| | IgG4 | 3 | 150,000 |
| IgA | * | 10 to 15 | 320,000 |
| IgM | * | 10 | 900,000 |
| IgD | * | 1% or less | 180,000 |
| IgE | * | 0.001% or less | 200,000 |

13. Method for Producing and Purifying Antibody and Bioactive Substance

In the methods for manufacturing an antibody of several embodiments, an antibody that is produced in the core layer of a polymer-coated crosslinked alginate gel fiber by culturing an antibody-producing cell and is capable of penetrating the polymer layer is not particularly limited, and examples thereof include antibodies having a class (isotype) selected from the group consisting of IgG, IgA, IgM, IgD, IgE and the like. In a case where the produced antibody is used as a biopharmaceutical, IgG antibodies are preferable.

In the methods for manufacturing an antibody of several embodiments, the molecular weight of an antibody that is produced in the core layer of a polymer-coated crosslinked alginate gel fiber by culturing an antibody-producing cell and is capable of penetrating the cationic polymer layer is not particularly limited, but is, for example, an antibody having a molecular weight within a range of approximately 45,000 to approximately 1,000,000 Da. In addition, the molecular weight of an antibody capable of penetrating the cationic polymer layer is, for example, an antibody having a molecular weight within a range of approximately 3,000 to approximately 1,000,000 Da, approximately 20,000 to approximately 1,000,000 Da, approximately 20,000 to approximately 400,000 Da, approximately 45,000 to approximately 400,000 Da, approximately 20,000 to approximately 200,000 Da or approximately 45,000 to approximately 200,000 Da.

In the methods for manufacturing a bioactive substance of several embodiments, the molecular weight of a bioactive substance that is produced in the core layer of a polymer-coated crosslinked alginate gel fiber by culturing a bioactive substance-producing cell and is capable of penetrating the cationic polymer layer is not particularly limited, but is, for example, a bioactive substance having a molecular weight within a range of approximately 3,000 to approximately 1,000,000 Da, approximately 20,000 to approximately 1,000,000 Da, approximately 45,000 to approximately 1,000,000 Da, approximately 20,000 to approximately 400,000 Da, approximately 45,000 to approximately 400,000 Da, approximately 20,000 to approximately 200,000 Da or approximately 45,000 to approximately 200,000 Da.

In the present specification, in the case of performing culturing by the above-described method for manufacturing an antibody using each of the above-described antibody-producing cells, an antibody corresponding to the antibody-producing cell used is produced. For example, in a case where a muromonab-CD3 producing CHO cell is used, muromonab-CD3 is produced as an antibody.

In the present specification, in the case of performing culturing by the above-described method for manufacturing a bioactive substance using each of the above-described bioactive substance-producing cells, a bioactive substance corresponding to the bioactive substance-producing cell used is produced.

Examples of the antibody to be produced include muromonab-CD3 (IgG; 150,000) produced using a muromonab-CD3-producing CHO cell, trastuzumab (IgG; 148,000) produced using a trastuzumab-producing CHO cell, rituximab (IgG; 144,510) produced using a rituximab-producing CHO cell, palivizumab (IgG; 147,700) produced using a palivizumab-producing NS0 cell, infliximab (IgG; 149,000) produced using an infliximab-producing Sp2/0 cell or an infliximab-producing CHO cell, basiliximab (IgG; 147,000) produced using a basiliximab-producing Sp2/0 cell, tocilizumab (IgG; 148,000) produced using a tocilizumab-producing CHO cell, gemtuzumab (IgG; 150,000) produced using a gemtuzumab-producing CHO cell, bevacizumab (IgG; 149,000) produced using a bevacizumab-producing CHO cell, ibritumomab (IgG; 148,000) produced using an ibritumomab-producing CHO cell, adalimumab (IgG; 148,000) produced using an adalimumab-producing CHO cell, cetuximab (IgG; 151,800) produced using a cetuximab-producing Sp2/0 cell, ranibizumab (IgG(FAb); 48,000) produced using a ranibizumab-producing CHO cell, omalizumab (IgG; 149,000) produced using an omalizumab-producing CHO cell, eculizumab (IgG; 145,235) produced using an eculizumab-producing NS0 cell, panitumumab (IgG; 147,000) produced using a panitumumab-producing CHO cell, ustekinumab (IgG; 148,079 to 149,690) produced using a ustekinumab-producing Sp2/0 cell, golimumab (IgG; 149,802 to 151,064) produced using a golimumab-producing Sp2/0 cell, canakinumab (IgG; 148,000) produced using a canakinumab-producing Sp2/0 cell, denosumab (IgG; 150,000) produced using a denosumab-producing CHO cell, mogamulizumab (IgG; 149,000) produced using a mogamulizumab-producing CHO cell, certolizumab (IgG(Fab'); 50,000) produced using a certolizumab-producing CHO cell, ofatumumab (IgG; 149,000) produced using an ofatumumab-producing NS0 cell, pertuzumab (IgG; 148,000) produced using a pertuzumab-producing CHO cell, brentuximab (IgG; 148,000) produced using a brentuximab-producing CHO cell, natalizumab (IgG; 146,178) produced using a natalizumab-producing NS0 cell, nivolumab (IgG; 145,000) produced using a nivolumab-producing CHO cell, alemtuzumab (IgG; 150,000) produced using an alemtuzumab-producing CHO cell, secukinumab (IgG; 151,000) produced using a secukinumab-producing CHO cell, ramucirumab (IgG; 147,000) produced using a ramucirumab-producing NS0 cell, ipilimumab (IgG; 148,000) produced using an ipilimumab-producing CHO cell, evolocumab (IgG; 141,789) produced using an evolocumab-producing CHO cell, mepolizumab (IgG; 149,000) produced using a mepolizumab-producing CHO cell, alirocumab (IgG; 145892. 049.) produced using an alirocumab-producing CHO cell, ixekizumab (IgG; 149,000) produced using an ixekizumab-producing CHO cell, brodalumab (IgG; 147,000) produced using a brodalumab-producing CHO cell, idarucizumab (IgG(Fab); 47,782) produced using an idarucizumab-producing CHO cell, elotuzumab (IgG; 148,000) produced using an elotuzumab-producing NS0 cell, pembrolizumab (IgG; 149,000) produced using a pembrolizumab-producing CHO cell, sarilumab (IgG; 150,000) produced using a sarilumab-producing CHO cell, bezlotoxumab (IgG; 148,000) produced using a bezlotoxumab-producing CHO cell, belimumab (IgG; 147,000) produced using a belimumab-producing NS0 cell, daratumumab (IgG; 148,000) produced using a daratumumab-producing CHO cell, avelumab (IgG; 147,000) produced using an avelumab-producing CHO cell, dupilumab (IgG; 152,000) produced using a dupilumab-producing CHO cell, atezolizumab (IgG; 144,611) produced using an atezolizumab-producing CHO cell, benralizumab (IgG; 148,000) produced using a benralizumab-producing CHO cell, inotuzumab (IgG; 149,000) produced using an inotuzumab-producing CHO cell, emicizumab (IgG; 148,000) produced using an emicizumab-producing CHO cell, guselkumab (IgG; 146,000) produced using a guselkumab-producing CHO cell, durvalumab (IgG; 149,000) produced using a durvalumab-producing CHO cell, obinutuzumab (IgG; 148,000 to 150,000) produced using an obinutuzumab-producing CHO cell, vedolizumab (IgG; 150,000) produced using a vedolizumab-producing CHO cell or an anti-GPVI antibody (IgG; 150,000) produced using an anti-GPVI antibody-producing CHO cell (in the parentheses after the antibody names, the classes (isotypes) and molecular weights of the antibodies are shown). Antibodies that can be obtained by the method for manufacturing an antibody of the present invention are not particularly limited to the above-described classes (isotypes) or subclasses.

The produced antibody is purified by performing, for example, the following three steps.

[Step 1] In order to remove almost all of proteins and solid matters other than the antibody in the culture medium, filtration or the like by a centrifugation method or with a filter is performed.

[Step 2] An intended antibody is purified by, for example, chromatography such as affinity chromatography (in the case of an antibody, affinity chromatography where protein A or protein G is used) or ion exchange chromatography.

[Step 3] In order to highly purify the intended antibody, an impurity that has been contaminated in the step 2 is removed by performing ion exchange chromatography, gel filtration chromatography, hydroxyapatite chromatography or the like.

The produced bioactive substance is purified by, for example, performing the above-described steps by the same methods.

Affinity chromatography where protein A or protein G is used:

As a method for purifying IgG, for example, a method for purifying an antibody using protein A or protein G is known. As a method for purifying an antibody using protein A, the following method is exemplified as one example. (1) A solution obtained by adding serum to a solution obtained by the method of the above-described [Step 1] is filtered using a column filled with beads to which protein A is fixed, whereby IgG bonds to the beads in the column, and other serum components flows out from the column. (2) After that, an acidic solution is passed through the column, whereby IgG bonding to the beads is cut and eluted to the outside of the column and thereby IgG is obtained. Since the bonding forces of Ig to protein A and to protein G differ depending on animal species or subclass, it is possible to properly use protein A or protein G depending on the target.

Ion Exchange Chromatography

This is a method for separating protein using the electric properties (charges) of the protein. Since positively charged basic protein ionically bonds to a cation exchanger (carrier) having a negative charge, and negatively charged acidic protein bonds to an anion exchanger having a positive charge, a sample comprising protein is passed through a column filled with an ion exchanger, whereby protein bonds to the ion exchanger. After that, the salt concentration of a solvent that passes through the column is increased, whereby the ionic bond between the protein and the ion exchanger becomes weak, and protein having a weak bonding force begins to sequentially detach from the ion exchanger and flows out from the column. Regarding the selection of a cation exchanger or an anion exchanger, the exchanger is selected based on the charge of protein that is used as a sample.

Gel Filtration Chromatography:

This is a method for separating protein using a difference in the molecular weight of the protein. When a sample is caused to flow through a column filled with a carrier with a small hole, since protein having a small molecular weight enters the small hole and flows out, but protein having a large molecular weight flows out without entering the small hole, the time taken for the protein having a small molecular weight to pass through the column is slow, and the time for the protein having a large molecular weight becomes fast, and thus it becomes possible to separate protein based on a difference in time.

Hydroxyapatite Chromatography:

This is a chromatography where hydroxyapatite, which is one kind of calcium phosphate, is used. This is a method for separating protein using a plurality of interactions mainly based on the metal affinity by a calcium ion and anion exchange by a phosphate group. A carboxyl group and an amino group of an amino acid are each adsorbed due to an interaction with a carrier, and high-concentration phosphoric acid or a solvent having a high salt concentration are caused to flow, thereby separating a target and impurities.

14. Physical Properties of Polymer-Coated Crosslinked alginate Gel Fiber

[Method for Confirming Stability of Polymer-Coated Crosslinked alginate Gel Fiber]

In the present specification, the stability of the polymer-coated crosslinked alginate gel fiber can be confirmed by, for example, the following testing methods. More specifically, the stability can be confirmed by methods to be described in the following examples.

<Shaking collapse test>: A polymer-coated crosslinked alginate gel fiber that is obtained by the above-described manufacturing method is suspended in phosphate buffered saline (PBS), the suspension is shaken for a certain time and then the collapse easiness (degree of shaking collapse) of the fiber is confirmed, whereby the physical strength can be measured. Examples of a specific testing method include a method to be described in the following examples.

<Tensile test test>: The rupture value (mN) is confirmed using a polymer-coated crosslinked alginate gel fiber that is obtained by the above-described manufacturing method and a tensile strength-measuring instrument, whereby the physical strength can be measured. Examples of a specific testing method include a method to be described in the following examples.

The strength of the polymer-coated crosslinked alginate gel fiber of the present invention is attributed to the fact that the crosslinked alginate gel, which configures the fiber and is contained in the core layer, and an electrostatic action between the crosslinked alginate gel and the cationic polymer, which is formed between the core layer and the cationic polymer layer, have optimal properties in terms of the strength of the fiber of the present invention.

The polymer-coated crosslinked alginate gel fiber of the present invention has high physical stability, also has appropriate permeability due to the fact that antibodies, bioactive substances or the like produced in the core layer are discharged from the core layer and, furthermore, are capable of penetrating the polymer layer(s) and is also a structure suitable for the production of antibodies, bioactive substances or the like.

15. Measurement of Introduction Rate of Reactive Group (Complementary Reactive Group) into Chemically Modified Alginic Acid Derivative The reactive group or complementary reactive group introduction rate means a value expressing the number of the reactive groups or the complementary reactive groups introduced per uronic acid monosaccharide unit, which is the repeating unit of alginic acid.

In the examples to be described below, the reactive group or complementary reactive group introduction rate (mol %) was calculated from the integral ratio in 41-NMR. In addition, the amount of alginic acid necessary for the calculation of the introduction rate can be measured by the carbazole sulfate method in which a calibration curve is used, and the amount of the reactive group or the complementary reactive group can also be measured by spectrophotometry in which a calibration curve is used.

16. Measurement of Molecular Weight of Chemically Modified Alginic Acid Derivative A solid of the chemically modified alginic acid derivative obtained in the examples to be described below was dissolved in a 10 mmol/L phosphate buffer solution comprising 0.15 mol/L of NaCl (pH: 7.4) to prepare a 0.1% or 0.2% solution, an insoluble matter was removed by passing the solution through a polyether sulfone filtration filter having a pore diameter of 0.22 μm (Minisart High Flow Filter, Sartorius AG), and then the solution was used as a gel filtration sample. The spectrum of each sample was measured with a spectrophotometer DU-800 (Beckman Coulter, Inc.), and the measurement wavelength in the gel filtration of each compound was determined. For compounds having no peculiar absorption wavelength, a differential refractometer was used.

200 μL of the gel filtration sample was fed into a Superose 6 Increase 10/300 GL column (GE Healthcare Corporation). Gel filtration was performed under conditions of room temperature and a flow rate of 0.8 mL/min using AKTA Explorer 10S as a chromatography device and a 10 mmol/L phosphate buffer solution comprising 0.15 mol/L of NaCl (pH: 7.4) as a developing solvent. The elution profile of the sample was produced by monitoring the absorption of the wavelength determined in each compound. The obtained chromatogram was analyzed with Unicorn 5.31 software (GE Healthcare Corporation), and the peak range was determined.

Regarding the molecular weight of alginic acid into which the reactive group or the complementary reactive group had been introduced, blue dextran (molecular weight: 2,000,000 Da, Sigma-Aldrich), thyroglobulin (molecular weight: 669,000 Da, GE Healthcare Corporation), ferritin (molecular weight: 440,000 Da, GE Healthcare Corporation), aldolase (molecular weight: 158,000 Da, GE Healthcare Corporation), conalbumin (molecular weight: 75,000 Da, GE Healthcare Corporation), ovalbumin (molecular weight: 44,000 Da, GE Healthcare Corporation), ribonuclease A (molecular weight: 13,700 Da, GE Healthcare Corporation) and aprotinin (molecular weight: 6,500 Da, GE Healthcare Corporation) were used as standard products, gel filtration was performed under the same conditions as for alginic acid into which the reactive group or the complementary reactive group had been introduced, and the amount of the eluate of each component was determined with Unicorn software.

The amount of the eluate of each component was plotted along the horizontal axis, the absolute value of the molecular weight was plotted along the vertical axis, respectively, and calibration curves were created by linear regression. Two calibration curves were created from blue dextran to ferritin and from ferritin to aprotinin.

The molecular weight (Mi) at an elution time i in the previously-obtained chromatogram was calculated using this calibration curve. Next, the absorbance at the elution time i was read and regarded as Hi. The weight-average molecular weight (Mw) was obtained from this data through the following formula.

$$Mw = \frac{\sum_{i=1}^{\infty}(H^i \times Mi)}{\sum_{i=1}^{\infty} Hi} \quad \text{[Math. 1]}$$

All publications, published publications, patent publications and other patent literature cited in the present specification are regarded as being incorporated by reference into the present specification regardless of purposes thereof.

In addition, the objective, characteristics, advantages and ideas of the present invention are clear to a person skilled in the art from the description of the present specification, and a person skilled in the art should be able to perform the present invention based on the description of the present specification. Embodiments, specific examples and the like for performing the invention show preferable embodiments of the present invention, are shown for exemplification or description, and do not limit the present invention thereto. It is clear to a person skilled in the art that a variety of modifications based on the description of the present specification are possible within the intention and scope of the present invention that are disclosed in the present specification.

EXAMPLES

Hereinafter, the present invention will be described with examples, but the present invention is not limited to the following examples.

[Method for Synthesizing Chemically Modified Alginic Acid Derivative]

In the measurement of a nuclear magnetic resonance spectrum (NMR), JEOL JNM-ECX 400 FT-NMR (JEOL Ltd.) was used. Liquid chromatography-mass spectrometry (LC-Mass) was measured by the following method. [UPLC] Waters ACQUITY UPLC system and BEH C18 column (2.1 mm×50 mm, 1.7 μm) (Waters Corporation) were used, and mobile phases and gradient conditions of acetonitrile:0.05% trifluoroacetate aqueous solution=5:95 (0 minutes) to 95:5 (1.0 minute) to 95:5 (1.6 minutes) to 5:95 (2.0 minutes) were used.

In $^{1}$H-NMR data, regarding the patterns of NMR signals, s means singlet, d means doublet, t means triplet, q means quartet, m means multiplet, br means broad, J means the coupling constant, Hz means hertz, $CDCl_3$ means deuterated chloroform, DMSO-$d_6$ means deuterated dimethyl sulfoxide, and D20 means deuterium oxide. Regarding signals that were broad bands and thus could not be confirmed such as protons of a hydroxyl group (OH), an amino group ($NH_2$) and a carboxyl group (COOH), data was not entered in the $^{1}$H-NMR data.

In LC-Mass data, M means the molecular weight, RT means the retention time, and $[M+H]^+$ and $[M+Na]^+$ mean molecular ionic peaks.

"Room temperature" or "r.t." in the examples normally indicates temperatures from approximately 0° C. to approximately 35° C. [DMT-MM] in the examples means 4-(4,6-dimethoxy-1,3,5-triazin-2-yl)-4-methylmorpholinium chloride (CAS REGISTRY NO.: 3945-69-5), and it is possible to use a commercially available product or a substance synthesized by a method well known by publications.

The reactive group introduction rate (mol %) in the examples is considered to indicate the proportion of the mole number of a reactive group introduced in the mole number of a monosaccharide (guluronic acid and mannuronic acid) unit that configures alginic acid calculated from the integral ratio of 41-NMR (D20).

In the examples, as sodium alginates, sodium alginates having physical property values shown in Table 8 (A-1 to A-3, B-2 and B-3) were used. In addition, filter sterilization was performed on sodium alginates or a variety of alginic acid derivatives as necessary.

Table 24-1 and Table 24-2 show the physical property values (specifically, reactive group introduction rate (mol %), molecular weight and weight-average molecular weight (Da)) of alginic acid derivatives into which a reactive group had been introduced and that were obtained in (Example 1) to (Example 18).

Table 25-1 to Table 25-3 show the data of $^{1}$H-NMR and LC-Mass of each intermediate in the examples.

(Examples 1a to i) Syntheses of dibenzocyclooctyne-amine Group-Introduced alginic acids (1-A2, 1-A1, 1-A3, 1-B2, 1-B2b, 1-B2c, 1-A2b, 1-A2c and 1-A2d)

[C63]

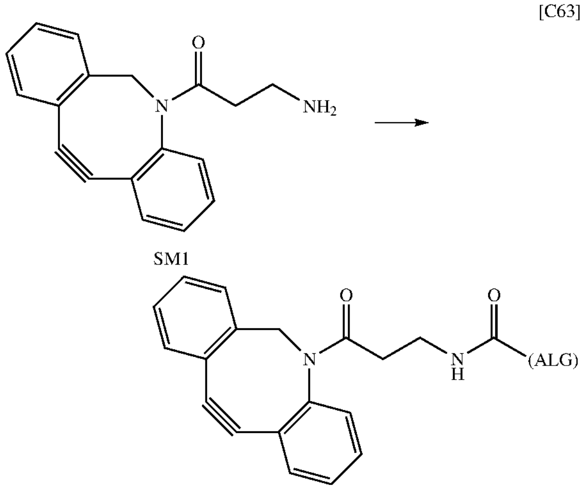

SM1

1-A2, 1-A1, 1-A3, 1-B2, 1-B2b, 1-B2c, 1-A2b, 1-A2c, 1-A2d

Compounds 1-A2, 1-A1, 1-A3, 1-B2, 1-B2b, 1-B2c, 1-A2b, 1-A2c and 1-A2d were synthesized by the following synthesis method under the following reaction conditions.

[Synthesis Method]

4-(4,6-Dimethoxy-1,3,5-triazin-2-yl)-4-methylmorpholinium chloride (DMT-MM) and 1-molar aqueous sodium bicarbonate solution were added to a sodium alginate (manufactured by MOCHIDA PHARMACEUTICAL CO., LTD.) aqueous solution prepared to 1 wt % or 2 wt %. An ethanol (EtOH 1) solution of commercially available dibenzocyclooctyne-amine (3-amino-1-(11,12-didehydrodibenz[b,f]azocin-5(6H)-yl)-1-propanone) [CAS REGISTRY NO.: 1255942-06-3] (SM1) was added dropwise to this solution and stirred at room temperature. Sodium chloride was added thereto, and then ethanol (EtOH 2) was added thereto and stirred at room temperature. An obtained precipitation was filtered, washed with ethanol and dried under reduced pressure, thereby obtaining a title compound. In Examples 1g, 1h and 1i, a solid obtained by the previous operation was dissolved in water, lyophilized, thereby obtaining a title compound.

[Reaction Conditions and Results]

TABLE 10

| Examples | 1a | 1b | 1c | 1d | 1e |
|---|---|---|---|---|---|
| Compound | 1-A2 | 1-A1 | 1-A3 | 1-B2 | 1-B2b |
| Sodium alginate | A-2 | A-1 | A-3 | B-2 | B-2 |
| 1 wt % sodium alginate aqueous solution (mL) | 43.6 | 19.32 | 15.06 | 53 | 35 |
| 2 wt % sodium alginate aqueous solution (mL) | * | * | * | * | * |
| DMT-MM (mg) | 111.65 | 49.47 | 38.57 | 111 | 14.7 |
| 1-molar aqueous sodium bicarbonate solution (μL) | 403.5 | 178.8 | 139.4 | 134 | 17.7 |
| SM1 (mg) | 83.62 | 37.05 | 28.88 | 36.9 | 4.9 |
| EtOH 1 (mL) | 2 | 4 | 2 | 5.3 | 3.5 |
| Reaction time (hours) | 18 | 20 | 23 | 3 | 3.5 |
| Reaction temperature | r.t. | r.t. | r.t. | 30° C. | 30° C. |
| NaCl (mg) | 400 | 200 | 150 | 530 | 350 |
| EtOH 2 (mL) | 87.2 | 38.64 | 60.24 | 101 | 70 |
| Post treatment stirring time (minutes) | 30 | 30 | 30 | 30 | 30 |
| Yield (mg) | 376 | 184 | 164 | 465 | 329 |
| Form (color/shape) | Light yellow solid | Light yellow solid | Light yellow solid | White solid | White solid |

TABLE 11

| Examples | 1f | 1g | 1h | 1i |
|---|---|---|---|---|
| Compound | 1-B2c | 1-A2b | 1-A2c | 1-A2d |
| Sodium alginate | B-2 | A-2 | A-2 | A-2 |
| 1 wt % sodium alginate aqueous solution (mL) | 60 | 120 | 120 | * |
| 2 wt % sodium alginate aqueous solution (mL) | * | * | * | 250 |
| DMT-MM (mg) | 67 | 335 | 67 | 279 |
| 1-molar aqueous sodium bicarbonate solution (μL) | 60.5 | 303 | 61 | 252 |
| SM1 (mg) | 16.7 | 84 | 17 | 70 |
| EtOH 1 (mL) | 6 | 12 | 12 | 25 |
| Reaction time (hours) | 3 | 3 | 3.5 | 3 |
| Reaction temperature | 30° C. | 30° C. | 30° C. | 32° C. |
| NaCl (mg) | 600 | 1200 | 1200 | 5000 |
| EtOH 2 (mL) | 120 | 240 | 240 | 500 |
| Post treatment stirring time (minutes) | 30 | 105 | 30 | 30 |
| Yield (mg) | 558 | 1174 | 1138 | 4600 |
| Form (color/shape) | White solid | White solid | White solid | White solid |

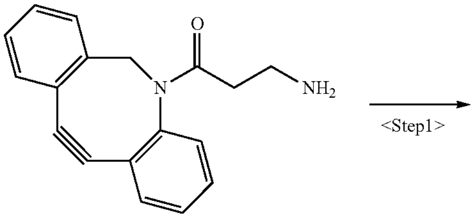

SM1

TABLE 11-continued (Example 2) Synthesis of 5-amino-1-(11,12-didehydrodibenz[b,f]azocin-5(6H)-yl)-1-pentanone group (ADIBO-05-amine)-Introduced alginic acid (2-B2)

[C64]

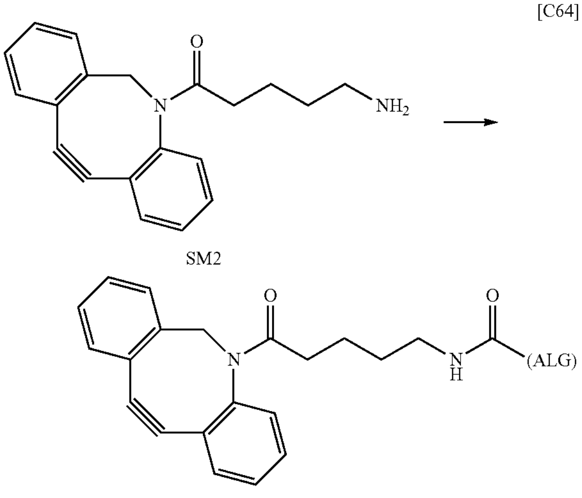

SM2

2-B2

DMT-MM (60 mg), an ethanol (2.9 mL) solution of ADIBO-05-amine [CAS REGISTRY NO.: 2401876-29-5] (SM2) (22 mg) obtained by a method well known by publications and 1-molar aqueous sodium bicarbonate solution (72 μL) were added to a sodium alginate (manufactured by MOCHIDA PHARMACEUTICAL CO., LTD.: B-2) aqueous solution (28.5 mL) prepared to 1 wt % and stirred at 30° C. for three hours. Sodium chloride (285 mg) was added thereto, then, ethanol (57 mL) was added thereto and stirred at room temperature for 30 minutes. An obtained precipitation was filtered, washed with ethanol and dried under reduced pressure, thereby obtaining a title compound (277 mg) as a white solid.

(Example 3) Synthesis of 2-amino-N-[3-(11,12-didehydrodibenz[b,f]azocin-5(6H)-yl)-3-oxopropyl] acetamide Group-Introduced alginic acid (3-A2)

[C65]

-continued

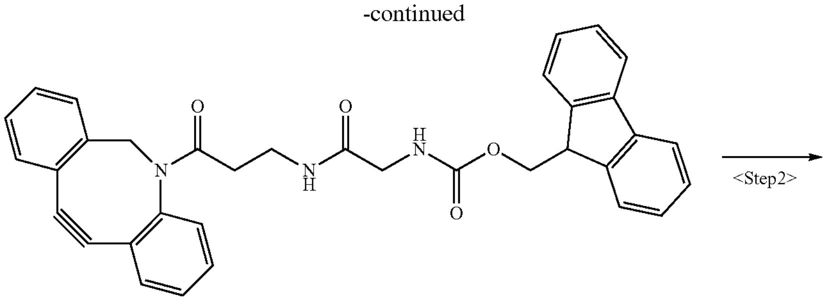

IM3-1

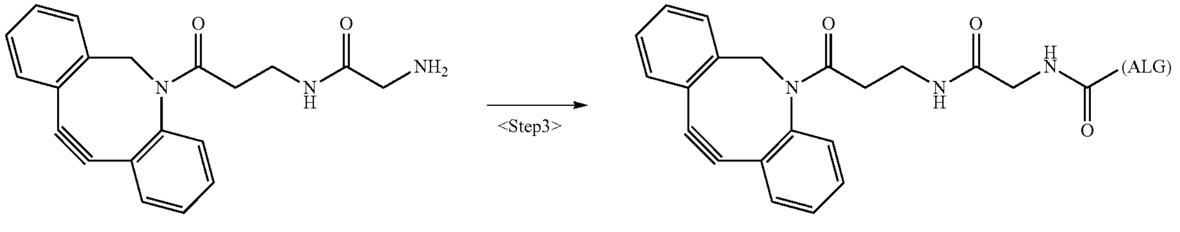

IM3-2 3-A2

<Step 1> Synthesis of (9H-fluoren-9-yl)methyl-N-[3-(11,12-didehydrodibenz[b,f]azocin-5(6H)-yl)-3-oxopropyl]acetamido-2-carbamate (IM3-1)

A compound of Formula SM1 (50 mg) and N-[(9H-fluoren-9-ylmethoxy)carbonyl]glycine [CAS REGISTRY NO.: 29022-11-5] (54 mg) were dissolved in acetonitrile (1.5 mL). 0-(7-azabenzotriazol-1-yl)-N,N,N',N'-tetramethyluronium hexafluorophosphate (76 mg) and N,N-diisopropylethylamine (70 μL) were added thereto and stirred at room temperature for 4.5 hours. Ethyl acetate (15 mL) and water (5 mL) were added to a reaction liquid, liquid was separated, and then an organic layer was sequentially washed with water and brine. The organic layer was dried with anhydrous sodium sulfate, then, concentrated under reduced pressure and purified by silica gel column chromatography, thereby obtaining a title compound (63 mg) as thin beige amorphous.

<Step 2> Synthesis of 2-amino-N-[3-(11,12-didehydrodibenz[b,f]azocin-5(6H)-yl)-3-oxopropyl]acetamide (IM3-2)

An N,N-dimethylformamide (315 μL) solution of piperidine (56 μL) was added to the compound of Formula IM3-1 (63 mg) obtained in <Step 1> of (Example 3) and stirred at room temperature for 30 minutes. Ethyl acetate (15 mL) and water (5 mL) were added to a reaction liquid, liquid was separated, and then an organic layer was sequentially washed with water and brine. The organic layer was dried with anhydrous sodium sulfate and then concentrated under reduced pressure. tert-Butyl methyl ether (5 mL) was added to an obtained solid, triturated and then filtered, thereby obtaining a title compound (10 mg) as thin beige solid. In addition, the title compound (11 mg) was additionally recovered from the filtrate and obtained as a light yellow gummy substance.

<Step 3> Synthesis of 2-amino-N-[3-(11,12-didehydrodibenz[b,f]azocin-5(6H)-yl)-3-oxopropyl]acetamide Group-Introduced alginic acid (3-A2)

DMT-MM (106 mg), an ethanol (1.9 mL) solution of a compound of Formula IM3-2 (21 mg) obtained in <Step 2> of (Example 3) and 1-molar aqueous sodium bicarbonate solution (48 μL) were added to a sodium alginate (manufactured by MOCHIDA PHARMACEUTICAL CO., LTD.: A-2) aqueous solution (19 mL) prepared to 1 wt %. The components were stirred at 30° C. for three hours, and then sodium chloride (0.19 g) and ethanol (38 mL) were sequentially added thereto and stirred at room temperature for 30 minutes. An obtained precipitation was filtered, washed with ethanol and dried under reduced pressure. An obtained solid was dissolved in water, then, lyophilized, thereby obtaining a title compound (188 mg) as a white solid.

(Examples 4a to g) Syntheses of N-(4-(aminomethyl)benzyl)-2-(cyclooct-2-yn-1-yloxy)acetamide Group-Introduced alginic acids (4-B2, 4-A2, 4-B2b, 4-A2b, 4-A2c, 4-A2d and 4-A3)

[C66]

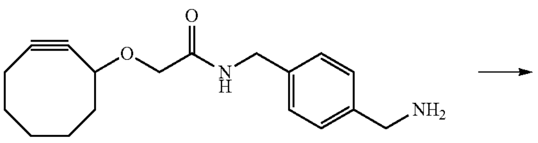

SM4

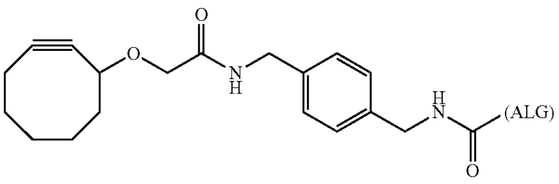

4-B2, 4-A2, 4-B2b, 4-A2b, 4-A2c, 4-A2d, 4-A3

Compounds 4-B2, 4-A2, 4-B2b, 4-A2b, 4-A2c, 4-A2d and 4-A3 were synthesized by the following synthesis method under the following reaction conditions.

[Synthesis Method]

DMT-MM was added to a sodium alginate (manufactured by MOCHIDA PHARMACEUTICAL CO., LTD.) aqueous solution prepared to 1 wt % or 2 wt % at room temperature under stirring. Subsequently, an ethanol (EtOH 1) solution of N-[[4-(aminomethyl)benzyl]-2-(2-cyclooctyn-1-yloxy)-acetamide [CAS REGISTRY NO.: 2401876-33-1] (SM4) obtained by a method well known by publications was added dropwise at room temperature and stirred. The solution was cooled to room temperature, then, sodium chloride was added thereto, and then ethanol (EtOH 2) was added thereto and stirred. An obtained precipitation was filtered, washed with ethanol (2 mL) three times and dried under reduced pressure, thereby obtaining a title compound. In Examples 4b, 4c, 4d, 4e, 4f and 4g, a solid obtained by the previous operation was dissolved in water, lyophilized, thereby obtaining the title compound.

[Reaction Conditions and Results]

TABLE 12

| Examples | 4a | 4b | 4c | 4d |
|---|---|---|---|---|
| Compound | 4-B2 | 4-A2 | 4-B2b | 4-A2b |
| Sodium alginate | B-2 | A-2 | B-2 | A-2 |
| 1 wt % sodium alginate aqueous solution (mL) | 50.86 | 30.1 | 200 | 120 |
| 2 wt % sodium alginate aqueous solution (mL) | * | * | * | * |
| DMT-MM (mg) | 118 | 83.7 | 335.0 | 73.7 |
| 1-molar aqueous sodium bicarbonate solution (μL) | * | 75.7 | 303 | 66.6 |
| SM4 (mg) | 35 | 22.7 | 98.9 | 22.2 |
| EtOH 1 (mL) | 3 | 3 | 20 | 6 |
| Reaction time (hours) | 4 | 3 | 4 | 3 |
| Reaction temperature | 40° C. | 30° C. | 30° C. | 32° C. |
| NaCl (mg) | 500 | 300 | 2.0 (g) | 1200 |
| EtOH 2 (mL) | 101.72 | 60 | 400 | 240 |
| Post treatment stirring time (minutes) | 30 | 30 | 30 | 60 |
| Yield (mg) | 521 | 285 | 1.96 (g) | 1100 |
| Form (color/shape) | White solid | White solid | White solid | White solid |

TABLE 13

| Examples | 4e | 4f | 4g |
|---|---|---|---|
| Compound | 4-A2c | 4-A2d | 4-A3 |
| Sodium alginate | A-2 | A-2 | A-3 |
| 1 wt % sodium alginate aqueous solution (mL) | * | * | 100 |
| 2 wt % sodium alginate aqueous solution (mL) | 250 | 600 | * |
| DMT-MM (mg) | 279.1 | 670 | 56 |
| 1-molar aqueous sodium bicarbonate solution (μL) | 252 | 606 | 50 |
| SM4 (mg) | 84.2 | 202 | 17 |
| EtOH 1 (mL) | 25 | 60 | 5 |
| Reaction time (hours) | 3 | 3.25 | 3 |
| Reaction temperature | 32° C. | 32° C. | 32° C. |
| NaCl (mg) | 5000 | 12000 | 1000 |
| EtOH 2 (mL) | 500 | 1200 | 200 |
| Post treatment stirring time (minutes) | 30 | 75 | 30 |
| Yield (mg) | 4570 | 10690 | 940 |
| Form (color/shape) | White solid | White solid | White solid |

(Examples 5a and b) Syntheses of N-(4-(2-amino-ethoxy)benzyl)-2-(cyclooct-2-yn-1-yloxy)acetamide Group-Introduced alginic acids (5-A2 and 5-B2)

[C67]

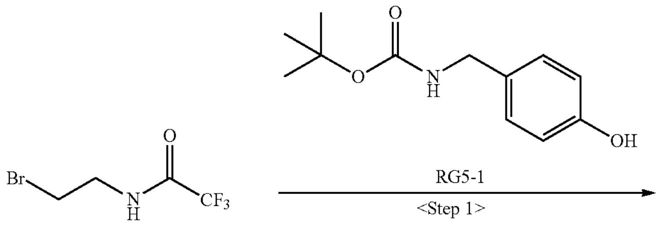

SM5

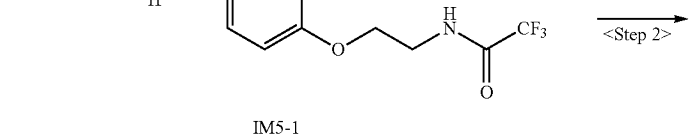

IM5-1

-continued

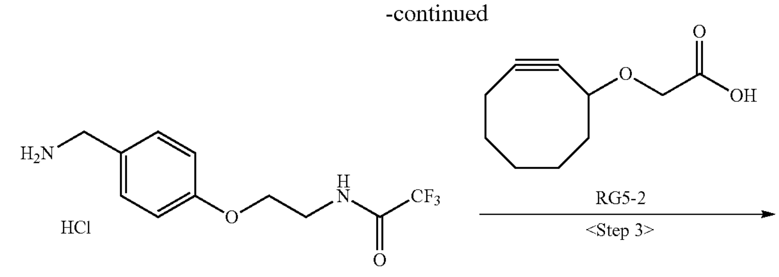

IM5-2

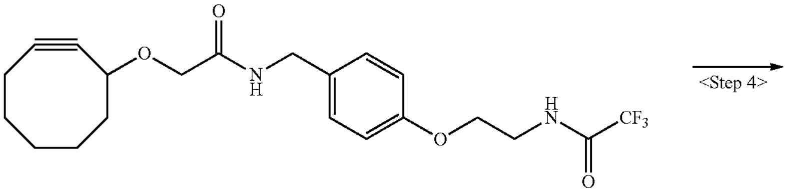

IM5-3

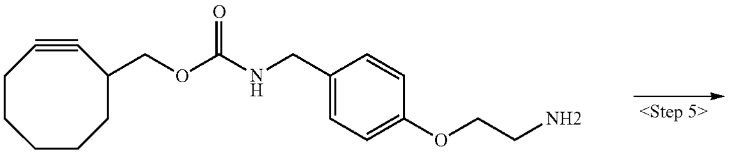

IM5-4

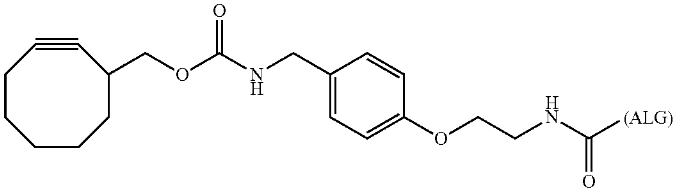

5-A2, 5-B2

<Step 1> Synthesis of tert-butyl (4-(2-(2,2,2-trifluoroacetamido)ethoxy)benzyl)carbamate (IM-5-1)

Potassium carbonate (0.45 g) was added to a mixture of commercially available tert-butyl (4-hydroxybenzyl)carbamate (Formula RG5-1, CAS REGISTRY NO.: 149505-94-2) (0.36 g), N-(2-bromoethyl)-2,2,2-trifluoroacetamide commercially available or synthesized and obtained by a method well known by publications (Formula SM5, CAS REGISTRY NO.: 75915-38-7] (0.46 g), potassium iodide (0.35 g) and N-methylpyrrolidone (3.6 mL) and stirred at 140° C. for five hours. After the end of a reaction, a reaction mixture was cooled to room temperature and diluted with water (10 mL). An organic layer was extracted three times with methyl tert-butyl ether (10 mL), sequentially washed with a 1 N-sodium hydroxide aqueous solution (5 mL) twice, water (5 mL) and brine (5 mL) and dried with anhydrous sodium sulfate. The organic layer was filtered and then concentrated under reduced pressure, thereby obtaining a crude product. The obtained crude product was purified by silica gel column chromatography (n-heptane/ethyl acetate), and a title compound (0.202 g) was obtained as white amorphous.

<Step 2> Synthesis of N-(2-(4-(aminomethyl)phenoxy)ethyl)-2,2,2-trifluoroacetamide hydrochloride (IM5-2)

4N-hydrogen chloride/1,4-dioxane (1.4 mL) was added to a mixture of a compound of Formula IM5-1 (0.2 g) obtained in <Step 1> of (Example 5) and 1,4-dioxane (1.4 mL) under water cooling and stirring and then stirred at room temperature for seven hours. Diisopropyl ether (20 mL) was added to a reaction liquid, and a suspension was stirred at room temperature for one day. A precipitate was filtered, and a recovered solid was dried under reduced pressure, thereby obtaining a title compound (0.15 g) as a white solid.

<Step 3> Synthesis of N-(2-(4-42-(cyclooct-2-yn-1-yloxy)acetamido)methyl)phenoxy)ethyl)-2,2,2-trifluoroacetamide (IM5-3)

DMT-MM (137.22 mg) and triethylamine (38.25 μL) were added to a mixture of 2-(2-cyclooctyne-1-yloxy)-acetic acid (Formula RG5-2) [CAS REGISTRY NO.: 917756-42-4] (50 mg) synthesized according to a method well known by a publication (Org. Process Res. Dev. (2018) 22: 108 to 110), a compound of Formula IM5-2 (81.96 mg) synthesized in <Step 2> of (Example 5) and ethanol (1 mL) under ice cooling and stirring and stirred at room temperature for 1 hour 30 minutes. After the end of a reaction, water (2 mL) was added thereto, a suspension was stirred, and methyl tert-butyl ether (0.5 mL) was added thereto. A separated water layer was extracted twice with methyl tert-butyl ether (5 mL), sequentially washed with water (5 mL) and brine (5 mL) and dried with anhydrous sodium sulfate. A dried organic layer was filtered and concentrated under reduced pressure. A crude product was purified by silica gel column chromatography (n-heptane/ethyl acetate), and a title compound (99 mg) was obtained as white amorphous.

<Step 4> Synthesis of N-(4-(2-aminoethoxy)benzyl-2-(cyclooct-2-yn-1-yloxy)acetamide (IM5-4)

Potassium carbonate (64.17 mg) and water (495 μL) were added to a mixture of a compound of Formula IM5-3 (99 mg) obtained in <Step 3> of (Example 5) and methanol (1485 μL) under water cooling and stirring and stirred at room temperature for 15 hours. After the end of a reaction, methanol was concentrated under reduced pressure, and a generated water layer was extracted with ethyl acetate (5 mL) three times. An organic layer was sequentially washed with water (5 mL) and brine (5 mL) and dried with anhydrous sodium sulfate. The dried organic layer was filtered and then concentrated under reduced pressure, thereby obtaining a crude product of a title compound (68 mg) as a yellow oily substance.

<Step 5> Syntheses of N-(4-(2-aminoethoxy)benzyl)-2-(cyclooct-2-yn-1-yloxy)acetamide Group-Introduced alginic acids (5-A2 and 5-B2)

Compounds of Formulae 5-A2 and 5-B2 were synthesized by the following synthesis method under the following reaction conditions.

[Synthesis Method]

DMT-MM was added to a sodium alginate (manufactured by MOCHIDA PHARMACEUTICAL CO., LTD.) aqueous solution prepared to 1 wt % at room temperature under stirring. Subsequently, a water (1 mL) and ethanol (EtOH 1) solution of a compound of Formula IM5-4 obtained in <Step 4> of (Example 5) was added dropwise at room temperature and stirred at the same temperature, and then sodium chloride and ethanol (EtOH 2) were sequentially added thereto and stirred at room temperature. An obtained precipitation was filtered, washed with ethanol and dried under reduced pressure. An obtained solid was dissolved in water, then, lyophilized, thereby obtaining a title compound.

[Reaction Conditions and Results]

TABLE 14

| Examples | 5a | 5b |
|---|---|---|
| Compound | 5-A2 | 5-B2 |
| Sodium alginate | A-2 | B-2 |
| 1 wt % sodium alginate aqueous solution (mL) | 49.44 | 40.08 |
| DMT-MM (mg) | 152.54 | 123.66 |
| IM5-4(mg) | 37.79 | 30.64 |
| EtOH 1 (mL) | 1 | 1 |
| Reaction time (hours) | 15 | 15 |
| Reaction temperature | r.t. | r.t. |
| NaCl (mg) | 500 | 400 |
| EtOH 2 (mL) | 98.88 | 80.16 |
| Post treatment stirring time (minutes) | 30 | 30 |
| Yield (mg) | 479 | 356 |
| Form (color/shape) | White solid | White solid |

(Examples 6a, 6b and 6c) Syntheses of N-(2-aminoethyl)-2-(cyclooct-2-yn-1-yloxy)acetamide Group-Introduced alginic acids (6-A2, 6-B2 and 6-B2b)

[C68]

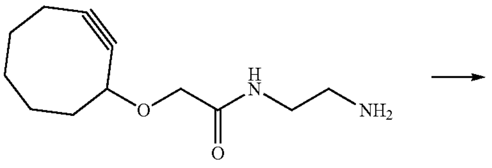

SM6

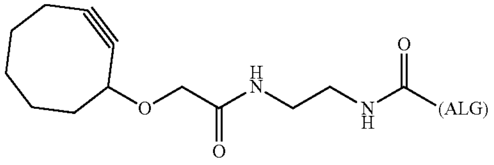

6-A2, 6-B2, 6-B2b

Compounds 6-A2, 6-B2 and 6-B2b were synthesized by the following synthesis method under the following reaction conditions.

[Synthesis Method]

DMT-MM, an ethanol (EtOH 1) solution of N-(2-aminoethyl)-2-(2-cyclooctyne-1-yloxy)-acetamide [CAS REGISTRY NO.: 1809789-76-1] (SM6) obtained by a method well known by publications and 1-molar aqueous sodium bicarbonate solution were sequentially added to a sodium alginate (manufactured by MOCHIDA PHARMACEUTICAL CO., LTD.) aqueous solution prepared to 1 wt % at room temperature under stirring and stirred. Sodium chloride was added to a reaction liquid, and then ethanol (EtOH 2) was added thereto and stirred. An obtained precipitation was filtered, washed with ethanol and dried under reduced pressure, thereby obtaining a title compound. A solid obtained by the previous operation was dissolved in water, lyophilized, thereby obtaining a title compound.

[Reaction Conditions and Results]

TABLE 15

| Examples | 6a | 6b | 6c |
|---|---|---|---|
| Compound | 6-A2 | 6-B2 | 6-B2b |
| Sodium alginate | A-2 | B-2 | B-2 |
| 1 wt % sodium alginate aqueous solution (mL) | 30 | 120 | 120 |
| DMT-MM (mg) | 84 | 335 | 167 |
| SM6 (mg) | 17 | 68 | 34 |
| EtOH 1 (mL) | 3 | 12 | 12 |
| 1-molar aqueous sodium bicarbonate solution (μL) | 76 | 303 | 151 |
| Reaction time (hours) | 3 | 3 | 3 |
| Reaction temperature | 30° C. | 30° C. | 30° C. |
| NaCl (mg) | 300 | 1200 | 1200 |
| EtOH 2 (mL) | 60 | 240 | 240 |
| Post treatment stirring time (minutes) | 90 | 90 | 90 |
| Yield (mg) | 290 | 1160 | 1120 |
| Form (color/shape) | White solid | White solid | White solid |

(Example 7) Synthesis of N-(2-(2-aminoethoxy) ethyl)-2-(cyclooct-2-yn-1-yloxy)acetamide Group-Introduced alginic acid (7-A2)

[C69]

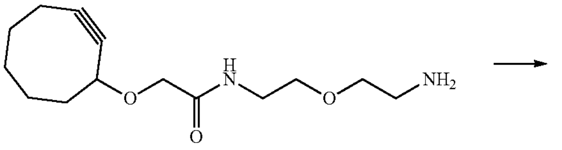

SM7

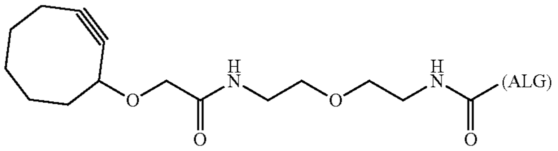

7-A2

DMT-MM (112 mg), an ethanol (4.0 mL) solution of N-[2-(2-aminoethoxy)ethyl]-2-(2-cyclooctyn-1-yloxy)-acetamide [CAS REGISTRY NO.: 2401876-51-3] (SM7) (30 mg) obtained by a method well known by publications and 1-molar aqueous sodium bicarbonate solution (101 μL) were sequentially added to a sodium alginate (manufactured by MOCHIDA PHARMACEUTICAL CO., LTD., A-2) aqueous solution (40 mL) prepared to 1 wt % at room temperature under stirring and stirred at 30° C. for three hours. Sodium chloride (0.4 g) was added to a reaction liquid, then, ethanol (80 mL) was added thereto and stirred for 30 minutes. An obtained precipitation was filtered, washed with ethanol and dried under reduced pressure. An obtained solid was dissolved in water, lyophilized, thereby obtaining a title compound (410 mg) as a white solid.

(Examples 8a and 8b) Syntheses of N-(2-aminoethyl)-2-(2-(cyclooct-2-yn-1-yloxy)acetamide) acetamide Group-Introduced alginic acids (8-A2 and 8-B2)

[C70]

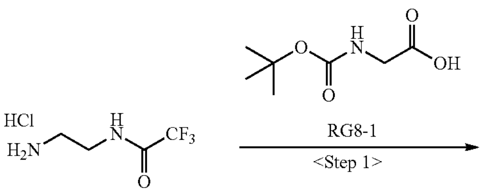

SM8

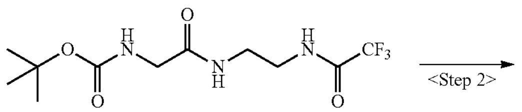

IM8-1

-continued

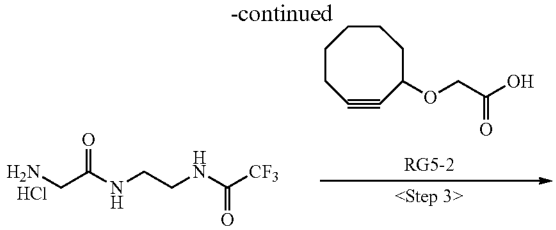

IM8-2

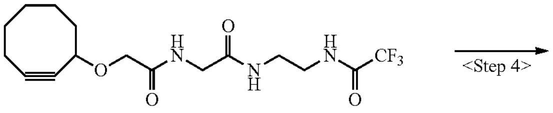

IM8-3

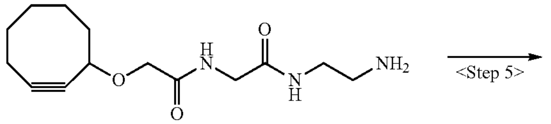

IM8-4

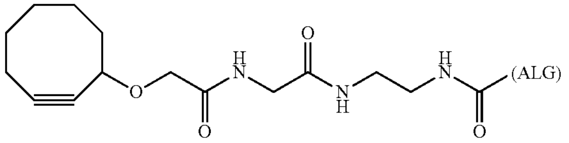

8-A2, 8-B2

<Step 1> Synthesis of tert-butyl (2-oxo-2-((2-(2,2,2-trifluoroacetamido)ethyl)amino)ethyl)carbamate (IM8-1)

N-(2-aminoethyl)-2,2,2-trifluoroacetamide hydrochloride (Formula SM8) [CAS REGISTRY NO.: 496946-73-7] (100 mg) and N-(tert-butoxycarbonyl)glycine (Formula RG8-1) [CAS REGISTRY NO.: 4530-20-5] (91 mg) obtained by methods well known by publications were dissolved in acetonitrile (3.0 mL). O-(7-azabenzotriazol-1-yl)-N,N,N',N'-tetramethyluronium hexafluorophosphate (217 mg) and N,N-diisopropylethylamine (281 μL) were added thereto and stirred at room temperature for 3.5 hours. Ethyl acetate (15 mL) and water (5 mL) were added to a reaction liquid, liquid was separated, and then an organic layer was sequentially washed with water and brine. The organic layer was dried with anhydrous sodium sulfate and then concentrated under reduced pressure. A residue was purified by silica gel column chromatography (elution solvent: 40% ethyl acetate/n-heptane→ethyl acetate), and a title compound (180 mg) was obtained as light beige amorphous.

<Step 2> Synthesis of N-(2-(2-aminoacetamido) ethyl)-2,2,2-trifluoroacetamide hydrochloride (IM8-2)

4N-hydrogen chloride/1,4-dioxane (1.2 mL) was added to a compound of Formula IM8-1 (180 mg) obtained in <Step 1> of (Example 8) under ice cooling and then stirred at room temperature for 0.8 hours. Diisopropyl ether (3.6 mL) was added to a reaction liquid and stirred for 30 minutes. An obtained solid was filtered, thereby obtaining a title compound (114 mg) as a white solid.

<Step 3> Synthesis of N-(2-(2-(2-(cyclooct-2-yn-1-yloxy)acetamido)acetamido)ethyl)-2,2,2-trifluoroacetamide (IM8-3)

Ethanol (1.6 mL), DMT-MM (219 mg) and triethylamine (67 μL) were added to 2-(2-cyclooctyne-1-yloxy)-acetic acid (Formula RG5-2) [CAS REGISTRY NO.: 917756-42-4] (80 mg) obtained by a method well known by publications and a compound of Formula IM8-2 (110 mg) obtained in <Step 2> of (Example 8) and stirred at room temperature for three hours. Water (3.2 mL) was added to a reaction liquid and stirred at room temperature for 30 minutes, then, a solid was filtered and washed with water. Ethyl acetate/ethanol (1/1, 10 mL) was added to the obtained solid, and an insoluble matter was removed. A filtrate was concentrated under reduced pressure, thereby obtaining a title compound (101 mg) as a white solid.

<Step 4> Synthesis of N-(2-(aminoethyl)-2-(2-(cyclooct-2-yn-1-yloxy)acetamide)acetamide A water (0.3 mL) solution of potassium carbonate (59 mg) was added to a methanol (1.8 mL) solution of a compound of Formula IM8-3 (60 mg) obtained in <Step 3> of (Example 8) and stirred at room temperature for four hours. A reaction liquid was concentrated under reduced pressure, then, water (2 mL) was added thereto, and the reaction liquid was saturated with sodium chloride. An organic layer was extracted with ethyl acetate (15 mL, 10 mL×4) and concentrated under reduced pressure. Ethyl acetate (10 mL) and ethanol (1 mL) were added to a residue, and an insoluble matter was removed. An obtained filtrate was concentrated under reduced pressure, thereby obtaining a title compound (49 mg) as a colorless gummy substance.

<Step 5> Syntheses of N-(2-aminoethyl)-2-(2-(cyclooct-2-yn-1-yloxy)acetamide) acetamide Group-Introduced alginic acids (8-A2 and 8-B2)

Compounds of Formulae 8-A2 and 8-B2 were synthesized by the following synthesis method under the following reaction conditions.

[Synthesis Method]

DMT-MM, an ethanol (EtOH 1) solution of a compound of Formula IM8-4 and 1-molar aqueous sodium bicarbonate solution were added to a sodium alginate (manufactured by MOCHIDA PHARMACEUTICAL CO., LTD.) aqueous solution prepared to 1 wt % and stirred, then, sodium chloride and ethanol (EtOH 2) were sequentially added thereto and stirred at room temperature. An obtained precipitation was filtered, washed with ethanol and dried under reduced pressure. An obtained solid was dissolved in water, then, lyophilized, thereby obtaining a title compound as a white solid. A solid obtained by the previous operation was dissolved in water, lyophilized, thereby obtaining a title compound.

[Reaction Conditions and Results]

TABLE 16

| Examples | 8a | 8b |
|---|---|---|
| Compound | 8-A2 | 8-B2 |
| Sodium alginate | A-2 | B-2 |
| 1 wt % sodium alginate aqueous solution (mL) | 38 | 38 |
| DMT-MM (mg) | 106 | 64 |
| IM8-4 (mg) | 30.3 | 18.2 |

TABLE 16-continued

| Examples | 8a | 8b |
|---|---|---|
| EtOH 1 (mL) | 3.8 | 3.8 |
| 1-molar aqueous sodium bicarbonate solution (μL) | 96 | 58 |
| Reaction time (hours) | 3.2 | 3.2 |
| Reaction temperature | 30° C. | 30° C. |
| NaCl (mg) | 380 | 380 |
| EtOH 2 (mL) | 76 | 76 |
| Post treatment stirring time (minutes) | 30 | 30 |
| Yield (mg) | 381 | 366 |
| Form (color/shape) | White solid | White solid |

(Example 9) Synthesis of N-(2-aminoethyl)-3-(2-(cyclooct-2-yn-1-yloxy)acetamide)propanamide Group-Introduced alginic acid (9-A2)

[C71]

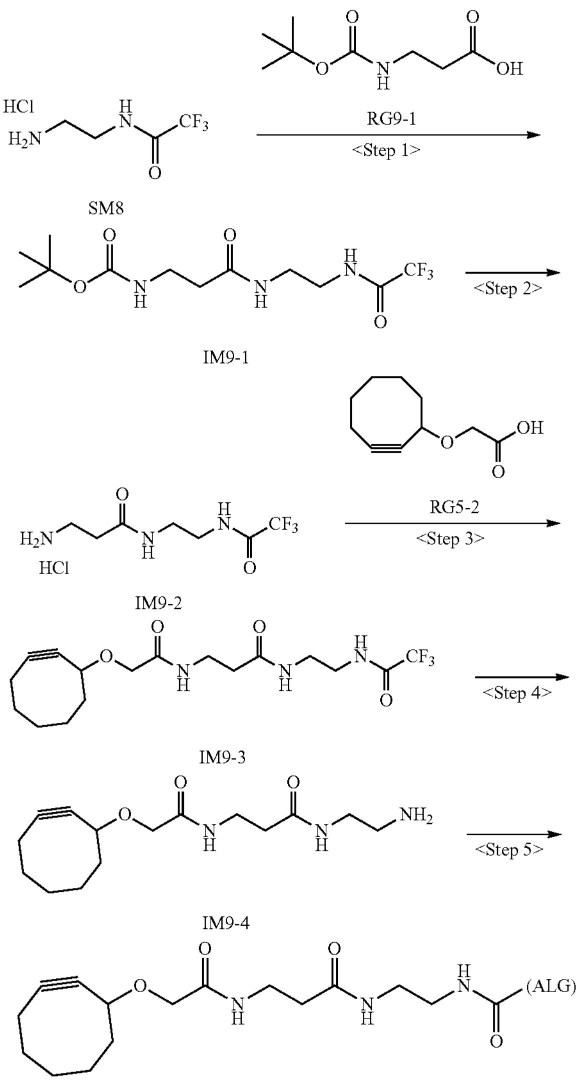

9-A2

<Step 1> Synthesis of tert-butyl (3-oxo-3-((2-(2,2,2-trifluoroacetamido)ethyl)amino)propyl)carbamate N-(2-aminoethyl)-2,2,2-trifluoroacetamide hydrochloride (Formula SM8) (110 mg) and N-(tert-butoxycarbonyl)-O-alanine (Formula RG9-1) [CAS REGISTRY NO.: 3303-84-2] (113.5 mg) obtained by methods well known by publications were dissolved in acetonitrile (3.3 mL), 0-(7-azabenzotriazol-1-yl)-N,N,N',N'-tetramethyluronium hexafluorophosphate (261 mg) and N,N-diisopropylethylamine (319 μL) were added thereto and stirred at room temperature for three hours. Ethyl acetate (15 mL) and water (5 mL) were added to a reaction liquid, liquid was separated, and then an organic layer was sequentially washed with water and brine. The organic layer was dried with anhydrous sodium sulfate, then, concentrated under reduced pressure and triturated with methyl tert-butyl ether (20 mL). A solid was filtered and dissolved in ethyl acetate (20 mL). The organic layer was sequentially washed with 1N-citric acid, water and brine, then, dried with anhydrous sodium sulfate and then concentrated under reduced pressure. A residue was triturated with methyl tert butyl ether (10 mL), and then a solid was filtered, thereby obtaining a title compound (80 mg) as a white solid.

<Step 2> Synthesis of 3-amino-N-(2-(2,2,2-trifluoroacetamido)ethyl)propanamide hydrochloride (IM9-2)

4N-hydrogen chloride/1,4-dioxane (1.1 mL) was added to a compound of Formula IM9-1 (80 mg) obtained in <Step 1> of (Example 9) under ice cooling and then stirred at room temperature for two hours. Diisopropyl ether (3.4 mL) was added to a reaction liquid and stirred for 1.5 hours. An obtained solid was filtered, thereby obtaining a title compound (61 mg) as a white solid.

<Step 3> Synthesis of 3-(2-(cyclooct-2-yn-1-yloxy)acetamide)-N-(2-(2,2,2-trifluoroacetamido)ethyl)propanamide (IM9-3)

Ethanol (1.2 mL), DMT-MM (115 mg) and triethylamine (39 μL) were added to a compound of Formula RG5-2 (44 mg) obtained by a method well known by publications and a compound of Formula IM9-2 (61 mg) obtained in <Step 2> of (Example 9) and stirred at room temperature for two hours. Water (3.7 mL) was added to a reaction liquid, and an organic layer was extracted with ethyl acetate (15 mL, 5 mL). The organic layer was sequentially washed with water and brine, dried with anhydrous sodium sulfate and then concentrated under reduced pressure. tert-Butyl methyl ether (10 mL) was added to the obtained solid, triturated and filtered. The obtained solid was purified by silica gel column chromatography (80% ethyl acetate/n-heptane→ethyl acetate→20% methanol/ethyl acetate), and a title compound (60 mg) was obtained as light yellow solid.

<Step 4> Synthesis of N-(2-(aminoethyl)-3-(2-(cyclooct-2-yn-1-yloxy)acetamide)propanamide (IM9-4)

A water (0.3 mL) solution of potassium carbonate (42 mg) was added to a methanol (3.0 mL) solution of a compound of Formula IM9-3 (60 mg) obtained in <Step 3> of (Example 9) and stirred at room temperature for three hours, then, furthermore, a water (0.3 mL) solution of potassium carbonate (42 mg) was added thereto and stirred at room temperature for 16.5 hours. A reaction liquid was concentrated under reduced pressure, then, brine (2 mL) was added thereto, and, furthermore, the reaction liquid was saturated with sodium chloride. A layer was extracted with ethyl acetate (15 mL, 10 mL×4), and the extracted layer was dried with anhydrous sodium sulfate and then concentrated under reduced pressure. Ethyl acetate (5 mL) and several droplets of methanol were added to a residue, and an insoluble matter was removed. An obtained filtrate was concentrated under reduced pressure, thereby obtaining a title compound (31 mg) as a colorless oily substance.

<Step 5> Synthesis of N-(2-aminoethyl)-3-(2-(cyclooct-2-yn-1-yloxy)acetamide)propanamide Group-Introduced alginic acid (9-A2)

DMT-MM (114 mg), an ethanol (4.1 mL) solution of a compound of Formula (30.5 mg) obtained in <Step 4> of (Example 9) and 1-molar aqueous sodium bicarbonate solution (103 μL) were added to a sodium alginate (manufactured by MOCHIDA PHARMACEUTICAL CO., LTD.: A-2) aqueous solution (41 mL) prepared to 1 wt %. The components were stirred at 30° C. for three hours, and then sodium chloride (0.41 g) and ethanol (82 mL) were sequentially added thereto and stirred at room temperature for 30 minutes. An obtained precipitation was filtered, washed with ethanol and dried under reduced pressure. The obtained solid was dissolved in water, then, lyophilized, thereby obtaining a title compound (406 mg) as a white solid.

(Example 10) Synthesis of 3-amino-N-(2-(2-(2-(cyclooct-2-yn-1-yloxy)acetamido)ethoxy)ethyl)propanamide Group-Introduced alginic acid (10-A2)

[C72]

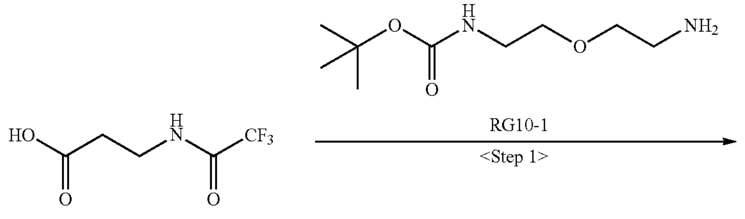

SM10

-continued

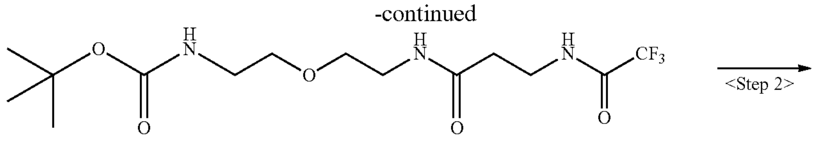

IM10-1

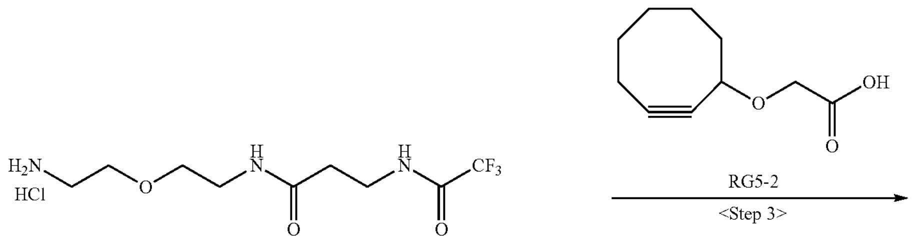

IM10-2

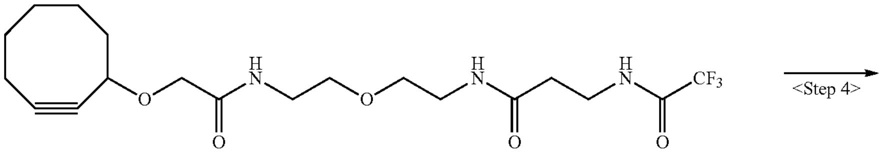

IM10-3

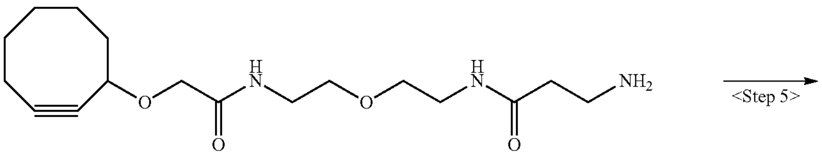

IM10-4

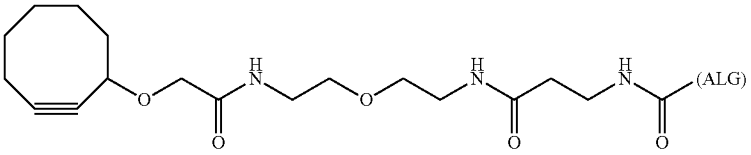

10-A2

<Step 1> Synthesis of tert-butyl (2-(2-(3-(2,2,2-trifluoroacetamido)propanamido)ethoxy)ethyl)carbamate (IM10-1)

DMT-MM (897 mg) was added to a compound of Formula SM10 [CAS REGISTRY NO.: 50632-82-1] (400 mg) obtained by a method well known by publications and an ethanol (4.0 mL) solution of a compound of Formula RG10-1 that was a commercially available product or obtained by a method well known by publications (tert-butyl (2-(2-aminoethoxy)ethyl) carbamate, CAS REGISTRY NO.: 127828-22-2) (441 mg) and stirred for 3.5 hours. Water (5 mL) was added to a reaction liquid, and an organic layer was extracted with ethyl acetate (20 mL, 10 mL) and then sequentially washed with water and brine. The organic layer was dried with anhydrous sodium sulfate and then concentrated under reduced pressure, and a residue was purified by silica gel column chromatography ([elution solvent/ratio %] ethyl acetate:n-heptane=30:70→ethyl acetate:n-heptane=100:0), thereby obtaining a title compound (451 mg) as a colorless oily substance.

<Step 2> Synthesis of N-(2-(2-aminoethoxy)ethyl)-3-(2,2,2-trifluoroacetamide)propanamide hydrochloride (IM10-2)

4N-hydrogen chloride/1,4-dioxane (3.16 mL) was added to a compound of Formula IM10-1 (451 mg) obtained in <Step 1> of (Example 10) under ice cooling and stirred at room temperature for three hours. Diisopropyl ether (6.4 mL) was added to a reaction liquid and concentrated under reduced pressure, thereby obtaining a title compound (433 mg) as a colorless gummy substance.

<Step 3> Synthesis of N-(2-(2-(2-(cyclooct-2-yn-1-yloxy)acetamido)ethoxy)ethyl-3-(2,2,2-trifluoroacetamido)propanamide (IM10-3)

Ethanol (1.7 mL), DMT-MM (253 mg) and triethylamine (102 μL) were added to a compound of Formula RG5-2 (111 mg) obtained by a method well known by publications and a compound of Formula IM10-2 (215 mg) obtained in <Step 2> of (Example 10) and stirred at room temperature for 21 hours. Water (5 mL) was added to a reaction liquid, and an organic layer was extracted with ethyl acetate (15 mL). The organic layer was sequentially washed with water and brine, dried with anhydrous sodium sulfate and then concentrated under reduced pressure. An obtained residue was purified by silica gel column chromatography ([elution solvent/ratio %] ethyl acetate:n-heptane=30:70→ethyl acetate:n-heptane=100:0→methanol:ethyl acetate=15:85), thereby obtaining a title compound (35 mg) as a colorless oily substance.

<Step 4> Synthesis of 3-amino-N-(2-(2-(2-(cyclooct-2-yn-1-yloxy)acetamido)ethoxy)ethyl)propanamide (IM10-4)

An aqueous solution (175 μL) of potassium carbonate (33 mg) was added to a methanol (700 μL) solution of a compound of Formula IM10-3 (35 mg) obtained in <Step 3> of (Example 10) and stirred at room temperature for 16.5 hours. A reaction liquid was concentrated under reduced pressure, then, water (2 mL) was added thereto, and the reaction liquid was saturated with sodium chloride. A layer was extracted with ethyl acetate (10 mL×5), and the extracted layer was dried with anhydrous sodium sulfate and then concentrated under reduced pressure. Ethyl acetate (10 mL) and several droplets of methanol were added to a residue, and an insoluble matter was removed. An obtained filtrate was concentrated under reduced pressure, thereby obtaining a title compound (24 mg) as a colorless gummy substance.

<Step 5> Synthesis of 3-amino-N-(2-(2-(2-(cyclooct-2-yn-1-yloxy)acetamido)ethoxy)ethyl)propanamide Group-Introduced alginic acid (10-A2)

DMT-MM (78 mg), an ethanol (2.8 mL) solution of a compound of Formula IM10-4 (24 mg) obtained in <Step 4> of (Example 10) and 1-molar aqueous sodium bicarbonate solution (71 μL) were added to a sodium alginate (manufactured by MOCHIDA PHARMACEUTICAL CO., LTD.: A-2) aqueous solution (28 mL) prepared to 1 wt %. The components were stirred at 30° C. for 3.5 hours, and then sodium chloride (0.28 g) and ethanol (56 mL) were sequentially added thereto and stirred at room temperature for 30 minutes. An obtained precipitation was filtered, washed with ethanol and dried under reduced pressure. The obtained solid was dissolved in water, then, lyophilized, thereby obtaining a title compound (272 mg) as a white solid.

(Examples 11a to m) Syntheses of 4-(2-aminoethoxy)-N-(3-azidopropyl)benzamide Group-Introduced alginic acids (11-A2, 11-A1, 11-A3, 11-B2, 11-B2b, 11-B2c, 11-A2b, 11-A2c, 11-B2d, 11-A2d, 11-A2e, 11-A3 and 11-A2f)

[C73]

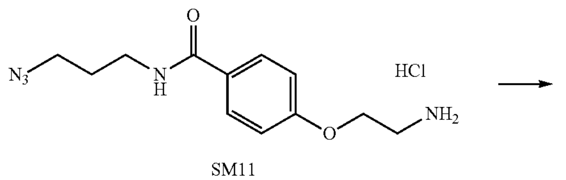

SM11

-continued

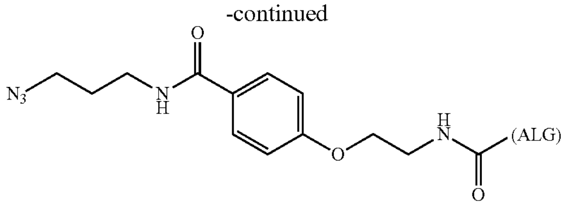

11-A2, 11-A1, 11-A3, 11-B2, 11-B2b, 11-B2c, 11-A2b, 11-A2c, 11-B2d 11-A2d, 11=A2e, 11-A3, 11-A2f

Compounds 11-A2, 11-A1, 11-A3, 11-B2, 11-B2b, 11-B2c, 11-A2b, 11-A2c, 11-B2d, 11-A2d, 11-A2e, 11-A3 and 11-A2f were synthesized by the following synthesis method under the following reaction conditions.

[Synthesis Method]

DMT-MM, a compound of Formula SM11 (4-(2-aminoethoxy)-N-(3-azidopropyl)benzamide hydrochloride; CAS REGISTRY NO.: 2401876-19-3] synthesized by a method well known by publications and 1-molar aqueous sodium bicarbonate solution were added to a sodium alginate (manufactured by MOCHIDA PHARMACEUTICAL CO., LTD.) aqueous solution prepared to 1 wt % or 2 wt % and stirred. Sodium chloride was added thereto, and then ethanol (EtOH 2) was added thereto and stirred at room temperature. An obtained precipitation was filtered, washed with ethanol and dried under reduced pressure, thereby obtaining a title compound as solid. In Examples 11g, 11h, 11i, 11j, 11k, 111 and 11m, a solid obtained by the previous operation was dissolved in water, lyophilized, thereby obtaining a title compound.

[Reaction Conditions and Results]

TABLE 17

| Examples | 11a | 11b | 11c | 11d |
|---|---|---|---|---|
| Compound | 11-A2 | 11-A1 | 11-A3 | 11-B2 |
| Sodium alginate | A-2 | A-1 | A-3 | B-2 |
| 0.67 wt % sodium alginate aqueous solution (mL) | * | * | * | * |
| 1 wt % sodium alginate aqueous solution (mL) | 19.6 | 19.32 | 15.06 | 60.0 |
| 2 wt % sodium alginate aqueous solution (mL) | * | * | * | * |
| DMT-MM (mg) | 50.19 | 49.47 | 38.57 | 125.6 |
| 1-molar aqueous sodium bicarbonate solution (μL) | 181.4 | 178.8 | 139.4 | 211.8 |
| SM11 (mg) | 54.37 | 53.59 | 41.78 | 45.4 |
| Reaction time (hours) | 5 | 20 | 5 | 3 |
| Reaction temperature | r.t. | r.t. | r.t. | 30° C. |
| NaCl (mg) | 200 | 200 | 150 | 600 |
| EtOH 2 (mL) | 39.2 | 38.64 | 60.24 | 120 |
| Post treatment stirring time (minutes) | 30 | 30 | 30 | 30 |
| Yield (mg) | 198 | 221 | 155 | 553 |
| Form (color/shape) | White solid | White solid | White solid | White solid |

TABLE 18

| Examples | 11e | 11f | 11g | 11h |
|---|---|---|---|---|
| Compound | 11-B2b | 11-B2c | 11-A2b | 11-A2c |
| Sodium alginate | B-2 | B-2 | A-2 | A-2 |
| 0.67 wt % sodium alginate aqueous solution (mL) | * | * | * | * |
| 1 wt % sodium alginate aqueous solution (mL) | 35.0 | 60.0 | 120 | 120 |

TABLE 18-continued

| Examples | 11e | 11f | 11g | 11h |
|---|---|---|---|---|
| 2 wt % sodium alginate aqueous solution (mL) | * | * | * | * |
| DMT-MM (mg) | 14.7 | 67.0 | 335.0 | 200.97 |
| 1-molar aqueous sodium bicarbonate solution (μL) | 26.5 | 90.8 | 453.9 | 272.4 |
| SM11 (mg) | 5.3 | 18.1 | 90.7 | 54.4 |
| Reaction time (hours) | 3.5 | 3 | 3 | 3.5 |
| Reaction temperature | 30° C. | 30° C. | 30° C. | 30° C. |
| NaCl (mg) | 350 | 600 | 1200 | 1200 |
| EtOH 2 (mL) | 70 | 120 | 240 | 240 |
| Post treatment stirring time (minutes) | 30 | 30 | 30 | 30 |
| Yield (mg) | 304 | 568 | 1171 | 1169 |
| Form (color/shape) | White solid | White solid | White solid | White solid |

TABLE 19

| Examples | 11i | 11j | 11k | 11l | 11m |
|---|---|---|---|---|---|
| Compound | 11-B2d | 11-A2d | 11-A2e | 11-A3 | 11-A2f |
| Sodium alginate | B-2 | A-2 | A-2 | A-3 | A-2 |
| 0.67 wt % sodium alginate aqueous solution (mL) | * | * | * | 150 | * |
| 1 wt % sodium alginate aqueous solution (mL) | 250 | * | * | * | * |
| 2 wt % sodium alginate aqueous solution (mL) | * | 300 | 225 | * | 300 |
| DMT-MM (mg) | 697.8 | 1005 | 754 | 167 | 1000 |
| 1-molar aqueous sodium bicarbonate solution (μL) | 945.7 | 1362 | 1021 | 227 | 1360 |
| SM11 (mg) | 189.0 | 272.1 | 204 | 45 | 272 |
| Reaction time (hours) | 3.5 | 3.6 | 3 | 3.5 | 3.5 |
| Reaction temperature | 30° C. | 32° C. | 32 | 32 | 32° C. |
| NaCl (mg) | 2500 | 6000 | 4500 | 1000 | 6000 |
| EtOH 2 (mL) | 500 | 600 | 450 | 300 | 600 |
| Post treatment stirring time (minutes) | 30 | 30 | 30 | 30 | 30 |
| Yield (mg) | 2420 | 5600 | 4160 | 860 | 5500 |
| Form (color/shape) | White solid | White solid | White solid | White solid | White solid |

(Example 12) Synthesis of 4-(3-aminopropoxy)-N-(2-(2-(2-azidoethoxy)ethoxy)ethyl)benzamide Group-Introduced alginic acid (12-A2)

[C74]

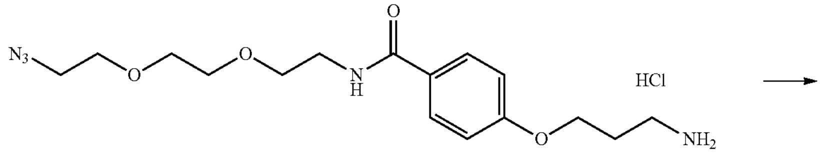

SM12

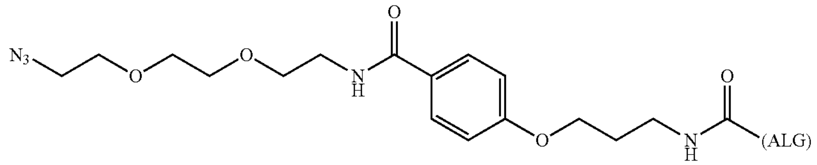

12-A2

DMT-MM (50.19 mg), a compound of Formula SM12 (4-(3-aminopropoxy)-N-(2-(2-(2-azidoethoxy)ethoxy)ethyl) benzamide hydrochloride; CAS REGISTRY NO.: 2401876-22-8] (70.35 mg) synthesized by a method well known by publications and 1-molar aqueous sodium bicarbonate solution (181.4 μL) were added to a sodium alginate (manufactured by MOCHIDA PHARMACEUTICAL CO., LTD., A-2) aqueous solution (19.6 mL) prepared to 1 wt % under ice cooling and stirring, and stirred at room temperature for five hours. Sodium chloride (200 mg) was added thereto, then, ethanol (39.2 mL) was added thereto and stirred at room temperature for 30 minutes. An obtained precipitation was filtered, washed with ethanol and dried under reduced pressure, thereby obtaining a title compound (199 mg) as a white solid.

(Examples 13a and b) Syntheses of N-(2-(2-aminoethoxy)ethyl)-4-(azidomethyl)benzamide Group-Introduced alginic acids (13-A2 and 13-A2b)

[C75]

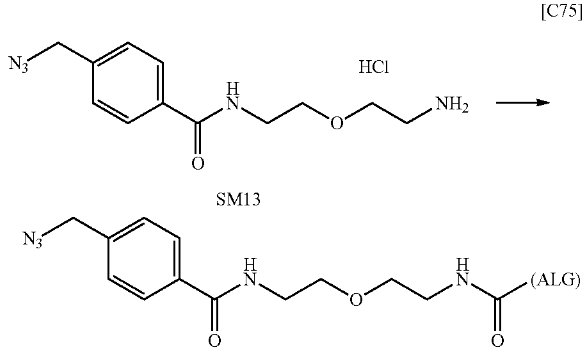

SM13

13-A2, 13-A2b

Compounds 13-A2 and 13-A2b were synthesized by the following synthesis method under the following reaction conditions.

[Synthesis Method]

DMT-MM, a compound of Formula SM13 (N-(2-(2-aminoethoxy)ethyl)-4-(azidomethyl)benzamide hydrochloride; CAS REGISTRY NO.: 2401876-38-6] synthesized by a method well known by publications and 1-molar aqueous sodium bicarbonate solution were added to a sodium alginate (manufactured by MOCHIDA PHARMACEUTICAL CO., LTD.) aqueous solution prepared to 1 wt % and stirred. Sodium chloride was added thereto, and then ethanol (EtOH 2) was added thereto and stirred at room temperature. An obtained precipitation was filtered, washed with ethanol and dried under reduced pressure, thereby obtaining a title compound as solid. The solid obtained by the previous operation was dissolved in water, lyophilized, thereby obtaining a title compound.

[Reaction Conditions and Results]

TABLE 20

| Examples | 13a | 13b |
|---|---|---|
| Compound | 13-A2 | 13-A2b |
| Sodium alginate | A-2 | A-2 |
| 1 wt % sodium alginate aqueous solution (mL) | 40 | 140 |

TABLE 20-continued

| Examples | 13a | 13b |
|---|---|---|
| DMT-MM (mg) | 112 | 234.5 |
| 1-molar aqueous sodium bicarbonate solution (μL) | 151 | 317.7 |
| SM13 (mg) | 30 | 63.5 |
| Reaction time (hours) | 3 | 3 |
| Reaction temperature | 30° C. | 32° C. |
| NaCl (mg) | 400 | 1400 |
| EtOH 2 (mL) | 80 | 280 |
| Post treatment stirring time (minutes) | 30 | 30 |
| Yield (mg) | 408 | 1320 |
| Form (color/shape) | White solid | White solid |

(Examples 14a to c) Syntheses of N-(2-aminoethyl)-4-(azidomethyl)benzamide Group-Introduced Alginic acids (14-A2, 14-B2 and 14-A2b)

[C76]

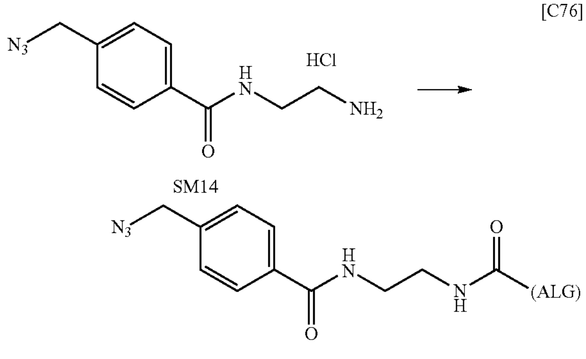

SM14

14-A2, 14-B2, 14-A2b

Compounds 14-A2, 14-B2 and 14-A2b were synthesized by the following synthesis method under the following reaction conditions.

[Synthesis Method]

DMT-MM, a compound of Formula SM14 (N-(2-aminoethyl)-4-(azidomethyl)benzamide hydrochloride; CAS REGISTRY NO.: 2401876-25-1] synthesized by a method well known by publications and 1-molar aqueous sodium bicarbonate solution were added to a sodium alginate (manufactured by MOCHIDA PHARMACEUTICAL CO., LTD.) aqueous solution prepared to 1 wt % and stirred. Sodium chloride was added thereto, and then ethanol (EtOH 2) was added thereto and stirred at room temperature. An obtained precipitation was filtered, washed with ethanol and dried under reduced pressure, thereby obtaining a title compound as solid. In Example 14c, a solid obtained by the previous operation was dissolved in water, lyophilized, thereby obtaining a title compound.

[Reaction Conditions and Results]

TABLE 21

| Examples | 14a | 14b | 14c |
|---|---|---|---|
| Compound | 14-A2 | 14-B2 | 14-A2b |
| Sodium alginate | A-2 | B-2 | A-2 |
| 1 wt % sodium alginate aqueous solution (mL) | 20 | 20 | 30 |

TABLE 21-continued

| Examples | 14a | 14b | 14c |
|---|---|---|---|
| DMT-MM (mg) | 84 | 84 | 83.7 |
| 1-molar aqueous sodium bicarbonate solution (μL) | 252 | 151 | 113.5 |
| SM14 (mg) | 52 | 26 | 19.3 |
| Reaction time (hours) | 3 | 3 | 3 |
| Reaction temperature | 30° C. | 30° C. | 30° C. |
| NaCl (mg) | 200 | 200 | 300 |
| EtOH 2 (mL) | 40 | 40 | 60 |
| Post treatment stirring time (minutes) | 30 | 30 | 30 |
| Yield (mg) | 185 | 187 | 276 |
| Form (color/shape) | White solid | White solid | White solid |

(Example 15) Synthesis of N-(2-(2-(2-aminoethoxy)ethoxy)ethyl)-4-(azidomethyl)benzamide Group-Introduced alginic acid (15-A2)

[C77]

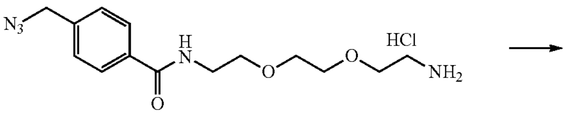

SM15

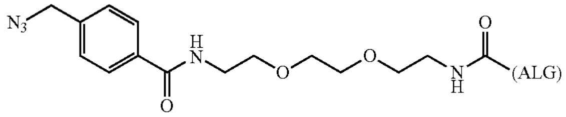

15-A2

DMT-MM (112 mg), an ethanol (4.0 mL) solution of a compound of Formula SM15 (N-(2-(2-(2-aminoethoxy)ethoxy)ethyl)-4-(azidomethyl)benzamide hydrochloride; CAS REGISTRY NO.: 2401876-41-1] (38 mg) synthesized by a method well known by publications and 1-molar aqueous sodium bicarbonate solution (151 μL) were added to a sodium alginate (manufactured by MOCHIDA PHARMACEUTICAL CO., LTD., A-2) aqueous solution (40 mL) prepared to 1 wt % and stirred at 30° C. for three hours. Sodium chloride (0.4 g) was added thereto, then, ethanol (80 mL) was added thereto and stirred at room temperature for 30 minutes. An obtained precipitation was filtered, washed with ethanol and dried under reduced pressure. The solid obtained by the previous operation was dissolved in water, lyophilized, thereby obtaining a title compound (416 mg) as a white solid.

(Examples 16a and b) Syntheses of N-(2-(2-amino-ethoxy)ethyl)-4-azidobenzamide Group-Introduced alginic acids (compounds: 16-A2 and 16-A2b)

[C78]

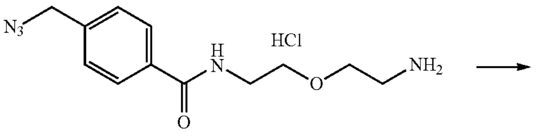

SM16

-continued

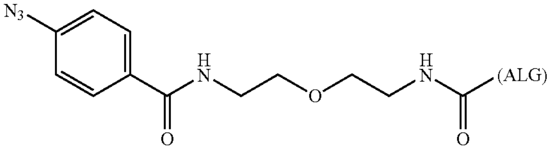

16-A2, 16-A2b

Compounds 16-A2 and 16-A2b were synthesized by the following synthesis method under the following reaction conditions.

[Synthesis Method]

DMT-MM, a compound of Formula SM16 (N-(2-(2-aminoethoxy)ethyl)-4-azidobenzamide hydrochloride; CAS REGISTRY NO.: 2401876-47-7] synthesized by a method well known by publications and 1-molar aqueous sodium bicarbonate solution were added to a sodium alginate (manufactured by MOCHIDA PHARMACEUTICAL CO., LTD.) aqueous solution prepared to 1 wt % and stirred. Sodium chloride was added thereto, and then ethanol (EtOH 2) was added thereto and stirred at room temperature. An obtained precipitation was filtered, washed with ethanol and dried under reduced pressure, thereby obtaining a title compound as solid. The solid obtained by the previous operation was dissolved in water, lyophilized, thereby obtaining a title compound.

[Reaction Conditions and Results]

TABLE 22

| Examples | 16a | 16b |
|---|---|---|
| Compound | 16-A2 | 16-A2b |
| Sodium alginate | A-2 | A-2 |
| 1 wt % sodium alginate aqueous solution (mL) | 40 | 140 |
| DMT-MM (mg) | 112 | 234 |
| 1-molar aqueous sodium bicarbonate solution (μL) | 151 | 318 |
| SM16 (mg) | 31 | 61 |
| Reaction time (hours) | 3 | 3 |
| Reaction temperature | 30° C. | 32° C. |
| NaCl (mg) | 400 | 1400 |
| EtOH 2 (mL) | 80 | 280 |
| Post treatment stirring time (minutes) | 30 | 30 |
| Yield (mg) | 400 | 1310 |
| Form (color/shape) | White solid | White solid |

(Examples 17a to c) Syntheses of N-(2-amino-ethyl)-4-azidobenzamide Group-Introduced Alginic Acids (17-B2, 17-B2b and 17-A2)

[C79]

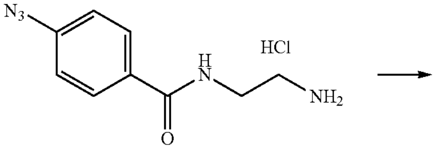

SM17

-continued

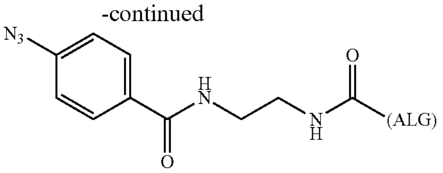

17-B2, 17-B2b, 17-A2

Compounds 17-B2, 17-B2b and 17-A2 were synthesized by the following synthesis method under the following reaction conditions.

[Synthesis Method]

DMT-MM, a compound of Formula SM17 (N-(2-aminoethyl)-4-azidobenzamide hydrochloride; CAS REGISTRY NO.: 164013-00-7] synthesized by a method well known by publications and 1-molar aqueous sodium bicarbonate solution were added to a sodium alginate (manufactured by MOCHIDA PHARMACEUTICAL CO., LTD.) aqueous solution prepared to 1 wt % and stirred. Sodium chloride was added thereto, and then ethanol (EtOH 2) was added thereto and stirred at room temperature. An obtained precipitation was filtered, washed with ethanol and dried under reduced pressure, thereby obtaining a title compound as solid. In Example 17c, a solid obtained by the previous operation was dissolved in water, lyophilized, thereby obtaining a title compound.

[Reaction Conditions and Results]

TABLE 23

| Examples | 17a | 17b | 17c |
|---|---|---|---|
| Compound | 17-B2 | 17-B2b | 17-A2 |
| Sodium alginate | B-2 | B-2 | A-2 |
| 1 wt % sodium alginate aqueous solution (mL) | 30.0 | 60.0 | 30 |
| DMT-MM (mg) | 63 | 67 | 84 |
| 1-molar aqueous sodium bicarbonate solution (μL) | 113 | 91 | 113 |
| SM17(mg) | 18 | 15 | 18 |
| Reaction time (hours) | 3 | 3 | 3 |
| Reaction temperature | 30° C. | 30° C. | 30° C. |
| NaCl (mg) | 300 | 600 | 300 |
| EtOH 2 (mL) | 60 | 120 | 60 |
| Post treatment stirring time (minutes) | 30 | 30 | 30 |

TABLE 23-continued

| Examples | 17a | 17b | 17c |
|---|---|---|---|
| Yield (mg) | 282 | 560 | 271 |
| Form (color/shape) | White solid | White solid | White solid |

(Example 18) Synthesis of N-(2-(2-(2-aminoethoxy)ethoxy)ethyl)-4-azidobenzamide Group-Introduced alginic acid (18-A2)

[C80]

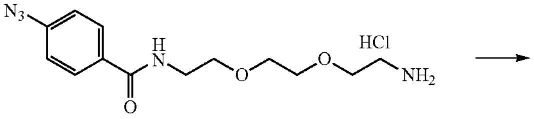

SM18

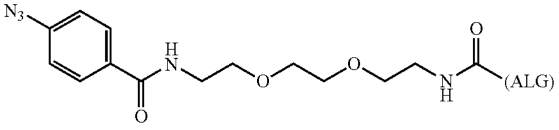

18-A2

DMT-MM (112 mg), an ethanol (4.0 mL) solution of a compound of Formula SM18 (N-(2-(2-(2-aminoethoxy)ethoxy)ethyl)-4-azidobenzamide hydrochloride; CAS REGISTRY NO.: 2401876-48-8) (45 mg) synthesized by a method well known by publications and 1-molar aqueous sodium bicarbonate solution (151 μL) were added to a sodium alginate (manufactured by MOCHIDA PHARMACEUTICAL CO., LTD., A-2) aqueous solution (40 mL) prepared to 1 wt % and stirred at 30° C. for three hours. Sodium chloride (0.4 g) was added thereto, then, ethanol (80 mL) was added thereto and stirred at room temperature for 30 minutes. An obtained precipitation was filtered, washed with ethanol and dried under reduced pressure. The solid obtained by the previous operation was dissolved in water, lyophilized, thereby obtaining a title compound (408 mg) as a white solid.

TABLE 24-1

| Ex. | Cpd. No. | MWL (nm) | MWD (Da) | WAMW (Da) | RGIR (mol %) ($) |
|---|---|---|---|---|---|
| 1a | 1-A2 | 280 | 12,000-2,650,000 | 1,530,000 | 6.9 |
| 1b | 1-A1 | 280 | 5,000-2,620,000 | 1,150,000 | 6.5 |
| 1c | 1-A3 | 280 | 27,000-2,660,000 | 1,710,000 | 6.6 |
| 1d | 1-B2 | 288 | 3,730-2,850,000 | 1,410,000 | 4.9 |
| 1e | 1-B2b | 287 | 13,700-2,520,000 | 1,400,000 | 0.8 |
| 1f | 1-B2c | 287 | 2,230-2,570,000 | 1,420,000 | 1.9 |
| 1g | 1-A2b | — | — | — | 4.9 |
| 1h | 1-A2c | — | — | — | 0.8 |
| 1i | 1-A2d | — | — | — | 0.9 |
| 2 | 2-B2 | 287 | 2,080-2,570,000 | 1,400,000 | 2.7 |
| 3 | 3-A2 | 290 | 1,000-2,690,000 | 1,260,000 | 4.3 |
| 4a | 4-B2 | 215 | 1,850-2,830,000 | 1,380,000 | 4.5 |
| 4b | 4-A2 | — | — | — | 4.4 |
| 4c | 4-B2b | — | — | — | 2.4 |
| 4d | 4-A2b | — | — | — | 0.6 |
| 4e | 4-A2c | — | 35,600-2,520,000 | 1,380,000 | 0.7 |
| 4f | 4-A2d | — | — | — | 0.7 |
| 4g | 4-A3 | — | — | — | 0.5 |
| 5a | 5-A2 | 220 | 8,000-2,650,000 | 1,420,000 | 4.6 |
| 5b | 5-B2 | 220 | 5,000-2,680,000 | 1,400,000 | 4.1 |

TABLE 24-1-continued

| Ex. | Cpd. No. | MWL (nm) | MWD (Da) | WAMW (Da) | RGIR (mol %) ($) |
|---|---|---|---|---|---|
| 6a | 6-A2 | # | 13,000-2,820,000 | 1,420,000 | 4.3 |
| 6b | 6-B2 | # | 13,000-2,590,000 | 1,410,000 | 4.2 |
| 6c | 6-B2b | # | 13,000-2,670,000 | 1,410,000 | 2.1 |
| 7 | 7-A2 | # | 13,000-3,640,000 | 1,400,000 | 3.2 |
| 8a | 8-A2 | # | 13,000-2,660,000 | 1,370,000 | 5.0 |
| 8b | 8-B2 | # | 17,000-2,540,000 | 1,380,000 | 2.4 |
| 9 | 9-A2 | # | 14,000-2,720,000 | 1,370,000 | 4.3 |
| 10 | 10-A2 | # | 13,000-2,580,000 | 1,350,000 | 4.4 |
| 11a | 11-A2 | 255 | 15,000-2,530,000 | 1,510,000 | 6.1 |
| 11b | 11-A1 | 255 | 5,000-2,590,000 | 1,140,000 | 9.4 |
| 11c | 11-A3 | 255 | 18,000-2,690,000 | 1,650,000 | 6.9 |
| 11d | 11-B2 | 249 | 7,630-2,590,000 | 1,420,000 | 3.7 |
| 11e | 11-B2b | 249 | 2,290-2,560,000 | 1,410,000 | 0.6 |
| 11f | 11-B2c | 249 | 11,800-2,540,000 | 1,420,000 | 1.5 |
| 11g | 11-A2b | — | — | — | 4.3 |
| 11h | 11-A2c | — | — | — | 2.7 |
| 11i | 11-B2d | — | — | — | 4.9 |
| 11j | 11-A2d | — | — | — | 3.1 |
| 11k | 11-A2e | 250 | 8,710-2,600,000 | 1,350,000 | 3.0 |
| 11l | 11-A3 | — | — | — | 3.0 |
| 11m | 11-A2f | — | — | — | 3.1 |
| 12 | 12-A2 | 255 | 10,000-2,850,000 | 1,460,000 | 4.3 |

Cpd. No.: compound number,
MWL: measurement wavelength,
MWD: molecular weight distribution,
WAMW: weight-average molecular weight,
RGIR: reactive group introduction rate,
#: differential refractometer,
$: NMR integral ratio

TABLE 24-2

| Ex. | Cpd. No. | MWL (nm) | MWD (Da) | WAMW (Da) | RGIR (mol %) ($) |
|---|---|---|---|---|---|
| 13a | 13-A2 | 230 | 7,740-2, 660,000 | 1,430,000 | 4.7 |
| 13b | 13-A2b | — | — | — | 2.7 |
| 14a | 14-A2 | 255 | 11,000-2,660,000 | 1,530,000 | 9.4 |
| 14b | 14-B2 | 232 | 5,190-2,660,000 | 1,410,000 | 11.1 |
| 14c | 14-A2b | — | — | — | 4.9 |
| 15 | 15-A2 | 230 | 7,120-2,710,000 | 1,450,000 | 4.2 |
| 16a | 16-A2 | 270 | 5,130-2,690,000 | 1,410,000 | 3.9 |
| 16b | 16-A2b | — | — | — | 2.7 |
| 17a | 17-B2 | 267 | 6,430-2,590,000 | 1,410,000 | 5.1 |
| 17b | 17-B2b | 267 | 1,820-2,560,000 | 1,410,000 | 2.0 |
| 17c | 17-A2 | — | — | — | 5.0 |
| 18 | 18-A2 | 270 | 5,020-2,670,000 | 1,430,000 | 4.2 |

Cpd. No.: compound number,
MWL: measurement wavelength,
MWD: molecular weight distribution,
WAMW: weight-average molecular weight,
RGIR: reactive group introduction rate,
#: differential refractometer,
$: NMR integral ratio

TABLE 25-1

| IM No. | NMR Data (δ:ppm) | Mass MS-ESI(m/z), [M + H]+ | Mass RT(min) |
|---|---|---|---|
| IM3-1 | DMSO-$d_6$:7.88(2H, d, J = 8 Hz), 7.73-7.66(3H, m), 7.61-7.57(2H, m), 7.50-7.29(11H, m), 5.02(1H, d, J = 14 Hz), 4.29-4.18(3H, m), 3.62(1H, d, J = 14 Hz), 3.46(2H, d, J = 6 Hz), 3.18-3.08(1H, m), 3.02-2.89(1H, m), 2.47-2.39(1H, m), 1.85-1.74(1H, m) | — | — |

TABLE 25-1-continued

| IM No. | NMR Data (δ:ppm) | Mass MS-ESI(m/z), [M + H]+ | Mass RT(min) |
|---|---|---|---|
| IM3-2 | DMSO-$d_6$:7.73(1H, brs), 7.64-7.58(2H, m), 7.51-7.29(6H, m), 5.04(1H, d, J = 14 Hz), 3.63(1H, d, J = 14 Hz), 3.18-3.06(1H, m), 3.04-2.95(1H, m), 2.95(2H, s), 2.47-2.39(1H, m), 1.87-1.78(1H, m) | 334 | 0.74 |
| IM5-1 | $CDCl_3$:7.22(2H, d, J = 8 Hz), 6.85(2H, d, J = 8 Hz), 6.74(1H, brs), 4.79(1H, brs), 4.25(2H, d, J = 6 Hz), 4.09(2H, t, J = 5 Hz), 3.78(2H, q, J = 5 Hz), 1.46(9H, s) | — | — |
| IM5-2 | DMSO-$d_6$:9.67(1H, brs), 8.14(3H, brs), 7.38(2H, d, J = 9 Hz), 6.98(2H, d, J = 9 Hz), 4.10(2H, t, J = 6 Hz), 3.94(2H, brs), 3.57(2H, q, J = 6 Hz) | *285 | 0.59 |
| IM5-3 | $CDCl_3$:7.23(2H, d, J = 9 Hz), 6.94(1H, brs), 6.85(2H, d, J = 9 Hz), 6.80-6.77(1H, m), 4.42(2H, d, J = 6 Hz), 4.25-4.21(1H, m), 4.11-4.05(3H, m), 3.92(1H, d, J = 15 Hz), 3.78(2H, q, J = 6 Hz), 2.28-2.05(3H, m), 1.99-1.55(6H, m), 1.48-1.39(1H, m) | 427 | 1.02 |
| IM5-4 | $CDCl_3$:7.22(2H, d, J = 9 Hz), 6.87(2H, d, J = 9 Hz), 6.75(1H, brs), 4.42(2H, d, J = 6 Hz), 4.25-4.20(1H, m), 4.10(1H, d, J = 15 Hz), 4.03-3.90(3H, m), 3.08(2H, t, J = 5 Hz), 2.28-2.07(3H, m), 1.99-1.55(6H, m), 1.48-1.40(1H, m) | 331 | 0.72 |

*[M + Na]+,
IM No. = intermediate number,
RT = retention time

TABLE 25-2

| IM No. | NMR Data (δ:ppm) | Mass MS-ESI(m/z), [M + H]+ | Mass RT(min) |
|---|---|---|---|
| IM8-1 | DMSO-$d_6$:9.39(1H, brs), 7.93(1H, brs), 6.92(1H, t, J = 6 Hz), 3.49(2H, d, J = 6 Hz), 3.25-3.17(4H, m), 1.38(9H, s) | — | — |
| IM8-2 | DMSO-$d_6$:9.50(1H, brs), 8.54(1H, brs), 8.01(3H, brs), 3.49(2H, s), 3.28-3.24(4H, m) | — | — |
| IM8-3 | DMSO-$d_6$:9.41(1H, brs), 8.03(1H, t, J = 6 Hz), 7.78(1H, t, J=6 Hz), 4.35-4.29(1H, m), 3.93(1H, d, J = 15 Hz), 3.79(1H, d, J = 15 Hz), 3.68 (2H, dd, J = 6, 24 Hz), 3.27-3.16(4H, m), 2.28-2.05(3H, m), 1.99-1.69(4H, m), 1.65-1.54(2H, m), 1.46-1.36(1H, m) | 378 | 0.84 |
| IM8-4 | DMSO-$d_6$:7.83(1H, t, J = 6 Hz), 7.78(1H, t, J = 6 Hz), 4.33-4.29(1H, m), 3.92(1H, d, J = 15 Hz), 3.79(1H, d, J = 15 Hz), 3.69 (2H, dd, J = 6, 2 Hz), 3.05(2H, q, J = 6 Hz), 2.55(2H, t, J = 6 Hz), 2.28-2.05(3H, m), 1.99-1.69(4H, m), 1.63-1.56(2H, m), 1.46-1.36(1H, m) | 282 | 0.62 |
| IM9-1 | DMSO-$d_6$:9.39(1H, t, J = 5 Hz), 8.00(1H, t, J = 6 Hz), 6.74(1H, t, J = 6 Hz), 3.21(2H, t, J = 6 Hz), 3.17(2H, t, J = 6 Hz), 3.14-3.07(2H, m), 2.20(2H, t, J = 7 Hz), 1.37(9H, s) | — | — |
| IM9-2 | DMSO-$d_6$:9.47(1H, brs), 8.27(1H, t, J = 6 Hz), 7.74(3H, brs), 3.27-3.17(4H, m), 2.96(2H, t, J = 7 Hz), 2.43(2H, t, J = 7 Hz) | — | — |
| IM9-3 | DMSO-$d_6$:9.40(1H, t, J = 5 Hz), 8.04(1H, t, J = 6 Hz), 7.68(1H, t, J = 6 Hz), 4.29-4.23(1H, m), 3.85(1H, d, J = 15 Hz), 3.73(1H, d, J = 15 Hz), 3.32-3.13(6H, m), 2.25(2H, t, J = 7 Hz), 2.23-2.03(3H, m), 1.95-1.70(4H, m), 1.66-1.50(2H, m), 1.43-1.35(1H, m) | 392 | 0.83 |
| IM9-4 | DMSO-$d_6$:7.85(1H, t, J = 6 Hz), 7.68(1H, t, J = 6 Hz), 4.30-4.25(1H, m), 3.86(1H, d, J = 15 Hz), 3.74(1H, d, J = 15 Hz), 3.32-3.25(2H, m), 3.04(2H, q, J = 6 Hz), 2.55(2H, t, J = 6 Hz), 2.27(2H, t, J = 7 Hz), 2.25-2.04(3H, m), 1.96-1.71(4H, m), 1.67-1.51(2H, m), 1.45-1.35(1H, m) | 296 | 0.62 |

*[M + Na]+,
IM No. = intermediate number,
RT = retention time

TABLE 25-3

| | | Mass | |
|---|---|---|---|
| IM No. | NMR Data (δ: ppm) | MS-ESI(m/z), [M + H]+ | RT(min) |
| IM10-1 | $CDCl_3$: 7.73(1H, brs), 6.40(1H, brs), 4.86(1H, brs), 3.64(2H, q, J = 6 Hz), 3.56-3.50(4H, m), 3.47-3.43(2H, m), 3.30(2H, q, J = 5 Hz), 2.53-2.50(2H, m), 1.45(9H, s) | — | — |
| IM10-2 | DMSO-$d_6$: 9.50(1H, t, J = 5 Hz), 8.15(1H, t, J = 6 Hz), 8.01(3H, brs), 3.58((2H, t, J = 5 Hz), 3.43(2H, t, J = 6 Hz), 3.38(2H, q, J = 7 Hz), 3.24(2H, q, J = 6 Hz), 3.00-2.92(2H, m), 2.39(2H, t, J = 7 Hz) | — | — |
| IM10-3 | $CDCl_3$: 7.80(1H, brs), 6.80(1H, brs), 6.58(1H, brs), 4.29-4.23(1H, m), 4.06(1H, d, J = 15 Hz), 3.89(1H, d, J = 15 Hz), 3.64(2H, q, J = 6 Hz), 3.60-3.55(4H, m), 3.52-3.46(2H, m), 3.44(2H, q, J = 5 Hz), 2.52(2H, t, J = 6 Hz), 2.31-2.11(3H, m), 2.02-1.78(4H, m), 1.76-1.61(2H, m), 1.51-1.42(1H, m) | 436 | 0.82 |
| IM10-4 | $CDCl_3$: 7.33(1H, brs), 6.82(1H, brs), 4.28-4.23(1H, m), 4.06(1H, d, J = 15 Hz), 3.90(1H, d, J = 15 Hz), 3.56(4H, t, J = 5 Hz), 3.51-3.44(4H, m), 3.01(2H, t, J = 6 Hz), 2.35(2H, t, J = 6 Hz), 2.31-2.12(3H, m), 2.02-1.79(4H, m), 1.77-1.60(2H, m), 1.50-1.42(1H, m) | 340 | 0.64 |

* [M + Na]+,
IM No. = intermediate number,
RT = retention time (Example F1-A) Production of Crosslinked Alginate Gel Fiber (1)

A3 wt % alkyne aqueous solution (alkyne solution) that was prepared from the compound 4-A2d or the compound 1-A2d and a 3 wt % azide aqueous solution (azide solution) that was prepared from the compound 11-A2d, the compound 13-A2b or the compound 16-A2b were used, and equal volumes of the alkyne solution and the azide solution were mixed together in a combination shown in Table 26, thereby preparing a chemically modified alginic acid solution mixture (F1A-M1). The solution mixture F1A-M1 and a 3 wt % alginic acid aqueous solution (ALGS) prepared from sodium alginate (B-2) were mixed together in a ratio shown in Table 26, thereby producing an alginic acid solution mixture (F1A-M2). Subsequently, equal volumes of the solution mixture F1A-M2 and 1.8 wt % saline solution containing 20 mg/mL of blue dextran (manufactured by Cytiva, Blue Dextran 2000, code No. 17036001) were mixed together, thereby producing an alginic acid solution mixture (F1A-M3). A Hamilton syringe was filled with the alginic acid solution mixture F1A-M3, and a metal needle (Musashi Engineering, Inc., SNA-19G-B), a silicon tube (AS ONE Corporation, ϕ1×ϕ2) and a glass capillary (NARISHIGE Group, G-1) were sequentially connected to the syringe and set in a syringe pump. The tip of the glass capillary was immersed in a beaker containing 100 mmol/L of a calcium chloride aqueous solution, and the alginic acid solution mixture was injected into the calcium chloride aqueous solution at a flow rate of 250 μL/minute for one minute. A fibrous substance injected into the calcium chloride aqueous solution was placed still for 30 minutes or longer and was thereby obtained as a crosslinked alginate gel fiber (CLA-1A) (refer to CLA-1A No. in Table 26).

TABLE 26

| No. | Combination of alkyne compound/ azide compound in F1A-M1 | Mixing ratio of F1A-M1/ALGS | Final concentration of alkyne compound and azide compound in F1A-M3 (wt %) | CLA-1A No. |
|---|---|---|---|---|
| F1-A-1 | — | ALGS only | 0 | FB1-A-1 |
| F1-A-2 | 1-A2d/11-A2d | 5/10 | 0.5 | FB1-A-2 |
| F1-A-3 | 1-A2d/13-A2b | 5/10 | 0.5 | FB1-A-3 |
| F1-A-4 | 1-A2d/16-A2b | 5/10 | 0.5 | FB1-A-4 |
| F1-A-5 | 4-A2d/11-A2d | 2/13 | 0.2 | FB1-A-5 |
| F1-A-6 | 4-A2d/11-A2d | 5/10 | 0.5 | FB1-A-6 |
| F1-A-7 | 4-A2d/11-A2d | 10/5 | 1.0 | FB1-A-7 |
| F1-A-8 | 4-A2d/13-A2b | 5/10 | 0.5 | FB1-A-8 |
| F1-A-9 | 4-A2d/16-A2b | 5/10 | 0.5 | FB1-A-9 |

(Example F1-B) Production of Crosslinked Alginate Gel Fiber (2)

Equal volumes of a 3 wt % compound 4-A2d aqueous solution prepared from the compound 4-A2d and a 3 wt % compound 11-A2d aqueous solution prepared from the compound 11-A2d were mixed together, and a solution mixture (F1B-M1) of chemically modified alginic acid was prepared. The solution mixture F1B-M1 and a 3 wt % sodium alginate aqueous solution (ALGS) prepared from sodium alginate (B-2) were mixed together in a volume ratio of 1:2, thereby producing a 3 wt % alginic acid solution mixture (F1B-M1B). The solution mixture F1B-M1B was prepared to have a concentration shown in Table 27 (in Table 27; concentration of F1B-M2) and mixed with saline solution containing separately-prepared blue dextran (manufactured by Cytiva, Blue Dextran 2000, code No. 17036001) (F1B-BS: the concentration of blue dextran and the concentration of sodium chloride were as shown in Table 27) at a volume ratio shown in Table 27, thereby producing an alginic acid solution mixture (F1B-M3). The alginic acid solution mixture was prepared so that the blue dextran concentration (mg/mL) and the sodium chloride concentration (mg/mL) in the solution mixture F1B-M3 reached 10 mg/mL and 9 mg/mL, respectively. A Hamilton syringe was filled with the solution mixture F1B-M3. Subsequently, a metal needle (Musashi Engineering, Inc., SNA-19G-B), a silicon tube (AS ONE Corporation, ϕ1×ϕ2) and a glass capillary (NARISHIGE Group, G-1) were sequentially connected to the syringe and set in a syringe pump. The tip of the glass capillary was immersed in a beaker containing 100 mmol/L of a calcium chloride aqueous solution, and the alginic acid solution mixture was injected at a flow rate of 250 μL/minute for one minute. A fibrous substance injected into the calcium chloride aqueous solution was placed still for 30 minutes or longer and was thereby obtained as a crosslinked alginate gel fiber (CLA-1B) (refer to CLA-1B No. in Table 27).

TABLE 27

| No. | F1B-M2 concentration (wt %) | Concentration of blue dextran, NaCl in F1B-BS (mg/mL) | | Volume ratio between F1B-M2 and F1B-BS in F1B-M3 | Final concentration of alkyne compound and azide compound in F1B-M3 (wt %) | CLA-1B No. |
|---|---|---|---|---|---|---|
| F1-B-1 | 3.0 | 30 | 27 | 2/1 | 2.0 | FB1-B-1 |
| F1-B-2 | 2.0 | 20 | 18 | 1/1 | 1.0 | FB1-B-2 |
| F1-B-3 | 1.0 | 20 | 18 | 1/1 | 0.5 | FB1-B-3 |

(Example F1-C) Production of Polymer-Coated Crosslinked Alginate Gel Fiber (1)

The crosslinked alginate gel fiber in the calcium chloride aqueous solution, which was obtained in (Example F1-A) or (Example F1-B), was filtered and fractionated using a cell strainer. The fractionated crosslinked alginate gel fiber was added to an aqueous solution containing a cationic polymer having each composition shown in Table 28 and shaking-stirred at 37° C. and 125 rpm for 20 minutes, thereby coating the crosslinked alginate gel fiber with the polymer. The fiber in the aqueous solution was filtered and fractionated using the cell strainer and washed with 5 mL of physiological saline twice, thereby obtaining a polymer-coated crosslinked alginate gel fiber (CFB-1) (refer to CFB-1 No. in Table 29).

TABLE 28

| No. | Composition of cationic polymer-containing aqueous solution |
|---|---|
| F1-c1 | 0.1% poly-L-ornithine hydrobromide/100 mM calcium chloride |
| F1-c2 | 0.1% polyallylamine hydrochloride/100 mM calcium chloride |

TABLE 29

| No. | CLA-1A, 1B No. | Cationic polymer-containing aqueous solution | CFB-1 No. |
|---|---|---|---|
| F1-C-1 | FB1-A-1 | F1-c1 | FB1-A-1-c1 |
| F1-C-2 | FB1-A-2 | F1-c1 | FB1-A-2-c1 |
| F1-C-3 | FB1-A-3 | F1-c1 | FB1-A-3-c1 |
| F1-C-4 | FB1-A-4 | F1-c1 | FB1-A-4-c1 |
| F1-C-5 | FB1-A-6 | F1-c1 | FB1-A-6-c1 |
| F1-C-6 | FB1-A-7 | F1-c1 | FB1-A-7-c1 |
| F1-C-7 | FB1-A-8 | F1-c1 | FB1-A-8-c1 |
| F1-C-8 | FB1-A-9 | F1-c1 | FB1-A-9-c1 |
| F1-C-9 | FB1-B-1 | F1-c1 | FB1-B-1-c1 |
| F1-C-10 | FB1-B-2 | F1-c1 | FB1-B-2-c1 |
| F1-C-11 | FB1-A-6 | F1-c2 | FB1-A-6-c2 |

(Example F1-D) Stability of Polymer-Coated Crosslinked Alginate Gel Fiber (1) EDTA Treatment of Fiber The polymer-coated crosslinked alginate gel fiber (CFB-1) obtained in (Example F1-C) was added to 20 mM EDTA·2Na/physiological saline (5 mL) and shaking-stirred at 37° C. and 125 rpm for 20 minutes. The chelate-treated polymer-coated crosslinked alginate gel fiber was filtered and fractionated again using the cell strainer and washed with 5 mL of physiological saline twice. The obtained polymer-coated crosslinked alginate gel fiber was immersed in 5 mL of physiological saline until a stability evaluation test.

(2) Shaking Collapse Test

The EDTA-treated polymer-coated crosslinked alginate gel fiber was separated with using the cell strainer, added to a 25 mL centrifuge tube to which 10 mL of a PBS solution had been added and shaken at 37° C. for 24 hours.

The stability of the polymer-coated crosslinked alginate gel fiber after the EDTA treatment and after the shaking was evaluated based on the following indexes.

Stability Evaluation (Score)

3: The collapse/dissolution/deformation/blue dextran elution or the like of the fiber are all not recognized.

2: Collapse/dissolution/deformation/blue dextran elution (cumulatively less than 100 μg/mL) or the like are recognized in a part of the fiber.

1: Clear collapse/dissolution/deformation/blue dextran elution (cumulatively 100 μg/mL or more) or the like are recognized in the fiber.

TABLE 30

| | | Stability evaluation (score) | |
|---|---|---|---|
| No. | CFB-1 No. | EDTA treatment | After shaking |
| F1-D-1 | FB1-A-1-c1 | 1 | 1 |
| F1-D-2 | FB1-A-2-c1 | 3 | 3 |
| F1-D-3 | FB1-A-3-c1 | 3 | 3 |
| F1-D-4 | FB1-A-4-c1 | 3 | 3 |
| F1-D-5 | FB1-A-6-c1 | 3 | 3 |
| F1-D-6 | FB1-A-7-c1 | 3 | 3 |
| F1-D-7 | FB1-A-8-c1 | 3 | 3 |
| F1-D-8 | FB1-B-1-c1 | 3 | 3 |
| F1-D-9 | FB1-B-2-c1 | 3 | 3 |
| F1-D-10 | FB1-A-6-c2 | 2 | 2 |
| F1-D-11 | FB1-A-9-c1 | 3 | 3 |

(Example F2-A) Production of Antibody-Producing Cell-Containing Crosslinked Alginate Gel Fiber A G016 culture medium having a composition in Table 31 below was prepared. Subsequently, methotrexate (hereinafter, represented by MTX) was dissolved in D-PBS so as to become 1 mmol/L, thereby preparing a MTX solution. The MTX solution was diluted with the G016 culture medium such that the final concentration reached 1 μmol/L, and an antibody-producing culture medium solution was prepared.

TABLE 31

| | Sample | Maker | Added Amount (mL) | Final concentration |
|---|---|---|---|---|
| Culture medium | JX G016 | Irvine | 930 | |
| Additive | L-Glutamine 200 mM | SIGMA | 40 | 8 mM |
| | Penicillin Streptomycin | Invitrogen | 10 | 1% |
| | Soy Hydrolysate UF Solution 50X | SIGMA | 20 | 2% |

Equal volumes of an alkyne aqueous solution and an azide aqueous solution prepared according to formulations in Table 32 and Table 33 below were mixed together in a combination shown in Table 34, thereby preparing an alginic acid solution mixture (F2A-M1).

TABLE 32

| | 3 wt % alkyne aqueous solution (containing 0.9 wt % of sodium chloride) |
|---|---|
| F2A1 | Prepared by mixing 3.3 wt % compound 4-A2d aqueous solution and 9.9 wt % sodium chloride aqueous solution in ratio of 10/1 |
| F2A2 | Prepared by mixing 3.3 wt % compound 4-A2c aqueous solution and 9.9 wt % sodium chloride aqueous solution in ratio of 10/1 |
| F2A3 | Prepared by mixing 3.3 wt % compound 1-A2d aqueous solution and 9.9 wt % sodium chloride aqueous solution in ratio of 10/1 |

TABLE 33

| | 3 wt % azide aqueous solution (containing 0.9 wt % of sodium chloride) |
|---|---|
| F2N1 | Prepared by mixing 3.3 wt % compound 11-A2d aqueous solution and 9.9 wt % sodium chloride aqueous solution in ratio of 10/1 |
| F2N2 | Prepared by mixing 3.3 wt % compound 11-A2e aqueous solution and 9.9 wt % sodium chloride aqueous solution in ratio of 10/1 |
| F2N3 | Prepared by mixing 3.3 wt % compound 13-A2b aqueous solution and 9.9 wt % sodium chloride aqueous solution in ratio of 10/1 |
| F2N4 | Prepared by mixing 3.3 wt % compound 16-A2b aqueous solution and 9.9 wt % sodium chloride aqueous solution in ratio of 10/1 |

The solution mixture F2A-M1 and a 3 wt % alginic acid solution (containing 0.9% sodium chloride) (ALGS2) prepared from sodium alginate (B-2) and a 0.9 wt % sodium chloride aqueous solution or a 3 wt % alginic acid solution (containing 0.9% sodium chloride) (ALGS2A) prepared from sodium alginate (A-2) and a 0.9 wt % sodium chloride aqueous solution were mixed together in a ratio shown in Table 34, thereby producing an alginic acid solution mixture (F2A-M2). Subsequently, equal volumes of the solution mixture F2A-M2 and an antibody-producing culture medium solution containing an anti-GPVI antibody-producing cell ($2\times10^7$ cells/mL) were mixed together, thereby producing a solution mixture (F2A-M3). A Hamilton syringe was filled with the solution mixture F2A-M3, and a needle for luer lock syringe (KANTO CHEMICAL CO., INC., 15/23NL-F) was connected to the syringe and set in a syringe pump. The tip of the needle was immersed in a beaker containing 100 mmol/L of a calcium chloride aqueous solution, and the alginic acid solution mixture was injected into the calcium chloride aqueous solution at a flow rate of 250 μL/minute for two minutes. A fibrous substance injected into the calcium chloride aqueous solution was placed still for 30 minutes or longer, thereby obtaining an anti-GPVI antibody-producing cell-containing crosslinked alginate gel fiber (CLA-G) (refer to CLA-G No. in Table 34).

TABLE 34

| No. | Combination of alkyne compound/azide compound in F2A-M1 | Mixing ratio of F2A-M1/ALGS2 | Mixing ratio of F2A-M1/ALGS2A | Final concentration of alkyne compound and azide compound in F2A-M3 (wt %) | CLA-G No. |
|---|---|---|---|---|---|
| F2-A-1 | 1-A2d/11-A2d | 5/10 | * | 0.5 | FB2-A-1 |
| F2-A-2 | 1-A2d/13-A2b | 5/10 | * | 0.5 | FB2-A-2 |
| F2-A-3 | 1-A2d/16-A2b | 5/10 | * | 0.5 | FB2-A-3 |
| F2-A-4 | 4-A2d/11-A2d | 2/13 | * | 0.2 | FB2-A-4 |
| F2-A-5 | 4-A2d/11-A2d | 5/10 | * | 0.5 | FB2-A-5 |
| F2-A-6 | 4-A2c/11-A2e | * | 5/10 | 0.5 | FB2-A-6 |
| F2-A-7 | 4-A2d/11-A2d | 10/5 | * | 1.0 | FB2-A-7 |
| F2-A-8 | 4-A2d/13-A2b | 5/10 | * | 0.5 | FB2-A-8 |

TABLE 34-continued

| No. | Combination of alkyne compound/azide compound in F2A-M1 | Mixing ratio of F2A-M1/ ALGS2 | Mixing ratio of F2A-M1/ ALGS2A | Final concentration of alkyne compound and azide compound in F2A-M3 (wt %) | CLA-G No. |
|---|---|---|---|---|---|
| F2-A-9 | 4-A2d/16-A2b | 5/10 | * | 0.5 | FB2-A-9 |
| F2-A-10 | 4-A2c/11-A2e | F2A-M1 only | * | 1.5 | FB2-A-10 |

(Example F2-B) Production of Bioactive Substance-Producing Cell-Comprising Crosslinked Alginate Gel Fiber A complete medium having a composition in Table 35 below was prepared.

TABLE 35

| Culture medium composition | | | | |
|---|---|---|---|---|
| | Sample | Maker | Added Amount (mL) | Final concentration |
| Culture medium | Optimized DMEM | AddexBio | 420 | |
| Additive | Fetal bovine serum (FBS) | NICHIREI | 75 | 15% |
| | Penicillin Streptomycin | Gibco | 5 | 1% |
| | 2-mercaptoethanol | Gibco | 0.455 | 0.05 mM |

Equal volumes of an alkyne aqueous solution F2A1 and an azide aqueous solution F2N2 shown in Table 32 and Table 33 in (Example F2-A) were mixed together, thereby preparing a chemically modified alginic acid solution mixture (F2B-M1). The solution mixture F2B-M1 and a 3 wt % sodium alginate aqueous solution (containing 0.9% sodium chloride) prepared from sodium alginate (B-2) and a 0.9 wt % sodium chloride-containing aqueous solution were mixed together in a ratio of 1:2, thereby producing an alginic acid solution mixture (F2B-M2). Subsequently, equal volumes of the solution mixture F2B-M2 and a complete medium in Table 35 containing MING cells ($1\times10^7$ cells/mL) were mixed together, thereby producing a solution mixture F2B-M3. A Hamilton syringe was filled with the solution mixture F2B-M3, and a needle for luer lock syringe (KANTO CHEMICAL CO., INC., 15/23NL-F) was connected to the syringe and set in a syringe pump. The tip of the needle was immersed in a beaker containing 100 mmol/L of a calcium chloride aqueous solution, and the alginic acid solution mixture (F2B-M3) was injected into the calcium chloride aqueous solution at a flow rate of 125 μL/minute for two minutes. A fibrous substance injected into the calcium chloride aqueous solution was placed still for 30 minutes or longer and was thereby obtained as a MIN6 cell-containing crosslinked alginate gel fiber (CLA-M) (FB2-B-1).

(Example F2-C) Production of Cell-Containing Polymer-Coated Crosslinked Alginate Gel Fibers A crosslinked alginate gel fiber containing a variety of cells obtained in (Example F2-A) or (Example F2-B) was coated in the same manner as in the method described in (Example F1-C) (the shaking-stirring time was 30 minutes) using a solution containing a cationic polymer having each composition shown in Table 36, thereby obtaining a polymer-coated crosslinked alginate gel fiber (CFB-S) (refer to CFB-S No. in Table 37).

TABLE 36

| No. | Composition of cationic polymer-containing aqueous solution |
|---|---|
| F2-c1 | 0.1% poly-L-ornithine hydrobromide/100 mM calcium chloride |
| F2-c2 | 0.1% polyallylamine hydrochloride/100 mM calcium chloride |

TABLE 37

| No. | CLA-G, CLA-M No. | Cationic polymer-containing aqueous solution | CFB-S No. |
|---|---|---|---|
| F2-C-1 | FB2-A-1 | F2-c1 | FB2-A-1-c1 |
| F2-C-2 | FB2-A-2 | F2-c1 | FB2-A-2-c1 |
| F2-C-3 | FB2-A-3 | F2-c1 | FB2-A-3-c1 |
| F2-C-4 | FB2-A-4 | F2-c1 | FB2-A-4-c1 |
| F2-C-5 | FB2-A-5 | F2-c1 | FB2-A-5-c1 |
| F2-C-6 | FB2-A-6 | F2-c1 | FB2-A-6-c1 |
| F2-C-7 | FB2-A-7 | F2-c1 | FB2-A-7-c1 |
| F2-C-8 | FB2-A-8 | F2-c1 | FB2-A-8-c1 |
| F2-C-9 | FB2-A-9 | F2-c1 | FB2-A-9-c1 |
| F2-C-10 | FB2-A-5 | F2-c2 | FB2-A-5-c2 |
| F2-C-11 | FB2-B-1 | F2-c1 | FB2-B-1-c1 |
| F2-C-12 | FB2-A-10 | F2-c1 | FB2-A-10-c1 |

(Example F3) Confirmation of Coating of Crosslinked Alginate Gel Fiber with Cationic Polymer A crosslinked alginate gel fiber (FB1-A-6) produced under conditions shown in No. F1-A-6 of (Example F1-A) was immersed in an aqueous solution containing 0.1% poly-L-lysine-FITC label/100 mM calcium chloride. After the same operation as in (Example F1-C) was performed, the surface of an obtained fiber was observed with using a fluorescence microscope.

Figure 7:
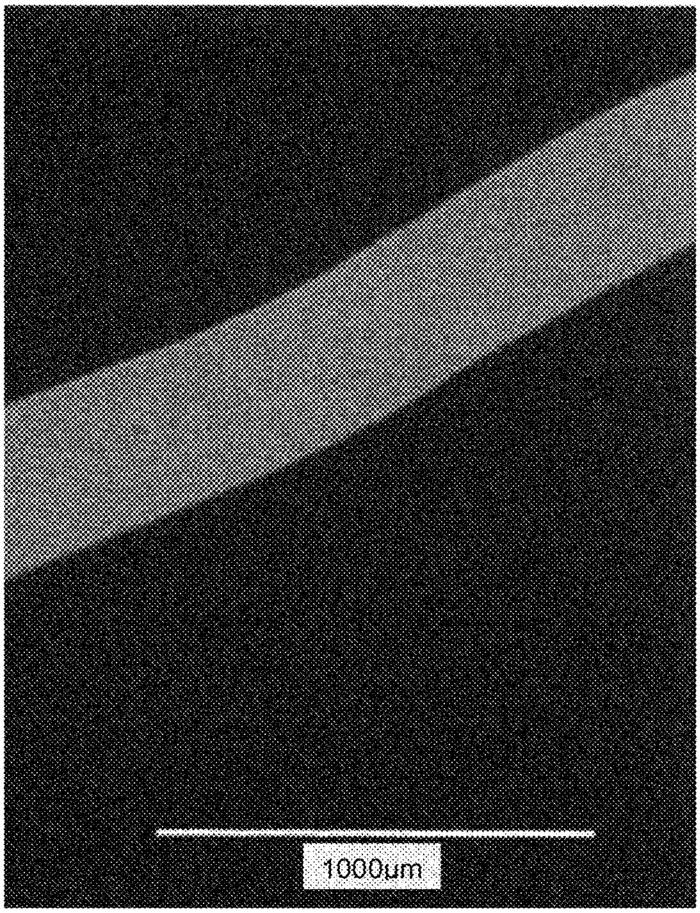
FIG. 7 is a fluorescence microscopic photograph of a polymer-coated crosslinked alginate gel fiber produced in (Example F3).
Figure 8:
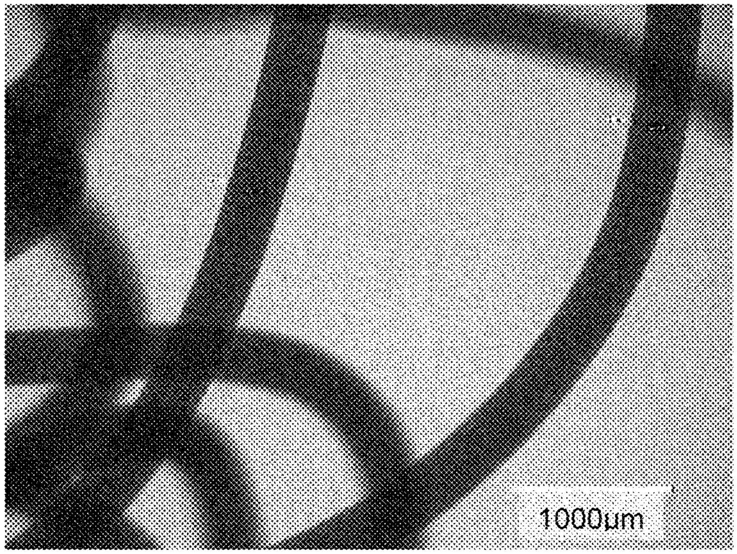
FIG. 8 is a photograph of a polymer-coated crosslinked alginate gel fiber (FB9-3-c3) of (Example F9) before culture.
Figure 9:
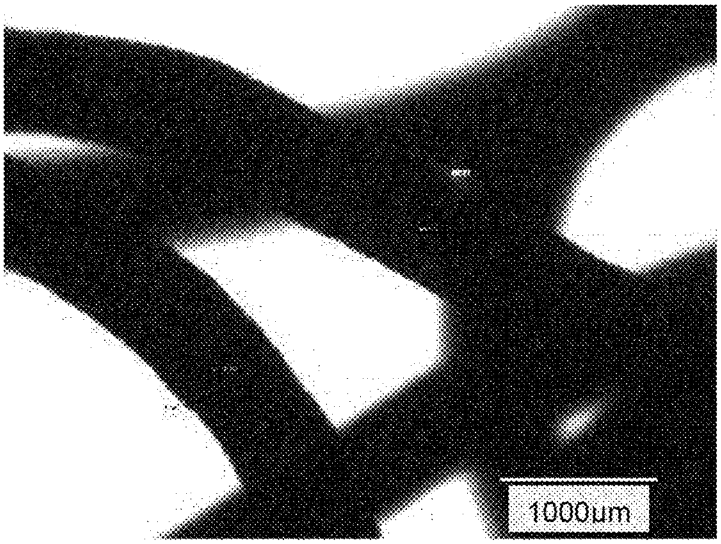
FIG. 9 is a photograph of the polymer-coated crosslinked alginate gel fiber (FB9-3-c3) of (Example F9) after culture.
Figure 10:
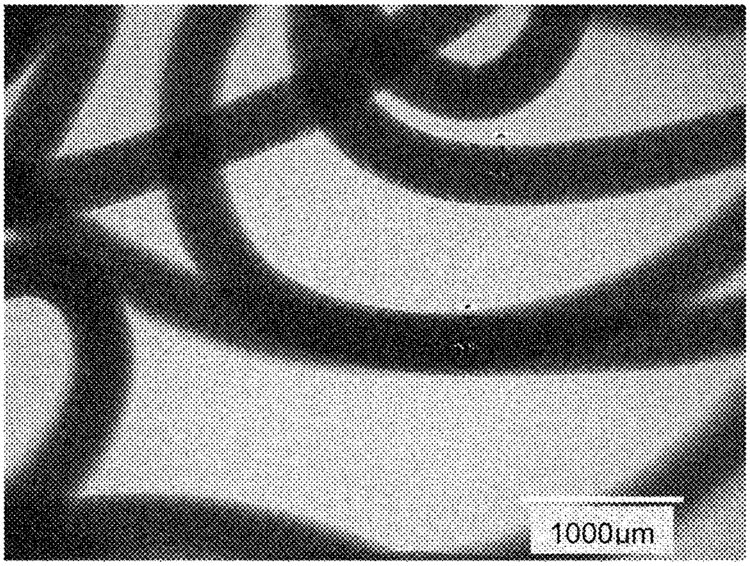
FIG. 10 is a photograph of a polymer-coated crosslinked alginate gel fiber (FB9-2-c2) of (Example F9) before culture.
Figure 11:
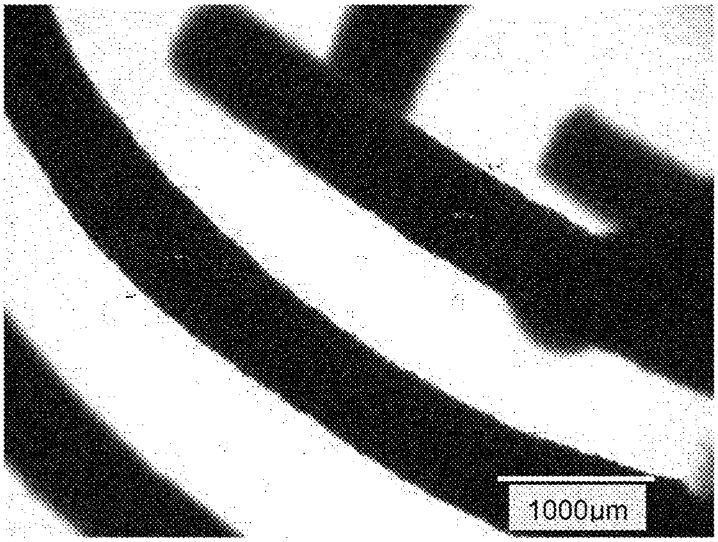
FIG. 11 is a photograph of the polymer-coated crosslinked alginate gel fiber (FB9-2-c2) of (Example F9) after culture.
Figure 12:
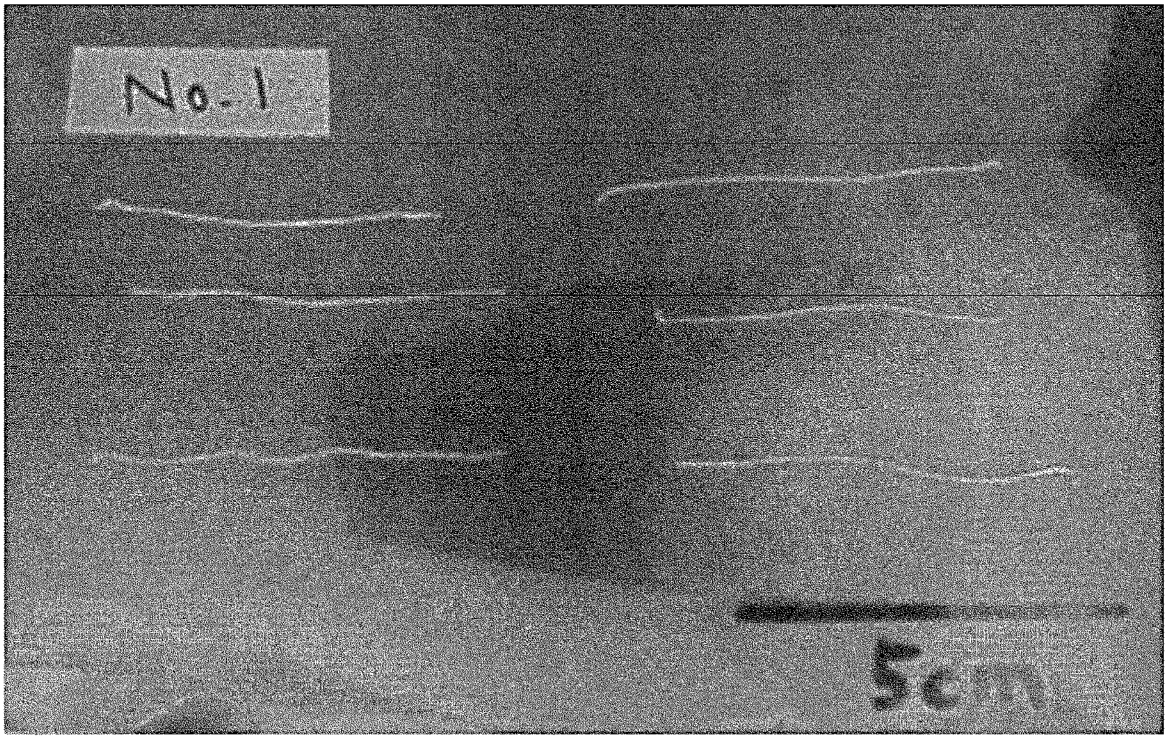
FIG. 12 is a photograph of a crosslinked alginate gel fiber (CLA-16A) of (Example F16-A).
Figure 13:
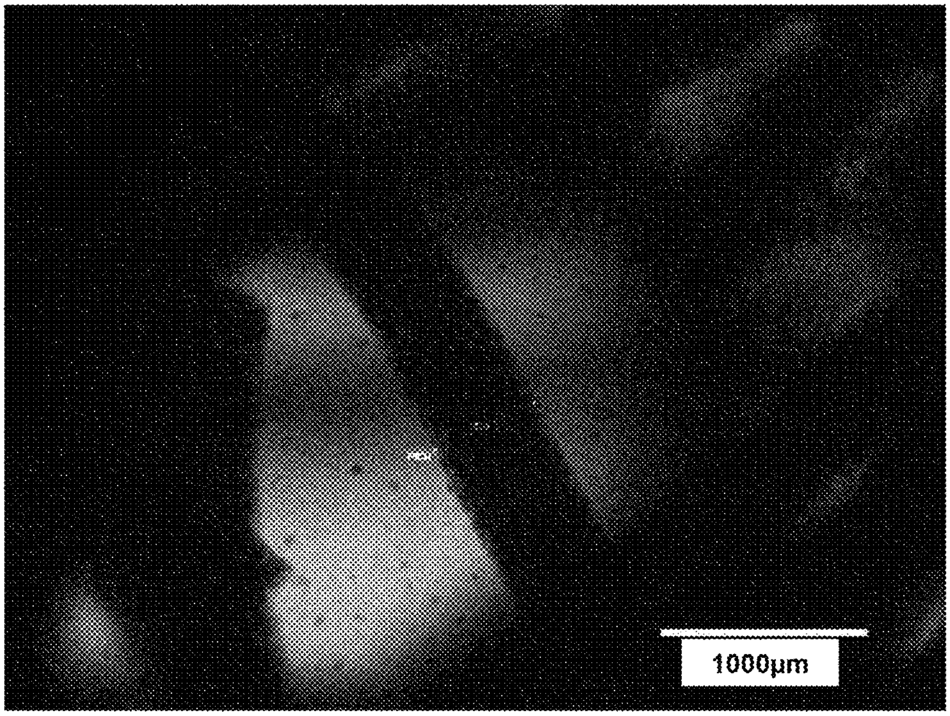
FIG. 13 is a photograph of a polymer-coated crosslinked alginate gel fiber (FB17-1-c1) of (Example FI-17) after culture.
Figure 14:
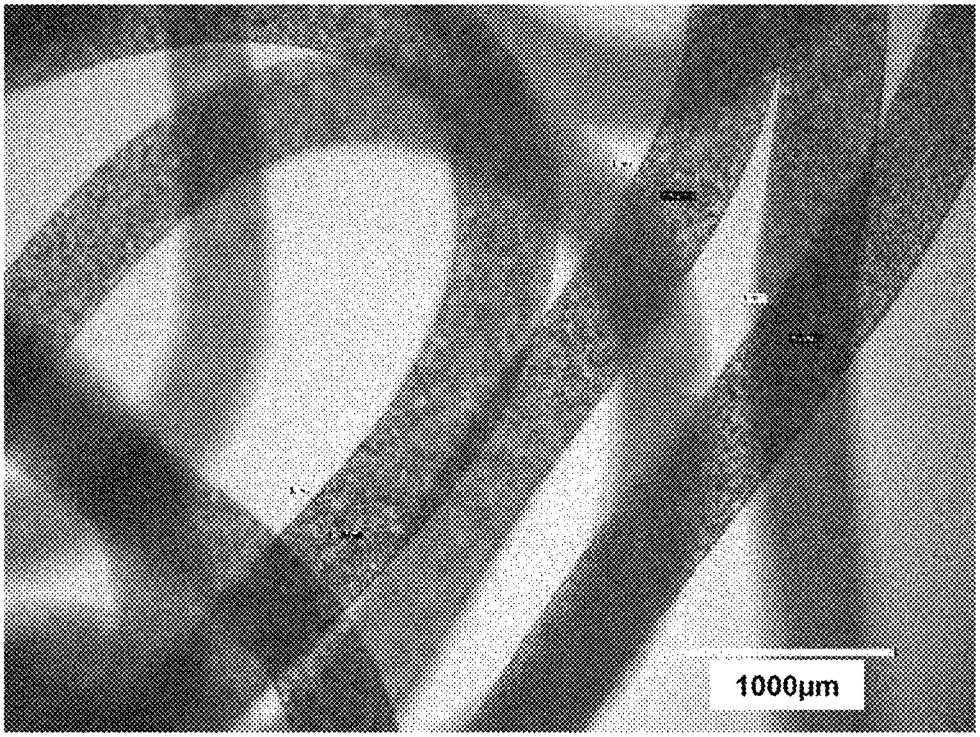
FIG. 14 is a photograph of a polymer-coated crosslinked alginate gel fiber (FB17-2-c1) of (Example FI-17) before culture.
Figure 15:
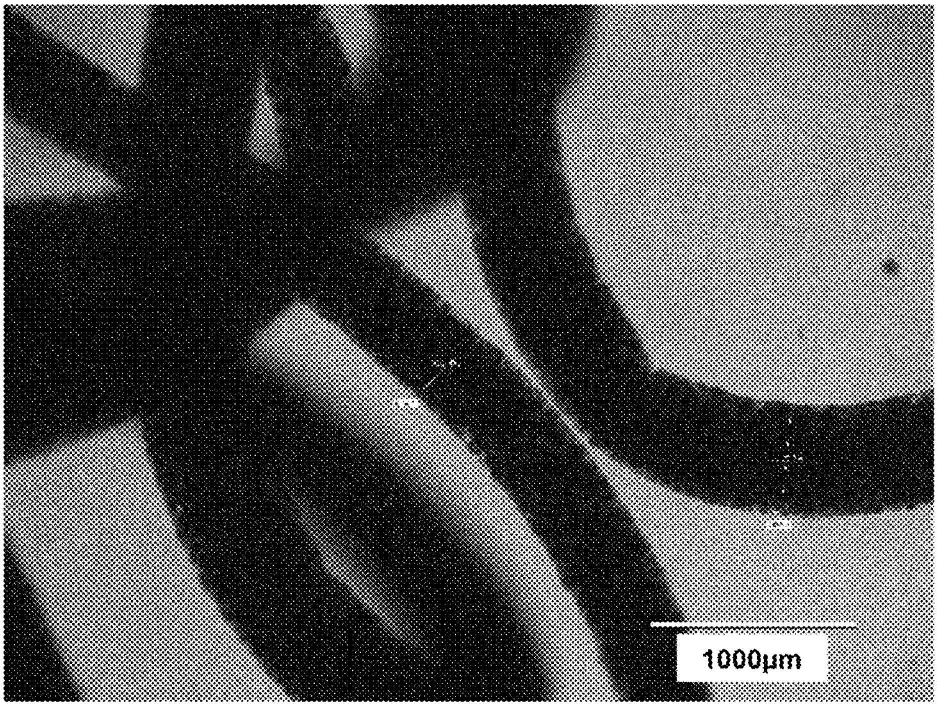
FIG. 15 is a photograph of the polymer-coated crosslinked alginate gel fiber (FB17-2-c1) of (Example FI-17) after culture.
Figure 16:
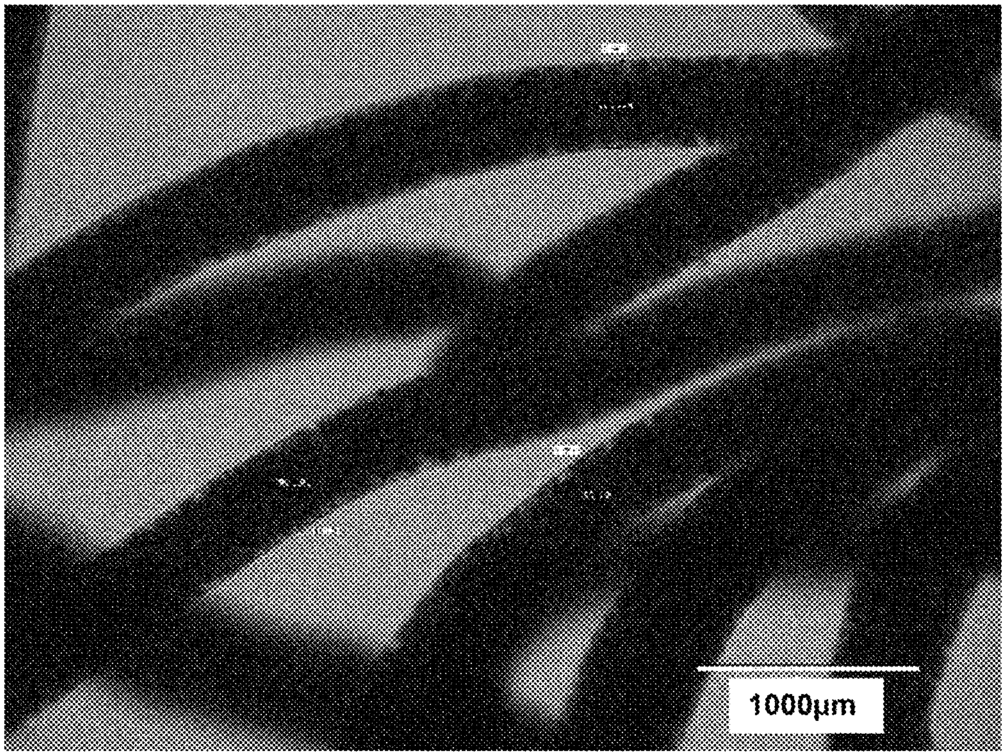
FIG. 16 is a photograph of a polymer-coated crosslinked alginate gel fiber (FB17-3-c1) of (Example FI-17) after culture.
Figure 17:
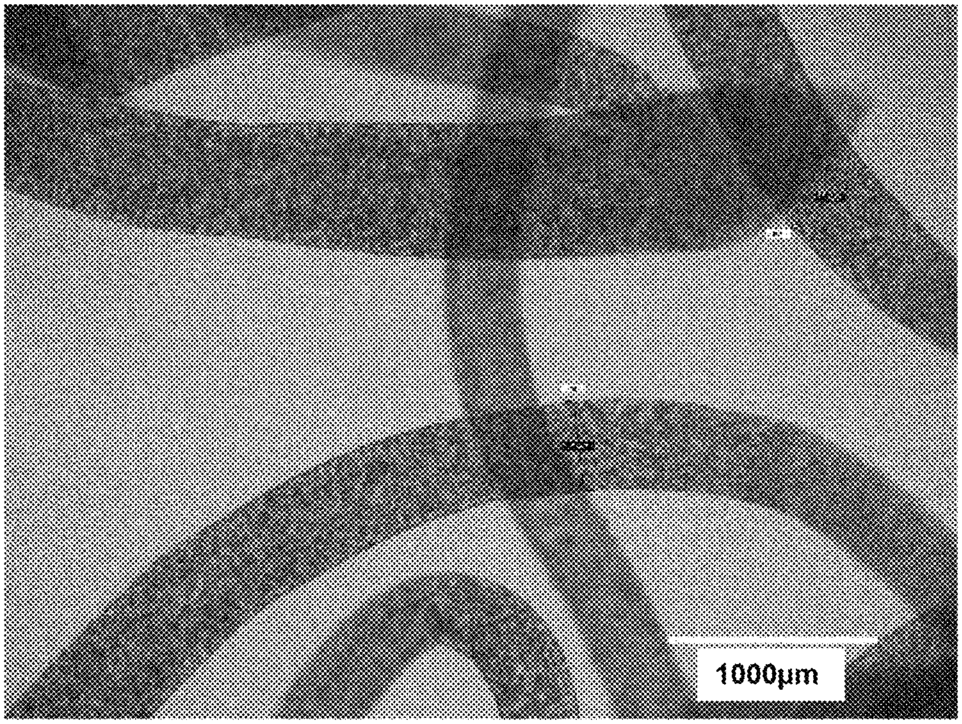
FIG. 17 is a photograph of a polymer-coated crosslinked alginate gel fiber (FB17-4-c1) of (Example FI-17) before culture.
Figure 18:
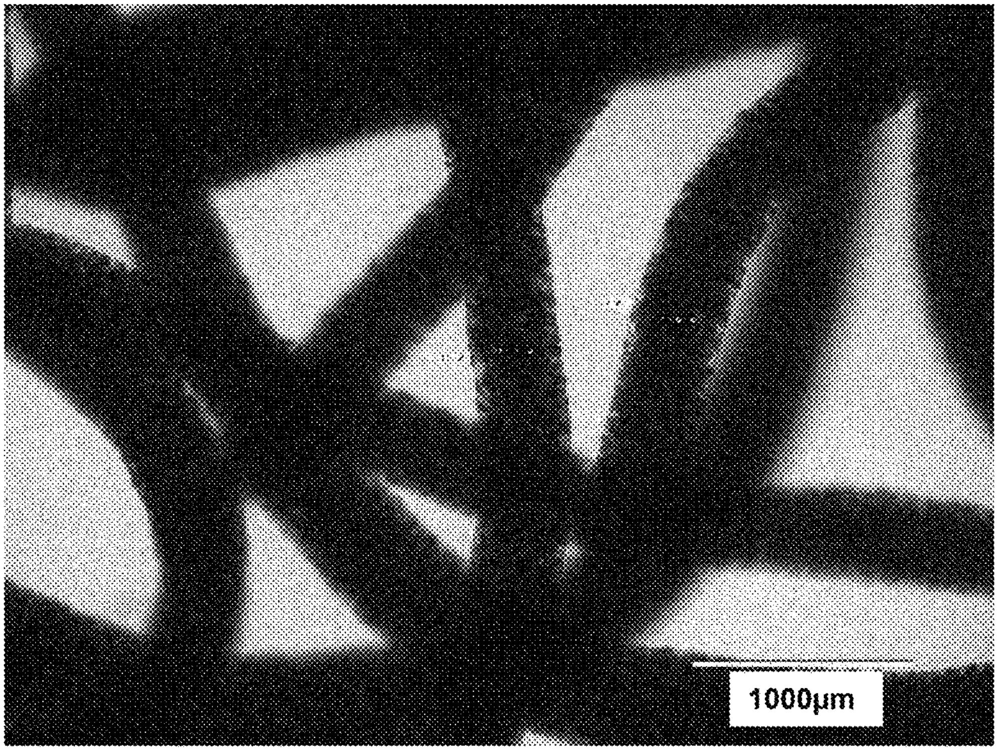
FIG. 18 is a photograph of the polymer-coated crosslinked alginate gel fiber (FB17-4-c1) of (Example FI-17) after culture.
Figure 19:
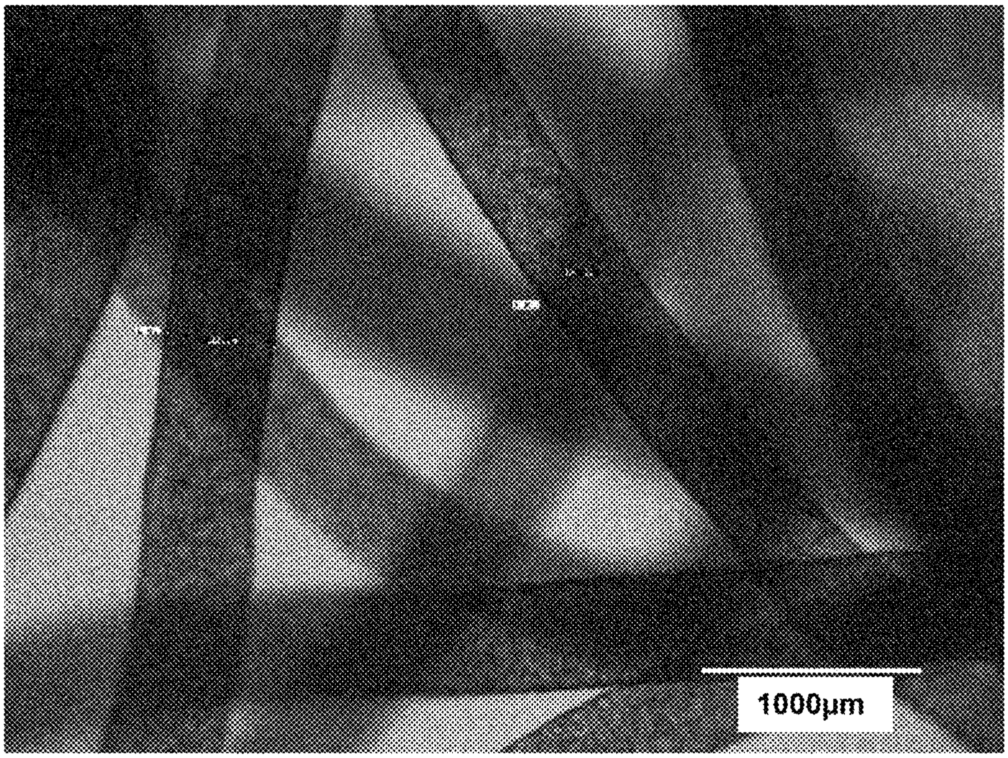
FIG. 19 is a photograph of a polymer-coated crosslinked alginate gel fiber (FB18-1-c1) of (Example FI-18) before culture.
Figure 20:
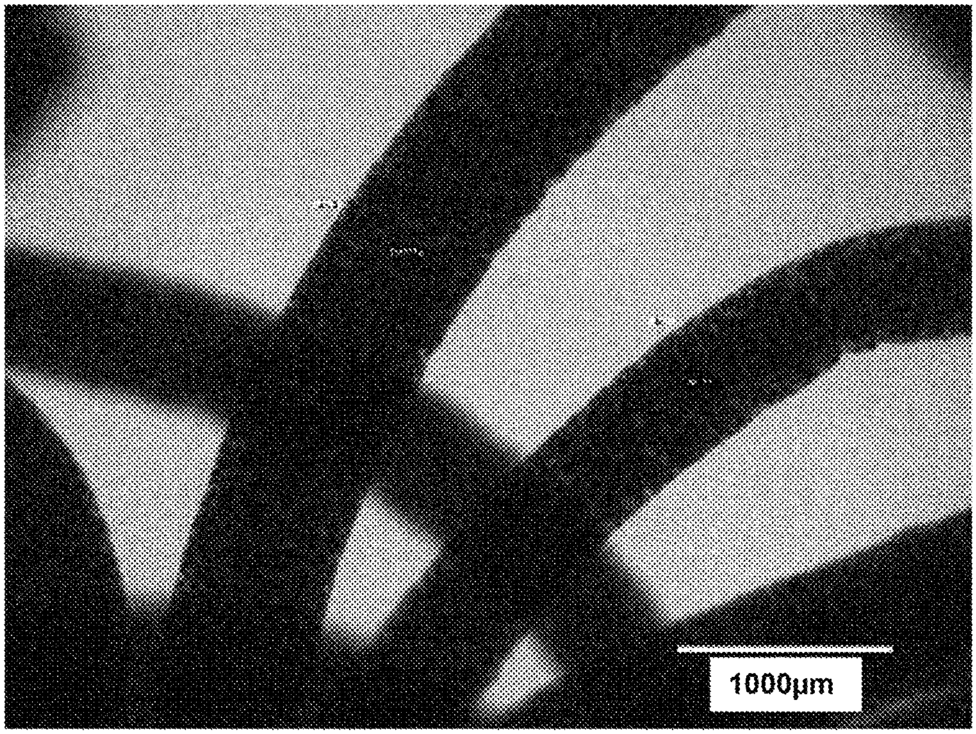
FIG. 20 is a photograph of the polymer-coated crosslinked alginate gel fiber (FB18-1-c1) of (Example FI-18) after culture.
Figure 21:
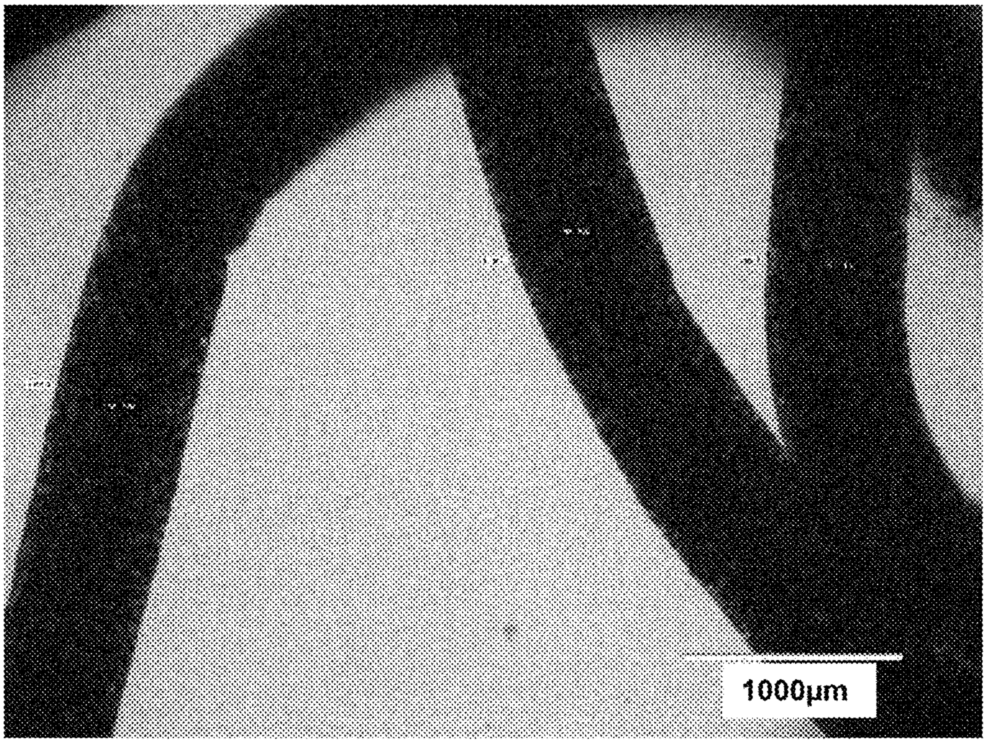
FIG. 21 is a photograph of a polymer-coated crosslinked alginate gel fiber (FB18-2-c1) of (Example FI-18) after culture.
Figure 22:
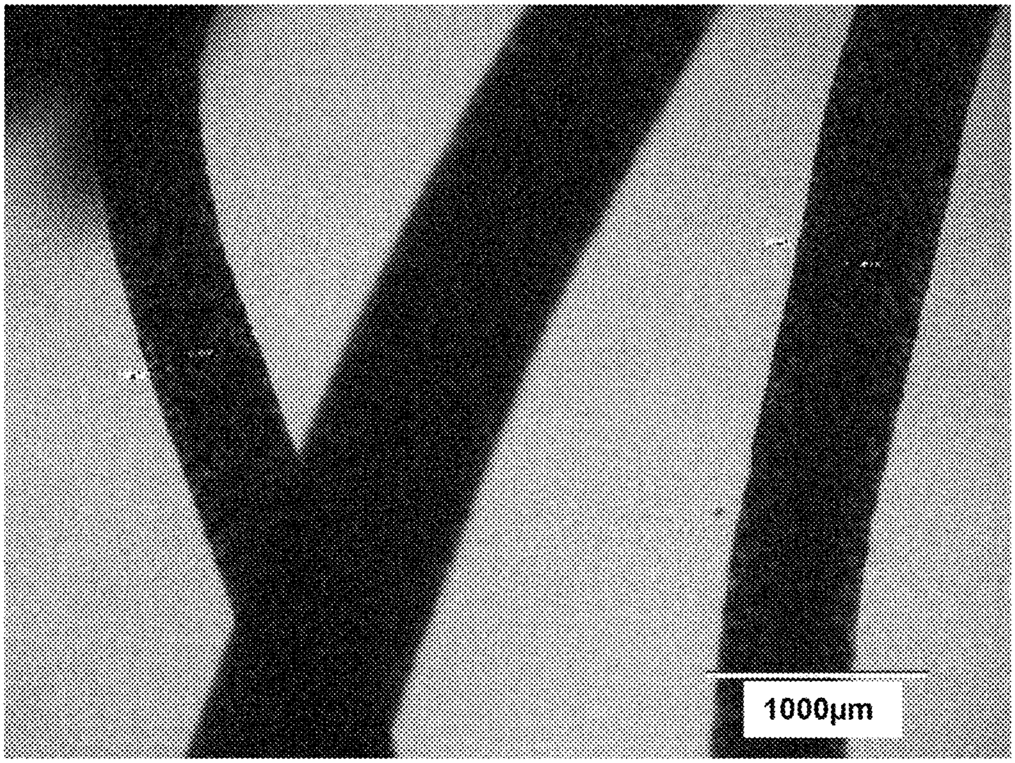
FIG. 22 is a photograph of a polymer-coated crosslinked alginate gel fiber (FB18-3-c1) of (Example FI-18) after culture.
Figure 23:
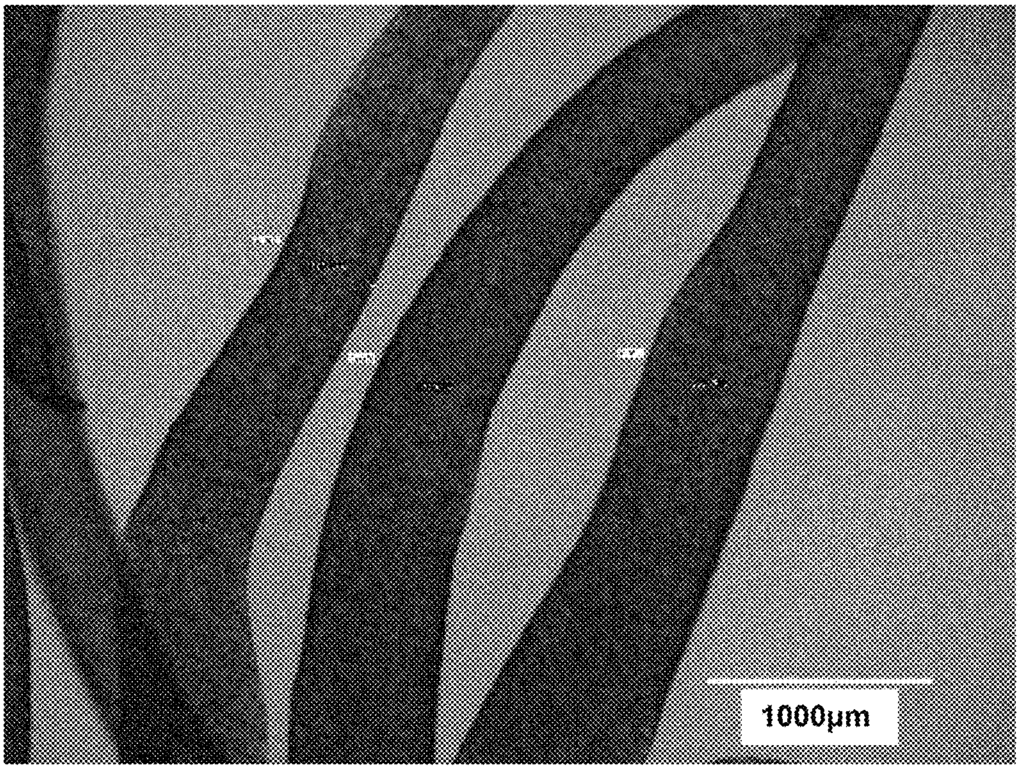
FIG. 23 is a photograph of a polymer-coated crosslinked alginate gel fiber (CFB19-G19) of (Example FI-19) before culture.
Figure 24:
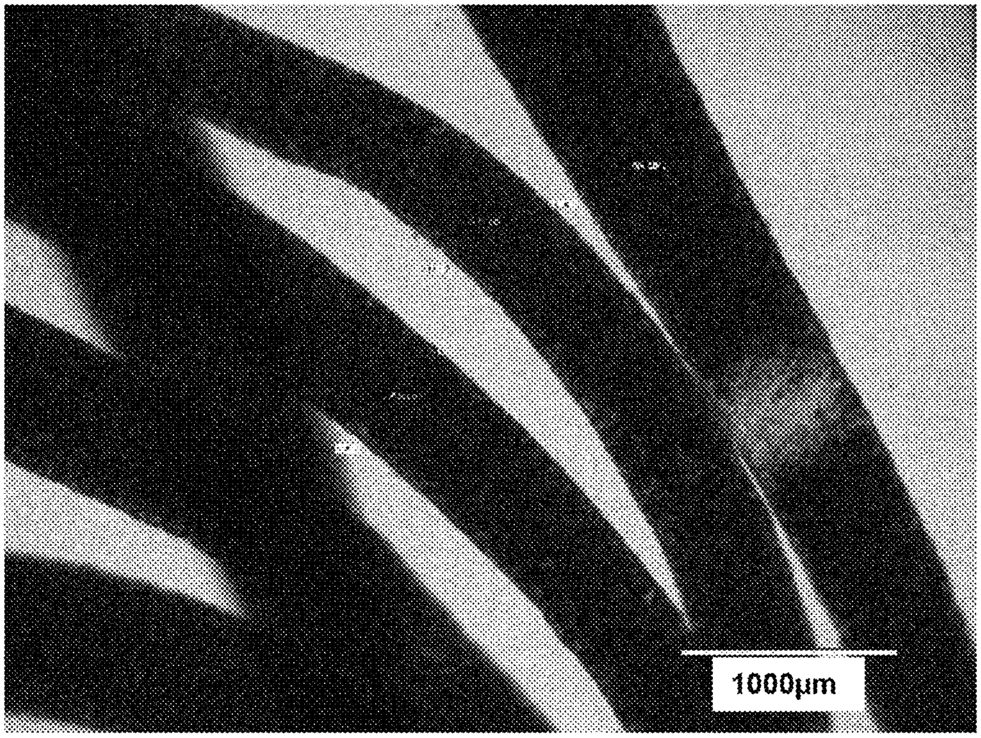
FIG. 24 is a photograph of the polymer-coated crosslinked alginate gel fiber (CFB19-G19) of (Example FI-19) after culture.

The observation result is shown in FIG. 7. It was confirmed that the surface of the gel fiber was coated with poly-L-lysine-FITC (the portion with a color inverted with respect to the (black) background of FIG. 7 is poly-L-lysine-FITC). This result suggests that the crosslinked alginate gel fiber was coated with the cationic polymer.

(Example F4-A) Production of Crosslinked Alginate Gel Fiber (3)

A3 wt % alginic acid aqueous solution (containing 0.9 wt % sodium chloride) (ALGS2) was prepared from sodium alginate (B-2) and saline for injection (manufactured by Otsuka Pharmaceutical Factory, Inc.) (INs). Subsequently, an alkyne aqueous solution and an azide aqueous solution were prepared according to formulations in Table 38 and Table 39 below.

TABLE 38

| 3 wt % alkyne aqueous solution and azide aqueous solution (containing 0.9 wt % of sodium chloride) | |
|---|---|
| F4A1 | Prepared by mixing 3.3 wt % compound 4-A2d aqueous solution and 9.9 wt % sodium chloride aqueous solution in ratio of 10/1 |
| F4N1 | Prepared by mixing 3.3 wt % compound 11-A2d aqueous solution and 9.9 wt % sodium chloride aqueous solution in ratio of 10/1 |

TABLE 39

| 3 wt % alkyne aqueous solution and azide aqueous solution | |
|---|---|
| F4A2 | 3 wt % compound 1-A2d aqueous solution |
| F4N2 | 3 wt % compound 13-A2b aqueous solution |
| F4N3 | 3 wt % compound 16-A2b aqueous solution |

Equal volumes of the alkyne aqueous solutions (F4A1 and F4A2) and the azide aqueous solutions ($F4N_1$, $F4N_2$ and $F4N_3$) were mixed together in a combination in the following table, thereby producing a chemically modified alginic acid solution mixture (F4A-M1). The solution mixture F4A-M1 and ALGS2 were mixed together in a ratio of 1:2, thereby producing an alginic acid solution mixture (F4A-M2). Subsequently, an alginic acid solution mixture (F4A-M2), a 9.9 wt % sodium chloride aqueous solution and saline for injection (manufactured by Otsuka Pharmaceutical Factory, Inc.) (INs) were prepared according to a formulation in Table 40 below, thereby producing a solution mixture (F4A-M3). The concentration of all alginic acid that was contained in F4A-M3 is approximately 1.5 wt %. Subsequently, a Hamilton syringe was filled with the alginic acid solution mixture F4A-M3, and a metal needle (Musashi Engineering, Inc., SNA-19G-B), a silicon tube (AS ONE Corporation, ϕ1×ϕ2) and a glass capillary (NARISHIGE Group, G-1) were sequentially connected to the syringe and set in a syringe pump. The tip of the glass capillary was immersed in a beaker containing 100 mmol/L of a calcium chloride aqueous solution, and the alginic acid solution mixture was injected into the calcium chloride aqueous solution at a flow rate of 250 μL/minute for one minute. A fibrous substance injected into the calcium chloride aqueous solution was placed still for 30 minutes or longer, thereby obtaining a crosslinked alginate gel fiber (CLA-X1) (refer to CLA-X1 No. in Table 40).

TABLE 40

| No. | Combination of alkyne compound/azide compound in F4A-M1 | Mixing ratio of F4A-M2/9.9 wt % sodium chloride aqueous solution/INs | CLA-X1 No. |
|---|---|---|---|
| F4-A-1 | 1-A2d/11-A2d | 125/4/142 | FB4-A-1 |
| F4-A-2 | 1-A2d/13-A2b | 125/2/146 | FB4-A-2 |
| F4-A-3 | 1-A2d/16-A2b | 125/2/146 | FB4-A-3 |
| F4-A-4 | 4-A2d/11-A2d | 125/0/146 | FB4-A-4 |
| F4-A-5 | 4-A2d/13-A2b | 125/4/142 | FB4-A-5 |
| F4-A-6 | 4-A2d/16-A2b | 125/4/142 | FB4-A-6 |

(Example F4-A2) Production of Crosslinked Alginate Gel Fiber (3a)

A 0.9 wt % sodium chloride aqueous solution (prepared with sodium chloride and water) was added to a compound 4-A2d or a compound 11-A2d to prepare a 3 wt % alkyne aqueous solution and an azide aqueous solution (containing 0.9 wt % of sodium chloride) (the alkyne is indicated by F4A3, and the azide is indicated by F4N4). Subsequently, 3 wt % sodium alginate aqueous solutions (containing 0.9 wt % of sodium chloride) were prepared from a variety of sodium alginates and a 0.9 wt % sodium chloride aqueous solution according to formulations in Table 41 below.

TABLE 41

| 3 wt % sodium alginate aqueous solution (containing 0.9 wt % of sodium chloride) | |
|---|---|
| No. | Composition |
| ALGS2 | Sodium alginate(B-2)/0.9 wt % sodium chloride aqueous solution |
| ALGS2A | Sodium alginate(A-2)/0.9 wt % sodium chloride aqueous solution |
| ALGS3A | Sodium alginate(A-3)/0.9 wt % sodium chloride aqueous solution |

Equal volumes of the alkyne aqueous solution (F4A3) and the azide aqueous solution (F4N4) were mixed together, thereby producing a chemically modified alginic acid solution mixture (F4A2-M1). Subsequently, the solution mixture F4A2-M1 and a 3 wt % sodium alginate aqueous solution (containing 0.9 wt % of sodium chloride) were mixed together in a combination shown in Table 42 below and a ratio of 5:10, thereby producing an alginic acid solution mixture (F4A2-M2). Equal volumes of the alginic acid solution mixture F4A2-M2 and saline for injection (manufactured by Otsuka Pharmaceutical Factory, Inc.) (INs) were mixed together, thereby producing a solution mixture (F4A2-M3). The concentration of all alginic acid that was contained in F4A-M3 was 1.5 wt %. Subsequently, a Hamilton syringe was filled with the solution mixture F4A2-M3, and a needle for luer lock syringe (KANTO CHEMICAL CO., INC., 15/23NL-F) was connected to the syringe and set in a syringe pump. The tip of the needle was immersed in a beaker containing 20 mmol/L of a barium chloride aqueous solution containing 0.9% sodium chloride, and the alginic acid solution mixture was injected into the barium chloride aqueous solution at a flow rate of 250 μL/minute for 0.8 minutes. A fibrous substance injected into the aqueous solution was placed still for 30 minutes or longer, thereby obtaining a crosslinked alginate gel fiber (CLA-X1A) (refer to CLA-X1A No. in Table 42).

TABLE 42

| No. | Combination of F4A2-M1/3 wt % sodium alginate (containing 0.9% sodium chloride) | CLA-X1A No. |
|---|---|---|
| F4-A2-1 | F4A2-M1/ALGS2 | FB4-A2-1 |
| F4-A2-2 | F4A2-M1/ALGS2A | FB4-A2-2 |
| F4-A2-3 | F4A2-M1/ALGS3A | FB4-A2-3 |

(Example F4-B) Production of Crosslinked Alginate Gel Fiber (4)

Equal volumes of the alkyne aqueous solution (F4A1) and the azide aqueous solution ($F4N_1$) described in (Example F4-A) were mixed together, thereby producing a chemically modified alginic acid solution mixture (F4B-M1). The solution mixture F4B-M1 and the ALGS2 were prepared according to a formulation in Table 43 below, thereby producing an alginic acid solution mixture (F4B-M2). Subsequently, a solution mixture (F4B-M3) was prepared in a mixing ratio between the alginic acid solution mixture (F4B-M2) and INs shown in Table 43 below. Subsequently, a Hamilton syringe was filled with the alginic acid solution mixture F4B-M3, and a metal needle (Musashi Engineering, Inc., SNA-19G-B), a silicon tube (AS ONE Corporation, ϕ1×ϕ2) and a glass capillary (NARISHIGE Group, G-1) were sequentially connected to the syringe and set in a syringe pump. The tip of the glass capillary was immersed in a beaker containing 100 mmol/L of a calcium chloride aqueous solution, and the alginic acid solution mixture was injected into the calcium chloride aqueous solution at a flow rate of 250 μL/minute for one minute. A fibrous substance injected into the calcium chloride aqueous solution was placed still for 30 minutes or longer, thereby obtaining a crosslinked alginate gel fiber (CLA-X2) (refer to CLA-X2 No. in Table 43).

TABLE 43

| No. | Mixing ratio of F4B-M1/ ALGS2 | Mixing ratio of F4B-M2/INs | Final concentration of alkyne compound and azide compound in F4B-M3 (wt %) | Total alginic acid concentration (wt %) | CLA-X2 No. |
|---|---|---|---|---|---|
| F4-B-1 | 17/108 | 1/1 | 0.2 | 1.5 | FB4-B-1 |
| F4-B-2 | 2/1 | 1/1 | 1.0 | 1.5 | FB4-B-2 |
| F4-B-3 | 56/111 | 167/83 | 0.67 | 2.0 | FB4-B-3 |
| F4-B-4 | 1/2 | 83/167 | 0.33 | 1.0 | FB4-B-4 |
| F4-B-5 | 1/2 | 21/104 | 0.17 | 0.5 | FB4-B-5 |
| F4-B-6 | F4B-M1 only | 1/1 | 1.5 | 1.5 | FB4-B-6 |

(Example F4-C) Production of Polymer-Coated Crosslinked Alginate Gel Fiber (2a)

The crosslinked alginate gel fibers (CLA-X1 and CLA-X2) in the calcium chloride aqueous solution, which was obtained in (Example F4-A) or (Example F4-B), were filtered and fractionated using a cell strainer. The fractionated crosslinked alginate gel fibers were added to an aqueous solution of 0.1% poly-L-ornithine hydrobromide/100 mM calcium chloride and shaking-stirred at 37° C. and 125 rpm for 30 minutes, thereby coating the crosslinked alginate gel fiber with the polymer. The fiber in the aqueous solution was filtered and fractionated using the cell strainer and washed with 5 mL of physiological saline twice, thereby obtaining a polymer-coated crosslinked alginate gel fiber (CFB-X) (refer to CFB-X No. in Table 44).

TABLE 44

| No. | CLA-X1 No. | CLA-X2 No. | CFB-X No. |
|---|---|---|---|
| F4-C-1 | FB4-A-1 | — | FB4-A-1-c |
| F4-C-2 | FB4-A-2 | — | FB4-A-2-c |
| F4-C-3 | FB4-A-3 | — | FB4-A-3-c |
| F4-C-4 | FB4-A-4 | — | FB4-A-4-c |
| F4-C-5 | FB4-A-5 | — | FB4-A-5-c |
| F4-C-6 | FB4-A-6 | — | FB4-A-6-c |
| F4-C-7 | — | FB4-B-1 | FB4-B-1-c |
| F4-C-8 | — | FB4-B-2 | FB4-B-2-c |
| F4-C-9 | — | FB4-B-3 | FB4-B-3-c |
| F4-C-10 | — | FB4-B-4 | FB4-B-4-c |
| F4-C-11 | — | FB4-B-5 | FB4-B-5-c |
| F4-C-12 | — | FB4-B-6 | FB4-B-6-c |

(Example F4-C2) Production of Polymer-Coated Crosslinked Alginate Gel Fiber (2)

A 1% poly-L-ornithine aqueous solution containing 1% poly-L-ornithine hydrobromide, 9.2 mmol/L of hydroxyethylpiperazine ethane sulfonic acid and 154 mmol/L of sodium chloride was prepared. The 1% poly-L-ornithine aqueous solution was diluted using an aqueous solution containing 0.9% sodium chloride and 20 mmol/L of barium chloride, thereby producing a 0.1% poly-L-ornithine aqueous solution. Subsequently, the crosslinked alginate gel fiber (CLA-X1A) in the barium chloride aqueous solution obtained in (Example F4-A2) was filtered and fractionated using a cell strainer. The fractionated crosslinked alginate gel fiber was added to the 0.1% poly-L-ornithine aqueous solution and shaking-stirred at 37° C. and 125 rpm for 30 minutes, thereby coating the crosslinked alginate gel fiber with the polymer. The fiber in the aqueous solution was filtered and fractionated using the cell strainer and washed with 10 mL of physiological saline once, thereby obtaining a polymer-coated crosslinked alginate gel fiber (CFB-X2) (refer to CFB-X2 No. in Table 45).

TABLE 45

| No. | CLA-X1A No. | CFB-X2 No. |
|---|---|---|
| F4-C2-1 | FB4-A2-1 | FB4-A2-1-c |
| F4-C2-2 | FB4-A2-2 | FB4-A2-2-c |
| F4-C2-3 | FB4-A2-3 | FB4-A2-3-c |

(Example F4-D) Tensile Test of Polymer-Coated Crosslinked Alginate Gel Fiber

The tensile test of the polymer-coated crosslinked alginate gel fiber (CFB-X or CFB-X2) obtained in (Example F4-C) and (Example F4-C2) was measured by setting the fiber in a jig in saline for injection (manufactured by Otsuka Pharmaceutical Factory, Inc.) using a small desktop gel strength tester EZ-SX 5 N C1 (Shimadzu Corporation, No. I308256D0592) and a load cell SMT1-5N (S/N=913193). Regarding measurement values, stresses and strains when the fibers ruptured are shown in Table 46 in units of MPa and %, respectively.

TABLE 46

| No. | CFB-X No. | CFB-X2 No. | Stress (MPa) | Strain (%) |
|---|---|---|---|---|
| F4-D-1 | FB4-A-1-c | — | 0.248 | 116 |
| F4-D-2 | FB4-A-2-c | — | 0.290 | 137 |
| F4-D-3 | FB4-A-3-c | — | 0.285 | 127 |
| F4-D-4 | FB4-A-4-c | — | 0.331 | 141 |
| F4-D-5 | FB4-A-5-c | — | 0.199 | 103 |
| F4-D-6 | FB4-A-6-c | — | 0.219 | 121 |
| F4-D-7 | FB4-B-1-c | — | 0.205 | 107 |
| F4-D-8 | FB4-B-2-c | — | 0.436 | 174 |
| F4-D-9 | FB4-B-3-c | — | 0.253 | 140 |
| F4-D-10 | FB4-B-4-c | — | 0.165 | 111 |
| F4-D-11 | FB4-B-5-c | — | 0.063 | 72 |

TABLE 46-continued

| No. | CFB-X No. | CFB-X2 No. | Stress (MPa) | Strain (%) |
|---|---|---|---|---|
| F4-D-12 | FB4-B-6-c | — | 0.482 | 174 |
| F4-D-13 | — | FB4-A2-1-c | 0.438 | 176 |
| F4-D-14 | — | FB4-A2-2-c | 0.564 | 191 |
| F4-D-15 | — | FB4-A2-3-c | 0.825 | 233 |

In Table 46, it was confirmed that Nos. F4-D-1 to F4-D-10 and F4-D-12 to F4-D-15 were polymer-coated crosslinked alginate gel fibers showing a tensile strength of 0.1 MPa or higher and a strain (elongation) of 100% or more.

(Example FI-1) Culture of Antibody-Producing Cell-Containing Polymer-Coated Crosslinked Alginate Gel Fibers The antibody-producing cell-containing polymer-coated crosslinked alginate gel fibers (FB2-A-1-c1, FB2-A-2-c1, FB2-A-3-c1, FB2-A-4-c1, FB2-A-5-c1, FB2-A-6-c1, FB2-A-7-c1, FB2-A-8-c1, FB2-A-9-c1 and FB2-A-10-c1) obtained in (Example F2-C) were put into 125 mL polycarbonate Erlenmeyer flasks, the antibody-producing culture medium solution (30 mL) described in (Example F2-A) was added thereto, and the gel fibers were cultured in an incubator at 37° C. under a 5% $CO_2$ atmosphere for 14 days or 20 days while being shaken at 125 rpm. Once two to three days, 1.8 mL of a culture fluid was extracted, 1.8 mL of the antibody-producing culture medium solution or 1.8 mL of a feed solution (manufactured by Fujifilm Irvine Scientific, catalog No. JX F003) was added thereto, and the total amount of the culture medium was held at 30 mL. In addition, half the amount of the culture fluid was exchanged once a week. During the culture period, the IgG concentration of the culture fluid was measured as a human IgG concentration with a Cedex Bio analyzer (Roche Diagnostics K.K.). In the culture using the cell-encapsulated polymer-coated crosslinked alginate gel fiber, the cumulative antibody amounts and the concentrations of the anti-GPVI antibody-producing CHO cell that was detected in the culture fluid during the culture period were as shown in Table 47.

TABLE 47

| No. | CFB-S No. | Culture period | Concentration of leaky cell in culture fluid upon end of culture | Cumulative antibody (IgG) amount during culture period (mg/L) |
|---|---|---|---|---|
| FB1-A-1 | FB2-A-1-c1 | 14 days | Less than 1 × $10^4$ cells/mL | 312 |
| FB1-A-2 | FB2-A-2-c1 | 14 days | Less than 1 × $10^4$ cells/mL | 375 |
| FB1-A-3 | FB2-A-3-c1 | 14 days | Less than 1 × $10^4$ cells/mL | 405 |
| FB1-A-4 | FB2-A-4-c1 | 14 days | Less than 1 × $10^4$ cells/mL | 560 |
| FB1-A-5 | FB2-A-5-c1 | 14 days | Less than 1 × $10^4$ cells/mL | 328 |
| FB1-A-6 | FB2-A-6-c1 | 20 days | Less than 1 × $10^4$ cells/mL | 816 |
| FB1-A-7 | FB2-A-7-c1 | 14 days | Less than 1 × $10^4$ cells/mL | 314 |
| FB1-A-8 | FB2-A-8-c1 | 14 days | Less than 1 × $10^4$ cells/mL | 353 |
| FB1-A-9 | FB2-A-9-c1 | 14 days | Less than 1 × $10^4$ cells/mL | 396 |
| FB1-A-10 | FB2-A-10-c1 | 20 days | Less than 1 × $10^4$ cells/mL | 195 |

(Example FI-2) Culture of Bioactive Substance-Producing Cell-Containing Polymer-Coated Crosslinked Alginate Gel Fiber <Step 1> Culture of MIN6 Cell-Containing Polymer-Coated Crosslinked Alginate Gel Fiber The polymer-coated crosslinked alginate gel fiber (FB2-B-1-c1) obtained in (Example F2-C) was put into a 60 mm ultralow adhesive surface dish (manufactured by Corning Inc., product No.: 3261), the complete medium (5 mL) described in (Example F2-B) was added thereto, and the gel fiber was cultured for three days or 14 days by being placed still in an incubator at 37° C. under a 5% $CO_2$ atmosphere.

<Step 2> Insulin Secretory Ability Evaluation

The insulin secretory ability of the MIN6 cell in the MIN6 cell-encapsulated polymer-coated crosslinked alginate gel fiber, which had been cultured for three days or for 14 days in <Step 1> of (Example FI-2) was evaluated. The MIN6 cell-encapsulated polymer-coated crosslinked alginate gel fiber was cultured for two hours in 10 mL of a low glucose solution (2 mM glucose/KRBH/0.1% BSA), the solution was exchanged with 10 mL of a high glucose solution (20 mM glucose/KRBH/0.1% BSA), and then the gel fiber was further cultured for two hours. After that, the solution was exchanged with 10 mL of a low glucose solution, and the gel fiber was cultured for two hours. The insulin concentration in the solution was measured with using an ultra sensitive mouse insulin ELISA kit (manufactured by Morinaga Institute of Biological Science, Inc.) upon the end of each step. It was possible to confirm that insulin was discharged based on the glucose concentration.

TABLE 48

| | Low glucose solution | High glucose solution | Low glucose solution |
|---|---|---|---|
| Insulin concentration on third day (ng/mL) | 3.9 | 43.4 | 2.0 |
| Insulin concentration on $14^{th}$ day (ng/mL) | 10.5 | 48.9 | 11.4 |

(Example F5-A) Production of Antibody-Producing Cell-Containing Crosslinked Alginate Gel Fiber 3 wt % aqueous solutions (containing 0.9 wt % sodium chloride) of the compound 4-A2d and the compound 11-A2d were prepared according to formulations in Table 32 and Table 33 described in (Example F2-A), and then equal volumes of the individual aqueous solutions were mixed together, thereby preparing a chemically modified alginic acid solution mixture (F5A-M1). The solution mixture F5A-M1 and a 3 wt % alginic acid aqueous solution (containing 0.9% sodium chloride) (ALGS2) prepared from sodium alginate (B-2) and saline for injection (manufactured by Otsuka Pharmaceutical Factory, Inc.) (INs) were mixed together in a ratio of F5A-M1:ALGS2=5:10, thereby producing an alginic acid solution mixture (F5A-M2). Subsequently, equal volumes of the solution mixture F5A-M2 and a G016 culture medium having the composition described in (Example F2-A) and containing tocilizumab-producing CHO cells ($1\times10^8$ cells/mL) were mixed together, thereby producing a cell-containing alginic acid solution mixture (F5A-M3). A Hamilton syringe was filled with the solution mixture F5A-M3, and a needle for luer lock syringe (KANTO CHEMICAL CO., INC., 15/23NL-F) was connected to the syringe and set in a syringe pump. The tip of the needle was immersed in a beaker containing 100 mmol/L of a calcium chloride aqueous solution or 20 mmol/L of a barium chloride aqueous solution containing 0.9% sodium chloride, and the alginic acid solution mixture (F5A-M3) was injected into the calcium chloride or barium chloride aqueous solution at a flow rate of 250 μL/minute for 0.8 minute. A fibrous substance injected into the aqueous solution was placed still for 30 minutes or longer, thereby obtaining a tocilizumab-producing CHO cell-containing crosslinked alginate gel fiber (CLA-G5) (refer to CLA-G5 No. in Table 49).

TABLE 49

| No. | Final concentration of alkyne compound and azide compound in F5A-M3 (wt %) | Cationic species during gel fiber production | CLA-G5 No. |
|---|---|---|---|
| F5-A-1 | 0.5 | Ca | FB5-A-1 |
| F5-A-2 | 0.5 | Ba | FB5-A-2 |

(Example F5-B) Production of Antibody-Producing Cell-Containing Polymer-Coated Crosslinked Alginate Gel Fiber The antibody-producing cell-containing crosslinked alginate gel fiber (CLA-G5) obtained in (Example F5-A) was added to a cationic polymer-containing aqueous solution having each composition shown in Table 50 and shaking-stirred at 37° C. and 125 rpm for 30 minutes, thereby coating the cell-containing crosslinked alginate gel fiber with the polymer. The amount of the aqueous solution used for the polymer coating was set to 10 times the amount of fiber to be coated. The fiber in the aqueous solution was filtered and fractionated using the cell strainer and washed with 5 mL of physiological saline twice, thereby obtaining an antibody-producing cell-containing polymer-coated crosslinked alginate gel fiber (CFB-S2) (refer to CFB-S2 No. in Table 51).

TABLE 50

| No. | Composition of cationic polymer-containing aqueous solution |
|---|---|
| F5-c1 | 0.1% poly-L-ornithine hydrobromide/100 mM calcium chloride |
| F5-c2 | 0.1% poly-L-ornithine hydrobromide/0.9% sodium chloride/20 mM barium chloride |

TABLE 51

| No. | CLA-G5 No. | Cationic polymer-containing aqueous solution | CFB-S2 No. |
|---|---|---|---|
| F5-B-1 | FB5-A-1 | F5-c1 | FB5-A-1-c1 |
| F5-B-2 | FB5-A-2 | F5-c2 | FB5-A-2-c2 |

(Example FI-3) Culture of Antibody-Producing Cell-Containing Polymer-Coated Crosslinked Alginate Gel Fiber One antibody-producing cell-containing polymer-coated crosslinked alginate gel fiber (FB5-A-1-c1 or FB5-A-2-c2) obtained in (Example F5-B) was put into a 125 mL polycarbonate Erlenmeyer flask, the G016 culture medium (30 mL) described in (Example F2-A) was added thereto, the gel fiber began to be cultured in an incubator at 37° C. under a 5% $CO_2$ atmosphere while being shaken at 125 rpm, the culture temperature was changed to 30° C. after five days, and the gel fiber was continuously cultured at the same temperature. During this period, once two to three days, 1.8 mL of a culture fluid was extracted, 1.8 mL of the G016 culture medium or 1.8 mL of a feed solution (manufactured by Fujifilm Irvine Scientific, catalog No. JX F003) was added thereto, and the total amount of the culture medium was held at 30 mL. In addition, half the amount of the culture fluid was exchanged once a week. During the culture period, the IgG concentration of the culture fluid was measured as a human IgG concentration with a Cedex Bio analyzer (Roche Diagnostics K.K.). In the culture using the antibody-producing cell-encapsulated polymer-coated crosslinked alginate gel fiber, the cumulative antibody concentrations and the concentrations of the tocilizumab-producing CHO cell that was detected in the culture fluid at each measurement day were as shown in Table 52. From the culture results, it was possible to confirm that the amount of the antibody produced increased over time in the culture of each fiber.

TABLE 52

| No. | CFB-S2 No. | Measurement days | Concentration of leaky cell in culture fluid on each measurement day | Cumulative antibody (IgG) concentration on each measurement day (mg/L) |
|---|---|---|---|---|
| FI-3-1 | FB5-A-1-c1 | 14 | Less than 1 × $10^4$ cells/mL | 308 |
| | | 28 | 2 × $10^4$ cells/mL | 684 |
| | | 47 | Less than 1 × $10^4$ cells/mL | 994 |
| FI-3-2 | FB5-A-2-c2 | 14 | Less than 1 × $10^4$ cells/mL | 533 |
| | | 21 | 3.5 × $10^4$ cells/mL | 1009 |
| | | 28 | 1.5 × $10^4$ cells/mL | 1475 |
| | | 47 | Less than 1 × $10^4$ cells/mL | 2349 |

(Example F6) Production of Antibody-Producing Cell-Containing Polymer-Coated Crosslinked Alginate Gel Fiber Equal volumes of the G016 culture medium having the composition described in (Example F2-A) and containing tocilizumab-producing CHO cells (3×$10^7$ cells/mL or 1×$10^8$ cells/mL) and the solution mixture F5A-M2 prepared in (Example F5-A) were mixed together, thereby producing a cell-containing alginic acid solution mixture (F6A-M3). In the solution mixture F6A-M3, the final concentrations of the alkyne compound and the azide compound were 0.5 wt %, and the tocilizumab-producing CHO cells were contained at a concentration shown in Table 53. A Hamilton syringe was filled with the solution mixture F6A-M3, and a needle for luer lock syringe (KANTO CHEMICAL CO., INC., 15/23NL-F) was connected to the syringe and set in a syringe pump. The tip of the needle was immersed in a beaker containing 20 mmol/L of a barium chloride aqueous solution containing 0.9% sodium chloride, and the alginic acid solution mixture (F6A-M3) was injected into the aqueous solution at a flow rate of 250 µL/minute for a time shown in Table 53. A fibrous substance injected into the aqueous solution was placed still for 30 minutes or longer, thereby obtaining a tocilizumab-producing CHO cell-containing crosslinked alginate gel fiber. Subsequently, coating was performed in the same manner as in the method described in (Example F5-B) using an aqueous solution containing 0.1% poly-L-ornithine hydrobromide, 0.9% sodium chloride and 20 mmol/L barium chloride, thereby obtaining an antibody-producing cell-containing polymer-coated crosslinked alginate gel fiber (CFB-S3) (refer to CFB-S3 No. in Table 53).

TABLE 53

| No. | Tocilizumab-producing CHO cell concentration in G016 culture medium before mixing with F6A-M2 | Tocilizumab-producing CHO cell concentration in F6A-M3 | Injection time (minutes) | CFB-S3 No. |
|---|---|---|---|---|
| F6-1 | 3 × $10^7$ cells/mL | 1.5 × $10^7$ cells/mL | 1.2 | FB6-1-c1 |
| F6-2 | 3 × $10^7$ cells/mL | 1.5 × $10^7$ cells/mL | 4 | FB6-2-c1 |
| F6-3 | 3 × $10^7$ cells/mL | 1.5 × $10^7$ cells/mL | 6 | FB6-3-c1 |
| F6-4 | 1 × $10^8$ cells/mL | 5 × $10^7$ cells/mL | 4 | FB6-4-c1 |

(Example FI-4) Culture of Antibody-Producing Cell-Containing Polymer-Coated Crosslinked Alginate Gel Fiber The antibody-producing cell-containing polymer-coated crosslinked alginate gel fibers (one of FB6-1-c1, FB6-2-c1 or FB6-4-c1 and two FB6-5-c1) obtained in (Example F6) were put into a 125 mL polycarbonate Erlenmeyer flask, the G016 culture medium having a composition described in (Example F2-A) was added thereto, the total amount of the gel fibers and the G016 culture medium was set to 30 mL, the gel fibers began to be cultured in an incubator at 37° C. under a 5% $CO_2$ atmosphere while being shaken at 125 µm, the culture temperature was changed to 30° C. after five days, and the gel fiber was continuously cultured at the same temperature. After two days from the beginning of the culture, 1.8 mL of a culture fluid was extracted, 1.8 mL of a feed solution (manufactured by Fujifilm Irvine Scientific, catalog No. JX F003) was added thereto, and the total amount of the culture medium was held at 30 mL. After that, half the amount of the culture fluid was exchanged once two to three days. During the culture period, the IgG concentration of the culture fluid was measured as a human IgG concentration with a Cedex Bio analyzer (Roche Diagnostics K.K.). In the culture using the antibody-producing cell-encapsulated polymer-coated crosslinked alginate gel fiber, the cumulative antibody concentrations and the concentrations of the tocilizumab-producing CHO cell that was detected in the culture fluid at each measurement day were as shown in Table 54. From the culture results, it was possible to confirm that the amount of the antibody produced increased over time in the culture of each fiber.

TABLE 54

| No. | CFB-S3 No. | Measurement days | Concentration of leaky cell on each measurement day | Cumulative antibody (IgG) concentration on each measurement day (mg/L) |
|---|---|---|---|---|
| FI-4-1 | FB6-1-c1 | 14 | Less than 1 × $10^4$ cells/mL | 270 |
| | | 28 | 3.5 × $10^4$ cells/mL | 812 |
| | | 37 | 2 × $10^4$ cells/mL | 1119 |

TABLE 54-continued

| No. | CFB-S3 No. | Measurement days | Concentration of leaky cell on each measurement day | Cumulative antibody (IgG) concentration on each measurement day (mg/L) |
|---|---|---|---|---|
| FI-4-2 | FB6-2-c1 | 14 | Less than 1 × $10^4$ cells/mL | 1120 |
| | | 28 | Less than 1 × $10^4$ cells/mL | 2662 |
| | | 37 | Less than 1 ×$10^4$ cells/mL | 3295 |
| FI-4-3 | FB6-3-c1 | 14 | Less than 1 × $10^4$ cells/mL | 2401 |
| | | 28 | Less than 1 × $10^4$ cells/mL | 4587 |
| | | 37 | Less than 1 × $10^4$ cells/mL | 5312 |
| FI-4-4 | FB6-4-c1 | 14 | Less than 1 × $10^4$ cells/mL | 1806 |
| | | 28 | Less than 1 × $10^4$ cells/mL | 3416 |
| | | 37 | Less than 1 × $10^4$ cells/mL | 3849 |

(Example F7) Production of Antibody-Producing Cell-Containing Polymer-Coated Crosslinked Alginate Gel Fiber Equal volumes of the antibody-producing culture medium solution described in (Example F2-A) containing anti-GPVI antibody-producing cells (2×$10^7$ cells/mL) and the solution mixture F5A-M2 prepared in (Example F5-A) were mixed together, thereby producing a cell-containing alginic acid solution mixture (F7A-M3). In the solution mixture F7A-M3, an alkyne compound and an azide compound were contained in final concentrations of 0.5 wt %. A Hamilton syringe was filled with the solution mixture F7A-M3, and a needle for luer lock syringe (KANTO CHEMICAL CO., INC., 15/23NL-F) was connected to the syringe and set in a syringe pump. The tip of the needle was immersed in a beaker containing 20 mmol/L of a barium chloride aqueous solution containing 0.9% sodium chloride, and the alginic acid solution mixture (F7A-M3) was injected into the aqueous solution at a flow rate of 250 µL/minute for a time shown in Table 55. A fibrous substance injected into the aqueous solution was placed still for 30 minutes or longer, thereby obtaining an anti-GPVI antibody-producing cell-containing crosslinked alginate gel fiber. Subsequently, coating was performed in the same manner as in the method described in (Example F5-B) using an aqueous solution containing 0.1% poly-L-ornithine hydrobromide, 0.9% sodium chloride and 20 mmol/L barium chloride, thereby obtaining an antibody-producing cell-containing polymer-coated crosslinked alginate gel fiber (CFB-S4) (refer to CFB-S4 No. in Table 55).

TABLE 55

| No. | Injection time (minutes) | CFB-S4 No. |
|---|---|---|
| F7-1 | 1.2 | FB7-1-c1 |
| F7-2 | 4 | FB7-2-c1 |
| F7-3 | 6 | FB7-3-c1 |

(Example FI-5) Culture of Antibody-Producing Cell-Containing Polymer-Coated Crosslinked Alginate Gel Fiber The antibody-producing cell-containing polymer-coated crosslinked alginate gel fibers (one FB7-1-c1 or FB7-2-c1 and two FB7-3-c1) obtained in (Example F7) were put into a 125 mL polycarbonate Erlenmeyer flask, the antibody-producing culture medium solution described in (Example F2-A) was added thereto, the total amount of the gel fibers and the antibody-producing culture medium solution was set to 30 mL, the gel fibers were cultured in an incubator at 37° C. under a 5% $CO_2$ atmosphere while being shaken at 125 rpm. After two days from the beginning of the culture, 1.8 mL of a culture fluid was extracted, 1.8 mL of a feed solution (manufactured by Fujifilm Irvine Scientific, catalog No. JX F003) was added thereto, and the total amount of the culture medium was held at 30 mL. After that, half the amount of the culture fluid was exchanged using an antibody-producing culture medium solution once two to three days. During the culture period, the IgG concentration of the culture fluid was measured as a human IgG concentration with a Cedex Bio analyzer (Roche Diagnostics K.K.). In the culture using the antibody-producing cell-encapsulated polymer-coated crosslinked alginate gel fiber, the cumulative antibody concentrations and the concentrations of the anti-GPVI antibody-producing cell that was detected in the culture fluid at each measurement day were as shown in Table 56. From the culture results, it was possible to confirm that the amount of the antibody produced increased over time in the culture of each fiber.

TABLE 56

| No. | CFB-S4 No. | Measurement days | Concentration of leaky cell in culture fluid on each measurement day | Cumulative antibody (IgG) concentration on each measurement day (mg/L) |
|---|---|---|---|---|
| FI-5-1 | FB7-1-c1 | 14 | Less than 1 × $10^4$ cells/mL | 271 |
| | | 28 | 1 × $10^4$ cells | 589 |
| FI-5-2 | FB7-2-c1 | 14 | Less than 1 × $10^4$ cells/mL | 1021 |
| | | 28 | 0.5 × $10^4$ cells | 2584 |
| | | 37 | 3 × $10^4$ cells | 3772 |
| FI-5-3 | FB7-3-c1 | 14 | Less than 1 × $10^4$ cells/mL | 2512 |
| | | 28 | Less than 1 × $10^4$ cells/mL | 6050 |
| | | 37 | Less than 1 × $10^4$ cells/mL | 8050 |

(Example F8) Production of Antibody-Producing Cell-Containing Polymer-Coated Crosslinked Alginate Gel Fiber 3 wt % alginic acid aqueous solutions (containing 0.9 wt % sodium chloride) were prepared according to formulations shown in Table 57 below from a variety of sodium alginates and saline for injection (manufactured by Otsuka Pharmaceutical Factory, Inc.) (INs). Subsequently, 3 wt % alkyne aqueous solutions and azide aqueous solutions (containing 0.9 wt % of sodium chloride) were prepared according to formulations shown in Table 58 below.

TABLE 57

| 3 wt % sodium alginate aqueous solution (containing 0.9 wt % of sodium chloride) | |
|---|---|
| No. | Composition |
| ALGS2A | Sodium alginate(A-2)/INs |
| ALGS3 | Sodium alginate(B-3)/INs |
| ALGS3A | Sodium alginate(A-3)/INs |

TABLE 58

| 3 wt % alkyne aqueous solution and azide aqueous solution (containing 0.9 wt % of sodium chloride) | |
|---|---|
| No. | Composition |
| F8A1 | Prepared by mixing 3.3 wt % compound 4-A2d aqueous solution and 9.9 wt % sodium chloride aqueous solution in ratio of 10/1 |
| F8A2 | Compound 4-A3/INs |
| F8N1 | Prepared by mixing 3.3 wt % compound 11-A2d aqueous solution and 9.9 wt % sodium chloride aqueous solution in ratio of 10/1 |
| F8N2 | Compound 11-A3/INs |

Equal volumes of a 3 wt % alkyne aqueous solution and an azide aqueous solution (containing 0.9 wt % of sodium chloride) shown in Table 58 were mixed together in a formulation shown in Table 59, thereby preparing a chemically modified alginic acid solution mixture (F8A-M1). The solution mixture F8A-M1 and the 3 wt % sodium alginate aqueous solution (containing 0.9 wt % of sodium chloride) were mixed together so that the combination shown in Table 59 below reached 5:10, thereby preparing an alginic acid solution mixture (F8A-M2). Subsequently, equal volumes of the G016 culture medium having the composition described in (Example F2-A) and containing tocilizumab-producing CHO cells ($1\times10^8$ cells/mL) and the solution mixture F8A-M2 were mixed together, thereby producing a cell-containing alginic acid solution mixture (F8A-M3). In the solution mixture F8A-M3, an alkyne compound and an azide compound were contained in final concentrations of 0.5 wt %.

A Hamilton syringe was filled with the solution mixture F8A-M3, and a needle for luer lock syringe (KANTO CHEMICAL CO., INC., 15/23NL-F) was connected to the syringe and set in a syringe pump. The tip of the needle was immersed in a beaker containing 20 mmol/L of a barium chloride aqueous solution containing 0.9% sodium chloride, and the alginic acid solution mixture (F8A-M3) was injected into the aqueous solution at a flow rate of 250 μL/minute for 0.8 minutes. A fibrous substance injected into the aqueous solution was placed still for 30 minutes or longer, thereby obtaining a tocilizumab-producing CHO cell-containing crosslinked alginate gel fiber. Subsequently, coating was performed in the same manner as in the method described in (Example F5-B) using the obtained tocilizumab-producing CHO cell-containing crosslinked alginate gel fiber and an aqueous solution containing 0.1% poly-L-ornithine hydrobromide, 0.9% sodium chloride and 20 mmol/L barium chloride, thereby obtaining a polymer-coated crosslinked alginate gel fiber (CFB-S5) (refer to CFB-S5 No. in Table 59).

TABLE 59

| No. | Combination of alkyne compound/azide compound in F8A-M1 | Type of sodium alginate in F8A-M2 | CFB-S5 No. |
|---|---|---|---|
| F8-1 | F8A1/F8N1 | ALGS2A | FB8-1-c1 |
| F8-2 | F8A1/F8N1 | ALGS3 | FB8-2-c1 |
| F8-3 | F8A1/F8N1 | ALGS3A | FB8-3-c1 |
| F8-4 | F8A2/F8N2 | ALGS3A | FB8-4-c1 |
| F8-5 | F8A2/F8N2 | ALGS3 | FB8-5-c1 |

(Example FI-6) Culture of Antibody-Producing Cell-Containing Polymer-Coated Crosslinked Alginate Gel Fiber One antibody-producing cell-containing polymer-coated crosslinked alginate gel fiber (FB8-1-c1, FB8-2-c1, FB8-3-c1, FB8-4-c1 or FB8-5-c1) obtained in (Example F8) was put into a 125 mL polycarbonate Erlenmeyer flask, the G016 culture medium (30 mL) having the composition described in (Example F2-A) was added thereto, the gel fiber began to be cultured in an incubator at 37° C. under a 5% $CO_2$ atmosphere while being shaken at 125 rpm, the culture temperature was changed to 30° C. after five days, and the gel fiber was continuously cultured at the same temperature. During this period, once two to three days, 1.8 mL of a culture fluid was extracted, 1.8 mL of the G016 culture medium or 1.8 mL of a feed solution (manufactured by Fujifilm Irvine Scientific, catalog No. JX F003) was added thereto, and the total amount of the culture medium was held at 30 mL. In addition, half the amount of the culture fluid was exchanged once a week. During the culture period, the IgG concentration of the culture fluid was measured as a human IgG concentration with a Cedex Bio analyzer (Roche Diagnostics K.K.). In the culture using the antibody-producing cell-encapsulated polymer-coated crosslinked alginate gel fiber, the cumulative antibody concentrations and the concentrations of the tocilizumab-producing CHO cell that was detected in the culture fluid at each measurement day were as shown in Table 60. From the culture results, it was possible to confirm that the amount of the antibody produced increased over time in the culture of each fiber. In the present culture results, antibody production becomes higher depending on the stretchability of the fiber (the results of the tensile test in (Example F4-D)).

TABLE 60

| No. | CFB-S5 No. | Measurement days | Concentration of leaky cell in culture fluid on each measurement day | Cumulative antibody (IgG) concentration on each measurement day (mg/L) |
|---|---|---|---|---|
| FI-6-1 | FB8-1-c1 | 14 | Less than $1\times10^4$ cells/mL | 575 |
| | | 21 | $4.5\times10^4$ cells/mL | 1116 |
| FI-6-2 | FB8-2-c1 | 14 | Less than $1\times10^4$ cells/mL | 445 |
| | | 28 | Less than $1\times10^4$ cells/mL | 1103 |
| | | 38 | Less than $1\times10^4$ cells/mL | 1412 |
| FI-6-3 | FB8-3-c1 | 14 | Less than $1\times10^4$ cells/mL | 636 |
| | | 21 | $0.5\times10^4$ cells/mL | 1225 |
| | | 28 | $4\times10^4$ cells/mL | 1758 |
| | | 38 | $2.5\times10^4$ cells/mL | 2343 |
| FI-6-4 | FB8-4-c1 | 14 | Less than $1\times10^4$ cells/mL | 566 |
| | | 28 | Less than $1\times10^4$ cells/mL | 1559 |
| | | 38 | Less than $1\times10^4$ cells/mL | 2075 |
| FI-6-5 | FB8-5-c1 | 14 | Less than $1\times10^4$ cells/mL | 360 |
| | | 28 | Less than $1\times10^4$ cells/mL | 854 |
| | | 38 | Less than $1\times10^4$ cells/mL | 1050 |

(Example F9) Production of Antibody-Producing Cell-Containing Polymer-Coated Crosslinked Alginate Gel Fiber Equal volumes of the G016 culture medium having the composition described in (Example F2-A) and containing tocilizumab-producing CHO cells ($1\times10^8$ cells/mL) and the alginic acid solution mixture F5A-M2 prepared in (Example F5-A) were mixed together, thereby producing a cell-containing alginic acid solution mixture (F9A-M3). In the solution mixture F9A-M3, an alkyne compound and an azide compound were contained in final concentrations of 0.5 wt %. A Hamilton syringe was filled with the solution mixture F9A-M3, and a needle for luer lock syringe (KANTO CHEMICAL CO., INC., 15/23NL-F) was connected to the syringe and set in a syringe pump. The tip of the needle was immersed in a beaker containing 20 mmol/L of a barium chloride aqueous solution containing 0.9% sodium chloride, and the alginic acid solution mixture (F9A-M3) was injected into the aqueous solution at a flow rate of 250 μL/minute for 0.8 minutes. A fibrous substance injected into the aqueous solution was placed still for 30 minutes or longer, thereby obtaining a tocilizumab-producing CHO cell-containing crosslinked alginate gel fiber. The obtained cell-containing crosslinked alginate gel fiber was coated in the same manner as in the method described in (Example F5-B) using a cationic polymer-containing aqueous solution having each composition shown in Table 61, thereby obtaining an antibody-producing cell-containing polymer-coated crosslinked alginate gel fiber (CFB-S6) (refer to CFB-S6 No. in Table 62).

TABLE 61

| No. | Composition of cationic polymer-containing aqueous solution |
|---|---|
| F9-c1 | 0.1% poly-L-ornithine hydrobromide/0.9% sodium chloride/20 mM barium chloride |
| F9-c2 | 0.1% polymethylene-CO-guanidine hydrochloride/ 0.9% sodium chloride/20 mM barium chloride |
| F9-c3 | 0.075% linear polyethylene imine hydrochloride/ 0.9% sodium chloride/20 mM barium chloride |

TABLE 62

| No. | Cationic polymer-containing aqueous solution | CFB-S6 No. |
|---|---|---|
| F9-1 | F9-c1 | FB9-1-c1 |
| F9-2 | F9-c2 | FB9-2-c2 |
| F9-3 | F9-c3 | FB9-3-c3 |

(Example FI-7) Culture of Antibody-Producing Cell-Containing Polymer-Coated Crosslinked Alginate Gel Fiber One antibody-producing cell-containing polymer-coated crosslinked alginate gel fiber (FB9-1-c1, FB9-2-c2 or FB9-3-c3) obtained in (Example F9) was put into a 125 mL polycarbonate Erlenmeyer flask, the G016 culture medium (30 mL) described in (Example F2-A) was added thereto, the gel fiber began to be cultured in an incubator at 37° C. under a 5% $CO_2$ atmosphere while being shaken at 125 μm, the culture temperature was changed to 30° C. after five days, and the gel fiber was continuously cultured at the same temperature. During this period, once two to three days, 1.8 mL of a culture fluid was extracted, 1.8 mL of the G016 culture medium or 1.8 mL of a feed solution (manufactured by Fujifilm Irvine Scientific, catalog No. JX F003) was added thereto, or half the amount of the culture fluid was exchanged. During the culture period, the IgG concentration of the culture fluid was measured as a human IgG concentration with a Cedex Bio analyzer (Roche Diagnostics K.K.). In the culture using the antibody-producing cell-encapsulated polymer-coated crosslinked alginate gel fiber, the cumulative antibody concentrations and the concentrations of the tocilizumab-producing CHO cell that was detected in the culture fluid at each measurement day were as shown in Table 63. From the culture results, it was possible to confirm that the amount of the antibody produced increased over time in the culture of the fibers FB9-1-c1 and FB9-1-c3.

TABLE 63

| No. | CFB-S6 No. | Measurement days | Concentration of leaky cell in culture fluid on each measurement day | Cumulative antibody (IgG) concentration on each measurement day (mg/L) |
|---|---|---|---|---|
| FI-7-1 | FB9-1-c1 | 14 | Less than $1 \times 10^4$ cells/mL | 601 |
| | | 35 | $1.5 \times 10^4$ cells/mL | 1863 |
| FI-7-2 | FB9-2-c2 | 14 | $3.5 \times 10^4$ cells/mL | 606 |
| FI-7-3 | FB9-3-c3 | 14 | Less than $1 \times 10^4$ cells/mL | 543 |
| | | 35 | Less than $1 \times 10^4$ cells/mL | 1803 |

(Example F16-A) Production of Crosslinked Alginate Gel Fiber

A 3 wt % sodium alginate aqueous solution, an alkyne aqueous solution and an azide aqueous solution (containing 0.9 wt % sodium chloride) were prepared according to formulations in Table 64 below.

TABLE 64

| 3 wt % sodium alginate aqueous solution, alkyne aqueous solution and azide aqueous solution (containing 0.9 wt % sodium chloride) | |
|---|---|
| ALGS2B | Prepared by mixing 3.3 wt % B-2 aqueous solution and 9.9 wt % sodium chloride aqueous solution in ratio of 10/1 |
| F16A1 | Prepared by mixing 3.3 wt % compound 4-A2d aqueous solution and 9.9 wt % sodium chloride aqueous solution in ratio of 10/1 |
| F16N1 | Prepared by mixing 3.3 wt % compound 11-A2f aqueous solution and 9.9 wt % sodium chloride aqueous solution in ratio of 10/1 |

Equal volumes of the alkyne aqueous solution (F16A1) and the azide aqueous solution (F16N1) were mixed together, thereby preparing a chemically modified alginic acid solution mixture (F16A-M1). The solution mixture F16A-M1 and ALGS2B were mixed together in a ratio of F16A-M1:ALGS2B=5:10, thereby producing an alginic acid solution mixture (F16A-M2). Subsequently, equal volumes of the solution mixture F16A-M2 and a bead suspension (manufactured by Spheretech, Inc., Fluorescent UV Particles, code No.: FP-10040-2) were mixed together, thereby producing a bead-containing alginic acid solution mixture (F16A-M3). A Hamilton syringe was filled with the solution mixture F16A-M3, and a needle for luer lock syringe (KANTO CHEMICAL CO., INC., 15/23NL-F) was connected to the syringe and set in a syringe pump. The tip of the needle was immersed in a beaker containing 20 mmol/L of a barium chloride aqueous solution containing 0.9% sodium chloride, and the solution mixture was injected at a flow rate of 250 μL/minute for one minute. A fibrous substance immediately after being injected was cut using anatomical scissors every three seconds. The cut fibrous substances were placed still in the barium chloride aqueous solution for 30 minutes or longer, thereby obtaining a crosslinked alginate gel fiber (CLA-16A) having a length of approximately 5 cm.

(Example F16-B) Production of Polymer-Coated Crosslinked Alginate Gel Fiber

The crosslinked alginate gel fibers in the barium chloride aqueous solution, which were obtained in (Example F16-A), were filtered and fractionated using a cell strainer, the fractionated crosslinked alginate gel fibers were added to an aqueous solution containing a cationic polymer and shaking-stirred at 37° C. and 125 rpm for 30 minutes, thereby coating the crosslinked alginate gel fibers with the polymer. The fibers in the aqueous solution were filtered and fractionated using the cell strainer and washed with 5 mL of physiological saline twice, thereby obtaining polymer-coated crosslinked alginate gel fibers (CFB-16).

(Example F17-A) Production of Antibody-Producing Cell-Containing Crosslinked Alginate Gel Fiber A3 wt % alkyne aqueous solution and azide aqueous solutions (containing 0.9 wt % sodium chloride) were prepared according to formulations in Table 65 below.

TABLE 65

| | 3 wt % alkyne aqueous solution and azide aqueous solutions (containing 0.9 wt % sodium chloride) |
|---|---|
| F17A1 | Prepared by mixing 3.3 wt % compound 4-A2d aqueous solution and 9.9 wt % sodium chloride aqueous solution in ratio of 10/1 |
| F17N1 | Prepared by mixing 3.3 wt % compound 11-A2d aqueous solution and 9.9 wt % sodium chloride aqueous solution in ratio of 10/1 |
| F17N2 | Prepared by mixing 3.3 wt % compound 11-A2f aqueous solution and 9.9 wt % sodium chloride aqueous solution in ratio of 10/1 |

After a 3 wt % aqueous solution (containing 0.9 wt % sodium chloride) of the compound 4-A2d, the compound 11-A2d and the compound 11-A2f shown in Table 65 was prepared, equal volumes of the alkyne and azide aqueous solutions were mixed together in combinations shown in Table 66 below, thereby preparing a chemically modified alginic acid solution mixture (F17A-M1). The solution mixture F17A-M1 and a 3 wt % alginate aqueous solution (containing 0.9% sodium chloride) (ALGS2) prepared from sodium alginate (B-2) and saline for injection (manufactured by Otsuka Pharmaceutical Factory, Inc.) (INs) were mixed together in a ratio of F17A-M1:ALGS2=5:10, thereby producing an alginic acid solution mixture (F17A-M2). Subsequently, equal volumes of the solution mixture F17A-M2 and the G016 culture medium having the composition described in (Example F2-A) and containing tocilizumab-producing CHO cells ($3\times10^7$ cells/mL) were mixed together, thereby producing a cell-containing alginic acid solution mixture (F17A-M3). Operation was performed using the solution mixture F17A-M3 according to the following operation method (operation method A or B), thereby obtaining an antibody-producing cell-containing crosslinked alginate gel fiber (CLA-G17) (refer to CLA-G17 No. in Table 66).

(Operation method A) Operation method described in (Example F16-A)

(Operation method B) The tip of the needle was immersed in a beaker containing 20 mmol/L of a barium chloride aqueous solution containing 0.9% sodium chloride, and the alginic acid solution mixture was injected into the barium chloride aqueous solution at a flow rate of 250 μL/minute. A fibrous substance injected into the aqueous solution was placed still for 30 minutes or longer.

The fiber lengths of FB17-3 and FB17-4 were approximately 2 to 4 cm.

TABLE 66

| No. | Combination of alkyne compound/azide compound in F17A-M1 | CLA-G17 No. | Operation method |
|---|---|---|---|
| F17-A-1 | 4-A2d/11-A2d | FB17-1 | B |
| F17-A-2 | 4-A2d/11-A2d | FB17-2 | B |
| F17-A-3 | 4-A2d/11-A2d + 11-A2f | FB17-3 | A |
| F17-A-4 | 4-A2d/11-A2d + 11-A2f | FB17-4 | A |

(Example F17-B) Production of Antibody-Producing Cell-Containing Polymer-Coated Crosslinked Alginate Gel Fiber The antibody-producing cell-containing crosslinked alginate gel fiber (CLA-G17) obtained in (Example F17-A) was coated in the same manner as the method described in (Example F5-B) using an aqueous solution containing 0.1% poly-L-ornithine hydrobromide, 0.9% sodium chloride and 20 mmol/L of barium chloride, thereby obtaining an antibody-producing cell-containing polymer-coated crosslinked alginate gel fiber (CFB-G17). The amount of the fiber used in the coating is as shown in Table 67 below (refer to CFB-G17 No. in Table 67).

TABLE 67

| No. | CLA-G17 No. | Fiber amount (mL) | Fiber length/fiber | CFB-G17 No. |
|---|---|---|---|---|
| F17-B-1 | FB17-1 | 10 | Approximately 69 m | FB17-1-c1 |
| F17-B-2 | FB17-2 | 1 | Approximately 6.9 m | FB17-2-c1 |
| F17-B-3 | FB17-3 | 30 | Approximately 2 to 4 cm | FB17-3-c1 |
| F17-B-4 | FB17-4 | 3 | Approximately 2 to 4 cm | FB17-4-c1 |

(Example FI-17) Culture of Antibody-Producing Cell-Containing Polymer-Coated Crosslinked Alginate Gel Fiber An antibody-producing cell-containing polymer-coated crosslinked alginate gel fiber was cultured by performing operation according to the following operation method (operation method 1 or 2) using the polymer-coated crosslinked alginate gel fiber (CFB-G17) obtained in (Example F-17B).

(Operation Performed 1)

The G016 culture medium described in (Example F2-A) to which a 0.01% antifoam (manufactured by Sigma-Aldrich, Antiform C Emulsion, catalog No. A8011) had been added and the antibody-producing cell-containing polymer-coated crosslinked alginate gel fiber (FB17-1-c1 or FB17-3-c1) obtained in (Example F17-B) were put into a glass culture tank including a magnetic stirrer (culture tank having a total capacity of 500 mL) to make the total amount of the culture system reach 300 mL. The gel fiber began to be cultured at 37° C. under stirring at a speed shown in Table 68 below while a filter-sterilized air was ventilated at all time and $CO_2$ was ventilated appropriately so that the pH reached approximately seven in the culture tank containing the antibody-producing cell-containing polymer-coated crosslinked alginate gel fiber, the culture temperature was changed to 30° C. after five days, and the gel fiber was continuously cultured at the same temperature. The culture fluid was continuously replaced at a culture medium exchange speed (vessel volume/day; hereinafter referred to as vvd) shown in Table 68 below from the culture beginning day. For the exchange of the culture fluid, the G016 culture medium was used after a 0.01% antifoam had been added thereto.

(Operation Performed 2)

The antibody-producing cell-containing polymer-coated crosslinked alginate gel fiber (FB17-2-c1 or FB17-4-c1) obtained in (Example F17-B) was put into a 125 mL polycarbonate Erlenmeyer flask, and the G016 culture medium described in (Example F2-A) was added thereto to make the total amount of the culture system reach 30 mL. The gel fiber began to be cultured in an incubator at 37° C. under a 5% $CO_2$ atmosphere while being shaken at a stirring speed shown in Table 68 below, the culture temperature was changed to 30° C. after five days, and the gel fiber was continuously cultured at the same temperature. During this period, once two to three days, 1.8 mL of a culture fluid was extracted, 1.8 mL of the G016 culture medium or 1.8 mL of a feed solution (manufactured by Fujifilm Irvine Scientific, catalog No. JX F003) was added thereto or half the amount of the culture fluid was exchanged.

During the culture period, the IgG concentration of the culture fluid was measured as a human IgG concentration with a Cedex Bio analyzer (Roche Diagnostics K.K.). In the culture using the antibody-producing cell-containing polymer-coated crosslinked alginate gel fiber, the concentrations and the cumulative antibody concentrations of the tocilizumab-producing CHO cell that was detected in the culture fluid at the final day of the culture were as shown in Table 68.

TABLE 68

| No. | CFB-G17 No. | Measurement days | Stirring speed (rpm) | Turning speed (rpm) | Culture medium exchange speed (vvd) | Concentration of leaky cell in culture fluid on last day of culture | Cumulative antibody (IgG) concentration on last day of culture (mg/L) |
|---|---|---|---|---|---|---|---|
| FI-17-1 | FB17-1-c1 | 42 | 450 | — | 0.4 | Less than $1 \times 10^4$ cells/mL | 1257 |
| FI-17-2 | FB17-2-c1 | 42 | — | 125 | — | $0.5 \times 10^4$ cells/mL | 2056 |
| FI-17-3 | FB17-3-c1 | 21 | 125 | — | 0.5 | Less than $1 \times 10^4$ cells/mL | 3822 |
| FI-17-4 | FB17-4-c1 | 21 | — | 125 | — | Less than $1 \times 10^4$ cells/mL | 3308 |

The results in Table 68 suggest that the amount of the antibodies produced in the reactor culture improved by shortening the fiber lengths compared with the flask culture.

(Example F18-A) Production of Antibody-Producing Cell-Containing Crosslinked Alginate Gel Fiber 3 wt % aqueous solutions (containing 0.9 wt % of sodium chloride) of the compound 4-A2d and the compound 11-A2d were prepared according to the same formulations as in Table 32 and Table 33 described in (Example F2-A), and then equal volumes of the individual aqueous solutions were mixed together, thereby preparing a chemically modified alginic acid solution mixture (F18A-M1). The solution mixture F18A-M1 and a 3 wt % alginate aqueous solution (containing 0.9% sodium chloride) prepared from sodium alginate (A-3) and saline for injection (manufactured by Otsuka Pharmaceutical Factory, Inc.) (INs) (ALGS3A) were mixed together in a ratio of F18A-M1:ALGS3A=5:10, thereby producing an alginic acid solution mixture (F18A-M2). Subsequently, equal volumes of the solution mixture F18A-M2 and the antibody-producing culture medium solution described in (Example F2-A) containing an anti-GPVI antibody-producing cell ($2\times10^7$ cells/mL) were mixed together, thereby producing a cell-containing alginic acid solution mixture (F18A-M3). The same operation as (operation method B) described in (Example F17-A) was performed using the solution mixture F18A-M3, thereby obtaining an antibody-producing cell-containing crosslinked alginate gel fiber (CLA-G18).

(Example F18-B) Production of Antibody-Producing Cell-Containing Polymer-Coated Crosslinked Alginate Gel Fiber The antibody-producing cell-containing crosslinked alginate gel fiber (CLA-G18) obtained in (Example F18-A) was coated in the same manner as the method described in (Example F5-B) using an aqueous solution containing 0.1% poly-L-ornithine hydrobromide, 0.9% sodium chloride and 20 mmol/L of barium chloride, thereby obtaining an antibody-producing cell-containing polymer-coated crosslinked alginate gel fiber (CFB-G18). The amount of the fiber used in the coating is as shown in Table 69 below (refer to CFB-G18 No. in Table 69).

TABLE 69

| No. | Fiber amount (mL) | CFB-G18 No. |
|---|---|---|
| F18-B-1 | 3 | FB18-1-c1 |
| F18-B-2 | 6 | FB18-2-c1 |
| F18-B-3 | 9 | FB18-3-c1 |

(Example FI-18) Culture of Antibody-Producing Cell-Containing Polymer-Coated Crosslinked Alginate Gel Fiber The antibody-producing cell-containing polymer-coated crosslinked alginate gel fiber (FB18-1-c1, FB18-2-c1 or FB18-3-c1) obtained in (Example F18-B) was put into a 125 mL polycarbonate Erlenmeyer flask, and the antibody-producing culture medium solution described in (Example F2-A) was added thereto, and the total amount of the culture system was set to 30 mL. The gel fiber began to be cultured while the Erlenmeyer flask was shaken in an incubator at 37° C. under a 5% $CO_2$ atmosphere at 125 μm, and the gel fiber was continuously cultured at the same temperature. During this period, once two to three days, 1.8 mL of a culture fluid was extracted, 1.8 mL of a feed solution (manufactured by Fujifilm Irvine Scientific, catalog No. JX F003) was added thereto or half the amount of the culture fluid was exchanged. For the exchange of half the amount of the culture fluid, aside from the antibody-producing culture medium solution described in (Example F2-A), a glucose-added antibody-producing culture medium solution obtained by adding 1/100 or 1/50 volume of a 45% D-(+) glucose solution (manufactured by Sigma-Aldrich, Catalog No. G8769) to the antibody-producing culture medium solution was used. During the culture period, the IgG concentration of the culture fluid was measured as a human IgG concentration with a Cedex Bio analyzer (Roche Diagnostics K.K.). In the culture using the antibody-producing cell-containing polymer-coated crosslinked alginate gel fiber, the cumulative antibody concentrations and the concentrations of the anti-GPVI antibody-producing cell that was detected in the culture fluid at each measurement day were as shown in Table 70. From the culture results, it was possible to confirm that the amount of the antibody produced increased over time in the culture of the fiber FB18-1-c1, FB18-2-c1 or FB18-3-c1.

TABLE 70

| No. | CFB-S3 No. | Measurement days | Concentration of leaky cell on each measurement day | Cumulative antibody (IgG) concentration on each measurement day (mg/L) |
|---|---|---|---|---|
| FI-18-1 | FB18-1-c1 | 15 | Less than $1 \times 10^4$ cells/mL | 2970 |
| | | 30 | Less than $1 \times 10^4$ cells/mL | 6344 |
| FI-18-2 | FB18-2-c1 | 15 | Less than $1 \times 10^4$ cells/mL | 4517 |
| | | 30 | Less than $1 \times 10^4$ cells/mL | 10460 |
| FI-18-3 | FB18-3-c1 | 15 | Less than $1 \times 10^4$ cells/mL | 4616 |
| | | 30 | Less than $1 \times 10^4$ cells/mL | 11954 |

(Example F19-A) Production of Antibody-Producing Cell-Containing Crosslinked Alginate Gel Fiber 3 wt % aqueous solutions (containing 0.9 wt % of sodium chloride) of the compound 4-A2d and the compound 11-A2f were prepared according to the same formulations as in Table 64 described in (Example F16-A), and then equal volumes of the individual aqueous solutions were mixed together, thereby preparing a chemically modified alginic acid solution mixture (F19A-M1). The solution mixture F19A-M1 and a 3 wt % alginate aqueous solution (containing 0.9% sodium chloride) prepared from sodium alginate (A-3) and saline for injection (manufactured by Otsuka Pharmaceutical Factory, Inc.) (INs) (ALGS3A) were mixed together in a ratio of F19A-M1:ALGS3A=5:10, thereby producing an alginic acid solution mixture (F19A-M2). Subsequently, equal volumes of the solution mixture F19A-M2 and the antibody-producing culture medium solution described in (Example F2-A) containing an anti-GPVI antibody-producing cell ($2\times10^7$ cells/mL) were mixed together, thereby producing a cell-containing alginic acid solution mixture (F19A-M3). Operation was performed according to (Example F16-A) using the solution mixture F19A-M3, thereby obtaining 60 mL of an antibody-producing cell-containing crosslinked alginate gel fiber (CLA-19A) having a fiber length of approximately 2 to 4 cm.

(Example F19-B) Production of Antibody-Producing Cell-Containing Polymer-Coated Crosslinked Alginate Gel Fiber The antibody-producing cell-containing crosslinked alginate gel fiber (CLA-G19) obtained in (Example F19-A) was coated in the same manner as the method described in (Example F5-B) using an aqueous solution containing 0.1% poly-L-ornithine hydrobromide, 0.9% sodium chloride and 20 mmol/L of barium chloride, thereby obtaining an antibody-producing cell-containing polymer-coated crosslinked alginate gel fiber (CFB-G19).

(Example FI-19) Culture of Antibody-Producing Cell-Containing Polymer-Coated Crosslinked Alginate Gel Fiber The antibody-producing cell culture medium solution described in (Example F2-A) and the antibody-producing cell-containing polymer-coated crosslinked alginate gel fiber (CFB-G19) obtained in (Example F19-B) were put into a glass culture tank including a magnetic stirrer (culture tank having a total capacity of 500 mL), and the total amount of the culture system was set to 300 mL. The gel fiber began to be cultured at 37° C. under stirring at 350 rpm while a filter-sterilized air was ventilated at all time and $CO_2$ was ventilated appropriately so that the pH reached approximately seven in the culture tank containing the antibody-producing cell-containing polymer-coated crosslinked alginate gel fiber. After one day, the stirring speed was changed to 210 rpm, and the gel fiber was continuously cultured at 37° C. and the same speed. The culture fluid was continuously replaced at approximately 0.5 vvd in the same manner as in (Example FI-17) from one day after the beginning of the culture. For the exchange of the culture fluid, the antibody-producing cell culture medium solution described in (Example F2-A) or the antibody-producing cell culture medium solution to which a 0.01% antifoam (manufactured by Sigma-Aldrich, Antiform C Emulsion, catalog No.

A8011) had been added were used. During the culture period, the IgG concentration of the culture fluid was measured as a human IgG concentration with a Cedex Bio analyzer (Roche Diagnostics K.K.). In the culture using the antibody-producing cell-containing polymer-coated crosslinked alginate gel fiber, the cumulative antibody concentrations and the concentrations of the anti-GPVI antibody-producing cell that was detected in the culture fluid at each measurement day were as shown in Table 71.

TABLE 71

| No. | Measurement days | Concentration of leaky cell on each measurement day | Cumulative antibody (IgG) concentration on each measurement day (mg/L) |
|---|---|---|---|
| FI-19 | 13 | Less than $1 \times 10^4$ cells/mL | 2897 |
| | 24 | Less than $1 \times 10^4$ cells/mL | 7680 |

The results of (Example FI-19) suggest that, in the reactor culture using the antibody-producing cell-containing polymer-coated crosslinked alginate gel fiber, anti-GPVI antibody-producing cells produce antibodies.

INDUSTRIAL APPLICABILITY

Here, a polymer-coated crosslinked alginate gel fiber in which a core layer comprising a cell enabling production of antibodies, bioactive substances or the like and crosslinked alginate gel is coated with a cationic polymer (cationic polymer layer) is provided. In addition, it is possible to provide a method for manufacturing the fiber and a method for culturing an antibody, a bioactive substance or the like using the fiber.

REFERENCE SIGNS LIST a Diameter of core layer of polymer-coated crosslinked alginate gel fiber
b Thickness of cationic polymer layer of polymer-coated crosslinked alginate gel fiber
c Outer diameter of polymer-coated crosslinked alginate gel fiber
4 Cationic polymer layer
5 Core layer
6 Cell (cell enabling production of antibodies, bioactive substances or the like)
XX Device
YY Extrusion tube
1 Introduction port
2 Discharge port
DD Container (for example, beaker) (divalent metal ion-containing solution)
EE Container (for example, beaker) (cationic polymer-containing solution)
CLA Crosslinked alginate gel fiber
CFB Polymer-coated crosslinked alginate gel fiber

The invention claimed is:

1. A polymer-coated crosslinked alginate gel fiber consisting of:

a core layer; and a cationic polymer layer, wherein the cationic polymer layer is selected from the group consisting of poly-L-ornithine (PLO), polymethylene-CO-guanidine (PMCG), polyallylamine (PAA), and polyethyleneimine, wherein the core layer comprises an antibody-producing cell or a bioactive substance-producing cell embedded in crosslinked alginate gel that is obtained by performing a crosslinking reaction using chemically modified alginic acid derivatives represented by Formula (I) and Formula (II), and the cationic polymer layer coats the surface of the core layer, wherein the polymer-coated crosslinked alginate gel fiber has a length within a range of 0.01 to 100 m and is suitable for use in the production of at least one member selected from the group consisting of an antibody and a bioactive substance, and wherein the chemically modified alginic acid derivative represented by Formula (I) is a chemically modified alginic acid derivative represented by Formula (I) below:

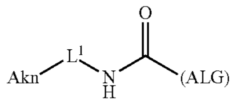

(I)

in Formula (I), (ALG) represents alginic acid; —NHCO— represents an amide bond through an arbitrary carboxyl group of the alginic acid; wherein Akn represents a cyclic alkyne group; $-L^1-$ is a divalent linker that bonds to the cyclic alkyne group (Akn), $Akn-L^1-$ is a group selected from the group consisting of the partial structural formulae shown in the following table, wherein in each formula, the right side of the broken line is not included:

| No. | $Akn—L^1—$ | |
|---|---|---|
| ALK-1a | 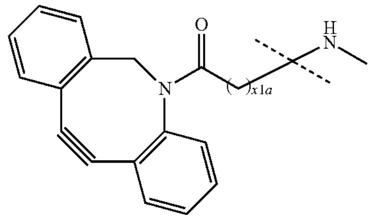 | x1a = 1-6 |
| ALK-1b | 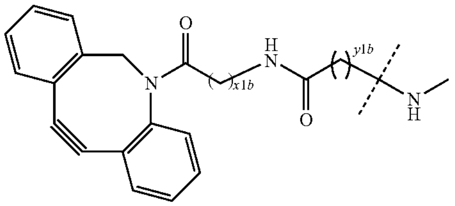 | x1b = 1-6 y1b = 1-6 |
| ALK-2 | 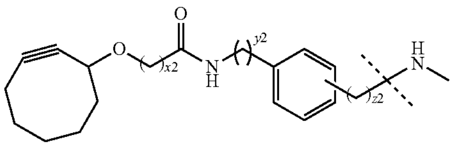 | x2 = 1-6 y2 = 0-6 z2 = 1-6 |
| ALK-3a | 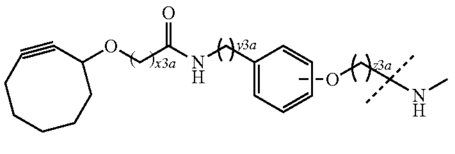 | x3a = 1-6 y3a = 0-6 z3a = 2-6 |

-continued

| No. | Akn—L¹— | |
|---|---|---|
| ALK-3b | 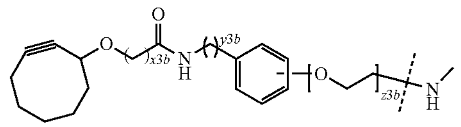 | x3b = 1-6 y3b = 0-6 z3b = 1-6 |
| ALK-4 | 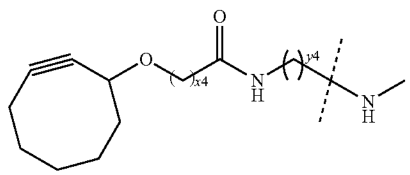 | x4 = 1-6 y4 = 2-6 |
| ALK-5a | 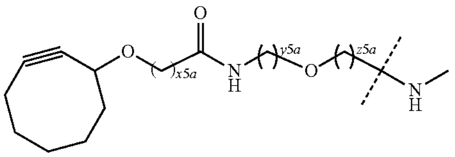 | x5a = 1-6 y5a = 2-6 z5a = 2-6 |
| ALK-5b | 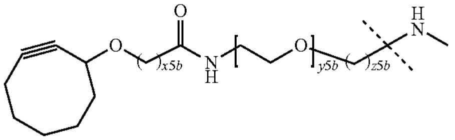 | x5b = 1-6 y5b = 1-6 z5b = 2-6 |

TABLE 72-2

| No. | Akn—L¹— | |
|---|---|---|
| ALK-6 | 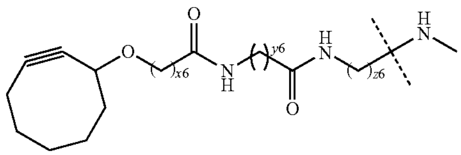 | x6 = 1-6 y6 = 1-6 z6 = 2-6 |
| ALK-7a | 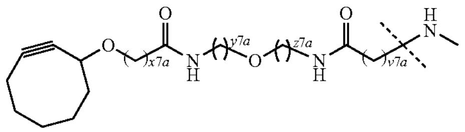 | x7a = 1-6 y7a = 2-6 z7a = 2-6 v7a = 1-6 |
| ALK-7b | 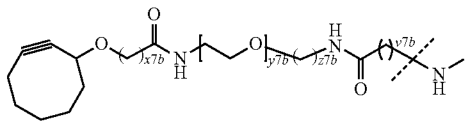 | x7b = 1-6 y7b = 1-6 z7b = 2-6 v7b = 1-6 |

and the chemically modified alginic acid derivative represented by Formula (II) is a chemically modified alginic acid derivative represented by Formula (II) below:

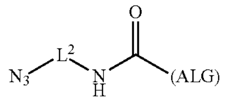

(II)

in Formula (II), (ALG) represents alginic acid; —NHCO— represents an amide bond through an arbitrary carboxyl group of the alginic acid; -L²- represents a linker selected from the group consisting of partial structural formulae, wherein in each formula, the outsides of the broken lines at both ends are not included, shown in the following table:

| No. | —L²— | |
|---|---|---|
| LN-1 | 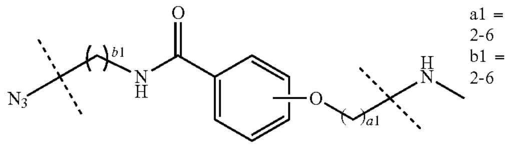 | a1 = 2-6 b1 = 2-6 |
| LN-2 | 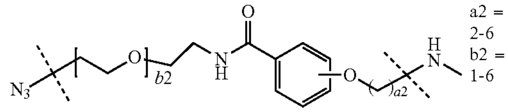 | a2 = 2-6 b2 = 1-6 |
| LN-3 | 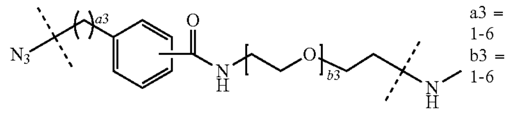 | a3 = 1-6 b3 = 1-6 |
| LN-4 | 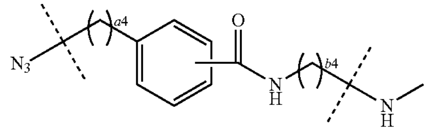 | a4 = 1-6 b4 = 2-6 |
| LN-5 | 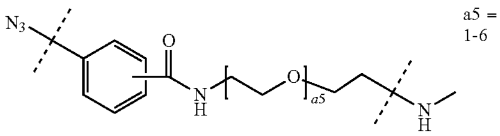 | a5 = 1-6 |
| LN-6 | 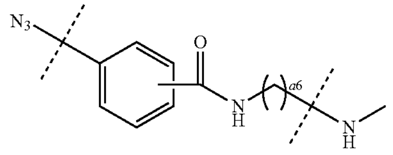 | a6 = 2-6. |

2. The polymer-coated crosslinked alginate gel fiber according to claim 1, wherein the antibody-producing cell that is contained in the core layer is an antibody-producing genetically modified animal cell, wherein a host cell of the genetically modified cell is selected from the group consisting of a CHO cell, a CHO cell subline, a COS cell, an Sp2/0 cell, an NS0 cell, an SP2 cell, a PERC6 cell, a YB2/0 cell, a YE2/0 cell, a 1R983F cell, a Namalwa cell, a Wil-2 cell, a Jurkat cell, a Vero cell, a Molt-4 cell, an HEK293 cell, a BHK cell, an HT-1080 cell, a KGH6 cell, a P3X63Ag8.653 cell, a C127 cell, a JC cell, an LA7 cell, a ZR-45-30 cell, an hTERT cell, an NM2C5 cell and a UACC-812 cell.

3. The polymer-coated crosslinked alginate gel fiber according to claim 1, wherein the bioactive substance-producing cell that is contained in the core layer is a cell selected from the group consisting of an insulin-secreting cell, a pancreatic islet, a pancreatic islet cell, a dopamine-secreting cell, a pituitary cell, a growth hormone-secreting cell, a parathyroid cell, a nerve growth factor-secreting cell, a blood coagulation factor-secreting cell, a hepatocyte, a parathyroid cell, an erythropoietin-secreting cell, a norepinephrine-secreting cell and a cell transformed with a bioactive substance expression vector (genetically modified cell).

4. The polymer-coated crosslinked alginate gel fiber according to claim 1, wherein the core layer further comprises at least one component selected from the group consisting of an alginic acid solution, alginate gel which has only ionic crosslinked gel formed by divalent metal ion with alginic acid, a culture fluid, a collagen solution, methylcellulose and a sucrose solution.

5. The polymer-coated crosslinked alginate gel fiber according to claim 1, wherein Akn-$L^1$- in the chemically modified alginic acid derivative represented by Formula (I) is a group selected from the group consisting of the following partial structural formulae, wherein in each formula, the right side of the broken line is not included:

ALK-1a-3a

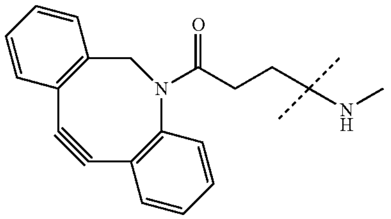

ALK-1a-3b

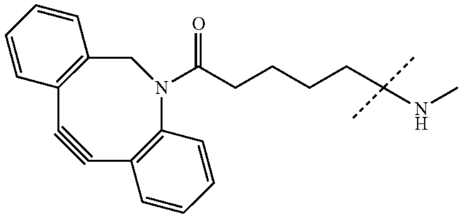

ALK-1b-3

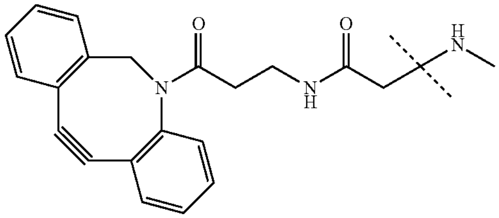

-continued

ALK-2-3

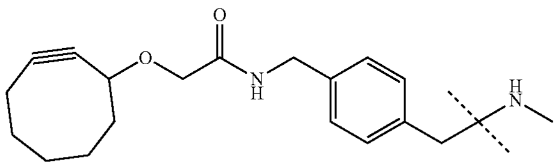

ALK-3a-3

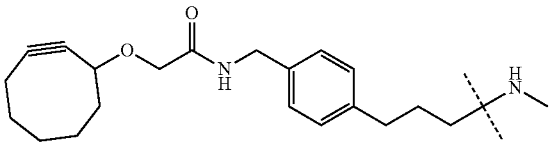

ALK-4-3

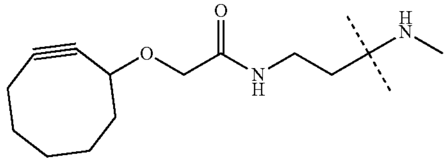

ALK-5a-3

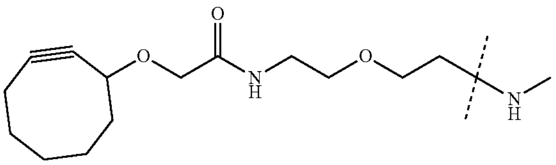

ALK-6-3a

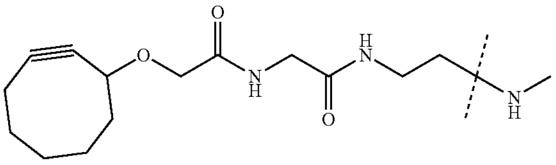

ALK-6-3b

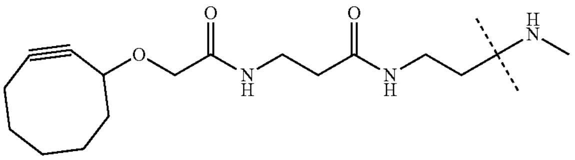

ALK-7a-3

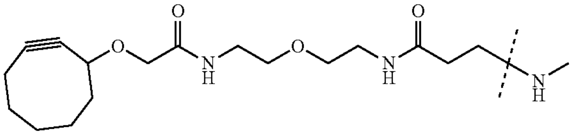

and

-$L^2$- in the chemically modified alginic acid derivative represented by Formula (II) is a group selected from the group consisting of the following partial structural formulae, wherein in each formula, the outsides of the broken lines at both ends are not included:

LN-1-3

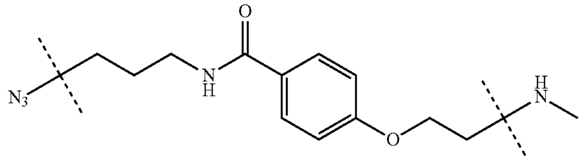

LN-2-3

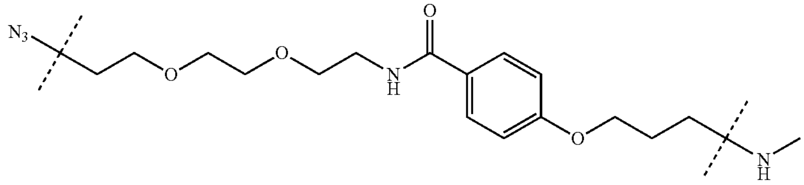

LN-3-3a

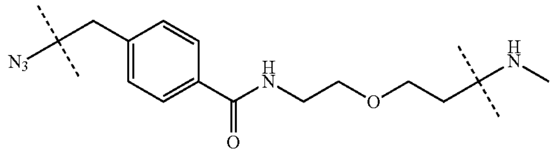

LN-3-3b

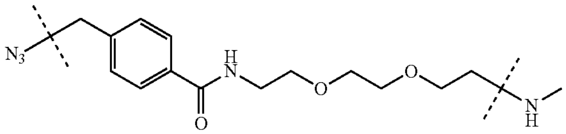

LN-4-3

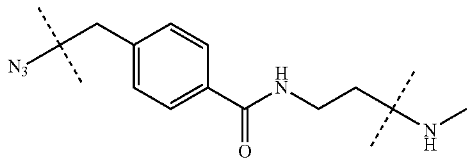

LN-5-3a

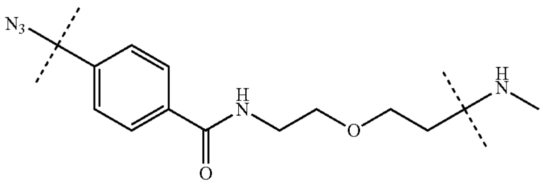

LN-5-3b

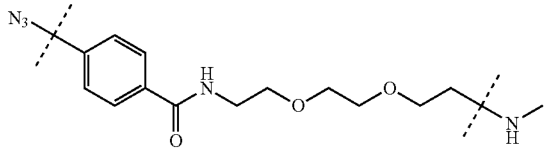

LN-6-3

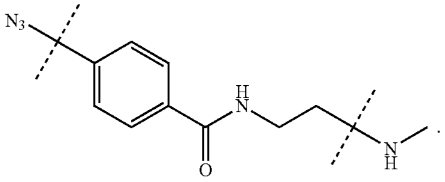

6. The polymer-coated crosslinked alginate gel fiber according to claim 1, wherein Akn-$L^1$- in the chemically modified alginic acid derivative represented by Formula (I) is a group selected from the group consisting of the following partial structural formulae, wherein in each formula, the right side of the broken line is not included:

ALK-1a-3a

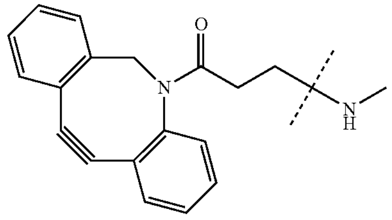

-continued

ALK-2-3

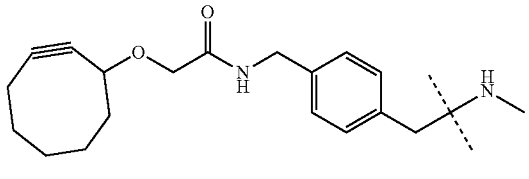

and

-$L^2$- in the chemically modified alginic acid derivative represented by Formula (II) is a group selected from the group consisting of the following partial structural formulae, wherein in each formula, the outsides of the broken lines at both ends are not included:

LN-1-3

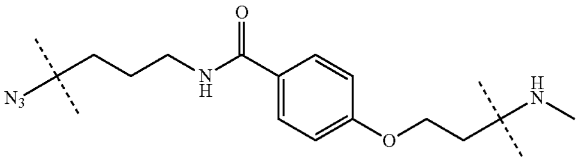

LN-3-3a

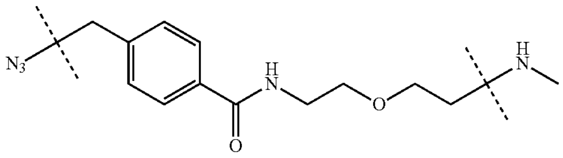

LN-5-3a

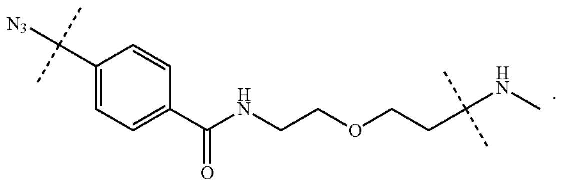

7. The polymer-coated crosslinked alginate gel fiber according to claim 2, wherein the antibody-producing cell that is contained in the core layer is an antibody-producing genetically modified animal cell in which a host cell of the genetically modified animal cell is selected from the group consisting of a CHO cell, a CHO cell subline, a COS cell, an Sp2/0 cell, an NS0 cell, an SP2 cell and a PERC6 cell.

8. The polymer-coated crosslinked alginate gel fiber according to claim 1, wherein the bioactive substance-producing cell that is contained in the core layer is an insulin-secreting cell.

9. The polymer-coated crosslinked alginate gel fiber according to claim 1, wherein the concentration of a solution mixture of the chemically modified alginic acid derivative represented by Formula (I) and the chemically modified alginic acid derivative represented by Formula (II), which are used to form the crosslinked alginate gel that is contained in the core layer of the polymer-coated crosslinked alginate gel fiber is within a range of 0.15 to 1.5 wt %.

10. The polymer-coated crosslinked alginate gel fiber according to claim 4, wherein the core layer further comprises at least one component selected from the group consisting of an alginic acid solution, and an alginate gel that is formed from an alginic acid solution.

11. The polymer-coated crosslinked alginate gel fiber according to claim 10, wherein the concentration ($C_{ALG}$) of the alginic acid solution is within a range of $0<C_{ALG}\leq1.7$ wt %.

12. The polymer-coated crosslinked alginate gel fiber according to claim 11, wherein the total concentration ($C_{TOL}$) of the concentration of the solution mixture comprising the chemically modified alginic acid derivatives represented by Formula (I) and Formula (II), and the concentration of the alginic acid solution is within the range of $0<C_{TOL}\leq2.0$ wt %.

13. The polymer-coated crosslinked alginate gel fiber according to claim 1, wherein the polymer-coated crosslinked alginate gel fiber has an outer diameter within a range of 0.1 to 2000 μm.

14. The polymer-coated crosslinked alginate gel fiber according to claim 1, wherein the polymer-coated crosslinked alginate gel fiber has a length within a range of 0.01 to 75 m.

15. The polymer-coated crosslinked alginate gel fiber according to claim 1, wherein the crosslinked alginate gel that is contained in the core layer of the polymer-coated crosslinked alginate gel fiber comprises a chemical crosslink through a group represented by Formula (III-L) below:

(III-L)

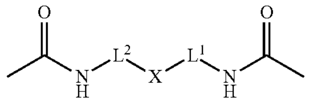

in Formula (III-L), —CONH— and —NHCO— at both ends represent amide bonds through arbitrary carboxyl groups of the alginic acid;

—X— is a cyclic group selected from the group of partial structural formulae shown in the following table:

| No. | —X— |
|---|---|
| CL-1 | 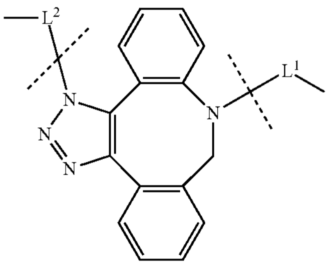 |
| CL-1-r | 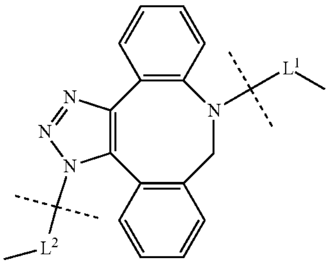 |
| CL-2 | 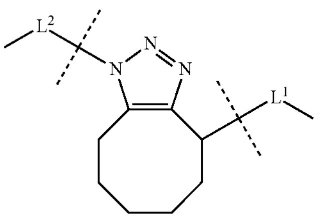 |

-continued

| No. | —X— |
|---|---|
| CL-2-r | 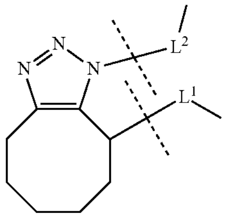 |

in a case where —X— is (CL-1) or (CL-1-r), -$L^1$- is a divalent linker, wherein in each formula, the outsides of the broken lines at both ends are not included, selected from the group of partial structural formulae shown in the following table:

| —$L^1$— | |
|---|---|
| 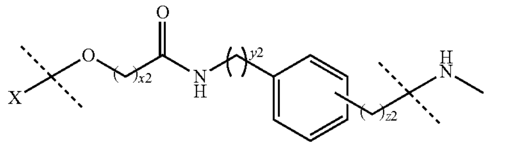 | x1a = 1-6 |
| 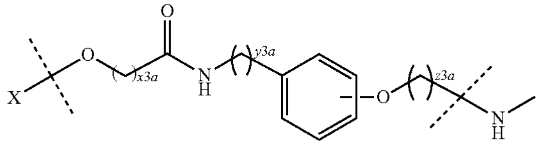 | x1b = 1-6<br>y1b = 1-6 |

and, in a case where —X— is (CL-2) or (CL-2-r), -$L^1$- is a divalent linker, wherein in each formula, the outsides of the broken lines at both ends are not included, selected from the group of partial structural formulae shown in the following table:

| —$L^1$— | |
|---|---|
| 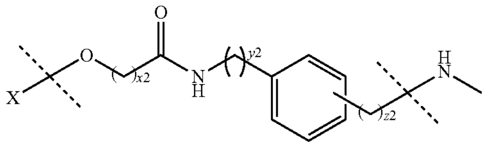 | x2 = 1-6<br>y2 = 0-6<br>z2 = 1-6 |
| 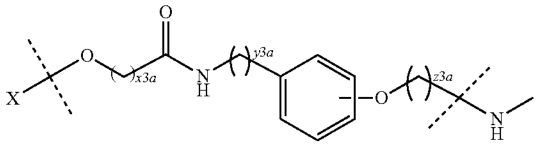 | x3a = 1-6<br>y3a = 0-6<br>z3a = 2-6 |
| 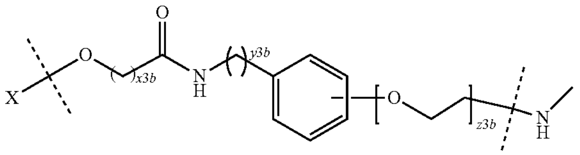 | x3b = 1-6<br>y3b = 0-6<br>z3b = 1-6 |

-continued
| —$L^1$— | |
|---|---|
| 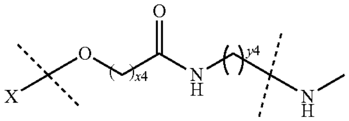 | x4 = 1-6<br>y4 = 2-6 |
| 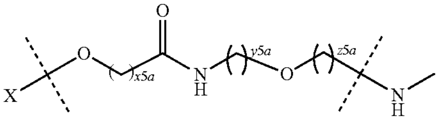 | x5a = 1-6<br>y5a = 2-6<br>z5a = 2-6 |
| 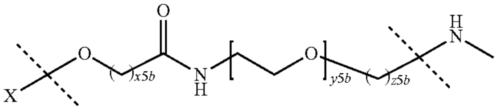 | x5b = 1-6<br>y5b = 1-6<br>z5b = 2-6 |
| 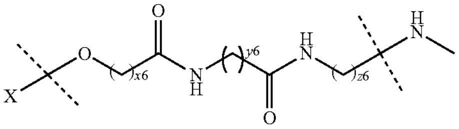 | x6 = 1-6<br>y6 = 1-6<br>z6 = 2-6 |
| 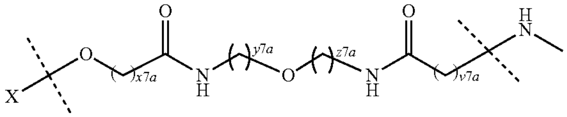 | x7a = 1-6<br>y7a = 2-6<br>z7a = 2-6<br>v7a = 1-6 |
| 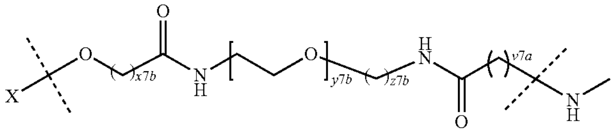 ; | x7b = 1-6<br>y7b = 1-6<br>z7b = 2-6<br>v7b = 1-6 |
and
-$L^2$- is a linker selected from the group consisting of partial structural formulae, wherein in each formula, the outsides of the broken lines at both ends are not included, shown in the following table:
| —$L^2$— | |
|---|---|
| 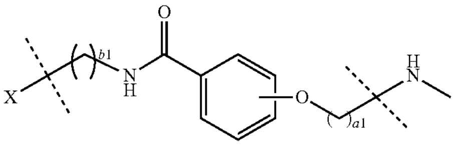 | a1 = 2-6<br>b1 = 2-6 |
| 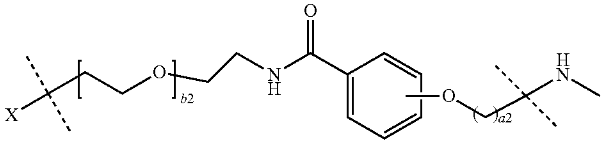 | a2 = 2-6<br>b2 = 1-6 |
| 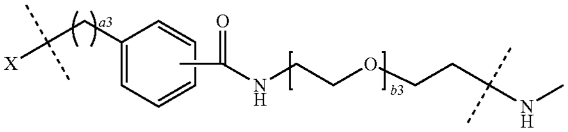 | a3 = 1-6<br>b3 = 1-6 |

-continued

| —$L^2$— | |
|---|---|
| 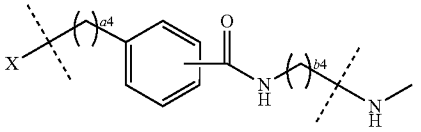 | a4 = 1-6<br>b4 = 2-6 |
| 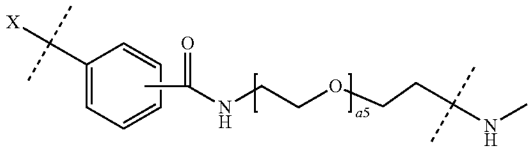 | a5 = 1-6 |
| 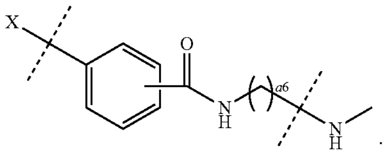 | a6 = 2-6 |

16. The polymer-coated crosslinked alginate gel fiber according to claim 1, wherein the bioactive substance-producing cell that is contained in the core layer is a pancreatic islet.

17. The polymer-coated crosslinked alginate gel fiber according to claim 1, wherein said cell can grow in said core layer of the fiber and said antibody and bioactive substance can continuously penetrate the cationic polymer layer and be discharged outside the fiber.

18. The polymer-coated crosslinked alginate gel fiber according to claim 1, wherein the polymer-coated crosslinked alginate gel fiber has a length within a range of 0.01 to 50 m.

19. The polymer-coated crosslinked alginate gel fiber according to claim 1, wherein the polymer-coated crosslinked alginate gel fiber has a length within a range of 0.01 to 10 m.

20. The polymer-coated crosslinked alginate gel fiber according to claim 1, wherein the polymer-coated crosslinked alginate gel fiber is circular in cross section and consists of said core layer and said cationic polymer layer and said cationic polymer layer is applied to said core layer, including both ends of said fiber, to directly adhere said cationic polymer layer onto said core layer by electrostatic interaction, the polymer-coated crosslinked alginate gel fiber has a length within a range of 0.01 to 10 m, the diameter of the core layer is 20 to 1000 μm, the thickness of the cationic polymer layer is 5 μm to 200 μm and the diameter of the cross section of the core layer is less than the diameter of the fiber cross section and is 50% or more.

* * * * *